US007138259B2

(12) United States Patent
Beavo et al.

(10) Patent No.: US 7,138,259 B2
(45) Date of Patent: Nov. 21, 2006

(54) PDES AND USES THEREOF

(75) Inventors: Joseph A. Beavo, Seattle, WA (US); Thomas Seebeck, Ortschwaben (CH); Scott Haydn Soderling, Beaverton, OR (US); Ana Rascon, Caracas (VE); Roya Zoraghi, Nashville, TN (US); Stefan Kunz, Bern (CH); Kewei Gong, Los Angeles, CA (US); Natalie Glavas, Daly City, CA (US)

(73) Assignees: University of Washington, Seattle, WA (US); University of Bern, Bern (CH)

( * ) Notice: Subject to any disclaimer, the term of this patent is extended or adjusted under 35 U.S.C. 154(b) by 600 days.

(21) Appl. No.: 10/380,437

(22) PCT Filed: Sep. 12, 2001

(86) PCT No.: PCT/US01/28503
§ 371 (c)(1),
(2), (4) Date: Mar. 12, 2003

(87) PCT Pub. No.: WO02/22661
PCT Pub. Date: Mar. 21, 2002

(65) Prior Publication Data
US 2005/0058998 A1 Mar. 17, 2005

Related U.S. Application Data

(60) Provisional application No. 60/240,500, filed on Oct. 12, 2000, provisional application No. 60/232,445, filed on Sep. 12, 2000.

(51) Int. Cl.
C12N 9/16 (2006.01)
C12N 15/79 (2006.01)
C12N 15/80 (2006.01)
C12N 15/81 (2006.01)
C12Q 1/68 (2006.01)

(52) U.S. Cl. ............... 435/196; 435/252.3; 435/320.1; 536/23.2; 436/6

(58) Field of Classification Search ............... 435/6, 435/196, 252.3, 320.1; 536/23.2
See application file for complete search history.

(56) References Cited

U.S. PATENT DOCUMENTS

| | | | | |
|---|---|---|---|---|
| 4,358,535 | A | 11/1982 | Falkow et al. | 435/5 |
| 4,777,019 | A | 10/1988 | Dandekar | 422/82.02 |
| 4,816,397 | A | 3/1989 | Boss et al. | 435/69.6 |
| 4,816,567 | A | 3/1989 | Cabilly et al. | 530/387.6 |
| 4,965,188 | A | 10/1990 | Mullis et al. | 435/6 |
| 5,110,802 | A | 5/1992 | Cantin et al. | 514/44 |
| 5,194,428 | A | 3/1993 | Agrawal et al. | 514/44 |
| 5,539,082 | A | 7/1996 | Nielsen et al. | 530/300 |
| 5,932,423 | A | * | 8/1999 | Au-Young et al. | 435/6 |

OTHER PUBLICATIONS

Abdullah, Khalid M. et al., "A Neutral Glycoprotease of *Pasteurella haemolytica* A1 Specifically Cleaves O-Sialoglycoporteins," *Infection and Immunity*, 1992, 60:56-62 (Exhibit 9).
Alexandre, Sylvie et al., "Differential expression of a family of putative adenylate/guanylate cyclase genes in *Trypanosoma brucei*," *Molecular and Biochemical Parasitology*, 1990, 43:279-88 (Exhibit 10).
Alexandre, Sylvie et al., "Families of adenylate cyclase genes in *Trypanosoma brucei*," *Molecular and Biochemical Parasitology*, 1996, 77:173-82 (Exhibit 11).
Altschul, Stephen F. et al., "Basic Local Alignment Search Tool," *Journal of Molecular Biology*, 1990, 215:403-10 (Exhibit 12).
Aravind, L. and Christopher P. Ponting, "The GAF domain: an evolutionary link between diverse phototransducing proteins," *Trends in Biochemical Sciences*, 1997, 22:458-9 (Exhibit 13).
Arnon, Ruth et al., "Monoclonal Antibodies for Immunotargeting of Drugs in Cancer Therapy," *Monoclonal Antibodies and Cancer Therapy*, Reisfeld and Sell (eds.), Alan R. Liss, Inc., NY, 1985, pp. 243-256 (Exhibit 14).
Arthur, Jill F. et al., "A comparison of gene transfer methods in human dendritic cells," *Cancer Gene Therapy*, 1997, 4:17-25 (Exhibit 15).
Ashley, David M. et al., "Bone Marrow-generated Dendritic Cells Pulsed with Tumor Extracts of Tumor RNA Induce Antitumor Immunity against Central Nervous System Tumors," *Journal of Experimental Medicine*, 1997, 186:1177-82 (Exhibit 16).
Atienza, Josephine M. and John Colicelli, "Yeast Model System for Study of Mammalian Phosphodiesterases," *Methods*, 1998, 14:35-42 (Exhibit 17).
Baiget, Montserrat et al., "Identifcación de dos mutaciones allicas en el gen de la subunidad beta de la fosfodiesterasa en una familia española afectada de retinosis pigmetaria autosómica recesiva," *Medicina Clínica*, 1998, 111:420-422 (Exhibit 18).
Bastin, Philippe et al., "A novel epitope tag system to study protein targeting and organelle biogenesis in *Trypanosoma brucei*," *Molecular and Biochemical Parasitology*, 1996, 77:235-9 (Exhibit 19).
Beavo, Joseph A. and David H. Reifsnyder, "Primary sequence of cyclic nucleotide phosphodiesterase isozymes and the design of selective inhibitors," *Trends in Pharmacological Sciences*, 1990, 11:150-5 (Exhibit 20).
Benashski, Sharon E. et al., "Dimerization of the Highly Conserved Light Chain Shared by Dynein and Myosin V," *Journal of Biological Chemistry*, 1997, 272:20929-35 (Exhibit 21).
Berent, Susan L. et al., "Comparison of Oligonucleotide and Long DNA Fragments as Probes in DNA and RNA Dot, Southern, Northern, Colony and Plaque Hybridizations," *Biotechniques*, 1985, 3:208-18 (Exhibit 22).

(Continued)

Primary Examiner—Tekchand Saidha
(74) Attorney, Agent, or Firm—Townsend and Townsend and Crew LLP

(57) ABSTRACT

The present invention provides isolated full-length nucleic acid molecules encoding the novel PDE protein of the invention, and methods for uses thereof. The nucleic acid molecules of the invention also include peptide nucleic acids (PNA), and antisense molecules that react with the nucleic acid molecules of the invention. The invention also relates to agonists, antibodies, antagonists or inhibitors of the activity of novel PDE proteins. These compositions are useful for the diagnosis, prevention or treatment of conditions associated with the presence or the deficiency of novel PDE proteins.

13 Claims, 52 Drawing Sheets

OTHER PUBLICATIONS

Berkner, Kathleen L., "Development of Adenovirus Vectors for the Expression of Heterologous Genes," *Biotechniques*, 1988, 6:616-29 (Exhibit 23).

Bitter, Grant A. et al., "Expression and Secretion Vectors for Yeast," *Methods in Enzymology*, Wu and Grossman (eds.), 153:516-44, 19987 (Exhibit 24).

Bloom, Timothy J. et al., "Identification and tissue-specific expression of PDE7 phosphodiesterase splice variants," *Proceedings of the National Academy Sciences USA*, 1996, 93:14188-92 (Exhibit 25).

Bodley, Annette L. et al., "Drug Cytotoxicity Assay for African Trypanosomes and *Leishmania* Species," *Journal of Infectious Diseases*, 1995, 172:1157-9 (Exhibit 26).

Borden, Katherine L. B., "RING fingers and B-boxes: zinc-binding protein-protein interaction domains," *Biochemistry and Cell Biology*, 1998, 76:351-8 (Exhibit 27).

Borrebaeck, Carl A. K. et al., "Human monoclonal antibodies produced by primary *in vitro* immunization of peripheral blood lymphocytes," *Proceedings of the National Academy of Sciences USA*, 1988, 85:3995-9 (Exhibit 28).

Brisson, N. et al., "Expression of a bacterial gene in plants by using a viral vector," *Nature*, 1984, 310:511-4 (Exhibit 29).

Broglie, Richard et al., "Light-Regulated Expression of a Pea Ribulose-1,5-Biphosphate Carboxylase Small Subunit Gene in Transformed Plant Cells," *Science*, 1984, 224:838-43 (Exhibit 30).

Brun, R. et al., "Cultivation of vertebrate infective forms derived from metacyclic forms of pleomorphic *Trypanosoma brucei* stocks," *Acta Tropica*, 1979, 36:387-90 (Exhibit 31).

Capecchi, Mario R., "Altering the Genome by Homologous Recombination," *Science*, 1989, 244:1288-92 (Exhibit 32).

Charbonneau, Harry et al., "Identification of a conserved domain among cyclic nucleotide phosphodiesterases from diverse species," *Proceedings of the National Academy of Sciences USA*, 1986, 83:9308-12 (Exhibit 33).

Clayton, Christine et al., "Short communication: Genetic nomenclature for *Trypanosoma* and *Leishmania*," *Molecular and Biochemical Parasitology*, 1998, 97:221-4 (Exhibit 34).

Cohen, Stanley N. et al., "Nonchromosomal Antibiotic Resistance in Bacteria: Genetic Transformation of *Escherichia coli* by R-Factor DNA," *Proceedings of the National Academy of Sciences*, 1972, 69:2110-4 (Exhibit 35).

Colbére-Garapin, Florence et al., "A New Dominant Hybrid Selective Marker for Higher Eukaryotic Cells," *Journal of Molecular Biology*, 1981, 150:1-14 (Exhibit 36).

Corruzi, Gloria et al., "Tissue-specific and light-regulated expression of a pea nuclear gene encoding the small subunit of ribulose-1, 5-bisphosphate carboxylase," *EMBO Journal*, 1984, 3:1671-9 (Exhibit 37).

Crépieux, Pascale et al., "IκBα Physically Interacts with a Cytoskeleton-Associated Protein through Its Signal Response Domain," *Molecular and Cellular Biology*, 1997, 17:7375-85 (Exhibit 38).

Dekomien, G. and J. T. Epplen, "Short communication: Exclusion of the PDE6A gene for generalized progressive retinal atrophy in 11 breeds of dog," *Animal Genetics*, 2000, 31:135-9 (Exhibit 39).

Dickinson, Natalie T. et al., "Activation of cGMP-stimulated phosphodiesterase by nitroprusside limits cAMP accumulation in human platelets: effects on platelet aggregation," *Biochemical Journal*, 1997, 323:371-7 (Exhibit 40).

Dousa, Thomas P., "Cyclic-3',5'-nucleotide phosphodiesterase isozymes in cell biology and pathophysiology of the kidney," *Kidney International*, 1999, 55:29-62 (Exhibit 41).

Dugas, Hermann and Christopher Penney, *Bioorganic Chemistry*, Springer-Verlag, NY, 54-92 (Exhibit 42).

Dunlap, Paul V. and Sean M. Callahan, "Characterization of a Periplasmic 3':5'-Cyclic Nucleotide Phosphodiesterase Gene, *cpdP*, from the Marine Symbiotic Bacterium *Vibrio fischeri*," *Journal of Bacteriology*, 1993, 175:4615-24 (Exhibit 43).

Ekholm, Dag et al., "Differential Expression of Cyclic Nucleotide Phosphodiesterase 3 and 4 Activities in Human T Cell Clones Specific for Myelin Basic Protein," *Journal of Immunology*, 1997, 159:1520-9 (Exhibit 44).

Elghetany, M. Tarek, "Surface marker abnormalities in myelodysplastic syndromes," *Haematologica*, 1998, 83:1104-15 (Exhibit 45).

Engelhard, E. K. et al., "The insect tracheal system: A conduit for the systemic spread of *Autographa californica* M nuclear polyhedrosis virus," *Proceedings of the National Academy of Sciences USA*, 1994, 91:3224-7 (Exhibit 46).

Erdogan, Suat and Miles D. Houslay, "Challenge of human Jurkat T-cells with the adenylate cyclase activator forskolin elicits major changes in cAMP phosphodiesterase (PDE) expression by upregulating PDE3 and inducing PDE4D1 and PDE4D2 splice variants as well as down-regulating a novel PDE4A splice variant," *Biochemical Journal*, 1997, 321:165-75 (Exhibit 47).

Fawcett, Lindsay et al., "Molecular cloning and characterization of a distinct human phosphodiesterase gene family: PDE11A," *Proceedings of the National Academy of Sciences USA*, 2000, 97:3702-7 (Exhibit 48).

Fell, H. Perry et al., "Homologous recombination in hybridoma cells: Heavy chain chimeric antibody produced by gene targeting," *Proceedings of the National Academy of Sciences USA*, 1989, 86:8507-11 (Exhibit 49).

Fields, Stanley and Ok-kyu Song, "A novel genetic system to detect protein-protein interactions," *Nature*, 1989, 340:245-6 (Exhibit 50).

Fisher, Douglas A. et al., "Isolation and Characterization of PDE8A, a Novel Human cAMP-Specific Phosphodiesterase," *Biochemical and Biophysical Research Communications*, 1998, 246:570-7 (Exhibit 51).

Fisher, Douglas A. et al., "Isolation and Characterization of PDE9A, a Novel Human cGMP-specific Phosphodiesterase," *Journal of Biological Chemistry*, 1998, 273:15559-64 (Exhibit 52).

Foon, Kenneth A. et al., "Immune Response to the Carcinoembryonic Antigen in Patients Treated with an Anti-Idiotype Antibody Vaccine," *Journal of Clinical Investigation*, 1995, 96:334-42 (Exhibit 53).

Francis, Sharron H. et al., "Communication: Zinc Interactions and Conserved Motifs of the cGMP-binding cGMP-specific Phosphodiesterase Suggest That It Is a Zinc Hydrolase," *Journal of Biological Chemistry*, 1994, 269:22477-80 (Exhibit 54).

Freemont, Paul S., "Ubiquitination: RING for destruction?," *Current Biology*, 2000, 10:R84-7 (Exhibit 55).

Gekakis, Nicholas et al., "Isolation of *timeless* by PER Protein Interaction: Defective Interaction Between *timeless* Protein and Long-Period Mutant PER," *Science*, 1995, 270:811-5 (Exhibit 56).

Giembycz, Mark A. et al., "Identification of cyclic AMP phosphodiesterases 3, 4 and 7 in human CD4[+]and CD8[+]T-lymphocytes: role in regulating proliferation and the biosynthesis of interleukin-2," *British Journal of Pharmacology*, 1996, 118:1945-58 (Exhibit 57).

Gietz, R. Daniel et al., "Identification of proteins that interact with a protein of interest: Applications of the yeast two-hybrid system," *Molecular and Cellular Biochemistry*, 1997, 172:67-79 (Exhibit 58).

Graham, F. L. and A. J. Van Der Eb, "A New Technique for the Assay of Infectivity of Human Adenovrus 5 DNA," *Virology*, 1973, 52:456-67 (Exhibit 59).

Hanke, Jeffrey H. et al., "Discovery of a Novel, Potent, and Src Family-selective Tyrosine Kinase Inhibitor," *Journal of Biological Chemistry*, 1996, 271:695-701 (Exhibit 60).

Hannon, Gregory J. et al., "Isolation of the Rb-related p130 through its interaction with CDK2 and cyclins," *Genes & Development*, 1993, 7:2378-91 (Exhibit 61).

Hansen, R. Scott and J. A. Beavo, "Purification of two calcium/calmodulin-dependent forms of cyclic nucleotide phosphodiesterase by using conformation-specific monoclonal antibody chromatography," *Proceedings of the National Academy of Sciences USA*, 1982, 79:2788-92 (Exhibit 62).

Hartman, Standish C. and Richard C. Mulligan, "Two dominant-acting selectable markers for gene transfer studies in mammalian cells," *Proceedings of the National Academy of Sciences USA*, 1988, 85:8047-51 (Exhibit 63).

Hellström, Karl Erik et al., "Antibodies for Drug Delivery," *Controlled Drug Delivery* (2nd ed.), Robinson et al. (eds.), Marcel Dekker, Inc., 1987, pp. 623-653 (Exhibit 64).

Henderson, Robert A. et al., "Human Dendritic Cells Genetically Engineered to Express High Levels of the Human Epithelial tumor Antigen Mucin (MUC-1)," *Cancer Research*, 1996, 56:3763-9 (Exhibit 65).

Henras, Anthony et al., "Nhp2p and Nop10p are essential for the function of H/ACA snoRNPs," *EMBO Journal*, 1998, 17:7078-90 (Exhibit 66).

Herlyn, Dorothee et al., "Anti-idiotype cancer vaccines: past and future," *Cancer Immunology, Immunotherapy*, 1996, 43:65-76 (Exhibit 67).

Hesse, Friedemann et al., "A novel cultivation technique for long-term maintenance of bloodstream form trypanosomes in vitro," *Molecular and Biochemical Parasitology*, 1995, 70:157-66 (Exhibit 68).

Hoyer, L. L. et al., "A *Candida albicans* cyclic nucleotide phosphodiesterase: cloning and expression in *Saccharomyces cerevisiae* and biochemical characterization of the recombinant enzyme," *Microbiology*, 1994, 140:1533-42 (Exhibit 69).

Ichimura, Michio and Hiroshi Kase, "A New Cyclic Nucleotide Phosphodiesterase Isozyme Expressed in the T-lymphocyte Cell Lines," *Biochemical and Biophysical Research Communications*, 1993, 193:985-90 (Exhibit 70).

Jacobitz, Susanne et al., "Role of Conserved Histidines in Catalytic Activity and Inhibitor Binding of Human Recombinant Phosphodiesterase 4A," *Molecular Pharmacology*, 1997, 51:999-1006 (Exhibit 71).

Kauvar, Lawrence M., "Defective Cyclic Adenosine 3':5'-Monophosphate Phosphodiesterase in the *Drosophila* Memory Mutant *dunce*," *Journal of Neuroscience*, 1982, 2:1347-58 (Exhibit 72).

Kim, Doo Ho and Adam Lerner, "Type 4 Cyclic Adenosine Monophosphate Phosphodiesterase as a Therapeutic Target in Chronic Lymphocytic Leukemia," *Blood*, 1998, 92:2484-94 (Exhibit 73).

Köhler, G. and C. Milstein, "Continuous cultures of fused cells secreting antibody of predefined specificity," *Nature*, 1975, 256:495-7 (Exhibit 74).

Kozbor, Danuta and John C. Roder, "The production of monoclonal antibodies from human lymphocytes," *Immunology Today*, 1983, 4:72-9 (Exhibit 75).

Lacombe, Marie-Lisa et al., "Molecular Cloning and Developmental Expression of the Cyclic Nucleotide Phosphodiesterase Gene of *Dictyostelium discoideum*," *Journal of Biological Chemistry*, 1986, 261:16811-7 (Exhibit 76).

Lerner, Adam et al., "The cAMP Signaling Pathway as a Therapeutic Target in Lymphoid Malignancies," *Leukemia and Lymphoma*, 2000, 37:39-51 (Exhibit 77).

Li, Linsong et al., "CD3- and CD28-Dependent Induction of PDE7 Required for T Cell Activation," *Science*, 1999, 283:848-51 (Exhibit 78).

Lin, Jixun et al., "Increased cAMP and cAMP-Dependent Protein Kinase Activity Mediate Anti-CD2 Induced Suppression of Anti-CD3-Driven Interleukin-2 Production and CD25 Expression," *Pathobiology*, 1995, 63:175-87 (Exhibit 79).

Liu, He et al., "Constitutive and Antibody-induced Internalization of Prostate-specific Membrane Antigen," *Cancer Research*, 1998, 58:4055-60 (Exhibit 80).

Logan, John and Thomas Shenk, "*Adenovirus tripartite* leader sequence enhances translation of mRNAs late after infection," *Proceedings of the Nationall Academy of Sciences USA*, 1984, 81:3655-9 (Exhibit 81).

Lowy, Israel et al., "Isolation of Transforming DNA: Cloning the Hamster aprt Gene," *Cell*, 1980, 22:817-23 (Exhibit 82).

MacFarland, R. Trevor et al., "High Concentrations of a cGMP-stimulated Phosphodiesterase Mediate ANP-induced Decreases in cAMP and Steroidogenesis in Adrenal Glomerulosa Cells," *Journal of Biological Chemistry*, 1991, 266:136-42 (Exhibit 83).

Manfredi, John P. et al., "Yeast α Mating Factor Structure-Activity Relationship Derived from Genetically Selected Peptide Agonists and Antagonists of Ste2p," *Molecular and Cellular Biology*, 1996, 16:4700-9 (Exhibit 84).

Manning, Carol D. et al., "Suppression of human inflammatory cell function by subtype-selective PDE4 inhibitors correlates with inhibition of PDE4A and PDE4B," *British Journal of Pharmacology*, 1999, 128:1393-8 (Exhibit 85).

McAllister-Lucas, Linda M. et al., "An Essential Aspartic Acid at Each of Two Allosteri cGMP-binding Sites of a cGMP-specific Phosphodiesterase," *Journal of Biological Chemistry*, 1995, 270:30671-9 (Exhibit 86).

McLaughlin, Margaret E. et al., "Recessive mutations in the gene encoding the β-subunit of rod phosphodiesterase in patients with retinitis pigmentosa," *Nature Genetics*, 1993, 4:130-4 (Exhibit 87).

McPhee, Ian et al., "Association with the SRC Family Tyrosyl Kinase LYN Triggers a Conformational Change in the Catalytic Region of Human cAMP-specific Phosphodiesterase HSPDE4A4B," *Journal of Biological Chemistry*, 1999, 274:11796-810 (Exhibit 88).

Michaeli, Tamar et al., "Isolation and Characterization of a Previously Undetected Human cAMP Phosphodiesterase by Complementation of cAMP Phosphodiesterase-deficient *Saccharomyces cerevisiae*," *Journal of Biological Chemistry*, 1993, 268:12925-32 (Exhibit 89).

Morrison, Sherie L. et al., "Chimeric human antibody molecules: Mouse antigen-binding domains with human constant region domains," *Proceedings of the National Academy of Sciences USA*, 1984, 81:6851-5 (Exhibit 90).

Mumberg, Dominik et al., "Yeast vectors for the controlled expression of heterologous proteins in different genetic backgrounds," *Gene*, 1995, 156:119-22 (Exhibit 91).

Murphy, Noel B. et al., "*Trypanosoma brucei* Repeated Element with Unusual Structural and Transcriptional Properties," *Journal of Molecular Biology*, 1987, 195:855-71 (Exhibit 92).

Naula, C. and T. Seebeck, "Cyclic AMP Signaling in Trypanosomatids," *Parasitology Today*, 2000, 16:35-8 (Exhibit 93).

Neuberger, Michael S. et al., "Recombinant antibodies possessing novel effector functions," *Nature*, 1984, 312:604-8 (Exhibit 94).

Nielsen, Peter E. et al., "Peptide nucleic acids (PNAs): Potential anti-sense and anti-gene agents," *Anti-Cancer Drug Design*, 1993, 8:53-63 (Exhibit 95).

Nikawa, Jun-Ichi et al., "Cloning and Characterization of the Low-Affinity Cyclic AMP Phosphodiesterase Gene of *Saccharomyces cerevisiae*," *Molecular and Cellular Biology*, 1987, 7:3629-36 (Exhibit 96).

Olsson, Lennart and Henry S. Kaplan, "Human-Human Monoclonal Antibody-Producing Hybridomas: Technical Aspects," *Methods in Enzymology*, Langone and Vunakis (eds.), 1983, 92:3-16 (Exhibit 97).

Paveto, Cristina et al., "The Nitric Oxide Transduction Pathway in *Trypanosoma cruzi*," *Journal of Biological Chemistry*, 1995, 270:16576-9 (Exhibit 98).

Pillai, Rajeswari et al., "Use of a yeast expression system for the isolation and analysis of drug-resistant mutants of a mammalian phosphodiesterase," *Proceedings of the National Academy of Sciences USA*, 1993, 90:11970-4 (Exhibit 99).

Ponting, Chris P. et al., "SMART: Identification and annotation of domains from signalling and extracellular protein sequences," *Nucleic Acids Research*, 1999, 27:226-9 (Exhibit 100).

Powell, Leland D. and Ajit Varki, "The Oligosaccharide Binding Specificities of CD22β, a Sialic Acid-specific Lectin of B Cells," *Journal of Biological Chemistry*, 1994, 269:10628-36 (Exhibit 101).

Rascón, Ana et al., "Characterizatio of cyclic AMP phosphodiesterases in *Leishmania mexicana* and purification of a soluble form," *Molecular and Biochemical Parasitology*, 2000, 106:283-92 (Exhibit 102).

Reed, Sharon L. et al., "Effect of Theophylline on Differentiation of *Trypanosoma brucei*," *Infection and Immunity*, 1985, 49:844-7 (Exhibit 103).

Restifo, Nicholas P., "The new vaccines: building viruses that elicit antitumor immunity," *Current Opinion in Immunology*, 1996, 8:658-63 (Exhibit 104).

Ribas, Antoni et al., "Genetic Immunization for the Melanoma Antigen MART-1/Melan-A Using Recombinant Adenovirus-transduced Murine Dendritic Cells," *Cancer Research*, 1997, 57:2865-9 (Exhibit 105).

Rhodes, Carol A. et al., "Transformation of Maize by Electroporation of Embryos," *Methods in Molecular Biology*, 1995, 55:121-31 (Exhibit 106).

Rost, Burkhard and Chris Sander, "Combining Evolutionary Information and Neural Networks to Predict Protein Secondary Structure," *Proteins: Structure, Function and Genetics*, 1994, 19:55-72 (Exhibit 107).

Rowley, Janet D. et al., "Mapping chromosome band 11q23 in human acute leukemia with biotinylated probes: Identification of 11q23 translocation breakpoints with a yeast artificial chromosome," *Proceedings of the National Academy of Sciences USA*, 1990, 87:9358-62 (Exhibit 108).

Sbicego, Sandro et al., "The use of transgenic *Trypanosoma brucei* to identify compounds inducing the differentiation of bloodstream forms to procyclic forms," *Molecular and Biochemical Parasitology*, 1999, 104:311-22 (Exhibit 109).

Scharf, Klaus-Dieter et al., "Heat Stress Promoters and Transcription Factors," *Results and Problems in Cell Differentiation*, 1994, L. Nover (ed.), 20:125-62 (Exhibit 110).

Schilling, Roger J. et al., "A High-Throughput Assay for Cyclic Nucleotide Phosphodiesterase," *Analytical Biochemistry*, 1994, 216:154-8 (Exhibit 111).

Schuler, Gregory D. et al., "A Workbench for Multiple Alignment Construction and Analysis," *Proteins: Structure, Function and Genetics*, 1991, 9:180-90 (Exhibit 112).

Schultz, Jorg et al., "SMART, a simple modular architecture research tool: Identification of signaling domains," *Proceedings of the National Academy of Sciences USA*, 1998, 95:5857-64 (Exhibit 113).

Sgroi, Dennis et al., "CD22, a B Cell-specific Immunoglobulin Superfamily Member, Is a Sialic Acid-binding Lectin," *Journal of Biological Chemistry*, 1993, 268:7011-8 (Exhibit 114).

Shahinian, Arda et al., "Differential T Cell Costimulatory Requirements in CD28-Deficient Mice," *Science*, 1993, 261:609-12 (Exhibit 115).

Sharon, J. et al., "Expression of a $V_H C_\kappa$ chimaeric protein in mouse myeloma cells," *Nature*, 1984, 309:364-7 (Exhibit 116).

Shaulsky, Gad et al., "Developmental signal transduction pathways uncovered by genetic suppressors," *Proceedings of the National Academy of Sciences*, 1996, 93:15260-5 (Exhibit 117).

Shizuya, Hiroaki et al., "Cloning and stable maintenance of 300-kilobase-pair fragments of human DNA in *Escherichia coli* using an F-factor-based vector," Proceedings of the National Academy of Sciences USA, 1992, 89:8794-7 (Exhibit 118).

Smith, Carolyn J. et al., "Development of Decompensated Dilated Cardiomyopathy Is Associated With Decreased Gene Expression and Activity of the Milrinone-Sensitive cAMP Phosphodiesterase PDE3A," *Circulation*, 1997, 96:3116-23 (Exhibit 119).

Smith, Gale E. et al., "Molecular Engineering of the *Autographa californica* Nuclear Polyhedrosis Virus Genome: Deletion Mutations Within the Polyhedrin Gene," *Journal of Virology*, 1983, 46:584-93 (Exhibit 120).

Smith, Randall F. et al., "BCM Search Launcher—An Integrated Interface to Molecular Biology Date Base Search and Analysis Services Available on the World Wide Web," *Genome Research*, 1996, 6:454-62 (Exhibit 121).

Sodee, D. Bruce et al., "Preliminary Imaging Results Using In-111 Labeled CYT-356 (Prostascint) in the Detection of Recurrent Prostate Cancer," *Clinical Nuclear Medicine*, 1996, 21:759-67 (Exhibit 122).

Soderling, Scott H. et al., "Identification and Characterization of a Novel Family of Cyclic Nucleotide Phosphodiesterases," *Journal of Biological Chemistry*, 1998, 273:15553-8 (Exhibit 123).

Soderling, S. H. et al., "Cloning and characterization of a cAMP-specific cyclic nucleotide phosphodiesterase," *Proceedings of the National Academy of Sciences*, 1998, 95:8991-6 (Exhibit 124).

Soderling, Scott H. et al., "Regulation of cAMP and cGMP signaling: new phosphodiesterases and new functions," *Current Opinion in Cell Biology*, 2000, 12:174-9 (Exhibit 125).

Southern, E. M., "Detection of Specific Sequences Among DNA Fragments Separated by Gel Electrophoresis," *Journal of Molecular Biology*, 1975, 98:503-17 (Exhibit 126).

Stephens, R. E. and G. Prior, "Dynein from serotonin-activated cilia and flagella: extraction characteristics and distinct sites for cAMP-dependent protein phosphorylation," *Journal of Cell Science*, 1992, 103:999-1012 (Exhibit 127).

Takamatsu, Nobuhiko et al., "Expression of bacterial chloramphenicol actylytransferase gene in tobacco plants mediated by TMV-RNA," *EMBO Journal*, 1987, 6:307-11 (Exhibit 128).

Takeda, Shun-ichi et al., "Construction of chimaeric processed immunoglobulin genes containing mouse variable and human constant region sequences," *Nature*, 1985, 314:452-4 (Exhibit 129).

Tan, Lee K. et al., "A Human-Mouse Chimeric Immunoglobulin Gene with a Human Variable Region is Expressed in Mouse Myeloma Cells," *Journal of Immunology*, 1985, 135:3564-7 (Exhibit 130).

Teng, Nelson N. H. et al., "Construction and testing of mouse-human heteromyelomas for human monoclonal antibody production," *Proceedings of the National Academy of Sciences USA*, 1983, 80:7308-12 (Exhibit 131).

Thomas, Melissa K. et al., "Substrate- and Kinase-directed Regulation of Phosphorylation of a cGMP-binding Phosphodiesterase by cGMP," *Journal of Biological Chemistry*, 1990, 265:14971-8 (Exhibit 132).

Thorpe, Philip E. and Walter C. J. Ross, "The Preparation and Cytotoxic Properties of Antibody-Toxin Conjugates," *Immunological Reviews*, 1982, 62:119-58 (Exhibit 133).

Tsang, Stephen H. et al., "Retinal Degeneration in Mice Lacking the γ Subunit of the Rod cGMP Phosphodiesterase," *Science*, 1996, 272:1026-9 (Exhibit 134).

Turko, Illarion V. et al., "Identification of Key Amino Acids in a Conserved cGMP-binding Site of cGMP-binding Phosphodiesterases: A Putative NKXnD Motif for cGMP Binding," Journal of Biological Chemistry, 1996, 271:22240-4 (Exhibit 135).

Uren, Anthony G. and David L. Vaux, "TRAF proteins and meprins share a conserved domain," *Trends in Biochemical Sciences*, 1996, 21:244-5 (Exhibit 136).

Van Heeke, Gino and Sheldon M. Schuster, "Expression of Human Asparagine Synthetase in *Escherichia coli*," *Journal of Biological Chemistry*, 1989, 264:5503-9 (Exhibit 137).

Vassella, Erik et al., "Differentiation of African trypanosomes is controlled by a density sensing mechanism which signals cells cycle arrest via the cAMP pathway," *Journal of Cell Science*, 1997, 110:2661-71 (Exhibit 138).

Veillette, André et al., "Signal transduction through the CD4 receptor involves the activation of the internal membrane tyrosine-protein kinase p56*lck*," *Nature*, 1989, 338:257-9 (Exhibit 139).

Vickerman, Keith, "Developmental Cycles and Biology of Pathogenic Trypanosomes," *British Medical Bulletin*, 1985, 41:105-14 (Exhibit 140).

Vitetta, Ellen S. et al., "Immunotoxin Therapy," *Cancer: Principles & Practice of Oncology*, 1993, DeVita, Jr. V. T. et al. (ed.), J. B. Lippincott Co., Philadelphia, pp. 2624-2636 (Exhibit 141).

Wagner, U. et al., "Immunological Responses to the Tumor-Associated Antigen CA125 in Patients with Advanced Ovarian Cancer Induced by the Murine Monoclonal Anti-Idiotype Vaccine ACA125," *Hybridoma*, 1997, 16:33-40 (Exhibit 142).

Walter, Rolf D. and Fred R. Opperdoes, "Subcellular Distribution of Adenylate Cyclase, Cyclic-AMP Phosphodiesterase, Protein Kinases and Phosphoprotein Phosphotase in *Trypanosoma Brucei*," *Molecular and Biochemical Parasitology*, 1982, 6:287-95 (Exhibit 143).

Walter, Rolf D., "3':5'-Cyclic-AMP Phosphodiesterase from *Trypanosoma gambiense*," *Hoppe-Seyler's Z. Physiol. Chem.*, 1974, 355:1443-50 (Exhibit 144).

Walter, R. D. et al., "Effect of Cyclic AMP on Transformation and Proliferation of Leishmania Cells," *Tropenmed. Parasit.*, 1978, 29:439-42 (Exhibit 145).

Wang, Yu and Robert L. Rosenberg, "Ethaverine, a Derivative of Papverine, Inhibits Cardiac L-Type Calcium Channels," *Molecular Pharmacology*, 1995, 40:750-5 (Exhibit 146).

Wang, Zefeng et al., "Inhibition of *Trypanosoma brucei* Gene Expression by RNA Interference Using an Integratable Vector with Opposing T7 Promoters," *Journal of Biological Chemistry*, 2000, 275:40174-9 (Exhibit 147).

Wigler, Michael et al., "Transfer of Purified Herpes Virus Thymidine Kinase Gene to Cultured Mouse Cells," *Cell*, 1977, 11:223-32 (Exhibit 148).

Wigler, Michael et al., "DNA-mediated transfer of the adenine phosphoribosyltransferase locus into mammalian cells," *Proceedings of the National Academy of Sciences USA*, 1979, 76:1373-6 (Exhibit 149).

Wigler, M. et al., "Transformation of mammalian cells with an amplifiable dominant-acting gene," *Proceedings of the National Academy of Science USA*, 1980, 77:3567-70 (Exhibit 150).

Williams, Michael and Michael F. Jarvis, "Adenosine Antagonists as Potential Therapeutic Agents," *Pharmacology Biochemistry & Behavior*, 1988, 29:433-41 (Exhibit 151).

Winter, Jill and Ralph Sinibaldi, "The Expression of Heat Shock Protein and Cognate Genes During Plant Development," Results and Problems in Cell Differentiation, 1991, 17:85-105 (Exhibit 152).

Wyatt, Todd A. et al., "ANF elicits phosphorylation of the cGMP phosphodiesterase in vascular smooth muscle cells," American Journal of Physiology, 1998, 274:H448-55 (Exhibit 153).

Yan, Chen et al., "Molecular cloning and characterization of a clamodulin-dependent phosphodiesterase enriched in olfactory sensory neurons," *Proceedings of the National Academy of Sciences USA*, 1995, 92:9677-81 (Exhibit 154).

Yang, Meijia et al., "Protein-peptide interactions analyzed with the yeast two-hybrid system," *Nucleic Acids Research*, 1995, 23:1152-6 (Exhibit 155).

Zamecnik, Paul C. and Mary L. Stephenson, "Inhibition of *Rous sarcoma* virus replication and cell transformation by a specific oligodeoxynucleotide," *Proceedings of the National Academy of Sciences USA*, 1978, 75:280-4 (Exhibit 156).

Zamecnik, Paul C. et al, "Inhibition of replication and expression of human T-cell lymphotropic virus type III in cultured cells by exogenous synthetic oligonucleotides complementary to viral RNA," *Proceedings of the National Academy of Sciences USA*, 1986, 83:4143-6 (Exhibit 157).

Zhao, Allan Z. et al., "Attenuation of insulin secretion by insulin-like growth factor 1 is mediated through activation of phosphodiesterase 3B," *Proceedings of the National Academy of Sciences USA*, 1997, 94:3223-8 (Exhibit 158).

Zoraghi, Roya et al., "Characterization of TbPDE2A, a Novel Cyclic Nucleotide-specific Phosphodiesterase from the Protozoan Parasite *Trypanosoma brucei*," *Journal of Biological Chemistry*, 2001, 276:11559-66 (Exhibit 159).

\* cited by examiner

```
   1 acgcgagatccgcgctcgcctccgtccgcccaggcggcgatgacacggcgcccacggcggcccgaaggcgccgggtgggc  80

81 cgtttgctgaccggatcgcggctacccgccagcgtgtccgcggcgccgccgccagc ATG GGC TGT GCC CCG AGC  154
                                                                M   G   C   A   P   S     6
   1

155 ATC CAC ATT TCC GAG CGC CTG GTG GCC GAG GAC GCG CCT AGC CCC GCG GCA CCG CCG CTG  214
   7  I   H   I   S   E   R   L   V   A   E   D   A   P   S   P   A   A   P   P   L    26

215 TCG TCC GGC GGG CCG CGC CTC CCG CAG GGC CAG AAG ACG GCC GCC TTG CCC CGG ACC CGC  274
  27  S   S   G   G   P   R   L   P   Q   G   Q   K   T   A   A   L   P   R   T   R    46

275 GGC GCC GGC CTC TTG GAG TCG GAG GTT CGC GAC GGC AGC GGC AAG AAG GTA GCA GTA GCT  334
  47  G   A   G   L   L   E   S   E   V   R   D   G   S   G   K   K   V   A   V   A    66

335 GAT GTG CAG TTT GGC CCC ATG AGA TTT CAT CAA GAT CAA CTT CAG GTA CTT TTA GTG TTT  394
  67  D   V   Q   F   G   P   M   R   F   H   Q   D   Q   L   Q   V   L   L   V   F    86

395 ACC AAA GAA GAT AAC CAA TGT AAT GGA TTC TGC AGG GCA TGT GAA AAA GCA GGG TTT AAG  454
  87  T   K   E   D   N   Q   C   N   G   F   C   R   A   C   E   K   A   G   F   K   106

455 TGT ACA GTT ACC AAG GAG GCT CAG GCT GTC CTT GCC TGT TTC CTG GAC AAA CAT CAT GAC  514
 107  C   T   V   T   K   E   A   Q   A   V   L   A   C   F   L   D   K   H   H   D   126

515 ATT ATC ATC ATA GAC CAC AGA AAT CCT CGA CAG CTG GAT GCA GAG GCA CTG TGC AGG TCT  574
 127  I   I   I   I   D   H   R   N   P   R   Q   L   D   A   E   A   L   C   R   S   146

575 ATC AGA TCA TCA AAA CTC TCA GAA AAC ACA GTT ATT GTT GGT GTA GTA CGC AGG GTG GAT  634
 147  I   R   S   S   K   L   S   E   N   T   V   I   V   G   V   V   R   R   V   D   166

635 AGA GAA GAG TTG TCC GTA ATG CCT TTC ATT TCT GCT GGA TTT ACA AGG AGG TAT GTA GAA  694
 167  R   E   E   L   S   V   M   P   F   I   S   A   G   F   T   R   R   Y   V   E   186

695 AAC CCC AAC ATC ATG GCC TGC TAC AAT GAA CTG CTC CAG CTG GAG TTT GGA GAG GTG CGA  754
 187  N   P   N   I   M   A   C   Y   N   E   L   L   Q   L   E   F   G   E   V   R   206

755 TCA CAA CTG AAA CTC AGG GCT TGT AAC TCA GTA TTC ACT GCA TTA GAA AAC AGT GAA GAT  814
 207  S   Q   L   K   L   R   A   C   N   S   V   F   T   A   L   E   N   S   E   D   226

815 GCA ATT GAA ATT ACA AGC GAA GAC CGT TTT ATA CAG TAT GCA AAT CCT GCA TTT GAA ACA  874
 227  A   I   E   I   T   S   E   D   R   F   I   Q   Y   A   N   P   A   F   E   T   246

875 ACA ATG GGC TAT CAG TCA GGT GAA TTA ATA GGG AAG GAG TTA GGA GAA GTG CCT ATA AAT  934
 247  T   M   G   Y   Q   S   G   E   L   I   G   K   E   L   G   E   V   P   I   N   266

935 GAA AAA AAG GCT GAC TTG CTC GAT ACT ATA AAT TCA TGC ATC AGG ATA GGC AAG GAG TGG  994
 267  E   K   K   A   D   L   L   D   T   I   N   S   C   I   R   I   G   K   E   W   286

995 CAA GGA ATT TAC TAT GCC AAA AAG AAA AAC GGA GAT AAT ATA CAA CAA AAT GTG AAG ATA 1054
 287  Q   G   I   Y   Y   A   K   K   K   N   G   D   N   I   Q   Q   N   V   K   I   306

1055 ATA CCT GTC ATT GGA CAG GGA GGA AAA ATT AGA CAC TAT GTG TCC ATT ATC AGA GTG TGC 1114
 307  I   P   V   I   G   Q   G   G   K   I   R   H   Y   V   S   I   I   R   V   C   326

1115 AAT GGC AAC AAT AAG GCT GAG AAA ATA TCC GAA TGT GTT CAG TCT GAC ACT CGT ACA GAT 1174
 327  N   G   N   N   K   A   E   K   I   S   E   C   V   Q   S   D   T   R   T   D   346

1175 AAT CAG ACA GGC AAA CAT AAA GAC AGG AGA AAA GGC TCA CTA GAC GTC AAA GCT GTT GCC 1234
 347  N   Q   T   G   K   H   K   D   R   R   K   G   S   L   D   V   K   A   V   A   366

1235 TCC CGT GCA ACT GAA GTT TCC AGC CAG AGA CGA CAC TCT TCC ATG GCC CGG ATA CAT TCC 1294
 367  S   R   A   T   E   V   S   S   Q   R   R   H   S   S   M   A   R   I   H   S   386

1295 ATG ACA ATT GAG GCG CCC ATC ACC AAG GTA ATC AAT GTT ATC AAT GCT GCC CAG GAA AGT 1354
 387  M   T   I   E   A   P   I   T   K   V   I   N   V   I   N   A   A   Q   E   S   406

1355 AGT CCC ATG CCT GTG ACA GAA GCC CTA GAC CGT GTG CTG GAA ATT CTA AGA ACC ACT GAG 1414
 407  S   P   M   P   V   T   E   A   L   D   R   V   L   E   I   L   R   T   T   E   426

1415 TTA TAT TCA CCA CAG TTT GGT GCT AAA GAT GAT GAT CCC CAT GCC AAT GAC CTT GTT GGG 1474
 427  L   Y   S   P   Q   F   G   A   K   D   D   D   P   H   A   N   D   L   V   G   446

1475 GGC TTA ATG TCT GAT GGT TTG CGA AGA CTA TCA GGG AAT GAA TAT GTT CTT TCA ACA AAA 1534
 447  G   L   M   S   D   G   L   R   R   L   S   G   N   E   Y   V   L   S   T   K   466

1535 AAC ACT CAA ATG GTT TCA AGC AAT ATA ATC ACT CCC ATC TCC CTT GAT GAT GTC CCA CCA 1594
 467  N   T   Q   M   V   S   S   N   I   I   T   P   I   S   L   D   D   V   P   P   486
```

FIGURE 1A

```
1595 CGG ATA GCT CGG GCC ATG GAA AAT GAG GAA TAC TGG GAC TTT GAT ATT TTT GAA CTG GAG 1654
 487 R   I   A   R   A   M   E   N   E   E   Y   W   D   F   D   I   F   E   L   E   506

1655 GCT GCC ACC CAC AAT AGG CCT TTG ATT TAT CTT GGT CTC AAA ATG TTT GCT CGC TTT GGA 1714
 507 A   A   T   H   N   R   P   L   I   Y   L   G   L   K   M   F   A   R   F   G   526

1715 ATC TGT GAA TTC TTA CAC TGC TCC GAG TCA AAG CTA AGA TCA TGG TTA CAA ATT ATC GAA 1774
 527 I   C   E   F   L   H   C   S   E   S   K   L   R   S   W   L   Q   I   I   E   546

1775 GCC AAT TAT CAT TCC TCC AAT CCC TAC CAC AAT TCT ACA CAT TCT GCT GAT GTG CTT CAT 1834
 547 A   N   Y   H   S   S   N   P   Y   H   N   S   T   H   S   A   D   V   L   H   566

1835 GCC ACT GCC TAT TTT CTC TCC AAG GAG AGG ATA AAG GAA ACT TTA GAT CCA ATT GAT GAG 1894
 567 A   T   A   Y   F   L   S   K   E   R   I   K   E   T   L   D   P   I   D   E   586

1895 GTC GCT GCA CTC ATC GCA GCC ACC ATT CAT GAT GTG GAT CAC CCT GGG AGA ACC AAC TCC 1954
 587 V   A   A   L   I   A   A   T   I   H   D   V   D   H   P   G   R   T   N   S   606

1955 TTC CTG TGT AAT GCT GGA AGT GAG CTG GCC ATT TTG TAC AAT GAC ACT GTT GTG CTG GAG 2014
 607 F   L   C   N   A   G   S   E   L   A   I   L   Y   N   D   T   A   V   L   E   626

2015 AGC CAC CAT GCG GCC TTG GCC TTC CAG CTG ACC ACT GGA GAT GAT AAA TGC AAT ATA TTT 2074
 627 S   H   H   A   A   L   A   F   Q   L   T   T   G   D   D   K   C   N   I   F   646

2075 AAA AAC ATG GAG AGG AAT GAT TAT CGG ACA CTG CGC CAG GGG ATT ATC GAC ATG GTC TTA 2134
 647 K   N   M   E   R   N   D   Y   R   T   L   R   Q   G   I   I   D   M   V   L   666

2135 GCC ACA GAA ATG ACA AAG CAC TTT GAG CAT GTC AAC AAA TTT GTC AAC AGC ATC AAC AAA 2194
 667 A   T   E   M   T   K   H   F   E   H   V   N   K   F   V   N   S   I   N   K   686

2195 CCC TTG GCA ACA CTA GAA GAA AAT GGG GAA ACT GAT AAA AAC CAG GAA GTG ATA AAC ACT 2254
 687 P   L   A   T   L   E   E   N   G   E   T   D   K   N   Q   E   V   I   N   T   706

2255 ATG CTT AGG ACT CCA GAG AAC CGG ACC CTA ATC AAA CGA ATG CTG ATT AAA TGT GCT GAT 2314
 707 M   L   R   T   P   E   N   R   T   L   I   K   R   M   L   I   K   C   A   D   726

2315 GTG TCC AAT CCC TGC CGA CCC CTG CAG TAC TGC ATC GAG TGG GCT GCA CGC ATT TCG GAA 2374
 727 V   S   N   P   C   R   P   L   Q   Y   C   I   E   W   A   A   R   I   S   E   746

2375 GAA TAT TTT TCT CAG ACT GAT GAA GAG AAG CAG CAG GGC TTA CCT GTG GTG ATG CCA GTG 2434
 747 E   Y   F   S   Q   T   D   E   E   K   Q   Q   G   L   P   V   V   M   P   V   766

2435 TTT GAC AGA AAT ACC TGC AGC ATC CCC AAA TCC CAA ATC TCT TTC ATT GAT TAC TTC ATC 2494
 767 F   D   R   N   T   C   S   I   P   K   S   Q   I   S   F   I   D   Y   F   I   786

2495 ACA GAC ATG TTT GAT GCT TGG GAT GCC TTT GTA GAC CTG CCT GAT TTA ATG CAG CAT CTT 2554
 787 T   D   M   F   D   A   W   D   A   F   V   D   L   P   D   L   M   Q   H   L   806

2555 GAC AAC AAC TTT AAA TAC TGG AAA GGA CTG GAC GAA ATG AAG CTG CGG AAC CTC CGA CCA 2614
 807 D   N   N   F   K   Y   W   K   G   L   D   E   M   K   L   R   N   L   R   P   826

2615 CCT CCT GAA TAG tgggagacaccacccagagccctgaagctttgttccttcggtcatttggaattcctgagggcag 2690
 827 P   P   E   *                                                                    830

2691 ccagagctccttggtcctttcagtactaggcagaacagccccgatctgcatagcctgtgaaagcccacggggacatcag 2770

2771 taaccttctgcagccaccatccaatgccattactgtcaagtgagacttggccactgtagcctgggcctgctgcaggagct 2850

2851 cttcagaaagccacatgagcaccacggcttgcctaagtttctgctaaaacacaaggtctggagtgccctgcaaacggta 2930

2931 ttgatggacttcctgccagtgacagagcatgtctattgcaaacaattctctcagttacgttcagcacttaagaacggcta 3010

3011 atggcaataggatctttagcaacttttttcacatcatagaaggtgcaatcgctcacttgggaacactactgagagtgactt 3090

3091 ctcttttaaaattgagtagcagatgaaaaattaaaatttgaacttgattattaatatcaattaaaatgttttattttattt 3170

3171 tattaaaagctcaatatttctatgaattcaaaaatacttcagagccaaagccaacttcaaataccgtgaccaaatttac 3250

3251 atgattcatattcattatgcattacttggtatacagacttatttttcataatgcaaattaataaaatgacacttttactgc 3330

3331 tctatacaaatattcatctatgttaaactttctgattgacgctaactggaaaaagctggctcctattctaagtgctaa 3410

3411 agaaggctgcttctactgtatagaacccagggctctgaaacagctctagccgcctaatgcacttcacaggtaactcccca 3490

3491 aggtaaaactagactctcttgttggttcgcaaagaaaagttaggacttaacactttttttctaaaatctataattcaatt 3570
```

FIGURE 1A (continued)

```
3571 tccaaaagtctactctatttttatactgtttctacaaaatattccttataaaaacaaagaacaaaaattgaatatttaatg 3650
3651 aattgacattttataaccaacctgtttttatctacggtgggaatctttgatgccagaaatttataaagaggttctgtatc 3730
3731 ttcacaccttgaataagcataataccataaaaaatgacacttgacatgtcaatgtatttgtcatttcattttaaactcgt 3810
3811 atttgtggttttttttcccagataaaaatgaaattaaaccattccttttttaagaaaaaaaaaaaaaaaaa         3880
```

```
h8A,    1 MGCAPSIHISE-RLVAEDAPSPAAPPLSSGGPRLPQGQKTAALPRTRGAGLLESEVRDGS
m8A,    1 MGCAPSIHTSENRTFSHSDGEDEDVDVDVPGPAPRSIQRWSTAP-----GLVEPQPRDNG
          ******   *                  **    *     *     ** *   ** h8A,   60 GKKVAVADVQFGPMRFHQDQLQVLLVFTKEDNQCNGFCRACEKAGFKCTVTKEAQAVLAC
m8A,   56 ASKVSVADVQFGPMRFHQDQLQVLLVFTKEDSQCNGFHRACEKAGFKCTVTKEVQTVLTC
             ***************************** *************  * ** * h8A,  120 RLDKHHDIIIID
m8A,  116 RQDKLHDIIIID
          ** *******
```

FIGURE 1B

A.
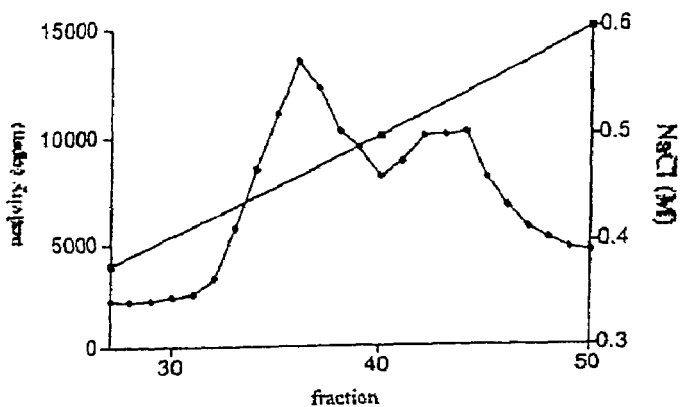
B.
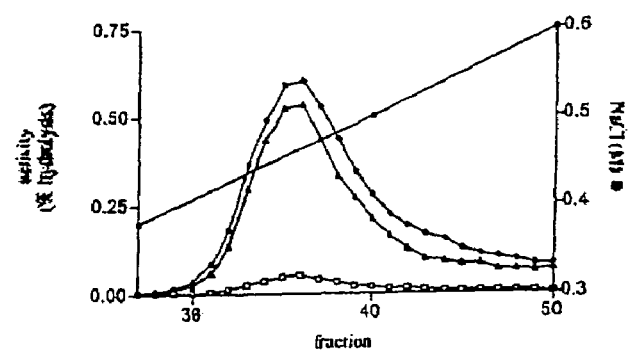
C.
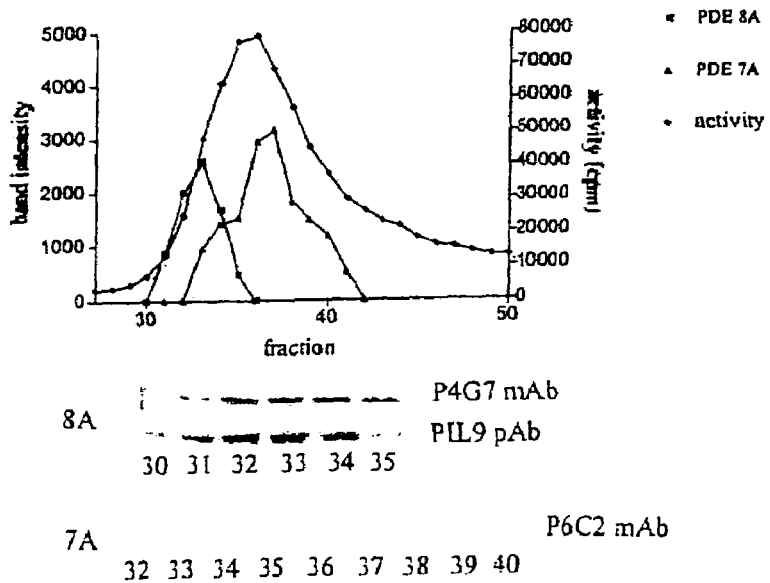
FIGURE 5

A.
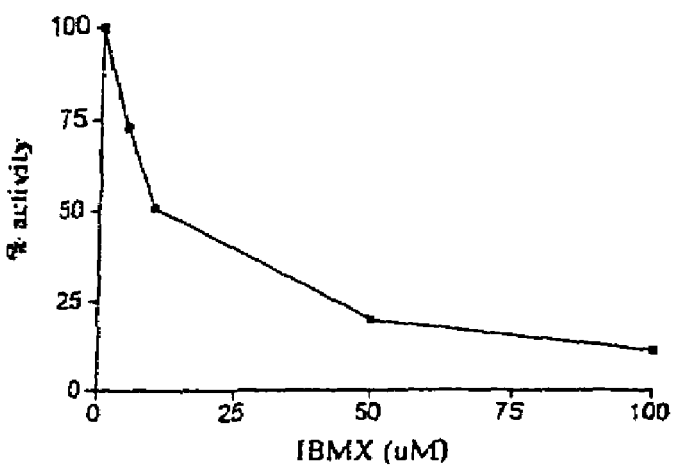
B.
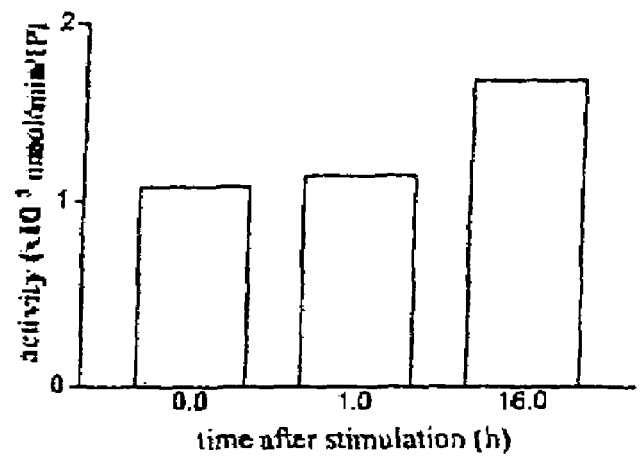
FIGURE 6

A.
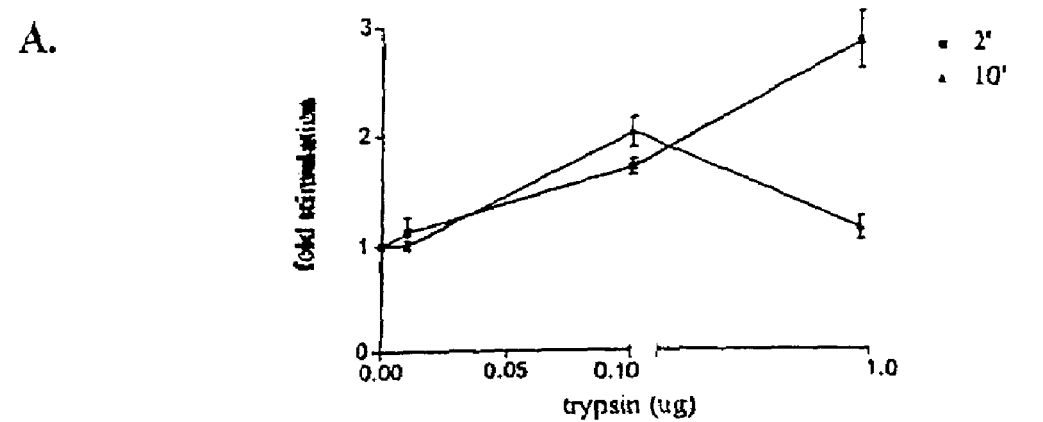
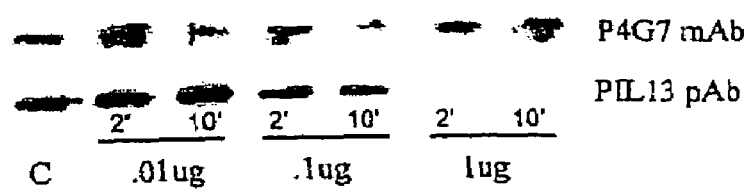
B.
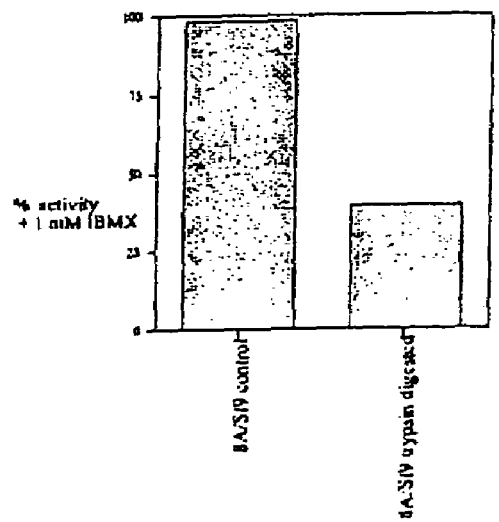
FIGURE 7 complete TA3 -> List

DNA sequence 2990 b.p. ATGGAAGTGTGT ... aaaaaaaaaaaa linear

```
         |   10       |   20       |   30       |   40       |   50       |   60
    1 ATCCAAGTGT  GTTAATAACT  CCCGGTACTG  CCCTGGACA  GGCCGGTCCC  CCAGCACGTC   60
   61 CTCAGCCGCC  GAGGAGTCAT  CAGCTTCAGC  TCCACCTCCG  CTCTCTTCCG  CTGCCCCAAT  120
  121 CCCCCGCAGC  TCTCTTCGAG  GCGTGGAGCT  ATTTCCTATG  ACAGTTCTGA  TCAGACTGCA  180
  181 TTATCCATTC  GTATCCTAGC  AGATGTAGGT  GTAACCAGCC  GAGTAGGATT  TGAATCAGAA  240
  241 ACAACAGGTT  CTCACCCATA  TATTGATTTT  CGTATTTTCC  ACTCTCAATC  TGAAATTGAA  300
  301 GTGTCTGTCT  CTGCAAGGAA  TATCAGAAGG  CTACTAAGTT  TTCACGCATA  TCTTAGATCT  360
  361 TCACGCTTTT  TTCGTGGTAC  TGCGGTTTTA  AATTCCCTAA  ACATTTTAGA  TGATGATTAT  420
  421 AATGGACAAG  CCAAGTGTAT  GCTGGAAAAA  GTTCGAAATT  GAAATTTGA   TATCTTTCTA  480
  481 TTTCATAGAC  TAACAAATCG  AAATAGTCTA  GTAAGCTTAA  GCTTTCATTT  ATTAGTCTT   540
  541 CATGGATTAA  TTGAGTACTT  CCATTTAGAT  ATGATGAAAC  TTGGTACATT  TTTAGTTATG  600
  601 ATTCAAGAAG  ATTACCACAG  TCAAAATTCT  TACCACAAAG  CAGTCCACGC  TGCGGATGTT  660
  661 ACTCAGGCCA  TGTACTGTTA  CTTAAAGGAA  CCTAAGCTTG  CTAATTCTGT  AACCTCTTCG  720
  721 GATATCTTGC  TGAGGTTAAT  TGCAGCTGCC  ACTCATGATC  TGGATCATCC  AGGTGTTAAT  780
  781 CAACCTTTCC  TTATTAAAAC  TAACCATTAC  TTCGCAACTT  TATACAAGAA  TACCTCAGTA  840
  841 CTGGAAAATC  ACCACTGCAG  ATCTGTAGTG  GGCTTAGTGA  GAGAATCAGG  CTTATTCTCA  900
  901 CATCTGCCAT  TAGAAACCAG  GCAACAAATC  GAGACACAGA  TAGCTGCTCT  GATACTAGCC  960
  961 ACAGACAATA  GTCCCCACAA  TGAGTATCTG  TCTTTGTTTA  GGTCCCATTT  GGATAGACGT 1020
 1021 GATTTATGCC  TAGAAGACAC  CAGACACAGA  CATTTGGTTT  TACACATGGC  TTTGAAATGT 1080
 1081 GCTGATATTT  GTACCCCATG  TCGGACGTGG  GAATTAAGCA  AGCAGTGGAG  TGAAAAAGTA 1140
 1141 ACGGAGGAAT  TCTTCCATCA  AGGAGATATA  GAAAAAAAAT  ATCATTTGGG  TGTGAGTCCA 1200
 1201 CTTTGCGATC  GTCACACTGA  ATCTATTGCC  AACATCCAGA  TTGGTAACTA  TTCATTATTA 1260
 1261 GACATAGCTG  GTTAGaaaaa  tgccacbgtt  tttatcaaga  aggcaaatat  attttgaaata 1320
 1321 taaaatatta  aaattatgct  cacttctatt  tttaaaaata  atttcagaaa  cttcacccct 1380
 1381 gtttccgtt   gttatcgctc  ttctaattct  cattcaattt  taggatgtaa  aaagtatatt 1440
 1441 tttgcagaac  aggcagcagc  aatcactcgt  ttctgtcttt  atgtcaataa  gaatccatta 1500
 1501 ttcgctcatg  tggaagcttc  tcttggatca  tttgggactg  ccatttaaaa  aaggatacgc 1560
 1561 aaacaaagaa  atcaccaaaa  tcaaatacat  aaaataaaaa  tgcataggtg  gtgaccact  1620
 1621 gagtctgatc  ataatcgaa   gaccggcttc  tgccaatgcc  tttccagact  cctaccactg 1680
 1681 cctgttgatt  aaatctaact  cttcaaaatc  ctagatagg   ccttataacc  ttgcttcaaa 1740
 1741 tgctgtgcag  ccatcttgcc  tcaacttccc  tcccatttgc  ctacagcatc  tcgggacgct 1800
 1801 tctgtgcttc  cccagtatac  gctgttcttt  cgctcttgt   gcttcgccag  tgctttccat 1850
 1861 gtgtctgta   cagttatttt  tctbgaagag  gcagctcaaa  tgtcacccttc tcccaaagct 1920
 1921 gctcttccact tgctttaggc  agagtcagtc  actcttcttc  tagattccaa  agtcctgat  1980
 1981 ccacttggtt  gtggattcct  ggagcctagc  accacaccag  aagcacgagg  ccttgagaa  2040
 2041 ccgtgtgttg  agtgaactaa  taactctatt  atagaaagca  taatgaaaat  gtcctgtgac 2100
 2101 tgaagtatct  gtagcttgtc  gcacgagtca  caggaaagtt  gactaggatt  gcctgtgttg 2160
 2161 ggctttgtgt  ataaaggagg  ggcattctac  ttgggcagta  gctcaacaag  gcatagaggg 2220
 2221 aggagtgtaa  ttttgggtagc  tggtgttgaa  tagggccttt  gagaattcaga ctgaacacag 2280
 2281 tgaatatgt   gcccaaagtt  cagaagatg   aagtttccag  aaaccaagaa  cgtagcacaa 2340
 2341 tatgtgccat  cataccagaa  aaggaagacc  atgccatcgg  gccagaaatt  cagaaacgca 2400
 2401 attcttacat  tgtgactgaa  atggatacc   atgaagaaa   gtgggtagtg  gccgattggc 2460
 2461 cttcagagtg  acaggaaag   aagggaagag  cgtgtagaac  tgtggccata  cttaggagt  2520
 2521 gtcagggatg  cagaacctcc  cagagagcac  acactgcca   ggaatgctga  gagtagcaga 2580
 2581 tcctttcctt  tcggtgagt   agtaaaacaa  tttagaacca  gatatgcttt  gtcttgattc 2640
 2641 tcagctagaa  taatcttaaa  atgcaaaaga  atacattaga  aatggacaaa  agtggctagg 2700
 2701 acccgtagct  catactttgta acccagcact  ttgcgaagcc  gagcggcct   gatcgcttga 2760
 2761 cgtcaggagt  tggagaccag  cctggccaaa  atagtgaaac  ccaogttttct actaaaaata 2820
 2821 caaaaattag  ctgggtgtca  tggccacttg  gcaggctgag  acaggagcat  cgcttgaacc 2880
 2881 tgggaggcag  aggttggagt  gagccaatat  cgtgccactg  cattccagcc  tgggcgacag 2940
 2941 aatgaaactc  catcactcca  tctcaaaaaa  aaaaaaaaaa  aaaaaaaaaa              2990
         |   10       |   20       |   30       |   40       |   50       |   60
```

FIGURE 8A

PDE7A3 protein -> List

Protein sequence    424 a.a.    MEVCYCLPVLPL .. QDGNYTYLDIAG

```
         |  10        |  20        |  30        |  40        |  50        |  60
   1 NEVCYQLPVL  PLDRFVKQHV  LSRRGAISPS  SSSALIGCPN  PRQLSCFFLA  ISYDSSDQTA   60
  61 LYIRMLGDJR  VRSRAGPBSE  RRGSHPYIIP  RIFHSQSSIE  VSVSAFNIRR  LLSPQRYLRS  120
 121 SRPFRGIAJS  NSLNILDDDY  NGQACMLEK   VGFA/FPDISL FDRD/INGMSL VSLTFHLPSL  180
 181 KGLICFHLD   MMKLFRPLVH  IQIDVHSQNP  YHDAVHAADV  IQAMICYLRI  PKLANSVIEM  240
 241 DILLSLIAAA  THILLHPGVR  QPPLIKIMHY  LATLYONTSV  LENFHWRSAV  GLLAESCLPS  300
 301 ELPLESRDIM  BIQIGALILA  TDISRQNBYL  SLFRSHLDRG  ILCLHDTRHR  HLVLQMPLFC  360
 361 ADICIPIRIN  BISHQTSIKV  TIREPHQCDI  BIRPHEG/SP  LCIFHTISLA  NIQIGNYTYL  420
 421 DLAG                                                                   424
         |  10        |  20        |  20        |  40        |  50        |  60
```

FIGURE 8B

A.
```
      381
7A1  TEEFFHQGDIEKKYHLGVSPLCDRHTESIANIQIGFMTYLVEPLFTEWARFSNTRLSQTM
     ::::::::::::::::::::::::::::::::::::::  :::
7A3  TEEFFHQGDIEKKYHLGVSPLCDRHTESIANIQIGNYTYLDIAG*
      441
7A1  .LGHVGLNKASWKGLQREQSSSEDTDAAFELNSQLLPQENRLS*
```
B. 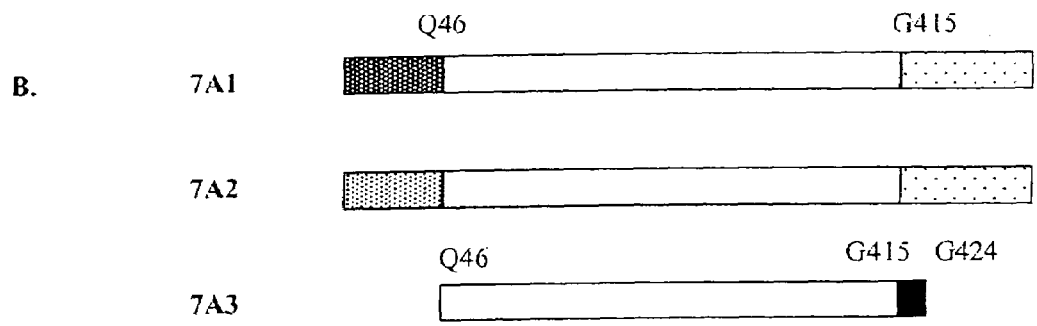
C. 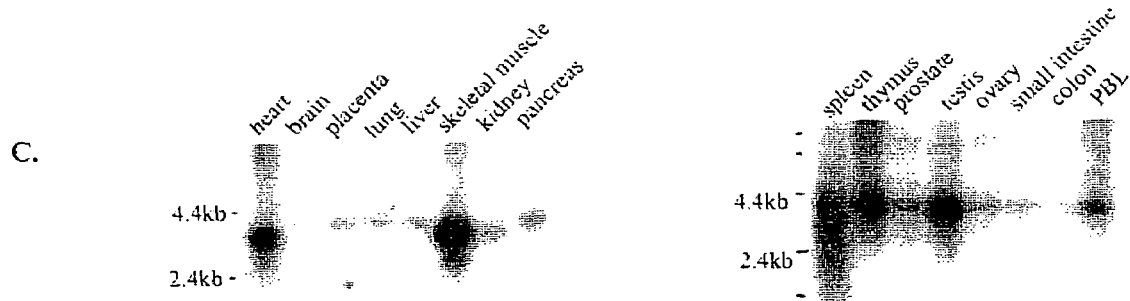
FIGURE 9

A.
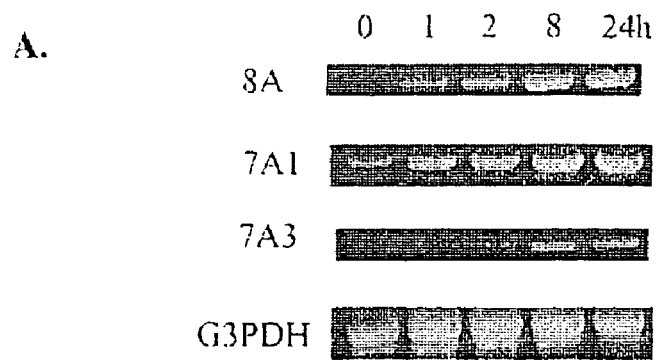
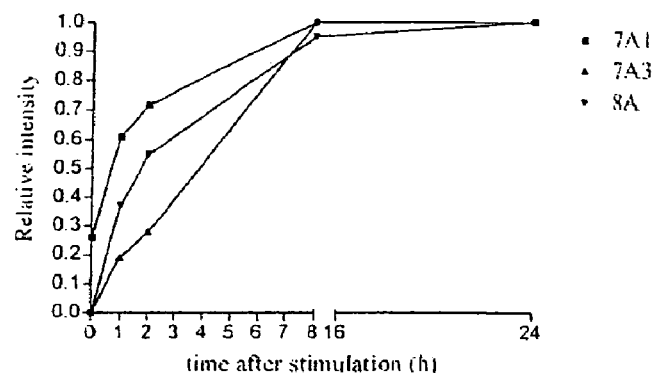
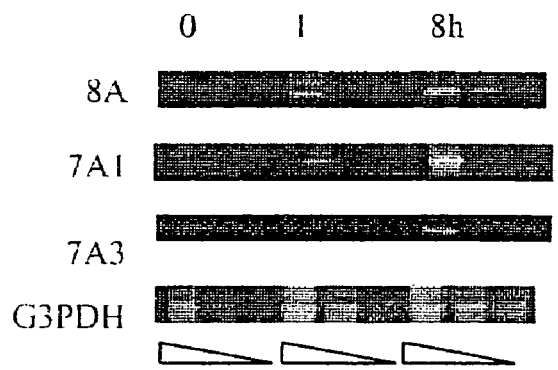
FIGURE 10

B. 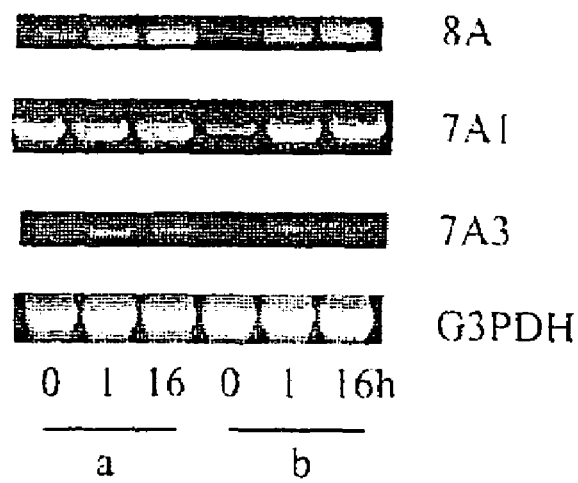
C. 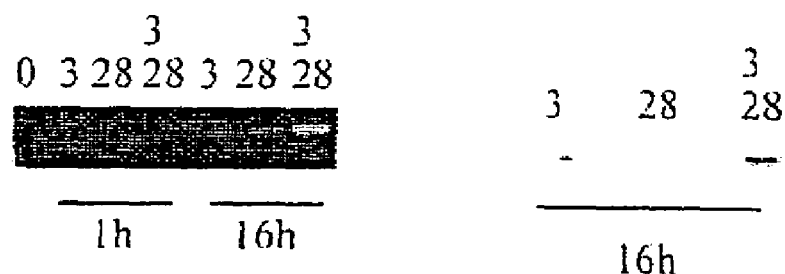
FIGURE 10 (continued)

```
       0      2      4      8h
```
7A1 
```
       0      2      4      8     16h
```
8A 
```
       0      1      2      8     24    48h
```
7A3 
```
       0      1      2      8     24    48h
```
7A 
FIGURE 11

A.
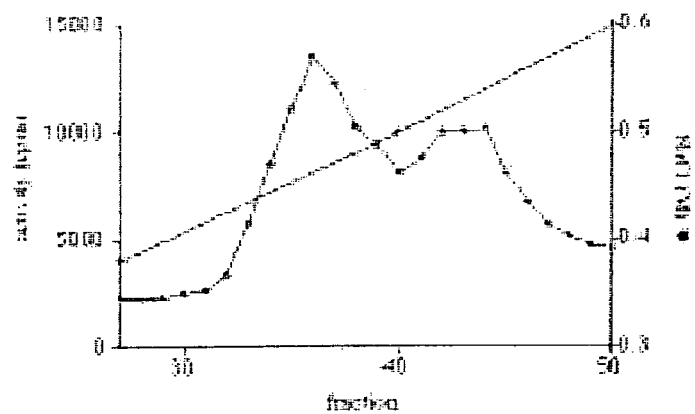
B.
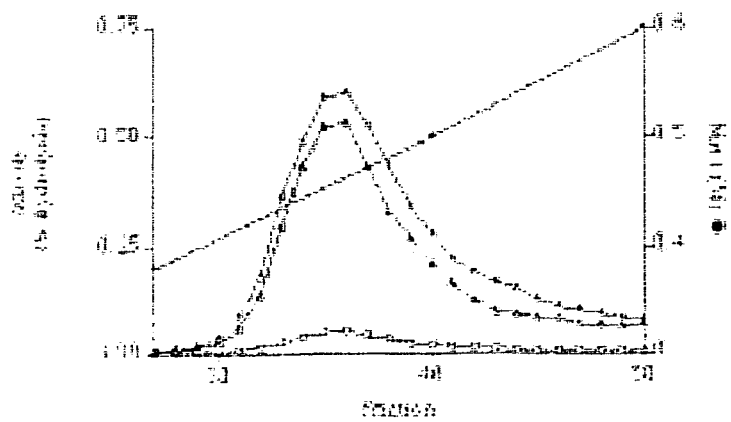
FIGURE 12

GAF A

GAF B

Catalytic
Domain

PDE1 PDE2 vector only
pde1 pde2 TBPDE2B vector
pde1 pde2 vector only
- heat shock    + heat shock
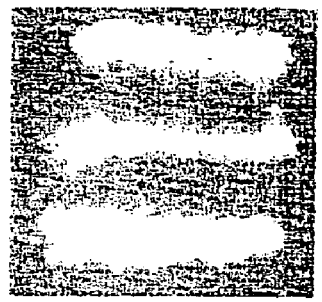
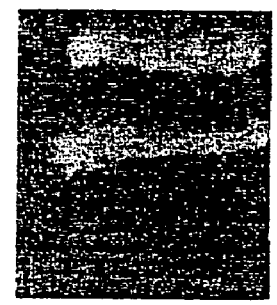
FIGURE 19

```
   1 ATGTATGTGC ACGACGTACG CATGTTCGCT GATTATTGTT ACTGCTTTTT

51 CTGCTTACTG AATGACGTGC CTTATTCTAT CTGCTGTTAT CTGGCGTTTG

101 CTCGTGGTTT ACAGGACGAT CCGCGCTTCA ACCGTGAGGT TGACAAACAA

151 CTTGGATACC GCACGCAGGC CATATTGTGC GAGCCCATCA TACTAAATGG

201 TGAGATCCTT GCTGTCGTGC AGCTCGTGAA CAAGCTTGAT TCATCTGGAG

251 AAGTGACTGT GTTTACCGAG GATGATCGTG ACACCTTCCG TGTGTTTCC

301 TTATTTGCAG GTATATCCAT CAACAACTCT CACCTGCTTG AGTTCGCTGT

351 GAAGGCCGGT CGTGAGGTGA TGGAATTAAA TGAACACCGA GCAACATTGT

401 TTAATAAGAA CGTTCCCTCA CGTGGAGTTA AACGAGTCAC TGCCATCACA

451 AATAGAGAAA GGGAGGCTGT TCTACGTATT GAGTTCCCCA ACGTGGATGT

501 TACGGATATT GACTTCGACT TGTTCCAGGC ACGTGAAAGC ACAGATAAAC

551 CGTTGGATGT CGCTGCTGCT ATTGCATACA GACTACTGCT TGGAAGCGGC

601 CTTCCACAAA AGTTTGGTTG CTCCGACGAG GTGCTTCTTA ACTTCATTCT

651 GCAATGCCGT AAGAAATACC GTAATGTCCC TTATCACAAC TTTTACCATG

701 TTGTGGATGT ATGCCAAACC ATTTACACAT TTTTGTACAG GGGAAATGTG

751 TATGAGAAGT TAACCGAGCT TGAGTGCTTT GTGCTGCTTA TCACCGCACT

801 GGTGCATGAT CTTGATCATA TGGGGTTGAA CAACAGTTTC TACCTGAAAA

851 CAGAATCTCC ACTTGGTATT CTTTCCAGCG CAAGTGGTAA CAAGTCTGTT

901 CTTGAGGTGC ATCACTGCAA CCTTGCTGTT GAGATCCTCT CTGATCCGGA

951 ATCTGATGTG TTTGGTGGTC TGGAGGGTGC AGAGCGTACT CTTGCGTTCC

1001 GATCGATGAT TGATTGTGTA CTTGCGACAG ATATGGCGAG ACATAGTGAA
```

FIGURE 21A

```
1051  TTTCTTGAGA AGTACCTAGA AATTATGAAA ACATCTTACA ACGTTGATGA

1101  TTCCGATCAT CGGCAAATGA CAATGGATGT GCTTATGAAA GCTGGAGATA

1151  TCTCTAACGT AACGAAACCG TTCGACATTT CCCGTCAGTG GGCAATGGCT

1201  GTGACGGAGG AGTTCTACCG TCAAGGAGAC ATGGAGAAGG AGAGGGTGT

1251  GGAAGTATTG CCCATGTTTG ACCGATCTAA GAATATGGAG CTTGCAAAAG

1301  GTCAAATTGG ATTCATTGAC TTTGTCGCAG CCCCATTTTT CCAGAAGATA

1351  GTTGATGCCT GCCTGCAAGG GATGCAATGG ACAGTCGACC GTACAAAGTC

1401  GAACCGCGCA CAGTGGGAGC GAGTTCTGGA AGCAAGGAGT ACAGGGGCTT

1451  CGTCTTAG
```

FIGURE 21 A (continued)

```
  1 MYVEEVRMEA DKGVGTYCLL RDVPYSICCY LAFARGLQDD PRPNREVCRQ LGYNTQAILC EPIIERGEIL
 71 AWVQLVNKLD SSGEVTVPTE OBRDTERVFS LFAGISINNS HLLEFAVRAC REVMELNEEP ASLPHKVVPS
141 RCVKRVEAIT NREREAVLRI EPPNVDVTDI DFDLPQARES TDKPLDVAAA IAYRLLLGSS LPQKFGCSDE
211 VLCMFILQCR KKYREVPYEM FYHVVDVCQT IYTPLYRGHV YEKLEELECF VLLITALVED LDHNGLNNSP
281 YLRTEGPLGI LSSASGNESV LEVHECNLAV EILSDPESDV FGGLEGAERT LAFRSHEDCV LATDMARIISE
351 FLERYLEIMK TSTNVDDSDE RQMTHDVLMK AGDISHVTKP FDVSRQNAMA VTEEFYRQGD MEKERGVEVL
421 PMFDRSKHME LAKGQIGPED FVAAPFFQKI VDACLQGHQW TVDRTKSNRA QWERVLEARS TGASS
```

FIGURE 21B

```
   1  ATGTTCATGA ACAAGCCCTT TGGCAGCAAG CGCTGCGAAC CCTTCCACGA
  51  GTCGGAGCAC CTTTGTGAGG CGTTTGCCAT CACTGAAGCA ATCCTCGCTC
 101  GCTATCAGCG TGGGAAACGC AGCTTTACGT CCTCCGAAAA AAGTGGACTG
 151  GCAGCCCTTA TCAAACGTAT TCCTTATGAT ATCCTTGTTG AGGTTCTCGA
 201  TCAAAGCGGA TTTACTCCAA CAAGCAATGC AACACCCCCC GTTGATTATT
 251  TAGCTATGAT GGAGCACACA ATGACGCACG GTGCGTCTAT TACACACGCC
 301  CTGCAGTACC TTAACGATTT GATGACTAAG TGTACCGGGT GCCCGGGGAT
 351  TCGTACATAT TACCATAACC CCAATGATGA CGTTCTGGCC GACCCCGTTC
 401  ACGACACGGC AGCATTGATT GATGAAACAA CAGCCGTGGG AAAGTCGGTT
 451  GTAACTAAAC AGTACCTTAA TATAGCTGGG GCTCACTACA TACCCTTGAT
 501  CCACGGAGAT ATTGTGGTTG GTTGTGTTGA GGTACCCCGC TTTTCGGGAA
 551  ATCTTGAGAA ATTGCCATCA TTCCCATCTC TCATAAGAGC TGTGACATGT
 601  ACCGCACACA AATTCATTGA GGAAGCGAGA ATCAACTGGA ACAGGGAGAA
 651  GGCGGAAGCT ATGTTGCAAA TGGCGACCAG GTTGGCCCGT GACAATCTTG
 701  ATGAAACAGT ACTTGCATCT TCTATCATGA ACACTGTCAA GAGTCTCACG
 751  GAAAGTGCGC GTTGCAGTCT CTTCCTTGTG AAAGACGACA AGCTTGAAGC
 801  GCATTTTGAG GATGGTAACG TCGTTTCCAT ACCCAAGGGA ACAGGCATTG
 851  TAGGGTATGT GGCGCAAACT GGTGAGACTG TTAATATTGT TGATGCCTAC
 901  GCCGATGACC GCTTTAACCG TGAGGTTGAC AAGGCTACTG GGTACCGTAC
 951  AAAGACGATA CTCTGCATGC CTGTGATGTA CGAAGGAACG ATTGTGGCTG
1001  TAACCCAGCT GATTAATAAA TTGGATCTGA CAACTGAGAG TGGATTGCGC
```

FIGURE 22A

```
1051  CTACCTCGTG TGTTCGGAAA ACGTGACGAG GAGCTGTTCC AAACCTTCTC

1101  TATGTTTGCT GGCGCCTCAC TACGTAACTG TCGTATCAAT GACCGACTCT

1151  TAAAGGAGAA GAAAAGAGT GACGTGATTC TCGATGTTGT TACTGTTCTC

1201  TCGAACACGG ATATCCGCGA TGTGGATGGT ATTGTTCGCC ACGCACTGCA

1251  CGGAGCAAAG AAACTACTGA ACGCGGATCG CTCTACTTTG TTTTTGGTGG

1301  ACAAGGAACG GAACGAACTT TGCAGTCGTA TGGCAGATAG CGTTGCTGGT

1351  AAGGAGATTC GGTTTCCGTG TGGCCAAGGT ATTGCGGGCA CTGTGGCGGC

1401  ATCTGGAGTT GGTGAGAATA TTCAGGACGC GTACCAGGAT CCGCGCTTCA

1451  ACCGTGAGGT TGACAAACAA CTTGGATACC GCACGCAGAC CATATTGTGC

1501  GAGCCCATCA TACTAAATGG TGAGATCCTT GCTGTCGTGC AGCTCGTGAA

1551  CAAGCTTGAT ACGTCTGGAG AAGTGACTGT GTTTACCGAG GATGATCGTG

1601  ACACCTTCCG TGTGTTTTCC TTATTTGCAG GTATATCCAT CAACAACTCT

1651  CACCTGCTTG AGTTCGCTGT GAAGGCGGGT CGTGAGGTGA TGGAATTAAA

1701  TGAACACCGA GCAACATTGT TTAATAAGAA CGTTCCCTCA CGCGCGGTTA

1751  AACGAGTCAC TGCCATTACG AAGGTTGAAA GGGAAGCGGT CTTGGTCTGT

1801  GAACTTCCAT CGTTTGATGT TACGGATGTT GAGTTCGACT TGTTCCGAGC

1851  ACGTGAAAGC ACAGATAAAC CGTTGGATGT CGCTGCTGCT ATTGCATACA

1901  GACTACTGCT TGGAAGCGGC CTTCCACAAA AGTTTGGTTG CTCTGACGAG

1951  GTGCTTCTTA ACTTCATTCT GCAATGCCGT AAGAAATACC GTAATGTCCC

2001  TTATCACAAC TTTTACCATG TTGTGGATGT ATGCCAAACC ATTCACACAT

2051  TCTTGTACAG GGGAAATGTG TATGAGAAGT TAACCGAGCT TGAGTGCTTT
```

FIGURE 22A (continued)

```
2101  GTGCTGCTTA TCACCGCACT GGTGCATGAT CTTGATCATA TGGGGCTGAA

2151  CAACAGTTTC TACCTGAAAA CAGAATCTCC ACTTGGTATT CTTTCCAGCG

2201  CAAGTGGTAA CACCTCTGTT CTTGAGGTGC ATCACTGCAA CCTTGCTGTT

2251  GAGATCCTCT CTGATCCGGA ATCTGATGTG TTTGATGGTC TGGAGGGTGC

2301  AGAGCGTACT CTTGCGTTCC GATCGATGAT TGATTGTGTA CTTGCGACAG

2351  ATATGGCGAA GCATGGAAGT GCATTAGAGG CGTTTCTTGC ATCTGCGGCG

2401  GACCAGTCGT CAGACGAGGC AGCGTTTCAC CGCATGACGA TGGAGATAAT

2451  CTTGAAAGCT GGAGATATCT CTAACGTAAC GAAACCGTTC GACATTTCCC

2501  GTCAGTGGGC AATGGCTGTG ACGGAGGAGT TCTACCGTCA AGGAGACATG

2551  GAGAAGGAGA GGGGTGTGGA AGTATTGCCC ATGTTTGACC GATCTAAGAA

2601  TATGGAGCTT GCAAAAGGTC AAATTGGATT CATTGACTTT GTTGCAGCCC

2651  CATTTTTCCA GAAGATAGTT GATGCCTGCC TGCAAGGGAT GCAATGGACA

2701  GTCGACCGTA TCAAATCGAA CCGCGCACAG TGGGAGCGAG TTCTGGAAAC

2751  AAGACTATCA ACGAGTTCTG GCAACAACAG CAGTACTCGT TGA
```

FIGURE 22A (continued)

```
  1  MFMNKPFGSK RCEPFHESEH LCEAFAITEA ILARYQRGKR SFTSSEKSGL
 51  AALIKRIPYD ILVEVLDQSG FTPTSNATPP VDYLAMMEHT MTHGASITHA
101  LQYLNDLMTK CTGCPGIRTY YHNPNDDVLA DPVHDTAALI DETTAVGKSV
151  VTKQYLNIAG AHYIPLIHGD IVVGCVEVPR FSGNLEKLPS FPSLIRAVTC
201  TAHKFIEEAR INWNREKAEA MLQMATRLAR DNLDETVLAS SIMNTVKSLT
251  ESARCSLFLV KDDKLEAHFE DGNVVSIPKG TGIVGYVAQT GETVNIVDAY
301  ADDRFNREVD KATGYRTKTI LCMPVMYEGT IVAVTQLINK LDLTTESGLR
351  LPRVFGKRDE ELFQTFSMFA GASLRNCRIN DRLLKEKKKS DVILDVVTVL
401  SNTDIRDVDG IVRHALHGAK KLLNADRSTL FLVDKERNEL CSRMADSVAG
451  KEIRFPCGQG IAGTVAASGV GENIQDAYQD PRFNREVDKQ LGYRTQTILC
501  EPIILNGEIL AVVQLVNKLD TSGEVTVFTE DDRDTFRVFS LFAGISINNS
551  HLLEFAVKAG REVMELNEHR ATLFNKNVPS RAVKRVTAIT KVEREAVLVC
601  ELPSFDVTDV EFDLFRARES TDKPLDVAAA IAYRLLLGSG LPQKFGCSDE
651  VLLNFILQCR KKYRNVPYHN FYHVVDVCQT IHTFLYRGNV YEKLTELECF
701  VLLITALVHD LDHMGLNNSF YLKTESPLGI LSSASGNTSV LEVHHCNLAV
751  EILSDPESDV FDGLEGAERT LAFRSMIDCV LATDMAKHGS ALEAFLASAA
801  DQSSDEAAFH RMTMEIILKA GDISNVTKPF DISRQWAMAV TEEFYRQGDM
851  EKERGVEVLP MFDRSKNMEL AKGQIGFIDF VAAPFFQKIV DACLQGMQWT
901  VDRIKSNRAQ WERVLETRLS TSSGNNSSTR
```

FIGURE 22B

```
   1  ATGGAATTAA ATGAACACCG AGCAACATTG TTTAATAAGA ACGTTCCCTC
  51  ACGTGCGGTT AAACGAGTCA CTGCCATTAC GAAGGTTGAA AGGGAAGCGG
 101  TCTTGGTCTG TGAACTTCCA TCGTTTGATG TTACGGATGT TGAGTTCGAC
 151  TTGTTCCGAG CACGTGAAAG CACAGATAAA TCGTTGGATG TCGCTGCTGC
 201  TATTGCATAC AGACTACTGC TTGGAAGCGG CCTTCCACAA AAGTTTGGTT
 251  GCTCTGACGA GGTGCTTCTT AACTTCATTC TGCAATGCCG TAAGAAATAC
 301  CGTAATGTCC CTTATCACAA CTTTTACCAT GTTGTGGATG TATGCCAAAC
 351  CATTCACACA TTCTTGTACA GGGGAAATGT GTATGAGAAG TTAACCGAGC
 401  TTGAGTGCTT TGTGCTGCTT ATCACCGCAC TGGTGCATGA TCTTGATCAT
 451  ATGGGGCTGA ACAACAGTTT CTACCTGAAA ACAGAATCTC CACTTGGTAT
 501  TCTTTCCAGC GCAAGTGGTA ACACCTCTGT TCTTGAGGTG CATCACTGCA
 551  ACCTTGCTGT TGAGATCCTC TCTGATCCGG AATCTGATGT GTTTGATGGT
 601  CTGGAGGGTG CAGAGCGTAC TCTTGCGTTC CGATCGATGA TTGATTGTGT
 651  ACTTGCGACA GATATGGCGA AGCATGGAAG TGCATTAGAG GCGTTTCTTG
 701  CATCTGCGGC GGACCAGTCG TCAGACGAGG CAGCGTTTCA CCGCATGACG
 751  ATGGAGATAA TCTTGAAAGC TGGAGATATC TCTAACGTAA CGAAACCGTT
 801  CGACATTTCC CGTCAGTGGG CAATGGCTGT GACGGAGGAG TTCTACCGTC
 851  AAGGAGACAT GGAGAAGGAG AGGGGTGTGG AAGTATTGCC CATGTTTGAC
 901  CGATCTAAGA ATATGGAGCT TGCAAAAGGT CAAATTGGAT TCATTGACTT
 951  TGTTGCAGCC CCATTTTTCC AGAAGATAGT TGATGCCTGC CTGCAAGGGA
1001  TGCAATGGAC AGTCGACCGT ATCAAATCGA ACCGCACA GTGGGAGCGA
```

FIGURE 23A

1051 GTTCTGGAAA CAAGACTATC AACGAGTTCT GGCAACAACA GCAGTACTCG

1101 TTGA

FIGURE 23 A (continued)

```
  1  MELNEHRATL FNKNVPSRAV KRVTAITKVE REAVLVCELP SFDVTDVEFD
 51  LFRARESTDK SLDVAAAIAY RLLLGSGLPQ KFGCSDEVLL NFILQCRKKY
101  RNVPYHNFYH VVDVCQTIHT FLYRGNVYEK LTELECFVLL ITALVHDLDH
151  MGLNNSFYLK TESPLGILSS ASGNTSVLEV HHCNLAVEIL SDPESDVFDG
201  LEGAERTLAF RSMIDCVLAT DMAKHGSALE AFLASAADQS SDEAAFHRMT
251  MEIILKAGDI SNVTKPFDIS RQWAMAVTEE FYRQGDMEKE RGVEVLPMFD
301  RSKNMELAKG QIGFIDFVAA PFFQKIVDAC LQGMQWTVDR IKSNRAQWER
351  VLETRLSTSS GNNSSTR
```

FIGURE 23B

| Inhibitor | IC50 values | |
|---|---|---|
| | For TbPDE2A | For TbPDE2C |
| Sildenafil | 9.4 | 42.4 |
| Dipyridamole | 5.9 | 14.6 |
| Etazolate | 30.3 | 30.57 |
| Ethaverine | 14.2 | 26.8 |
| Trequinsin | 5.4 | 13.3 |
| Km for cAMP | 2 µM | 7.9 µM |

FIGURE 30

```
  1 acgcgagatccgcgctcgcctccgtccgcccaggcggcgatgacacggcgcccacggcggcccgaaggcgccgggtgggc  80

81 cgtttgccgaccggatcgcggctaccgccagcgcgtccgcggcgccgccgccagc ATG GGC TGT GCC CCG AGC  154
  1                                                         M   G   C   A   P   S    6

155 ATC CAC ATT TCC GAG CGC CTG GTG GCC GAG GAC GCG CCT AGC CCC GCG GCA CCG CCG CTG  214
  7  I   H   I   S   E   R   L   V   A   E   D   A   P   S   P   A   A   P   P   L   26

215 TCG TCC GGC AGG CCG CGC CTC CCG CAG GGC CAG AAG ACG GCC GCC TTG CCC CGG ACC CGC  274
 27  S   S   G   R   P   R   L   P   Q   G   Q   K   T   A   A   L   P   R   T   R   46

275 GGC GCC GGC CTC TTG GAG TCG GAG GTT CGC GAC GGC AGC GGC AAG AAG GTA GCA GTA GCT  334
 47  G   A   G   L   L   E   S   E   V   R   D   G   S   G   K   K   V   A   V   A   66

335 GAT GTG CAG TTT GGC CCC ATG AGA TTT CAT CAA GAT CAA CTT CAG GTA CTT TTA GTG TTT  394
 67  D   V   Q   F   G   P   M   R   F   H   Q   D   Q   L   Q   V   L   L   V   F   86

395 ACC AAA GAA GAT AAC CAA TGT AAT GGA TTC TGC AGG GCA TGT GAA AAA GCA GGG TTT AAG  454
 87  T   K   E   D   N   Q   C   N   G   F   C   R   A   C   E   K   A   G   F   K  106

455 TGT ACA GTT ACC AAG GAG GCT CAG GCT GTC CTT GCC TGT TTC CTG GAC AAA CAT CAT GAC  514
107  C   T   V   T   K   E   A   Q   A   V   L   A   C   F   L   D   K   H   H   D  126

515 ATT ATC ATC ATA GAC CAC AGA AAT CCT CGA CAG CTG GAT GCA GAG GCA CTG TGC AGG TCT  574
127  I   I   I   I   D   H   R   N   P   R   Q   L   D   A   E   A   L   C   R   S  146

575 ATC AGA TCA TCA AAA CTC TCA GAA AAC ACA GTT ATT GTT GGT GTA GTA CGC AGG GTG GAT  634
147  I   R   S   S   K   L   S   E   N   T   V   I   V   G   V   V   R   R   V   D  166

635 AGA GAA GAG TTG TCC GTA ATG CCT TTC ATT TCT GCT GGA TTT ACA AGG AGG TAT GTA GAA  694
167  R   E   E   L   S   V   M   P   F   I   S   A   G   F   T   R   R   Y   V   E  186

695 AAC CCC AAC ATC ATG GCC TGC TAC AAT GAA CTG CTC CAG CTG GAG TTT GGA GAG GTG CGA  754
187  N   P   N   I   M   A   C   Y   N   E   L   L   Q   L   E   F   G   E   V   R  206

755 TCA CAA CTG AAA CTC AGG GCT TGT AAC TCA GTA TTC ACT GCA TTA GAA AAC AGT GAA GAT  814
207  S   Q   L   K   L   R   A   C   N   S   V   F   T   A   L   E   N   S   E   D  226

815 GCA ATT GAA ATT ACA AGC GAA GAC CGT TTT ATA CAG TAT GCA AAT CCT GCA TTT GAA ACA  874
227  A   I   E   I   T   S   E   D   R   F   I   Q   Y   A   N   P   A   F   E   T  246

875 ACA ATG GGC TAT CAG TCA GGT GAA TTA ATA GGG AAG GAG TTA GGA GAA GTG CCT ATA AAT  934
247  T   M   G   Y   Q   S   G   E   L   I   G   K   E   L   G   E   V   P   I   N  266

935 GAA AAA AAG GCT GAC TTG CTC GAT ACT ATA AAT TCA TGC ATC AGG ATA GGC AAG GAG TGG  994
267  E   K   K   A   D   L   L   D   T   I   N   S   C   I   R   I   G   K   E   W  286

995 CAA GGA ATT TAC TAT GCC AAA AAG AAA AAC GGA GAT AAT ATA CAA CAA AAT GTG AAG ATA 1054
287  Q   G   I   Y   Y   A   K   K   K   N   G   D   N   I   Q   Q   N   V   K   I  306

1055 ATA CCT GTC ATT GGA CAG GGA GGA AAA ATT AGA CAC TAT GTG TCC ATT ATC AGA GTG TGC 1114
307  I   P   V   I   G   Q   G   G   K   I   R   H   Y   V   S   I   I   R   V   C  326

1115 AAT GGC AAC AAT AAG GCT GAG AAA ATA TCC GAA TGT GTT CAG TCT GAC ACT CGT          1174
327  N   G   N   N   K   A   E   K   I   S   E   C   V   Q   S   D   T   R   ...   346

1175 AAT CAG ACA GGC AAA CAT AAA GAC AGG AGA AAA GGC TCA CTA GAC GTC AAA GCT GTT GCC 1234
347  N   Q   T   G   K   H   K   D   R   R   K   G   S   L   D   V   K   A   V   A  366

1235 TCC CGT GCA ACT GAA GTT TCC AGC CAG AGA CGA CAC TCT TCC ATG GCC GGG ATA CAT TCC 1294
367  S   R   A   T   E   V   S   S   Q   R   R   H   S   S   M   A   G   I   H   S  386

1295 ATG ACA ATT GAG GCG CCC ATC ACC AAG GTA ATC AAT GTT ATC AAT GCT GCC CAG GAA AGT 1354
387  M   T   I   E   A   P   I   T   K   V   I   N   V   I   N   A   A   Q   E   S  406

1355 AGT CCC ATG CCT GTG ACA GAA GCC CTA GAC CGT GTG CTG GAA ATT CTA AGA ACC ACT GAG 1414
407  S   P   M   P   V   T   E   A   L   D   R   V   L   E   I   L   R   T   T   E  426

1415 TTA TAT TCA CCA CAG TTT GGT GCT AAA GAT GAT GAT CCC CAT GCC AAT GAC TTT GTT GGG 1474
427  L   Y   S   P   Q   F   G   A   K   D   D   D   P   H   A   N   D   L   V   G  446

1475 GGC TTA ATG TCT GAT GGT TTG CGA AGA CTA TCA GGG AAT GAA TAT GTT CTT TCA ACA AAA 1534
447  G   L   M   S   D   G   L   R   R   L   S   G   N   E   Y   V   L   S   T   K  466

1535 AAC ACT CAA ATG GTT TCA AGC AAT ATA ATC ACT CCC ATC TCC TTG GAT GAT GTC CCA CCA 1594
467  N   T   Q   M   V   S   S   N   I   I   T   P   I   S   L   D   D   V   P   P  486

1595 CGG ATA GCT CGG GCC ATG GAA AAT GAG TAC TGG GAC TTT GAT ATT TTT GAA CTG GAG 1654
487  R   I   A   R   A   M   E   N   E   Y   W   D   F   D   I   F   E   L   E  506

1655 GCT GCC ACC CAC AAT AGG CCT TTG ATT TAT CTT GGT CTC AAA ATG TTT GCT CGC TTT GGA 1714
507  A   A   T   H   N   R   P   L   I   Y   L   G   L   K   M   F   A   R   F   G  526

1715 ATC TGT GAA TTC TTA CAC TGC TCC GAG TCA ACG CTA AGA TCA TGG TTA CAA ATT ATC GAA 1774
527  I   C   E   F   L   H   C   S   E   S   T   L   R   S   W   L   Q   I   I   E  546

1775 GCC AAT TAT CAT TCC TCC AAT CCC TAC CAC AAT TCT ACA CAT TCT GCT GAT GTG CTT TAT 1834
547  A   N   Y   H   S   S   N   P   Y   H   N   S   T   H   S   A   D   V   L   H  566

1835 GCC ACT GCC TAT TTT CTC TCC AAG GAG AGG ATA AAG GAA ACT TTA GAT CCA ATT GAT GAG 1894
567  A   T   A   Y   F   L   S   K   E   R   I   K   E   T   L   D   P   I   D   E  586

1895 GTC GCT GCA CTC ATC GCA GCC ACC ATT CAT GAT GTG GAT CAC CCT GGG AGA ACC AAC TCC 1954
```

FIGURE 33

```
1955 TTC CTG TGT AAT GCT GGA AGT GAG CTG GCC ATT TTG TAC AAT GAC ACT GCT GTG CTG GAG 2014
 607 F  L   C   N   A   G   S   E   L   A   I   L   Y   N   D   T   A   V   L   E   626

2015 AGC CAC CAT GCG GCC TTG GCC TTC CAG CTG ACC ACT GGA GAT GAT AAA TGC AAT ATA TTT 2074
 627 S   H   H   A   A   L   A   F   Q   L   T   T   G   D   D   K   C   N   I   F   646

2075 AAA AAC ATG GAG AGG AAT GAT TAT CGG ACA CTG CGC CAG GGG ATT ATC GAC ATG GTC TTA 2134
 647 K   N   M   E   R   N   D   Y   R   T   L   R   Q   G   I   I   D   M   V   L   666

2135 GCC ACA GAA ATG ACA AAG CAC TTT GAG CAT GTC AAC AAA TTT GTC AAC AGC ATC AAC AAA 2194
 667 A   T   E   M   T   K   H   F   E   H   V   N   K   F   V   N   S   I   N   K   686

2195 CCC TTG GCA ACA CTA GAA GAA AAT GGG GAA ACT GAT AAA AAC CAG GAA GTG ATA AAC ACT 2254
 687 P   L   A   T   L   E   E   N   G   E   T   D   K   N   Q   E   V   I   N   T   706

2255 ATG CTT ACG ACT CCA GAG AAC CGG ACC CTA ATC AAA CGA ATG CTG ATT AAA TGT GCT GAT 2314
 707 M   L   T   T   P   E   N   R   T   L   I   K   R   M   L   I   K   C   A   D   726

2315 GTG TCC AAT CCC TGC CGA CCC CTG CAG TAC TGC ATC GAG TGG GCT GCA CGC ATT TCG GAA 2374
 727 V   S   N   P   C   R   P   L   Q   Y   C   I   E   W   A   A   R   I   S   E   746

2375 GAA TAT TTT TCT CAG ACT GAT GAA GAG AAG CAG CAG GGC TTA CCT GTG GTG ATG CCA GTG 2434
 747 E   Y   F   S   Q   T   D   E   E   K   Q   Q   G   L   P   V   V   M   P   V   766

2435 TTT GAC AGA AAT ACC TGC AGC ATC CCC AAA TCC CAA ATC TCT TTC ATT GAT TAC TTC ATC 2494
 767 F   D   R   N   T   C   S   I   P   K   S   Q   I   S   F   I   D   Y   F   I   786

2495 ACA GAC ATG TTT GAT GCT TGG GAT GCC TTT GTA GAC CTG CCT GAT TTA ATG CAG CAT CTT 2554
 787 T   D   M   F   D   A   W   D   A   F   V   D   L   P   D   L   M   Q   H   L   806

2555 GAC AAC AAC TTT AAA TAC TGG AAA GGA CTG GAC GAA ATG AAG CTG CGG AAC CTC CGA CCA 2614
 807 D   N   N   F   K   Y   W   K   G   L   D   E   M   K   L   R   N   L   R   P   826

2615 CCT CCT GAA TAG tgggagacaccaccagagcctgaagctttgttccttcggtcatttggaattcctgaggcag 2690
 827 P   P   E   *                                                                   830

2691 ccagagctccttggtcctttcagtactaggcagaacagcccgatctgcatagcctgtgaaagcccacgggacatcag 2770

2771 taacctcctgcagccaccatccaatgccattactgtcaagtgagacttggccactgtagcctgggcctgctgcaggagct 2850

2851 cttcagaaaggcacatgaggaccacggttgcctcagttcctggtaaaacacaaggtctggagtgccctgcaaagggta 2930

2931 ttgatggacttcctgccagtgacagagcatgtctattgcaaacaattctctcagttacgttcagcacttaagaacgcta 3010

3011 atggcaataagatctttagcaacttcttcacatcatagaaggtgcaatcgctcacttgggaacactactgagagcgactt 3090

3091 ctcttttaaaasttgagtagcagatgaaaaattaaaatctgaacttgactattaatatcaattaaaatgttttatctattt 3170

3171 tattaaaagcttaatattttctatgaattcaaaaataacttcagagtcaaagccaacttcaaatacc gtgaacaaattac 3250

3251 atgattcatactcattatgcattacttggtatacagacttatttcataatgcaaattaataaaatgacacttttactgc 3330

3331 actatagaaatattcatgtatgtttaaacttttctgattgaggctaactggaaaaagctggggtcgtattctaagtgctaa 3410

3411 agaaggctgcttctaetgtatagaacccagggctctgaaacagctctagccgcctaatgcacttcacaggtaactcccca 3490

3491 aagtaaaactagactctcttgttggctcgcaaagaaaagttaggacttaacacttttttctaaaattttataattcaatt 3570

3571 cccaaaagtctactctatcttatacgttcctacaaaatatcctataaaacaaagaacaaaatcgaatacttaatg 3650

3651 aattgacattttataaccaacctgttttatctacggtgggaatcttcgatgccagaaatttataaagaggtctgtatc 3730

3731 ttcacaccttgaaaaagcataataccataaaaaatgacacttgacatgtcaatgtatttgtcattttcatttttaaaactcgt 3810

3811 attttgtcgtttcttcccagataaaaatgaaattaaaccattctttcttaagaaaaaaaaaaaaaaaaaaa 3880
```

FIGURE 33 (continued)

```
   1 acgcgagatccgcgctcgcctccgtccgcccaggcggcgatgacacggcgcccacggcggcccgaaggcgccgggtgggccgtttgctgaccggatcgcg 100

101 gctacccgccagcgtgtccgcggcgccgccgccagc ATG GGC TGT GCC CCG AGC ATC CAC ATT TCC GAG CGC CTG GTG GCC GAG 184
                                           M   G   C   A   P   S   I   H   I   S   E   R   L   V   A   E   16
                                           1

185 GAC GCG CCT AGC CCC GCG GCA CCG CCG CTG TCG TCC GGC GGG CCG CGC CTC CCG CAG GGC CAG AAG ACG GCC GCC 259
  17 D   A   P   S   P   A   A   P   P   L   S   S   G   G   P   R   L   P   Q   G   Q   K   T   A   A   41

260 TTG CCC CGG ACC CGC GGC GCC GGC CTC TTG GAG TCG GAG GTT CGC GAC GGC AGC GGC AAG AAG GTA GCA GTA GCT 334
  42 L   P   R   T   R   G   A   G   L   L   E   S   E   V   R   D   G   S   G   K   K   V   A   V   A   66

335 GAT GTG CAG TTT GGC CCC ATG AGA TTT CAT CAA GAT CAA CTT CAG GTA CTT TTA GTG TTT ACC AAA GAA GAT AAC 409
  67 D   V   Q   F   G   P   M   R   F   H   Q   D   Q   L   Q   V   L   L   V   F   T   K   E   D   N   91

410 CAA TGT AAT GGA TTC TGC AGG GCA TGT GAA AAA GCA GGG TTT AAG TGT ACA GTT ACC AAG GAG GCT CAG GCT GTC 484
  92 Q   C   N   G   F   C   R   A   C   E   K   A   G   F   K   C   T   V   T   K   E   A   Q   A   V   116

485 CTT GCC TGT TTC CTG GAC AAA CAT CAT GAC ATT ATC ATC ATA GAC CAC AGA AAT CCT CGA CAG CTG GAT GCA GAG 559
 117 L   A   C   F   L   D   K   H   H   D   I   I   I   I   D   H   R   N   P   R   Q   L   D   A   E   141

560 GCA CTG TGC AGG TCT ATC AGA TCA TCA AAA CTC TCA GAA AAC ACA GTT ATT GTT GGT GTA GTA CGC AGG GTG GAT 634
 142 A   L   C   R   S   I   R   S   S   K   L   S   E   N   T   V   I   V   G   V   V   R   R   V   D   166

635 AGA GAA GAG TTG TCC GTA ATG CCT TTC ATT TCT GCT GGA TTT ACA AGG AGG TAT GTA GAA AAC CCC AAC ATC ATG 709
 167 R   E   E   L   S   V   M   P   F   I   S   A   G   F   T   R   R   Y   V   E   N   P   N   I   M   191

710 GCC TGC TAC AAT GAA CTG CTC CAG CTG GAG TTT GGA GAG GTG CGA TCA CAA CTG AAA CTC AGG GCT TGT AAC TCA 784
 192 A   C   Y   N   E   L   L   Q   L   E   F   G   E   V   R   S   Q   L   K   L   R   A   C   N   S   216

785 GTA TTC ACT GCA TTA GAA AAC AGT GAA GAT GCA ATT GAA ATT ACA AGC GAA GAC CGT TTT ATA CAG TAT GCA AAT 859
 217 V   F   T   A   L   E   N   S   E   D   A   I   E   I   T   S   E   D   R   F   I   Q   Y   A   N   241

860 CCT GCA TTT GAA ACA ACA ATG GGC TAT CAG TCA GGT GAA TTA ATA GGG AAG GAG TTA GGA GAA GTG CCT ATA AAT 934
 242 P   A   F   E   T   T   M   G   Y   Q   S   G   E   L   I   G   K   E   L   G   E   V   P   I   N   266

935 GAA AAA AAG GCT GAC TTG CTC GAT ACT ATA AAT TCA TGC ATC AGG ATA GGC AAG GAG TGG CAA GGA ATT TAC TAT 1009
 267 E   K   K   A   D   L   L   D   T   I   N   S   C   I   R   I   G   K   E   W   Q   G   I   Y   Y   291

1010 GCC AAA AAG AAA AAC GGA GAT AAT ATA CAA CAA AAT GTG AAG ATA ATA CCT GTC ATT GGA CAG GGA GGA AAA ATT 1084
 292 A   K   K   K   N   G   D   N   I   Q   Q   N   V   K   I   I   P   V   I   G   Q   G   G   K   I   316

1085 AGA CAC TAT GTG TCC ATT ATC AGA GTG TGC AAT GGC AAC AAT AAG GCT GAG AAA ATA TCC GAA TGT GTT CAG TCT 1159
 317 R   H   Y   V   S   I   I   R   V   C   N   G   N   N   K   A   E   K   I   S   E   C   V   Q   S   341

1160 GAC ACT CAT ACA GAT AAT CAG ACA GGC TGT AAA GAC AGG AGA AAA GGC TCA CTA GAC GTC AAA GCT GTT GCC 1234
 342 D   T   H   T   D   N   Q   T   G   C   K   D   R   R   K   G   S   L   D   V   K   A   V   A   366

1235 TCC CGT GCA ACT GAA GTT TCC AGC CAG AGA CGA CAC TCT TCC ATG GCC CGG ATA CAT TCC ATG ACA ATT GAG GCG 1309
 367 S   R   A   T   E   V   S   S   Q   R   R   H   S   S   M   A   R   I   H   S   M   T   I   E   A   391

1310 CCC ATC ACC AAG GTA ATC AAT ATT ATC AAT GCT GCC CAG GAA AGT AGT CCC ATG CCT GTG ACA GAA GCC CTA GAC 1384
 392 P   I   T   K   V   I   N   I   I   N   A   A   Q   E   S   S   P   M   P   V   T   E   A   L   D   416

1385 CGT GTG CTG GAA ATT CTA AGA ACC ACT GAG TTA TAT TCA CCA CAG TTT GGT GCT AAA GAT GAT GAT CCC CAT GCC 1459
 417 R   V   L   E   I   L   R   T   T   E   L   Y   S   P   Q   F   G   A   K   D   D   D   P   H   A   441

1460 AAT GAC CTT GTT GGG GGC TTA ATG TCT GAT GGT TTG CGA AGA CTA TCA GGG AAT GAA TAT GTT CTT TCA ACA AAA 1534
 442 N   D   L   V   G   G   L   M   S   D   G   L   R   R   L   S   G   N   E   Y   V   L   S   T   K   466

1535 AAC ACT CAA ATG GTT TCA AGC AAT ATA ATC ACT CCC ATC TCC CTT GAT GAT GTC CCA CCA CGG ATA GCT CGG GCC 1609
 467 N   T   Q   M   V   S   S   N   I   I   T   P   I   S   L   D   D   V   P   P   R   I   A   R   A   491

1610 ATG GAA AAT GAG GAA TAC TGG GAC TTT GAT ATT TTT GAA CTG GAG GCT GCC ACC CAC AAT AGG CCT TTG ATT TAT 1684
 492 M   E   N   E   E   Y   W   D   F   D   I   F   E   L   E   A   A   T   H   N   R   P   L   I   Y   516

1685 CTT GGT CTC AAA ATG TTT GCT CGC TTT GGA ATC TGT GAA TTC TTA CAC TGC TCC GAG TCA ACG CTA AGA TCA TGG 1759
 517 L   G   L   K   M   F   A   R   F   G   I   C   E   F   L   H   C   S   E   S   T   L   R   S   W   541

1760 TTA CAA ATT ATC GAA GCC AAT TAT CAT TCC TCC AAT CCC TAC CAC AAT TCT ACA CAT TCT GCT GAT GTG CTT CAT 1834
 542 L   Q   I   I   E   A   N   Y   H   S   S   N   P   Y   H   N   S   T   H   S   A   D   V   L   H   566

1835 GCC ACT GCC TAT TTT CTC TCC AAG GAG AGG ATA AAG GAA ACT TTA GAT CCA ATT GAT GAG GTC GCT GCA CTC ATC 1909
 567 A   T   A   Y   F   L   S   K   E   R   I   K   E   T   L   D   P   I   D   E   V   A   A   L   I   591
```

ated with cardiac disease (Smith, C. J., Huang, R., Sun, D., Ricketts, S., Hoegler, C., Ding, J. Z., Moggio, R. A., Hintze, T. H. (1997) *Circulation* 96, 3116–23). A form of diabetes insipidus in the mouse has been associated with increased PDE4 activity (Dousa, T. P. (1999) *Kidney Int.* 55, 29–62). Furthermore, defects in PDE6 have also been associated with retinal disease, such as retinal degeneration in mouse (Tsung, S. H., Gouras, P., Yamashita, C. K., Kjeldbye, H., Fisher, J., Farber, D. B., Goff, S. P. (1996) *Science* 272, 1026–9), autosomal recessive retinitis in humans (Baiget, M., Calaf, M., Valverde, D., del Rio, E., Reig, C., Carballo, M., Calvo, M. T., Gonzales-Duarte, R. (1998) *Med. Clin.* 111, 420–422), and rod/cone dysplasia in some dogs (Dekomien, G., Epplen, J. T. (2000) *Anim. Genet.* 31, 135–139).

SEQUENCE LISTING

<160> NUMBER OF SEQ ID NOS: 61

<210> SEQ ID NO 1
<211> LENGTH: 3880
<212> TYPE: DNA
<213> ORGANISM: Homo sapiens

<400> SEQUENCE: 1

```
acgcgagatc cgcgctcgcc tccgtccgcc caggcggcga tgacacggcg cccacggcgg      60
cccgaaggcg ccgggtgggc cgtttgctga ccggatcgcg gctacccgcc agcgtgtccg     120
cggcgccgcc gccagcatgg gctgtgcccc gagcatccac atttccgagc gcctggtggc     180
cgaggacgcg cctagccccg cggcaccgcc gctgtcgtcc ggcgggccgc gcctcccgca     240
gggccagaag acggccgcct tgccccggac ccgcggcgcc ggcctcttgg agtcggaggt     300
tcgcgacggc agcggcaaga aggtagcagt agctgatgtg cagtttggcc ccatgagatt     360
tcatcaagat caacttcagg tacttttagt gtttaccaaa gaagataacc aatgtaatgg     420
attctgcagg gcatgtgaaa aagcagggtt taagtgtaca gttaccaagg aggctcaggc     480
tgtccttgcc tgtttcctgg acaaacatca tgacattatc atcatagacc acagaaatcc     540
tcgacagctg gatgcagagg cactgtgcag gtctatcaga tcatcaaaac tctcagaaaa     600
cacagttatt gttggtgtag tacgcagggt ggatagagaa gagttgtccg taatgccttt     660
catttctgct ggatttacaa ggaggtatgt agaaaacccc aacatcatgg cctgctacaa     720
tgaactgctc cagctggagt ttggagaggt gcgatcacaa ctgaaactca gggcttgtaa     780
ctcagtattc actgcattag aaaacagtga agatgcaatt gaaattacaa gcgaagaccg     840
ttttatacag tatgcaaatc ctgcatttga aacaacaatg ggctatcagt caggtgaatt     900 aataggaag gagttaggag aagtgcctat aaatgaaaaa aaggctgact tgctcgatac     960
tataaattca tgcatcagga taggcaagga gtggcaagga atttactatg ccaaaaagaa    1020
aaacggagat aatatacaac aaaatgtgaa gataatacct gtcattggac agggaggaaa    1080
aattagacac tatgtgtcca ttatcagagt gtgcaatggc aacaataagg ctgagaaaat    1140
atccgaatgt gttcagtctg acactcgtac agataatcag acaggcaaac ataaagacag    1200
```

| | |
|---|---|
| gagaaaaggc tcactagacg tcaaagctgt tgcctcccgt gcaactgaag tttccagcca | 1260 |
| gagacgacac tcttccatgg cccggataca ttccatgaca attgaggcgc ccatcaccaa | 1320 |
| ggtaatcaat gttatcaatg ctgcccagga aagtagtccc atgcctgtga cagaagccct | 1380 |
| agaccgtgtg ctggaaattc taagaaccac tgagttatat tcaccacagt ttggtgctaa | 1440 |
| agatgatgat ccccatgcca atgaccttgt tgggggctta atgtctgatg gtttgcgaag | 1500 |
| actatcaggg aatgaatatg ttcttttcaac aaaaaacact caaatggttt caagcaatat | 1560 |
| aatcactccc atctcccttg atgatgtccc accacggata gctcgggcca tggaaaatga | 1620 |
| ggaatactgg gactttgata tttttgaact ggaggctgcc acccacaata ggcctttgat | 1680 |
| ttatcttggt ctcaaaatgt ttgctcgctt tggaatctgt gaattcttac actgctccga | 1740 |
| gtcaacgcta agatcatggt tacaaattat cgaagccaat tatcattcct ccaatcccta | 1800 |
| ccacaattct acacattctg ctgatgtgct tcatgccact gcctattttc tctccaagga | 1860 |
| gaggataaag gaaactttag atccaattga tgaggtcgct gcactcatcg cagccaccat | 1920 |
| tcatgatgtg gatcaccctg ggagaaccaa ctccttcctg tgtaatgctg aagtgagct | 1980 |
| ggccattttg tacaatgaca ctgctgtgct ggagagccac catgcggcct tggccttcca | 2040 |
| gctgaccact ggagatgata aatgcaatat atttaaaaac atggagagga atgattatcg | 2100 |
| gacactgcgc caggggatta tcgacatggt cttagccaca gaaatgacaa agcactttga | 2160 |
| gcatgtcaac aaatttgtca acagcatcaa caaacccttg gcaacactag aagaaaatgg | 2220 |
| ggaaactgat aaaaaccagg aagtgataaa cactatgctt aggactccag agaaccggac | 2280 |
| cctaatcaaa cgaatgctga ttaaatgtgc tgatgtgtcc aatccctgcc gaccccctgca | 2340 |
| gtactgcatc gagtgggctg cacgcatttc ggaagaatat ttttctcaga ctgatgaaga | 2400 |
| gaagcagcag ggcttacctg tggtgatgcc agtgtttgac agaaatacct gcagcatccc | 2460 |
| caaatcccaa atctctttca ttgattactt catcacagac atgtttgatg cttgggatgc | 2520 |
| cttttgtagac ctgcctgatt taatgcagca tcttgacaac aactttaaat actggaaagg | 2580 |
| actggacgaa atgaagctgc ggaacctccg accacctcct gaatagtggg agacaccacc | 2640 |
| cagagccctg aagctttgtt ccttcggtca tttggaattc ctgagggcag ccagagctcc | 2700 |
| ttggtccttt cagtactagg cagaacagcc cccgatctgc atagcctgtg aaagcccacg | 2760 |
| gggacatcag taaccttctg cagccaccat ccaatgccat tactgtcaag tgagacttgg | 2820 |
| ccactgtagc ctgggcctgc tgcaggagct cttcagaaag gcacatgagg accacggttt | 2880 |
| gcctcagttt ctggtaaaac acaaggtctg gagtgccct gcaaagggta ttgatggact | 2940 |
| tcctgccagt gacagagcat gtctattgca aacaattctc tcagttacgt tcagcactta | 3000 |
| agaacggcta atgcaatag gatctttagc aactttttca catcatagaa ggtgcaatcg | 3060 |
| ctcacttggg aacactactg agagtgactt ctcttttaaa attgagtagc agatgaaaaa | 3120 |
| ttaaaatttg aacttgatta ttaatatcaa ttaaaatgtt ttatttattt tattaaaagc | 3180 |
| tcaatatttt ctatgaattc aaaaatactt cagagccaaa gccaacttca ataccgtga | 3240 |
| ccaaatttac atgattcata ttcattatgc attacttggt atacagactt attttcataa | 3300 |
| tgcaaattaa taaatgaca cttttactgc actatagaaa tattcatgta tgttaaactt | 3360 |
| ttctgattga ggctaactgg aaaaagctgg ggtcgtattc taagtgctaa agaaggctgc | 3420 |
| ttctactgta tagaacccag ggctctgaaa cagctctagc cgcctaatgc acttcacagg | 3480 |
| taactcccca aggtaaaaact agactctctt gttggttcgc aaagaaaagt taggacttaa | 3540 |
| cacttttttc taaaatttta taattcaatt tccaaaagtc tactctattt tatactgttt | 3600 |

```
ctacaaaata ttccttataa aaacaaagaa caaaaattga atatttaatg aattgacatt    3660
ttataaccaa cctgttttta tctacggtgg gaatctttga tgccagaaat ttataaagag    3720
gttctgtatc ttcacacctt gaataagcat aataccataa aaaatgacac ttgacatgtc    3780
aatgtatttg tcatttcatt ttaaactcgt atttgtggtt ttttcccag ataaaaatga    3840 aattaaacca tttctttta agaaaaaaaa aaaaaaaaa                           3880
```

<210> SEQ ID NO 2
<211> LENGTH: 829
<212> TYPE: PRT
<213> ORGANISM: Homo sapiens

<400> SEQUENCE: 2

```
Met Gly Cys Ala Pro Ser Ile His Ile Ser Glu Arg Leu Val Ala Glu
1               5                   10                  15

Asp Ala Pro Ser Pro Ala Ala Pro Pro Leu Ser Ser Gly Gly Pro Arg
            20                  25                  30

Leu Pro Gln Gly Gln Lys Thr Ala Ala Leu Pro Arg Thr Arg Gly Ala
        35                  40                  45

Gly Leu Leu Glu Ser Glu Val Arg Asp Gly Ser Gly Lys Lys Val Ala
    50                  55                  60

Val Ala Asp Val Gln Phe Gly Pro Met Arg Phe His Gln Asp Gln Leu
65                  70                  75                  80

Gln Val Leu Leu Val Phe Thr Lys Glu Asp Asn Gln Cys Asn Gly Phe
                85                  90                  95

Cys Arg Ala Cys Glu Lys Ala Gly Phe Lys Cys Thr Val Thr Lys Glu
            100                 105                 110

Ala Gln Ala Val Leu Ala Cys Phe Leu Asp Lys His His Asp Ile Ile
        115                 120                 125

Ile Ile Asp His Arg Asn Pro Arg Gln Leu Asp Ala Glu Ala Leu Cys
    130                 135                 140

Arg Ser Ile Arg Ser Ser Lys Leu Ser Glu Asn Thr Val Ile Val Gly
145                 150                 155                 160

Val Val Arg Arg Val Asp Arg Glu Glu Leu Ser Val Met Pro Phe Ile
                165                 170                 175

Ser Ala Gly Phe Thr Arg Arg Tyr Val Glu Asn Pro Asn Ile Met Ala
            180                 185                 190

Cys Tyr Asn Glu Leu Leu Gln Leu Glu Phe Gly Glu Val Arg Ser Gln
        195                 200                 205

Leu Lys Leu Arg Ala Cys Asn Ser Val Phe Thr Ala Leu Glu Asn Ser
    210                 215                 220

Glu Asp Ala Ile Glu Ile Thr Ser Glu Asp Arg Phe Ile Gln Tyr Ala
225                 230                 235                 240

Asn Pro Ala Phe Glu Thr Thr Met Gly Tyr Gln Ser Gly Glu Leu Ile
                245                 250                 255

Gly Lys Glu Leu Gly Glu Val Pro Ile Asn Glu Lys Lys Ala Asp Leu
            260                 265                 270

Leu Asp Thr Ile Asn Ser Cys Ile Arg Ile Gly Lys Glu Trp Gln Gly
        275                 280                 285

Ile Tyr Tyr Ala Lys Lys Lys Asn Gly Asp Asn Ile Gln Gln Asn Val
    290                 295                 300

Lys Ile Ile Pro Val Ile Gly Gln Gly Gly Lys Ile Arg His Tyr Val
305                 310                 315                 320
```

```
Ser Ile Ile Arg Val Cys Asn Gly Asn Asn Lys Ala Glu Lys Ile Ser
            325                 330                 335

Glu Cys Val Gln Ser Asp Thr Arg Thr Asp Asn Gln Thr Gly Lys His
            340                 345                 350

Lys Asp Arg Arg Lys Gly Ser Leu Asp Val Lys Ala Val Ala Ser Arg
            355                 360                 365

Ala Thr Glu Val Ser Ser Gln Arg Arg His Ser Ser Met Ala Arg Ile
        370                 375                 380

His Ser Met Thr Ile Glu Ala Pro Ile Thr Lys Val Ile Asn Val Ile
385                 390                 395                 400

Asn Ala Ala Gln Glu Ser Ser Pro Met Pro Val Thr Glu Ala Leu Asp
                405                 410                 415

Arg Val Leu Glu Ile Leu Arg Thr Thr Glu Leu Tyr Ser Pro Gln Phe
            420                 425                 430

Gly Ala Lys Asp Asp Pro His Ala Asn Asp Leu Val Gly Gly Leu
            435                 440                 445

Met Ser Asp Gly Leu Arg Arg Leu Ser Gly Asn Glu Tyr Val Leu Ser
    450                 455                 460

Thr Lys Asn Thr Gln Met Val Ser Ser Asn Ile Ile Thr Pro Ile Ser
465                 470                 475                 480

Leu Asp Asp Val Pro Pro Arg Ile Ala Arg Ala Met Glu Asn Glu Glu
                485                 490                 495

Tyr Trp Asp Phe Asp Ile Phe Glu Leu Glu Ala Ala Thr His Asn Arg
            500                 505                 510

Pro Leu Ile Tyr Leu Gly Leu Lys Met Phe Ala Arg Phe Gly Ile Cys
        515                 520                 525

Glu Phe Leu His Cys Ser Glu Ser Thr Leu Arg Ser Trp Leu Gln Ile
    530                 535                 540

Ile Glu Ala Asn Tyr His Ser Ser Asn Pro Tyr His Asn Ser Thr His
545                 550                 555                 560

Ser Ala Asp Val Leu His Ala Thr Ala Tyr Phe Leu Ser Lys Glu Arg
                565                 570                 575

Ile Lys Glu Thr Leu Asp Pro Ile Asp Glu Val Ala Ala Leu Ile Ala
            580                 585                 590

Ala Thr Ile His Asp Val Asp His Pro Gly Arg Thr Asn Ser Phe Leu
        595                 600                 605

Cys Asn Ala Gly Ser Glu Leu Ala Ile Leu Tyr Asn Asp Thr Ala Val
610                 615                 620

Leu Glu Ser His His Ala Ala Leu Ala Phe Gln Leu Thr Thr Gly Asp
625                 630                 635                 640

Asp Lys Cys Asn Ile Phe Lys Asn Met Glu Arg Asn Asp Tyr Arg Thr
                645                 650                 655

Leu Arg Gln Gly Ile Ile Asp Met Val Leu Ala Thr Glu Met Thr Lys
            660                 665                 670

His Phe Glu His Val Asn Lys Phe Val Asn Ser Ile Asn Lys Pro Leu
        675                 680                 685

Ala Thr Leu Glu Glu Asn Gly Glu Thr Asp Lys Asn Gln Glu Val Ile
    690                 695                 700

Asn Thr Met Leu Arg Thr Pro Glu Asn Arg Thr Leu Ile Lys Arg Met
705                 710                 715                 720

Leu Ile Lys Cys Ala Asp Val Ser Asn Pro Cys Arg Pro Leu Gln Tyr
                725                 730                 735

Cys Ile Glu Trp Ala Ala Arg Ile Ser Glu Glu Tyr Phe Ser Gln Thr
```

```
                    740                 745                 750
Asp Glu Glu Lys Gln Gln Gly Leu Pro Val Val Met Pro Val Phe Asp
            755                 760                 765

Arg Asn Thr Cys Ser Ile Pro Lys Ser Gln Ile Ser Phe Ile Asp Tyr
        770                 775                 780

Phe Ile Thr Asp Met Phe Asp Ala Trp Asp Ala Phe Val Asp Leu Pro
785                 790                 795                 800

Asp Leu Met Gln His Leu Asp Asn Asn Phe Lys Tyr Trp Lys Gly Leu
            805                 810                 815

Asp Glu Met Lys Leu Arg Asn Leu Arg Pro Pro Glu
            820                 825

<210> SEQ ID NO 3
<211> LENGTH: 131
<212> TYPE: PRT
<213> ORGANISM: Homo sapiens

<400> SEQUENCE: 3

Met Gly Cys Ala Pro Ser Ile His Ile Ser Glu Arg Leu Val Ala Glu
1               5                   10                  15

Asp Ala Pro Ser Pro Ala Ala Pro Leu Ser Ser Gly Gly Pro Arg
            20                  25                  30

Leu Pro Gln Gly Gln Lys Thr Ala Ala Leu Pro Arg Thr Arg Gly Ala
        35                  40                  45

Gly Leu Leu Glu Ser Glu Val Arg Asp Gly Ser Gly Lys Lys Val Ala
    50                  55                  60

Val Ala Asp Val Gln Phe Gly Pro Met Arg Phe His Gln Asp Gln Leu
65                  70                  75                  80

Gln Val Leu Leu Val Phe Thr Lys Glu Asp Asn Gln Cys Asn Gly Phe
                85                  90                  95

Cys Arg Ala Cys Glu Lys Ala Gly Phe Lys Cys Thr Val Thr Lys Glu
            100                 105                 110

Ala Gln Ala Val Leu Ala Cys Phe Leu Asp Lys His His Asp Ile Ile
        115                 120                 125

Ile Ile Asp
    130

<210> SEQ ID NO 4
<211> LENGTH: 127
<212> TYPE: PRT
<213> ORGANISM: Mus musculus

<400> SEQUENCE: 4

Met Gly Cys Ala Pro Ser Ile His Thr Ser Glu Asn Arg Thr Phe Ser
1               5                   10                  15

His Ser Asp Gly Glu Asp Glu Asp Val Asp Val Asp Val Pro Gly Pro
            20                  25                  30

Ala Pro Arg Ser Ile Gln Arg Trp Ser Thr Ala Pro Gly Leu Val Glu
        35                  40                  45

Pro Gln Pro Arg Asp Asn Gly Ala Ser Lys Val Ser Val Ala Asp Val
    50                  55                  60

Gln Phe Gly Pro Met Arg Phe His Gln Asp Gln Leu Gln Val Leu Leu
65                  70                  75                  80

Val Phe Thr Lys Glu Asp Ser Gln Cys Asn Gly Phe His Arg Ala Cys
                85                  90                  95

Glu Lys Ala Gly Phe Lys Cys Thr Val Thr Lys Glu Val Gln Thr Val
```

|  | 100 |  | 105 |  | 110 |  |
|---|---|---|---|---|---|---|
| Leu Thr Cys Phe Gln Asp Lys Leu His Asp Ile Ile Ile Asp |
|  | 115 |  | 120 |  | 125 |  |

<210> SEQ ID NO 5
<211> LENGTH: 2990
<212> TYPE: DNA
<213> ORGANISM: Homo sapiens

<400> SEQUENCE: 5

| atggaagtgt gttaccagct gccggtactg cccctggaca ggccggtccc ccagcacgtc | 60 |
|---|---|
| ctcagccgcc gaggagccat cagcttcagc tccagctccg ctctcttcgg ctgccccaat | 120 |
| ccccggcagc tctctcagag gcgtggagct atttcctatg acagttctga tcagactgca | 180 |
| ttatacattc gtatgctagg agatgtacgt gtaaggagcc gagcaggatt tgaatcagaa | 240 |
| agaagaggtt ctcacccata tattgatttt cgtattttcc actctcaatc tgaaattgaa | 300 |
| gtgtctgtct ctgcaaggaa tatcagaagg ctactaagtt ccagcgata tcttagatct | 360 |
| tcacgctttt ttcgtggtac tgcggtttca aattccctaa acattttaga tgatgattat | 420 |
| aatggacaag ccaagtgtat gctggaaaaa gttggaaatt ggaattttga tatctttcta | 480 |
| tttgatagac taacaaatgg aaatagtcta gtaagcttaa cctttcattt atttagtctt | 540 |
| catggattaa ttgagtactt ccatttagat atgatgaaac ttcgtagatt tttagttatg | 600 |
| attcaagaag attaccacag tcaaaatcct taccataacg cagtccacgc tgcggatgtt | 660 |
| actcaggcca tgcactgtta cttaaaggaa cctaagcttg ccaattctgt aactccttgg | 720 |
| gatatcttgc tgagcttaat tgcagctgcc actcatgatc tggatcatcc aggtgttaat | 780 |
| caacctttcc ttattaaaac taaccattac ttggcaactt tatacaagaa tacctcagta | 840 |
| ctggaaaatc accactggag atctgcagtg gcttattga gagaatcagg cttattctca | 900 |
| catctgccat tagaaagcag gcaacaaatg gagacacaga taggtgctct gatactagcc | 960 |
| acagacatca gtcgccagaa tgagtatctg tctttgttta ggtcccattt ggatagaggt | 1020 |
| gatttatgcc tagaagacac cagacacaga catttggttt tacagatggc tttgaaatgt | 1080 |
| gctgatattt gtaacccatg tcggacgtgg gaattaagca agcagtggag tgaaaaagta | 1140 |
| acggaggaat tcttccatca aggagatata gaaaaaaaat atcatttggg tgtgagtcca | 1200 |
| ctttgcgatc gtcacactga atctattgcc aacatccaga ttggtaacta tacatattta | 1260 |
| gatatagctg gttagaaaaa tgccactgtt tttatcaaga agggaaatat atttgaaata | 1320 |
| taaaatatta aaattatgct catttctatt tttaaaaata atttaagaaa ttttaccctt | 1380 |
| gttttccctt gttatggctc ttctaattct catttaattt taggatgtaa aaagtatatt | 1440 |
| tttgcagaac aggcagcagc aataacttgt ttctgttctt atgtaaataa gaatccatta | 1500 |
| ttcgctcatg tggaagcttc ttttgcatca tttgggactg ccatttaaaa aaggataggt | 1560 |
| aaacaaagaa atgacaaaaa taaataaat aaaataaaaa tggataggtg gtgacccact | 1620 |
| gagcctgatc ataatacgaa gaccagcttc tgccactgcc tttccagact cttaccactg | 1680 |
| cctgttgatt aaatctaact cttcaacatc ctagacaggc ccttataatc ttgcttcaaa | 1740 |
| tgctgtgcag ccatcttgcc tcaacttccc tctcatttgc ctacagcatc tcggacgct | 1800 |
| tctgtgtttc ccaagtatac gctgttcttt cgctctttgt gcttcgccag tgcttttccat | 1860 |
| gtgcctcgta gagttatttt tcttgaagag gcagctcaaa tgtcaccttc tccagaagct | 1920 |
| gctctccact tgctttaggc agagtcagtc acttttcttc tagattccaa agtgcctgat | 1980 |

```
ccacttggtt gtggattcct ggagcctagc accacaccag aagcacgagg cccttgagaa    2040
ctgtgtgttg agtgaactaa taactgtatt atagaaagca taatgaaaat gtcctgtgac    2100
tgaagtatgt gtagcttgtt gcaggagtca caggaaagtt gactaggatt gagtgtgttg    2160
ggctttgggt ataaggagg gggattctac gggggcagta gctcaacaag aatagaggg     2220 aggagtgtaa ttttggtagc tggtgttgaa tagggccttt gagaatcaga ctgaacacag    2280
tgaaatatgt gcccaaagtt cagaaagatg aagtttccag aaactaagaa ggtagcacaa    2340
tatgtggcat catactcaga aaggaagacc atgccatggg gccagaaatt cagaaacgta    2400
attcttacat tgtgattgca atggatactc atgaaagaaa gtgggtagtg ccgatttgc     2460 cttcagagtg acaggtagag aagggaagag cgtgtagaac tgtggccata ctttaggagt    2520
gtgagggatg ctgaatctcc cagagagctc acactggcca ggaatgctga gagtagcaga    2580
tgctttcttt ttgggaggat agtaaaacaa tttagaacca gatatgcttt gtcttgattc    2640
tcaagtagaa taatcttcaa atgcaaagaa atacattaga aatggacaaa agtggccagg    2700
agcggtagct catacttgta acccagcact ttgggaagcc gaggcgggct gatcgcttga    2760
ggtcaggagt tcgagaccag cctggccaaa atagtgaaac tcacgtttct actaaaaata    2820
caaaaattag ctgggtgtga tggccacttg ggaggctgag ataggagaat cgcttgaacc    2880
tgggaggcag aggttgcagt gagccaatat cgtgccactg cattccagcc tgggtgacag    2940
aatgaaactc catcactcca tctcaaaaaa aaaaaaaaa aaaaaaaaa                 2990

<210> SEQ ID NO 6
<211> LENGTH: 424
<212> TYPE: PRT
<213> ORGANISM: Homo sapiens

<400> SEQUENCE: 6

Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser
            20                  25                  30

Ser Ala Leu Phe Gly Cys Pro Asn Pro Arg Gln Leu Ser Gln Arg Arg
        35                  40                  45

Gly Ala Ile Ser Tyr Asp Ser Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110

Ser Phe Gln Arg Tyr Leu Arg Ser Ser Arg Phe Phe Arg Gly Thr Ala
        115                 120                 125

Val Ser Asn Ser Leu Asn Ile Leu Asp Asp Tyr Asn Gly Gln Ala
    130                 135                 140

Lys Cys Met Leu Glu Lys Val Gly Asn Trp Asn Phe Asp Ile Phe Leu
145                 150                 155                 160

Phe Asp Arg Leu Thr Asn Gly Asn Ser Leu Val Ser Leu Thr Phe His
                165                 170                 175

Leu Phe Ser Leu His Gly Leu Ile Glu Tyr Phe His Leu Asp Met Met
            180                 185                 190

Lys Leu Arg Arg Phe Leu Val Met Ile Gln Glu Asp Tyr His Ser Gln
```

```
                195                 200                 205
Asn Pro Tyr His Asn Ala Val His Ala Ala Asp Val Thr Gln Ala Met
            210                 215                 220

His Cys Tyr Leu Lys Glu Pro Lys Leu Ala Asn Ser Val Thr Pro Trp
225                 230                 235                 240

Asp Ile Leu Leu Ser Leu Ile Ala Ala Ala Thr His Asp Leu Asp His
                245                 250                 255

Pro Gly Val Asn Gln Pro Phe Leu Ile Lys Thr Asn His Tyr Leu Ala
            260                 265                 270

Thr Leu Tyr Lys Asn Thr Ser Val Leu Glu Asn His His Trp Arg Ser
        275                 280                 285

Ala Val Gly Leu Leu Arg Glu Ser Gly Leu Phe Ser His Leu Pro Leu
    290                 295                 300

Glu Ser Arg Gln Gln Met Glu Thr Gln Ile Gly Ala Leu Ile Leu Ala
305                 310                 315                 320

Thr Asp Ile Ser Arg Gln Asn Glu Tyr Leu Ser Leu Phe Arg Ser His
                325                 330                 335

Leu Asp Arg Gly Asp Leu Cys Leu Glu Asp Thr Arg His Arg His Leu
            340                 345                 350

Val Leu Gln Met Ala Leu Lys Cys Ala Asp Ile Cys Asn Pro Cys Arg
        355                 360                 365

Thr Trp Glu Leu Ser Lys Gln Trp Ser Glu Lys Val Thr Glu Glu Phe
    370                 375                 380

Phe His Gln Gly Asp Ile Glu Lys Lys Tyr His Leu Gly Val Ser Pro
385                 390                 395                 400

Leu Cys Asp Arg His Thr Glu Ser Ile Ala Asn Ile Gln Ile Gly Asn
                405                 410                 415

Tyr Thr Tyr Leu Asp Ile Ala Gly
            420

<210> SEQ ID NO 7
<211> LENGTH: 102
<212> TYPE: PRT
<213> ORGANISM: Homo sapiens

<400> SEQUENCE: 7

Thr Glu Glu Phe Phe His Gln Gly Asp Ile Glu Lys Lys Tyr His Leu
1               5                   10                  15

Gly Val Ser Pro Leu Cys Asp Arg His Thr Glu Ser Ile Ala Asn Ile
            20                  25                  30

Gln Ile Gly Phe Met Thr Tyr Leu Val Glu Pro Leu Phe Thr Glu Trp
        35                  40                  45

Ala Arg Phe Ser Asn Thr Arg Leu Ser Gln Thr Met Leu Gly His Val
    50                  55                  60

Gly Leu Asn Lys Ala Ser Trp Lys Gly Leu Gln Arg Glu Gln Ser Ser
65                  70                  75                  80

Ser Glu Asp Thr Asp Ala Ala Phe Glu Leu Asn Ser Gln Leu Leu Pro
                85                  90                  95

Gln Glu Asn Arg Leu Ser
            100

<210> SEQ ID NO 8
<211> LENGTH: 44
<212> TYPE: PRT
<213> ORGANISM: Homo sapiens
```

-continued

```
<400> SEQUENCE: 8

Thr Glu Glu Phe Phe His Gln Gly Asp Ile Glu Lys Lys Tyr His Leu
1               5                   10                  15

Gly Val Ser Pro Leu Cys Asp Arg His Thr Glu Ser Ile Ala Asn Ile
            20                  25                  30

Gln Ile Gly Asn Tyr Thr Tyr Leu Asp Ile Ala Gly
        35                  40

<210> SEQ ID NO 9
<211> LENGTH: 3019
<212> TYPE: DNA
<213> ORGANISM: Trypanosoma brucei

<400> SEQUENCE: 9
gctgggaaag acagagacag atgacacaca acggtggtcg tcatctgctt gaggcggtca        60
cgctatgcgg gtccattctt acccgctata agcggagcaa catgaagctc gacgaagctg       120
aggtaagggc attaaaggag ttattcgaga agtatcaaga tatcctcgtg gatggatctc       180 ctggttttgcc cacccacgct agcgggccca tgatccagcc tcccgttaca acatggtcg       240 ccccttatga ttcccccacg gataccatag tgaagttcgt tgagggaacg ataaacctgc       300
agagaccaat tgttgaggtc cttcacgtta tgaacgagca tttgtccctt gtccttcgcg       360
caaagaacac tcatgtcttt tatgtcgacc ccgttaataa cctgttatac gaccctatac       420
acggggtggc cgctgcactc gatgaatcat caccaatagg aaaggccata gtttcgggtg       480
agcgccttaa cgtagcgggg acactatata tacccatcat ctccgagggg atgccgttgg       540
gttgcgtact gagtccttgt ggaagggcag attaccacgc tctacgatg cttgagtcat        600 cactccgtgt tatttccaca tccctcaaaa acatcattca ggcagagaaa ctaaactgga       660
acaaagaaaa ggcggaggct atgctccgga tggcaacgca gctggcccgt gacaatcttg       720
aagaaacagt acttgcatct tctatcatga acactgtcaa gagtctcacg aaagtgcgc        780 gttgcagtct cttccttgtc agaggtgacg tacttgaagc gcattttgag gatggtaacg       840
tcgttacaat ccctagggt gcaggtattg ccggatatgt ggcgcaaact ggtgagactg        900
ttaatattgt tgatgcctac gccgatgacc gctttaaccg tgaggttgac aaggctactg       960
ggtaccgtac aaagacgata ctctgcatgc ctgtgatgta cgaaggaacg attgtggctg      1020
ttgcccaact gattaataaa ttggatctga caactgagag tggattgcgc ctacctcgtg      1080
tgttcggaaa acgtgacgag gagctgttcc aaaccttctc tatgtttgct ggcgcctcac      1140
tacgtaactg tcgtatcaac gaccgactct taaggagaa gaaaaagagt gacgtgattc       1200
tcgatgttgt tactgttctc tcgaacacgg atatccgcga tgtggatggt attgttcgcc      1260
acgcactgca cggagcaaag aaactactga acgcggatcg ctctactttg ttttttggtgg    1320 acaaggaacg gaacgaactt tgcagtcgta tggcagatag cgttgctggt aaggagattc      1380
gttttccgtg tggccaaggt attgcgggca ctgtggcggc atctggagtt ggtgagaata      1440
ttcaggacgc gtaccaggat ccgcgcttca accgtgaggt tgacaaacaa cttggatacc      1500
gcacgcagac catattgtgc gagcccatca tactaaatgg tgagatcctt gctgtcgtgc      1560
agctcgtgaa caagcttgat acgtctggag aagtgactgt gtttacggag gatgatcgtg      1620
agaccttccg tgtgttttcc ttatttgcag gtatatccat caacaactct cacctgcttg      1680
agttcgctgt gaaggcgggt cgtgaggtga tggaattaaa tgaacaccga gcaacattgt      1740
ttaataagaa cgttccctca cgtgcggtta acgagtcac tgccattacg aaggttgaaa      1800
```

```
gggaagcggt cttggtctgt gaacttccat cgtttgatgt tacgatgttt gagttcgact    1860
tgttccgagc gcgtgaaagc acagataaac cgttggatgt cgctgctgct attgcataca    1920
gactactgct tggaagcggc cttccacaaa agtttggttg ctctgacgag gtgcttctta    1980
acttcattct gcaatgccgt aagaaatacc gtaatgtccc ttatcacaac ttttaccatg    2040
ttgtggatgt atgccaaacc atttacacat ttttgtacag gggaaatgtg tatgagaagt    2100
taaccgagct tgagtgcttt gtgctgctta tcaccgcact ggtgcatgat cttgatcata    2160
tggggctgaa caacagtttc tacctgaaaa cagaatctcc acttggtatt ctttccagcg    2220
caagtggtaa cacctctgtt cttgaggtgc atcactgcaa ccttgctgtt gagatcctct    2280
ctgatccgga atctgatgtg tttggtggtc tggagggtgc agagcgtact cttgcgttcc    2340
gatcgatgat tgattgtgta cttgcgacag atatggcgaa gcatggaagt gcattagagg    2400
cgtttcttgc atctgcggcg gaccagtcgt cagacgaggc agcgtttcac cgcatgacga    2460
tggagataat cttgaaagct ggagatatct ctaacgtaac gaaaccgttc gacatttccc    2520
gtcagtgggc aatggctgtg acggaggagt tctatcgtca aggagacatg gagaaggaga    2580
ggggtgtgga agtattgccc atgtttgacc gatctaagaa tatggagctt gcaaaaggtc    2640
aaattggatt cattgacttt gttgcagccc cattttttcca gaagatagtt gatgcctgcc    2700
tgcaagggat gcaatggaca gtcgaccgta tcaaatcgaa ccgcgcacag tgggagcgag    2760
ttctggaaac aagactatca acgagttctg caacaacag cagtactcgt tgagtgaaat    2820
tgaagaagtc agttgaccgg tggtagatgt acgttcttgt caatggtgat ttgactgtgt    2880
atttaaaaag tgaaatggag ttctgggagt actgtagtgg atgtgaacac tatcacaatc    2940
aaatattttc catgcctaca gatatacatg atacgtttgg tacgtgggtt gccttcacgg    3000
aagtatgtac aaatcttac                                                 3019
```

<210> SEQ ID NO 10
<211> LENGTH: 930
<212> TYPE: PRT
<213> ORGANISM: Trypanosoma brucei

<400> SEQUENCE: 10

```
Met Thr His Asn Gly Gly Arg His Leu Leu Glu Ala Val Thr Leu Cys
1               5                   10                  15

Gly Ser Ile Leu Thr Arg Tyr Lys Arg Ser Asn Met Lys Leu Asp Glu
            20                  25                  30

Ala Glu Val Arg Ala Leu Lys Glu Leu Phe Glu Lys Tyr Gln Asp Ile
        35                  40                  45

Leu Val Asp Gly Ser Pro Gly Leu Pro Thr His Ala Ser Gly Pro Met
    50                  55                  60

Ile Gln Pro Pro Val Thr Asn Met Val Ala Pro Tyr Asp Ser Pro Thr
65                  70                  75                  80

Asp Thr Ile Val Lys Phe Val Glu Gly Thr Ile Asn Leu Gln Arg Pro
                85                  90                  95

Ile Val Glu Val Leu His Val Met Asn Glu His Leu Ser Leu Val Leu
            100                 105                 110

Arg Ala Lys Asn Thr His Val Phe Tyr Val Asp Pro Val Asn Asn Leu
        115                 120                 125

Leu Tyr Asp Pro Ile His Gly Val Ala Ala Leu Asp Glu Ser Ser
    130                 135                 140

Pro Ile Gly Lys Ala Ile Val Ser Gly Glu Arg Leu Asn Val Ala Gly
145                 150                 155                 160
```

-continued

```
Thr Leu Tyr Ile Pro Ile Ile Ser Glu Gly Met Pro Leu Gly Cys Val
                165                 170                 175

Leu Ser Pro Cys Gly Arg Ala Asp Tyr His Ala Ser Thr Met Leu Glu
            180                 185                 190

Ser Ser Leu Arg Val Ile Ser Thr Ser Leu Lys Asn Ile Ile Gln Ala
        195                 200                 205

Glu Lys Leu Asn Trp Asn Lys Glu Lys Ala Glu Ala Met Leu Arg Met
    210                 215                 220

Ala Thr Gln Leu Ala Arg Asp Asn Leu Glu Glu Thr Val Leu Ala Ser
225                 230                 235                 240

Ser Ile Met Asn Thr Val Lys Ser Leu Thr Glu Ser Ala Arg Cys Ser
                245                 250                 255

Leu Phe Leu Val Arg Gly Asp Val Leu Glu Ala His Phe Glu Asp Gly
            260                 265                 270

Asn Val Val Thr Ile Pro Arg Gly Ala Gly Ile Ala Gly Tyr Val Ala
        275                 280                 285

Gln Thr Gly Glu Thr Val Asn Ile Val Asp Ala Tyr Ala Asp Asp Arg
    290                 295                 300

Phe Asn Arg Glu Val Asp Lys Ala Thr Gly Tyr Arg Thr Lys Thr Ile
305                 310                 315                 320

Leu Cys Met Pro Val Met Tyr Glu Gly Thr Ile Val Ala Val Ala Gln
                325                 330                 335

Leu Ile Asn Lys Leu Asp Leu Thr Thr Glu Ser Gly Leu Arg Leu Pro
            340                 345                 350

Arg Val Phe Gly Lys Arg Asp Glu Glu Leu Phe Gln Thr Phe Ser Met
        355                 360                 365

Phe Ala Gly Ala Ser Leu Arg Asn Cys Arg Ile Asn Asp Arg Leu Leu
    370                 375                 380

Lys Glu Lys Lys Ser Asp Val Ile Leu Asp Val Val Thr Val Leu
385                 390                 395                 400

Ser Asn Thr Asp Ile Arg Asp Val Asp Gly Ile Val Arg His Ala Leu
                405                 410                 415

His Gly Ala Lys Lys Leu Leu Asn Ala Asp Arg Ser Thr Leu Phe Leu
            420                 425                 430

Val Asp Lys Glu Arg Asn Glu Leu Cys Ser Arg Met Ala Asp Ser Val
        435                 440                 445

Ala Gly Lys Glu Ile Arg Phe Pro Cys Gly Gln Gly Ile Ala Gly Thr
    450                 455                 460

Val Ala Ala Ser Gly Val Gly Glu Asn Ile Gln Asp Ala Tyr Gln Asp
465                 470                 475                 480

Pro Arg Phe Asn Arg Glu Val Asp Lys Gln Leu Gly Tyr Arg Thr Gln
                485                 490                 495

Thr Ile Leu Cys Glu Pro Ile Ile Leu Asn Gly Glu Ile Leu Ala Val
            500                 505                 510

Val Gln Leu Val Asn Lys Leu Asp Thr Ser Gly Glu Val Thr Val Phe
        515                 520                 525

Thr Glu Asp Asp Arg Glu Thr Phe Arg Val Phe Ser Leu Phe Ala Gly
    530                 535                 540

Ile Ser Ile Asn Asn Ser His Leu Leu Glu Phe Ala Val Lys Ala Gly
545                 550                 555                 560

Arg Glu Val Met Glu Leu Asn Glu His Arg Ala Thr Leu Phe Asn Lys
                565                 570                 575
```

-continued

```
Asn Val Pro Ser Arg Ala Val Lys Arg Val Thr Ala Ile Thr Lys Val
            580                 585                 590
Glu Arg Glu Ala Val Leu Val Cys Glu Leu Pro Ser Phe Asp Val Thr
        595                 600                 605
Asp Val Glu Phe Asp Leu Phe Arg Ala Arg Glu Ser Thr Asp Lys Pro
    610                 615                 620
Leu Asp Val Ala Ala Ile Ala Tyr Arg Leu Leu Gly Ser Gly
625                 630                 635                 640
Leu Pro Gln Lys Phe Gly Cys Ser Asp Glu Val Leu Leu Asn Phe Ile
                645                 650                 655
Leu Gln Cys Arg Lys Lys Tyr Arg Asn Val Pro Tyr His Asn Phe Tyr
            660                 665                 670
His Val Val Asp Val Cys Gln Thr Ile Tyr Thr Phe Leu Tyr Arg Gly
        675                 680                 685
Asn Val Tyr Glu Lys Leu Thr Glu Leu Glu Cys Phe Val Leu Leu Ile
    690                 695                 700
Thr Ala Leu Val His Asp Leu Asp His Met Gly Leu Asn Asn Ser Phe
705                 710                 715                 720
Tyr Leu Lys Thr Glu Ser Pro Leu Gly Ile Leu Ser Ser Ala Ser Gly
                725                 730                 735
Asn Thr Ser Val Leu Glu Val His His Cys Asn Leu Ala Val Glu Ile
            740                 745                 750
Leu Ser Asp Pro Glu Ser Asp Val Phe Gly Gly Leu Glu Gly Ala Glu
        755                 760                 765
Arg Thr Leu Ala Phe Arg Ser Met Ile Asp Cys Val Leu Ala Thr Asp
    770                 775                 780
Met Ala Lys His Gly Ser Ala Leu Glu Ala Phe Leu Ala Ser Ala Ala
785                 790                 795                 800
Asp Gln Ser Ser Asp Glu Ala Ala Phe His Arg Met Thr Met Glu Ile
                805                 810                 815
Ile Leu Lys Ala Gly Asp Ile Ser Asn Val Thr Lys Pro Phe Asp Ile
            820                 825                 830
Ser Arg Gln Trp Ala Met Ala Val Thr Glu Glu Phe Tyr Arg Gln Gly
        835                 840                 845
Asp Met Glu Lys Glu Arg Gly Val Glu Val Leu Pro Met Phe Asp Arg
    850                 855                 860
Ser Lys Asn Met Glu Leu Ala Lys Gly Gln Ile Gly Phe Ile Asp Phe
865                 870                 875                 880
Val Ala Ala Pro Phe Phe Gln Lys Ile Val Asp Ala Cys Leu Gln Gly
                885                 890                 895
Met Gln Trp Thr Val Asp Arg Ile Lys Ser Asn Arg Ala Gln Trp Glu
            900                 905                 910
Arg Val Leu Glu Thr Arg Leu Ser Thr Ser Ser Gly Asn Asn Ser Ser
        915                 920                 925
Thr Arg
    930
```

<210> SEQ ID NO 11
<211> LENGTH: 1458
<212> TYPE: DNA
<213> ORGANISM: Trypanosoma brucei

<400> SEQUENCE: 11
atgtatgtgc acgacgtacg catgttcgct gattattgtt actgcttttt ctgcttactg        60

```
aatgacgtgc cttattctat ctgctgttat ctggcgtttg ctcgtggttt acaggacgat    120
ccgcgcttca accgtgaggt tgacaaacaa cttggatacc gcacgcaggc catattgtgc    180
gagcccatca tactaaatgg tgagatcctt gctgtcgtgc agctcgtgaa caagcttgat    240
tcatctggag aagtgactgt gtttaccgag gatgatcgtg acaccttccg tgtgttttcc    300
ttatttgcag gtatatccat caacaactct cacctgcttg agttcgctgt gaaggccggt    360
cgtgaggtga tggaattaaa tgaacaccga gcaacattgt ttaataagaa cgttccctca    420
cgtggagtta aacgagtcac tgccatcaca aatagagaaa gggaggctgt tctacgtatt    480
gagttcccca acgtggatgt tacgatatt gacttcgact tgttccaggc acgtgaaagc    540
acagataaac cgttggatgt cgctgctgct attgcataca gactactgct tggaagcggc    600
cttccacaaa agtttggttg ctccgacgag gtgcttctta acttcattct gcaatgccgt    660
aagaaatacc gtaatgtccc ttatcacaac ttttaccatg ttgtggatgt atgccaaacc    720
atttacacat ttttgtacag gggaaatgtg tatgagaagt taaccgagct tgagtgcttt    780
gtgctgctta tcaccgcact ggtgcatgat cttgatcata tggggttgaa caacagtttc    840
tacctgaaaa cagaatctcc acttggtatt cttttccagcg caagtggtaa caagtctgtt    900
cttgaggtgc atcactgcaa ccttgctgtt gagatcctct ctgatccgga atctgatgtg    960
tttggtggtc tggagggtgc agagcgtact cttgcgttcc gatcgatgat tgattgtgta   1020
cttgcgacag atatggcgag acatagtgaa tttcttgaga agtacctaga aattatgaaa   1080
acatcttaca acgttgatga ttccgatcat cggcaaatga caatggatgt gcttatgaaa   1140
gctggagata tctctaacgt aacgaaaccg ttcgacattt cccgtcagtg ggcaatggct   1200
gtgacgaggg agttctaccg tcaaggagac atggagaagg agagggtgt ggaagtattg   1260 cccatgtttg accgatctaa gaatatggag cttgcaaaag gtcaaattgg attcattgac   1320
tttgtcgcag ccccattttt ccagaagata gttgatgcct gcctgcaagg gatgcaatgg   1380
acagtcgacc gtacaaagtc gaaccgcgca cagtgggagc gagttctgga agcaaggagt   1440 acagggggctt cgtcttag                                                1458
```

<210> SEQ ID NO 12
<211> LENGTH: 485
<212> TYPE: PRT
<213> ORGANISM: Trypanosoma brucei

<400> SEQUENCE: 12

```
Met Tyr Val His Asp Val Arg Met Phe Ala Asp Tyr Cys Tyr Cys Phe
1               5                   10                  15

Phe Cys Leu Leu Asn Asp Val Pro Tyr Ser Ile Cys Cys Tyr Leu Ala
            20                  25                  30

Phe Ala Arg Gly Leu Gln Asp Asp Pro Arg Phe Asn Arg Glu Val Asp
        35                  40                  45

Lys Gln Leu Gly Tyr Arg Thr Gln Ala Ile Leu Cys Glu Pro Ile Ile
    50                  55                  60

Leu Asn Gly Glu Ile Leu Ala Val Val Gln Leu Val Asn Lys Leu Asp
65                  70                  75                  80

Ser Ser Gly Glu Val Thr Val Phe Thr Glu Asp Asp Arg Asp Thr Phe
                85                  90                  95

Arg Val Phe Ser Leu Phe Ala Gly Ile Ser Ile Asn Asn Ser His Leu
            100                 105                 110

Leu Glu Phe Ala Val Lys Ala Gly Arg Glu Val Met Glu Leu Asn Glu
        115                 120                 125
```

His Arg Ala Thr Leu Phe Asn Lys Asn Val Pro Ser Arg Gly Val Lys
130                 135                 140

Arg Val Thr Ala Ile Thr Asn Arg Glu Arg Glu Ala Val Leu Arg Ile
145                 150                 155                 160

Glu Phe Pro Asn Val Asp Val Thr Asp Ile Asp Phe Asp Leu Phe Gln
                165                 170                 175

Ala Arg Glu Ser Thr Asp Lys Pro Leu Asp Val Ala Ala Ile Ala
            180                 185                 190

Tyr Arg Leu Leu Leu Gly Ser Gly Leu Pro Gln Lys Phe Gly Cys Ser
        195                 200                 205

Asp Glu Val Leu Leu Asn Phe Ile Leu Gln Cys Arg Lys Lys Tyr Arg
    210                 215                 220

Asn Val Pro Tyr His Asn Phe Tyr His Val Asp Val Cys Gln Thr
225                 230                 235                 240

Ile Tyr Thr Phe Leu Tyr Arg Gly Asn Val Tyr Glu Lys Leu Thr Glu
                245                 250                 255

Leu Glu Cys Phe Val Leu Leu Ile Thr Ala Leu Val His Asp Leu Asp
            260                 265                 270

His Met Gly Leu Asn Asn Ser Phe Tyr Leu Lys Thr Glu Ser Pro Leu
        275                 280                 285

Gly Ile Leu Ser Ser Ala Ser Gly Asn Lys Ser Val Leu Glu Val His
    290                 295                 300

His Cys Asn Leu Ala Val Glu Ile Leu Ser Asp Pro Glu Ser Asp Val
305                 310                 315                 320

Phe Gly Gly Leu Glu Gly Ala Glu Arg Thr Leu Ala Phe Arg Ser Met
                325                 330                 335

Ile Asp Cys Val Leu Ala Thr Asp Met Ala Arg His Ser Glu Phe Leu
            340                 345                 350

Glu Lys Tyr Leu Glu Ile Met Lys Thr Ser Tyr Asn Val Asp Asp Ser
        355                 360                 365

Asp His Arg Gln Met Thr Met Asp Val Leu Met Lys Ala Gly Asp Ile
    370                 375                 380

Ser Asn Val Thr Lys Pro Phe Asp Val Ser Arg Gln Trp Ala Met Ala
385                 390                 395                 400

Val Thr Glu Glu Phe Tyr Arg Gln Gly Asp Met Glu Lys Glu Arg Gly
                405                 410                 415

Val Glu Val Leu Pro Met Phe Asp Arg Ser Lys Asn Met Glu Leu Ala
            420                 425                 430

Lys Gly Gln Ile Gly Phe Ile Asp Phe Val Ala Ala Pro Phe Phe Gln
        435                 440                 445

Lys Ile Val Asp Ala Cys Leu Gln Gly Met Gln Trp Thr Val Asp Arg
    450                 455                 460

Thr Lys Ser Asn Arg Ala Gln Trp Glu Arg Val Leu Glu Ala Arg Ser
465                 470                 475                 480

Thr Gly Ala Ser Ser
            485

<210> SEQ ID NO 13
<211> LENGTH: 2793
<212> TYPE: DNA
<213> ORGANISM: Trypanosoma brucei

<400> SEQUENCE: 13
atgttcatga acaagccctt tggcagcaag cgctgcgaac ccttccacga gtcggagcac    60

-continued

```
ctttgtgagg cgtttgccat cactgaagca atcctcgctc gctatcagcg tgggaaacgc    120
agctttacgt cctccgaaaa aagtggactg gcagcccTta tcaaacgtat tccttatgat    180
atccttgttg aggttctcga tcaaagcgga tttactccaa caagcaatgc aacaccccccc   240
gttgattatt tagctatgat ggagcacaca atgacgcacg gtgcgtctat tacacacgcc    300
ctgcagtacc ttaacgattt gatgactaag tgtaccgggt gcccggggat tcgtacatat    360
taccataacc ccaatgatga cgttctggcc gaccccgttc acgacacggc agcattgatt    420
gatgaaacaa cagccgtggg aaagtcggtt gtaactaaac agtaccttaa tatagctggg    480
gctcactaca tacccttgat ccacggagat attgtggttg gttgtgttga ggtacccgc     540
ttttcgggaa atcttgagaa attgccatca ttcccatctc tcataagagc tgtgacatgt    600
accgcacaca aattcattga ggaagcgaga atcaactgga acagggagaa ggcggaagct    660
atgttgcaaa tggcgaccag gttggcccgt gacaatcttg atgaaacagt acttgcatct    720
tctatcatga acactgtcaa gagtctcacg gaaagtgcgc gttgcagtct cttccttgtg    780
aaagacgaca agcttgaagc gcattttgag gatggtaacg tcgtttccat acccaaggga    840
acaggcattg tagggtatgt ggcgcaaact ggtgagactg ttaatattgt tgatgcctac    900
gccgatgacc gctttaaccg tgaggttgac aaggctactg ggtaccgtac aaagacgata    960
ctctgcatgc ctgtgatgta cgaaggaacg attgtggctg taccagct gattaataaa     1020
ttggatctga caactgagag tggattgcgc ctacctcgtg tgttcggaaa acgtgacgag    1080
gagctgttcc aaaccttctc tatgtttgct ggcgcctcac tacgtaactg tcgtatcaat    1140
gaccgactct taaaggagaa gaaaaagagt gacgtgattc tcgatgttgt tactgttctc    1200
tcgaacacgg atatccgcga tgtggatggt attgttcgcc acgcactgca cggagcaaag    1260
aaactactga acgcggatcg ctctactttg ttttttggtgg acaaggaacg gaacgaactt    1320
tgcagtcgta tggcagatag cgttgctggt aaggagattc ggtttccgtg tggccaaggt    1380
attgcgggca ctgtggcggc atctggagtt ggtgagaata ttcaggacgc gtaccaggat    1440
ccgcgcttca accgtgaggt tgacaaacaa cttggatacc gcacgcagac catattgtgc    1500
gagcccatca tactaaatgg tgagatcctt gctgtcgtgc agctcgtgaa caagcttgat    1560
acgtctggag aagtgactgt gtttaccgag gatgatcgtg acaccttccg tgtgttttcc    1620
ttatttgcag gtatatccat caacaactct cacctgcttg agttcgctgt gaaggcgggt    1680
cgtgaggtga tggaattaaa tgaacaccga gcaacattgt taataagaa cgttccctca     1740
cgcgcggtta acgagtcac tgccattacg aaggttgaaa gggaagcggt cttggtctgt    1800
gaacttccat cgtttgatgt tacggatgtt gagttcgact tgttccgagc acgtgaaagc    1860
acagataaac cgttggatgt cgctgctgct attgcataca gactactgct tggaagcggc    1920
cttccacaaa agtttggttg ctctgacgag gtgcttctta acttcattct gcaatgccgt    1980
aagaaatacc gtaatgtccc ttatcacaac ttttaccatg ttgtggatgt atgccaaacc    2040
attcacacat tcttgtacag gggaaatgtg tatgagaagt taaccgagct tgagtgcttt    2100
gtgctgctta tcaccgcact ggtgcatgat cttgatcata tggggctgaa caacagtttc    2160
tacctgaaaa cagaatctcc acttggtatt cttttccagcg caagtggtaa cacctctgtt    2220
cttgaggtgc atcactgcaa ccttgctgtt gagatcctct ctgatccgga atctgatgtg    2280
tttgatggtc tggagggtgc agagcgtact cttgcgttcc gatcgatgat tgattgtgta    2340
cttgcgacag atatggcgaa gcatggaagt gcattagagg cgtttcttgc atctgcggcg    2400
```

-continued

```
gaccagtcgt cagacgaggc agcgtttcac cgcatgacga tggagataat cttgaaagct    2460
ggagatatct ctaacgtaac gaaaccgttc gacatttccc gtcagtgggc aatggctgtg    2520
acggaggagt tctaccgtca aggagacatg gagaaggaga ggggtgtgga agtattgccc    2580
atgtttgacc gatctaagaa tatggagctt gcaaaaggtc aaattggatt cattgacttt    2640
gttgcagccc cattttttcca gaagatagtt gatgcctgcc tgcaagggat gcaatggaca    2700
gtcgaccgta tcaaatcgaa ccgcgcacag tgggagcgag ttctggaaac aagactatca    2760
acgagttctg gcaacaacag cagtactcgt tga                                 2793
```

<210> SEQ ID NO 14
<211> LENGTH: 930
<212> TYPE: PRT
<213> ORGANISM: Trypanosoma brucei

<400> SEQUENCE: 14

```
Met Phe Met Asn Lys Pro Phe Gly Ser Lys Arg Cys Glu Pro Phe His
1               5                   10                  15

Glu Ser Glu His Leu Cys Glu Ala Phe Ala Ile Thr Glu Ala Ile Leu
            20                  25                  30

Ala Arg Tyr Gln Arg Gly Lys Arg Ser Phe Thr Ser Ser Glu Lys Ser
        35                  40                  45

Gly Leu Ala Ala Leu Ile Lys Arg Ile Pro Tyr Asp Ile Leu Val Glu
    50                  55                  60

Val Leu Asp Gln Ser Gly Phe Thr Pro Thr Ser Asn Ala Thr Pro Pro
65                  70                  75                  80

Val Asp Tyr Leu Ala Met Met Glu His Thr Met Thr His Gly Ala Ser
                85                  90                  95

Ile Thr His Ala Leu Gln Tyr Leu Asn Asp Leu Met Thr Lys Cys Thr
            100                 105                 110

Gly Cys Pro Gly Ile Arg Thr Tyr Tyr His Asn Pro Asn Asp Asp Val
        115                 120                 125

Leu Ala Asp Pro Val His Asp Thr Ala Ala Leu Ile Asp Glu Thr Thr
    130                 135                 140

Ala Val Gly Lys Ser Val Val Thr Lys Gln Tyr Leu Asn Ile Ala Gly
145                 150                 155                 160

Ala His Tyr Ile Pro Leu Ile His Gly Asp Ile Val Val Gly Cys Val
                165                 170                 175

Glu Val Pro Arg Phe Ser Gly Asn Leu Glu Lys Leu Pro Ser Phe Pro
            180                 185                 190

Ser Leu Ile Arg Ala Val Thr Cys Thr Ala His Lys Phe Ile Glu Glu
        195                 200                 205

Ala Arg Ile Asn Trp Asn Arg Glu Lys Ala Glu Ala Met Leu Gln Met
    210                 215                 220

Ala Thr Arg Leu Ala Arg Asp Asn Leu Asp Glu Thr Val Leu Ala Ser
225                 230                 235                 240

Ser Ile Met Asn Thr Val Lys Ser Leu Thr Glu Ser Ala Arg Cys Ser
                245                 250                 255

Leu Phe Leu Val Lys Asp Asp Lys Leu Glu Ala His Phe Glu Asp Gly
            260                 265                 270

Asn Val Ser Ile Pro Lys Gly Thr Gly Ile Val Gly Tyr Val Ala
        275                 280                 285

Gln Thr Gly Glu Thr Val Asn Ile Val Asp Ala Tyr Ala Asp Asp Arg
    290                 295                 300
```

```
Phe Asn Arg Glu Val Asp Lys Ala Thr Gly Tyr Arg Thr Lys Thr Ile
305                 310                 315                 320

Leu Cys Met Pro Val Met Tyr Glu Gly Thr Ile Val Ala Val Thr Gln
                325                 330                 335

Leu Ile Asn Lys Leu Asp Leu Thr Thr Glu Ser Gly Leu Arg Leu Pro
            340                 345                 350

Arg Val Phe Gly Lys Arg Asp Glu Glu Leu Phe Gln Thr Phe Ser Met
        355                 360                 365

Phe Ala Gly Ala Ser Leu Arg Asn Cys Arg Ile Asn Asp Arg Leu Leu
370                 375                 380

Lys Glu Lys Lys Lys Ser Asp Val Ile Leu Asp Val Val Thr Val Leu
385                 390                 395                 400

Ser Asn Thr Asp Ile Arg Asp Val Asp Gly Ile Val Arg His Ala Leu
                405                 410                 415

His Gly Ala Lys Lys Leu Leu Asn Ala Asp Arg Ser Thr Leu Phe Leu
            420                 425                 430

Val Asp Lys Glu Arg Asn Glu Leu Cys Ser Arg Met Ala Asp Ser Val
        435                 440                 445

Ala Gly Lys Glu Ile Arg Phe Pro Cys Gly Gln Gly Ile Ala Gly Thr
450                 455                 460

Val Ala Ala Ser Gly Val Gly Glu Asn Ile Gln Asp Ala Tyr Gln Asp
465                 470                 475                 480

Pro Arg Phe Asn Arg Glu Val Asp Lys Gln Leu Gly Tyr Arg Thr Gln
                485                 490                 495

Thr Ile Leu Cys Glu Pro Ile Ile Leu Asn Gly Glu Ile Leu Ala Val
            500                 505                 510

Val Gln Leu Val Asn Lys Leu Asp Thr Ser Gly Glu Val Thr Val Phe
        515                 520                 525

Thr Glu Asp Asp Arg Asp Thr Phe Arg Val Phe Ser Leu Phe Ala Gly
530                 535                 540

Ile Ser Ile Asn Asn Ser His Leu Leu Glu Phe Ala Val Lys Ala Gly
545                 550                 555                 560

Arg Glu Val Met Glu Leu Asn Glu His Arg Ala Thr Leu Phe Asn Lys
                565                 570                 575

Asn Val Pro Ser Arg Ala Val Lys Arg Val Thr Ala Ile Thr Lys Val
            580                 585                 590

Glu Arg Glu Ala Val Leu Val Cys Glu Leu Pro Ser Phe Asp Val Thr
        595                 600                 605

Asp Val Glu Phe Asp Leu Phe Arg Ala Arg Glu Ser Thr Asp Lys Pro
610                 615                 620

Leu Asp Val Ala Ala Ile Ala Tyr Arg Leu Leu Leu Gly Ser Gly
625                 630                 635                 640

Leu Pro Gln Lys Phe Gly Cys Ser Asp Glu Val Leu Leu Asn Phe Ile
                645                 650                 655

Leu Gln Cys Arg Lys Lys Tyr Arg Asn Val Pro Tyr His Asn Phe Tyr
            660                 665                 670

His Val Val Asp Val Cys Gln Thr Ile His Thr Phe Leu Tyr Arg Gly
        675                 680                 685

Asn Val Tyr Glu Lys Leu Thr Glu Leu Glu Cys Phe Val Leu Leu Ile
690                 695                 700

Thr Ala Leu Val His Asp Leu Asp His Met Gly Leu Asn Asn Ser Phe
705                 710                 715                 720

Tyr Leu Lys Thr Glu Ser Pro Leu Gly Ile Leu Ser Ser Ala Ser Gly
```

```
                725                 730                 735
Asn Thr Ser Val Leu Glu Val His His Cys Asn Leu Ala Val Glu Ile
            740                 745                 750
Leu Ser Asp Pro Glu Ser Asp Val Phe Asp Gly Leu Glu Gly Ala Glu
            755                 760                 765
Arg Thr Leu Ala Phe Arg Ser Met Ile Asp Cys Val Leu Ala Thr Asp
            770                 775                 780
Met Ala Lys His Gly Ser Ala Leu Glu Ala Phe Leu Ala Ser Ala Ala
785                 790                 795                 800
Asp Gln Ser Ser Asp Glu Ala Ala Phe His Arg Met Thr Met Glu Ile
            805                 810                 815
Ile Leu Lys Ala Gly Asp Ile Ser Asn Val Thr Lys Pro Phe Asp Ile
            820                 825                 830
Ser Arg Gln Trp Ala Met Ala Val Thr Glu Glu Phe Tyr Arg Gln Gly
            835                 840                 845
Asp Met Glu Lys Glu Arg Gly Val Glu Val Leu Pro Met Phe Asp Arg
            850                 855                 860
Ser Lys Asn Met Glu Leu Ala Lys Gly Gln Ile Gly Phe Ile Asp Phe
865                 870                 875                 880
Val Ala Ala Pro Phe Phe Gln Lys Ile Val Asp Ala Cys Leu Gln Gly
            885                 890                 895
Met Gln Trp Thr Val Asp Arg Ile Lys Ser Asn Arg Ala Gln Trp Glu
            900                 905                 910
Arg Val Leu Glu Thr Arg Leu Ser Thr Ser Ser Gly Asn Asn Ser Ser
            915                 920                 925
Thr Arg
    930

<210> SEQ ID NO 15
<211> LENGTH: 1104
<212> TYPE: DNA
<213> ORGANISM: Trypanosoma brucei

<400> SEQUENCE: 15
atggaattaa atgaacaccg agcaacattg tttaataaga cgttccctc acgtgcggtt      60 aaacgagtca ctgccattac gaaggttgaa agggaagcgg tcttggtctg tgaacttcca     120
tcgtttgatg ttacggatgt tgagttcgac ttgttccgag cacgtgaaag cacagataaa     180
tcgttggatg tcgctgctgc tattgcatac agactactgc ttggaagcgg ccttccacaa     240
aagtttggtt gctctgacga ggtgcttctt aacttcattc tgcaatgccg taagaaatac     300
cgtaatgtcc cttatcacaa cttttaccat gttgtggatg tatgccaaac cattcacaca     360
ttcttgtaca ggggaaatgt gtatgagaag ttaaccgagc ttgagtgctt tgtgctgctt     420
atcaccgcac tggtgcatga tcttgatcat atggggctga caacagtttt ctacctgaaa     480
acagaatctc cacttggtat tctttccagc gcaagtggta cacctctgt tcttgaggtg      540 catcactgca accttgctgt tgagatcctc tctgatccgg aatctgatgt gtttgatggt     600
ctggagggtg cagagcgtac tcttgcgttc cgatcgatga ttgattgtgt acttgcgaca     660
gatatggcga agcatggaag tgcattagag gcgtttcttg catctgcggc ggaccagtcg     720
tcagacgagg cagcgtttca ccgcatgacg atggagataa tcttgaaagc tggagatatc     780
tctaacgtaa cgaaaccgtt cgacatttcc cgtcagtggg caatggctgt gacggaggag     840
ttctaccgtc aaggagacat ggagaaggag agggtgtgg aagtattgcc catgtttgac     900
```

-continued

```
cgatctaaga atatggagct tgcaaaaggt caaattggat tcattgactt tgttgcagcc    960
ccatttttcc agaagatagt tgatgcctgc ctgcaaggga tgcaatggac agtcgaccgt   1020
atcaaatcga accgcgcaca gtgggagcga gttctggaaa caagactatc aacgagttct   1080
ggcaacaaca gcagtactcg ttga                                          1104
```

<210> SEQ ID NO 16
<211> LENGTH: 367
<212> TYPE: PRT
<213> ORGANISM: Trypanosoma brucei

<400> SEQUENCE: 16

```
Met Glu Leu Asn Glu His Arg Ala Thr Leu Phe Asn Lys Asn Val Pro
1               5                   10                  15

Ser Arg Ala Val Lys Arg Val Thr Ala Ile Thr Lys Val Glu Arg Glu
            20                  25                  30

Ala Val Leu Val Cys Glu Leu Pro Ser Phe Asp Val Thr Asp Val Glu
        35                  40                  45

Phe Asp Leu Phe Arg Ala Arg Glu Ser Thr Asp Lys Ser Leu Asp Val
50                  55                  60

Ala Ala Ala Ile Ala Tyr Arg Leu Leu Leu Gly Ser Gly Leu Pro Gln
65                  70                  75                  80

Lys Phe Gly Cys Ser Asp Glu Val Leu Leu Asn Phe Ile Leu Gln Cys
                85                  90                  95

Arg Lys Lys Tyr Arg Asn Val Pro Tyr His Asn Phe Tyr His Val Val
            100                 105                 110

Asp Val Cys Gln Thr Ile His Thr Phe Leu Tyr Arg Gly Asn Val Tyr
        115                 120                 125

Glu Lys Leu Thr Glu Leu Glu Cys Phe Val Leu Leu Ile Thr Ala Leu
130                 135                 140

Val His Asp Leu Asp His Met Gly Leu Asn Asn Ser Phe Tyr Leu Lys
145                 150                 155                 160

Thr Glu Ser Pro Leu Gly Ile Leu Ser Ser Ala Ser Gly Asn Thr Ser
                165                 170                 175

Val Leu Glu Val His His Cys Asn Leu Ala Val Glu Ile Leu Ser Asp
            180                 185                 190

Pro Glu Ser Asp Val Phe Asp Gly Leu Glu Gly Ala Glu Arg Thr Leu
        195                 200                 205

Ala Phe Arg Ser Met Ile Asp Cys Val Leu Ala Thr Asp Met Ala Lys
210                 215                 220

His Gly Ser Ala Leu Glu Ala Phe Leu Ala Ser Ala Ala Asp Gln Ser
225                 230                 235                 240

Ser Asp Glu Ala Ala Phe His Arg Met Thr Met Glu Ile Ile Leu Lys
                245                 250                 255

Ala Gly Asp Ile Ser Asn Val Thr Lys Pro Phe Asp Ile Ser Arg Gln
            260                 265                 270

Trp Ala Met Ala Val Thr Glu Glu Phe Tyr Arg Gln Gly Asp Met Glu
        275                 280                 285

Lys Glu Arg Gly Val Glu Val Leu Pro Met Phe Asp Arg Ser Lys Asn
290                 295                 300

Met Glu Leu Ala Lys Gly Gln Ile Gly Phe Ile Asp Phe Val Ala Ala
305                 310                 315                 320

Pro Phe Phe Gln Lys Ile Val Asp Ala Cys Leu Gln Gly Met Gln Trp
                325                 330                 335
```

```
Thr Val Asp Arg Ile Lys Ser Asn Arg Ala Gln Trp Glu Arg Val Leu
        340                 345                 350

Glu Thr Arg Leu Ser Thr Ser Ser Gly Asn Asn Ser Ser Thr Arg
        355                 360                 365

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Primer
      sequence 7A1p1

<400> SEQUENCE: 17
gatatttgta acccatgtcg gacg                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer
      sequence 7A1p2

<400> SEQUENCE: 18
gaaagcttgg cggtactcta cgat                                          24

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Primer
      sequence 7A3p1

<400> SEQUENCE: 19
acgcaggaat tcttccatca aggagat                                       27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Primer
      sequence 7A3p2

<400> SEQUENCE: 20
agcttccaca tgagcgaata atggatt                                       27

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Primer
      sequence 8A1p1

<400> SEQUENCE: 21
gtaatgcctt tcaattctgc tggatttaca                                    30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Primer
      sequence 8A1p2
```

-continued

```
<400> SEQUENCE: 22
acgagtgtca gactgaacac attcggatat                                        30

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: mAbPIL9

<400> SEQUENCE: 23

Met Gly Cys Ala Pro Ser Ile His Thr Ser Glu Asn Arg Thr Phe
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: mAb PIL13

<400> SEQUENCE: 24

Lys Gly Leu Asp Glu Met Lys Leu Arg Asn Leu Arg Pro Pro Pro Glu
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: mAb 6976

<400> SEQUENCE: 25

Gln Ile Gly Asn Tyr Thr Tyr Leu Asp Ile Ala Gly
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence: Flag tag

<400> SEQUENCE: 26

Met Asp Tyr Lys Asp Asp Asp Lys Gly Ser Tyr Asn Met Glu Trp
1               5                   10                  15

Gln Gly Ile

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Primer
      sequence AA06.1s

<400> SEQUENCE: 27
ggagctgttc caaaccttct ctatgtttg                                         29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Primer
``` sequence AA06.2s

<400> SEQUENCE: 28
ctggcgcctc actacgtaac tgtcgtatc                                   29

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Primer
      sequence AA06.1as

<400> SEQUENCE: 29
gttgtttgtc aactcacggt tgaagcg                                     27

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Primer
      sequence AA06.2as

<400> SEQUENCE: 30
cctggtacgc gtcctgaata ttctcacc                                    28

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Primer
      sequence W8.1s

<400> SEQUENCE: 31
gaagttaaga agcaccgtaa tgtccc                                      26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Primer
      sequence W8.1as

<400> SEQUENCE: 32
gattccggat cagagaggat ctcaac                                      26

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Primer
      sequence W8.2as

<400> SEQUENCE: 33
gcaaggttgc agtgatgcac ctcaag                                      26

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Primer
      sequence AA.c5

```
<400> SEQUENCE: 34
gtaagatttg tacatacttc cgtgaaggc                                        29

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Primer
      sequence GAF.1s

<400> SEQUENCE: 35
gctgggaaag acagagacag atgacac                                          27

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Primer
      sequence AP1

<400> SEQUENCE: 36
gtaatacgac tcactatagg gc                                               22

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Primer
      sequence AP2

<400> SEQUENCE: 37
actatagggc acgcgtggt                                                   19

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Primer
      sequence pdetyfor

<400> SEQUENCE: 38
atgacaatgg atggatgtgc ttat                                             24

<210> SEQ ID NO 39
<211> LENGTH: 46
<212> TYPE: DNA
<213> ORGANISM: Artificial Sequence
<220> FEATURE:
<223> OTHER INFORMATION: Description of Artificial Sequence: Primer
      sequence pdetyrev

<400> SEQUENCE: 39
cttctcgagg gatccctatc catgggcaga cgaagcccct gtactc                     46

<210> SEQ ID NO 40
<211> LENGTH: 39
<212> TYPE: DNA
<213> ORGANISM: Artificial Sequence
<220> FEATURE:
<223> OTHER INFORMATION: Description of Artificial Sequence: Primer
      sequence pde2gf2
```

-continued

```
<400> SEQUENCE: 40
gagaattcaa acatgtatgt gcacgacgta cgcatgttc                                39

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Primer
      sequence pde2gr

<400> SEQUENCE: 41
ttcaacccca tatgatcaag atcatgcacc ag                                       32

<210> SEQ ID NO 42
<211> LENGTH: 42
<212> TYPE: DNA
<213> ORGANISM: Artificial Sequence
<220> FEATURE:
<223> OTHER INFORMATION: Description of Artificial Sequence: Primer
      sequence pde2gf1

<400> SEQUENCE: 42
gagaattcaa acatggaagt taacgaacac cgagcaacat tg                            42

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence:
      Hemagglutinin tag

<400> SEQUENCE: 43

Tyr Pro Tyr Asp Val Pro Asp Tyr Ala Gly Ile Pro Met
1               5                   10

<210> SEQ ID NO 44
<211> LENGTH: 49
<212> TYPE: DNA
<213> ORGANISM: Artificial Sequence
<220> FEATURE:
<223> OTHER INFORMATION: Description of Artificial Sequence: Primer
      sequence Htfor

<400> SEQUENCE: 44
catggttacc catacgatgt cccagattac gccggtattc caatgtagg                     49

<210> SEQ ID NO 45
<211> LENGTH: 49
<212> TYPE: DNA
<213> ORGANISM: Artificial Sequence
<220> FEATURE:
<223> OTHER INFORMATION: Description of Artificial Sequence: Primer
      sequence Htrev

<400> SEQUENCE: 45
gatccctaca ttggaatacc ggcgtaatct gggacatcgt atgggtaac                     49

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Primer
      sequence Kozak
```

-continued

```
<400> SEQUENCE: 46
ctaaacatga gtcgacctcg agt                                                 23

<210> SEQ ID NO 47
<211> LENGTH: 10
<212> TYPE: PRT
<213> ORGANISM: Artificial Sequence
<220> FEATURE:
<223> OTHER INFORMATION: Xaa is any amino acid
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid

<400> SEQUENCE: 47

His Asp Xaa Xaa His Xaa Gly Xaa Xaa Asn
1               5                   10

<210> SEQ ID NO 48
<211> LENGTH: 3874
<212> TYPE: DNA
<213> ORGANISM: Homo sapiens

<400> SEQUENCE: 48
acgcgagatc cgcgctcgcc tccgtccgcc caggcggcga tgacacggcg cccacggcgg       60
cccgaaggcg ccgggtgggc cgtttgctga ccggatcgcg gctacccgcc agcgtgtccg      120
cggcgccgcc gccagcatgg gctgtgcccc gagcatccac atttccgagc gcctggtggc      180
cgaggacgcg cctagccccg cggcaccgcc gctgtcgtcc ggcgggccgc gcctcccgca      240
gggccagaag acggccgcct tgccccggac ccgcggcgcc ggcctcttgg agtcggaggt      300
tcgcgacggc agcggcaaga aggtagcagt agctgatgtg cagtttggcc ccatgagatt      360
tcatcaagat caacttcagg tactttagt gtttaccaaa aagataacc aatgtaatgg       420 attctgcagg gcatgtgaaa aagcagggtt taagtgtaca gttaccaagg aggctcaggc      480
tgtccttgcc tgtttcctgg acaaacatca tgacattatc atcatagacc acagaaatcc      540
tcgacagctg gatgcagagg cactgtgcag gtctatcaga tcatcaaaac tctcagaaaa      600
cacagttatt gttggtgtag tacgcagggt ggatagagaa gagttgtccg taatgccttt      660
catttctgct ggatttacaa ggaggtatgt agaaaacccc aacatcatgg cctgctacaa      720
tgaactgctc cagctggagt ttggagaggt gcgatcacaa ctgaaactca gggcttgtaa      780
ctcagtattc actgcattag aaaacagtga agatgcaatt gaaattacaa gcgaagaccg      840
ttttatacag tatgcaaatc ctgcatttga acaacaatg ggctatcagt caggtgaatt      900
aatagggaag gagttaggag aagtgcctat aaatgaaaaa aaggctgact tgctcgatac      960
tataaattca tgcatcagga taggcaagga gtggcaagga atttactatg ccaaaaagaa     1020
aaacggagat aatatacaac aaaatgtgaa gataatacct gtcattggac agggaggaaa     1080
aattagacac tatgtgtcca ttatcagagt gtgcaatggc aacaataagg ctgagaaaat     1140
atccgaatgt gttcagtctg acactcgtaa tcagacaggc aaacataaag acaggagaaa     1200
aggctcacta gacgtcaaag ctgttgcctc ccgtgcaact gaagtttcca gccagagacg     1260
```

-continued

| | | |
|---|---|---|
| acactcttcc atggcccgga tacattccat gacaattgag gcgcccatca ccaaggtaat | 1320 |
| caatgttatc aatgctgccc aggaaagtag tcccatgcct gtgacagaag ccctagaccg | 1380 |
| tgtgctggaa attctaagaa ccactgagtt atattcacca cagtttggtg ctaaagatga | 1440 |
| tgatccccat gccaatgacc ttgttggggg cttaatgtct gatggtttgc gaagactatc | 1500 |
| agggaatgaa tatgttcttt caacaaaaaa cactcaaatg gtttcaagca atataatcac | 1560 |
| tcccatctcc cttgatgatg tcccaccacg gatagctcgg gccatggaaa atgaggaata | 1620 |
| ctgggacttt gatattttg aactggaggc tgccacccac aataggcctt tgatttatct | 1680 |
| tggtctcaaa atgtttgctc gctttggaat ctgtgaattc ttacactgct ccgagtcaac | 1740 |
| gctaagatca tggttacaaa ttatcgaagc caattatcat tcctccaatc cctaccacaa | 1800 |
| ttctacacat tctgctgatg tgcttcatgc cactgcctat tttctctcca aggagaggat | 1860 |
| aaaggaaact ttagatccaa ttgatgaggt cgctgcactc atcgcagcca ccattcatga | 1920 |
| tgtggatcac cctgggagaa ccaactcctt cctgtgtaat gctggaagtg agctggccat | 1980 |
| tttgtacaat gacactgctg tgctggagag ccaccatgcg gccttggcct tccagctgac | 2040 |
| cactggagat gataaatgca atatatttaa aaacatggag aggaatgatt atcggacact | 2100 |
| gcgccagggg attatcgaca tggtcttagc cacagaaatg acaaagcact ttgagcatgt | 2160 |
| caacaaattt gtcaacagca tcaacaaacc cttggcaaca ctagaagaaa atggggaaac | 2220 |
| tgataaaaac caggaagtga taaacactat gcttaggact ccagagaacc ggaccctaat | 2280 |
| caaacgaatg ctgattaaat gtgctgatgt gtccaatccc tgccgacccc tgcagtactg | 2340 |
| catcgagtgg gctgcacgca tttcggaaga atatttttct cagactgatg aagagaagca | 2400 |
| gcagggctta cctgtggtga tgccagtgtt tgacagaaat acctgcagca tccccaaatc | 2460 |
| ccaaatctct ttcattgatt acttcatcac agacatgttt gatgcttggg atgcctttgt | 2520 |
| agacctgcct gatttaatgc agcatcttga caacaacttt aaatactgga aaggactgga | 2580 |
| cgaaatgaag ctgcggaacc tccgaccacc tcctgaatag tgggagacac cacccagagc | 2640 |
| cctgaagctt tgttccttcg gtcatttgga attcctgagg gcagccagag ctccttggtc | 2700 |
| cttttcagtac taggcagaac agcccccgat ctgcatagcc tgtgaaagcc cacggggaca | 2760 |
| tcagtaaccct tctgcagcca ccatccaatg ccattactgt caagtgagac ttggccactg | 2820 |
| tagcctgggc ctgctgcagg agctcttcag aaaggcacat gaggaccacg gtttgcctca | 2880 |
| gtttctggta aaacacaagg tctggagtgc ccctgcaaag ggtattgatg gacttcctgc | 2940 |
| cagtgacaga gcatgtctat tgcaaacaat tctctcagtt acgttcagca cttaagaacg | 3000 |
| gctaatggca ataggatctt tagcaacttt ttcacatcat agaaggtgca atcgctcact | 3060 |
| tgggaacact actgagagtg acttctcttt taaaattgag tagcagatga aaattaaaa | 3120 |
| tttgaacttg attattaata tcaattaaaa tgttttattt attttattaa aagctcaata | 3180 |
| ttttctatga attcaaaaat acttcagagc caaagccaac ttcaaatacc gtgaccaaat | 3240 |
| ttacatgatt catattcatt atgcattact tggtatacag acttattttc ataatgcaaa | 3300 |
| ttaataaaat gacacttta ctgcactata gaaatattca tgtatgttaa acttttctga | 3360 |
| ttgaggctaa ctggaaaaag ctggggtcgt attctaagtg ctaaagaagg ctgcttctac | 3420 |
| tgtatagaac ccagggctct gaaacagctc tagccgccta atgcacttca caggtaactc | 3480 |
| cccaaggtaa aactagactc tcttgttggt tcgcaaagaa aagttaggac ttaacacttt | 3540 |
| tttctaaaat tttataattc aatttccaaa agtctactct attttatact gtttctacaa | 3600 |
| aatattcctt ataaaaacaa agaacaaaaa ttgaatattt aatgaattga cattttataa | 3660 |

```
ccaacctgtt tttatctacg gtgggaatct ttgatgccag aaatttataa agaggttctg    3720
tatcttcaca ccttgaataa gcataatacc ataaaaaatg acacttgaca tgtcaatgta    3780
tttgtcattt catttttaaac tcgtatttgt ggttttttc ccagataaaa atgaaattaa    3840
accatttctt tttaagaaaa aaaaaaaaaa aaaa                                3874
```

<210> SEQ ID NO 49
<211> LENGTH: 827
<212> TYPE: PRT
<213> ORGANISM: Homo sapiens

<400> SEQUENCE: 49

Met Gly Cys Ala Pro Ser Ile His Ile Ser Glu Arg Leu Val Ala Glu
1               5                   10                  15

Asp Ala Pro Ser Pro Ala Ala Pro Leu Ser Ser Gly Gly Pro Arg
            20                  25                  30

Leu Pro Gln Gly Gln Lys Thr Ala Ala Leu Pro Arg Thr Arg Gly Ala
        35                  40                  45

Gly Leu Leu Glu Ser Glu Val Arg Asp Gly Ser Gly Lys Lys Val Ala
    50                  55                  60

Val Ala Asp Val Gln Phe Gly Pro Met Arg Phe His Gln Asp Gln Leu
65                  70                  75                  80

Gln Val Leu Leu Val Phe Thr Lys Glu Asp Asn Gln Cys Asn Gly Phe
                85                  90                  95

Cys Arg Ala Cys Glu Lys Ala Gly Phe Lys Cys Thr Val Thr Lys Glu
            100                 105                 110

Ala Gln Ala Val Leu Ala Cys Phe Leu Asp Lys His His Asp Ile Ile
        115                 120                 125

Ile Ile Asp His Arg Asn Pro Arg Gln Leu Asp Ala Glu Ala Leu Cys
130                 135                 140

Arg Ser Ile Arg Ser Ser Lys Leu Ser Glu Asn Thr Val Ile Val Gly
145                 150                 155                 160

Val Val Arg Arg Val Asp Arg Glu Glu Leu Ser Val Met Pro Phe Ile
                165                 170                 175

Ser Ala Gly Phe Thr Arg Arg Tyr Val Glu Asn Pro Asn Ile Met Ala
            180                 185                 190

Cys Tyr Asn Glu Leu Leu Gln Leu Glu Phe Gly Val Arg Ser Gln
        195                 200                 205

Leu Lys Leu Arg Ala Cys Asn Ser Val Phe Thr Ala Leu Glu Asn Ser
    210                 215                 220

Glu Asp Ala Ile Glu Ile Thr Ser Glu Asp Arg Phe Ile Gln Tyr Ala
225                 230                 235                 240

Asn Pro Ala Phe Glu Thr Thr Met Gly Tyr Gln Ser Gly Leu Ile
                245                 250                 255

Gly Lys Glu Leu Gly Glu Val Pro Ile Asn Glu Lys Lys Ala Asp Leu
            260                 265                 270

Leu Asp Thr Ile Asn Ser Cys Ile Arg Ile Gly Lys Glu Trp Gln Gly
        275                 280                 285

Ile Tyr Tyr Ala Lys Lys Lys Asn Gly Asp Asn Ile Gln Gln Asn Val
    290                 295                 300

Lys Ile Ile Pro Val Ile Gly Gln Gly Gly Lys Ile Arg His Tyr Val
305                 310                 315                 320

Ser Ile Ile Arg Val Cys Asn Gly Asn Asn Lys Ala Glu Lys Ile Ser
                325                 330                 335

```
Glu Cys Val Gln Ser Asp Thr Arg Asn Gln Thr Gly Lys His Lys Asp
            340                 345                 350

Arg Arg Lys Gly Ser Leu Asp Val Lys Ala Val Ala Ser Arg Ala Thr
        355                 360                 365

Glu Val Ser Ser Gln Arg Arg His Ser Ser Met Ala Arg Ile His Ser
    370                 375                 380

Met Thr Ile Glu Ala Pro Ile Thr Lys Val Ile Asn Val Ile Asn Ala
385                 390                 395                 400

Ala Gln Glu Ser Ser Pro Met Pro Val Thr Glu Ala Leu Asp Arg Val
                405                 410                 415

Leu Glu Ile Leu Arg Thr Thr Glu Leu Tyr Ser Pro Gln Phe Gly Ala
            420                 425                 430

Lys Asp Asp Pro His Ala Asn Asp Leu Val Gly Leu Met Ser
        435                 440                 445

Asp Gly Leu Arg Arg Leu Ser Gly Asn Glu Tyr Val Leu Ser Thr Lys
    450                 455                 460

Asn Thr Gln Met Val Ser Ser Asn Ile Ile Thr Pro Ile Ser Leu Asp
465                 470                 475                 480

Asp Val Pro Pro Arg Ile Ala Arg Ala Met Glu Asn Glu Glu Tyr Trp
                485                 490                 495

Asp Phe Asp Ile Phe Glu Leu Glu Ala Ala Thr His Asn Arg Pro Leu
            500                 505                 510

Ile Tyr Leu Gly Leu Lys Met Phe Ala Arg Phe Gly Ile Cys Glu Phe
    515                 520                 525

Leu His Cys Ser Glu Ser Thr Leu Arg Ser Trp Leu Gln Ile Ile Glu
    530                 535                 540

Ala Asn Tyr His Ser Ser Asn Pro Tyr His Asn Ser Thr His Ser Ala
545                 550                 555                 560

Asp Val Leu His Ala Thr Ala Tyr Phe Leu Ser Lys Glu Arg Ile Lys
                565                 570                 575

Glu Thr Leu Asp Pro Ile Asp Glu Val Ala Ala Leu Ile Ala Ala Thr
            580                 585                 590

Ile His Asp Val Asp His Pro Gly Arg Thr Asn Ser Phe Leu Cys Asn
    595                 600                 605

Ala Gly Ser Glu Leu Ala Ile Leu Tyr Asn Asp Thr Ala Val Leu Glu
    610                 615                 620

Ser His His Ala Ala Leu Ala Phe Gln Leu Thr Thr Gly Asp Asp Lys
625                 630                 635                 640

Cys Asn Ile Phe Lys Asn Met Glu Arg Asn Asp Tyr Arg Thr Leu Arg
                645                 650                 655

Gln Gly Ile Ile Asp Met Val Leu Ala Thr Glu Met Thr Lys His Phe
            660                 665                 670

Glu His Val Asn Lys Phe Val Asn Ser Ile Asn Lys Pro Leu Ala Thr
    675                 680                 685

Leu Glu Glu Asn Gly Glu Thr Asp Lys Asn Gln Glu Val Ile Asn Thr
    690                 695                 700

Met Leu Arg Thr Pro Glu Asn Arg Thr Leu Ile Lys Arg Met Leu Ile
705                 710                 715                 720

Lys Cys Ala Asp Val Ser Asn Pro Cys Arg Pro Leu Gln Tyr Cys Ile
                725                 730                 735

Glu Trp Ala Ala Arg Ile Ser Glu Glu Tyr Phe Ser Gln Thr Asp Glu
            740                 745                 750
```

```
Glu Lys Gln Gln Gly Leu Pro Val Met Pro Val Phe Asp Arg Asn
        755                 760                 765

Thr Cys Ser Ile Pro Lys Ser Gln Ile Ser Phe Ile Asp Tyr Phe Ile
770                 775                 780

Thr Asp Met Phe Asp Ala Trp Asp Ala Phe Val Asp Leu Pro Asp Leu
785                 790                 795                 800

Met Gln His Leu Asp Asn Asn Phe Lys Tyr Trp Lys Gly Leu Asp Glu
                805                 810                 815

Met Lys Leu Arg Asn Leu Arg Pro Pro Pro Glu
        820                 825

<210> SEQ ID NO 50
<211> LENGTH: 3880
<212> TYPE: DNA
<213> ORGANISM: Homo sapiens

<400> SEQUENCE: 50
```

| | | | | | |
|---|---|---|---|---|---|
| acgcgagatc | cgcgctcgcc | tccgtccgcc | caggcggcga | tgacacggcg | cccacggcgg | 60 |
| cccgaaggcg | ccgggtgggc | cgtttgctga | ccggatcgcg | gctacccgcc | agcgtgtccg | 120 |
| cggcgccgcc | gccagcatgg | gctgtgcccc | gagcatccac | atttccgagc | gcctggtggc | 180 |
| cgaggacgcg | cctagccccg | cggcaccgcc | gctgtcgtcc | ggcgggccgc | gcctcccgca | 240 |
| gggccagaag | acggccgcct | tgccccggac | ccgcggcgcc | ggcctcttgg | agtcggaggt | 300 |
| tcgcgacggc | agcggcaaga | aggtagcagt | agctgatgtg | cagtttggcc | ccatgagatt | 360 |
| tcatcaagat | caacttcagg | tactttagt | gtttaccaaa | gaagataacc | aatgtaatgg | 420 |
| attctgcagg | gcatgtgaaa | aagcagggtt | taagtgtaca | gttaccaagg | aggctcaggc | 480 |
| tgtccttgcc | tgtttcctgg | acaaacatca | tgacattatc | atcatagacc | acagaaatcc | 540 |
| tcgacagctg | gatgcagagg | cactgtgcag | gtctatcaga | tcatcaaaac | tctcagaaaa | 600 |
| cacagttatt | gttggtgtag | tacgcagggt | ggatagagaa | gagttgtccg | taatgccttt | 660 |
| catttctgct | ggatttacaa | ggaggtatgt | agaaaacccc | aacatcatgg | cctgctacaa | 720 |
| tgaactgctc | cagctggagt | ttggagaggt | gcgatcacaa | ctgaaactca | ggcttgtaa | 780 |
| ctcagtattc | actgcattag | aaaacagtga | agatgcaatt | gaaattacaa | gcgaagaccg | 840 |
| ttttatacag | tatgcaaatc | ctgcatttga | acaacaatg | ggctatcagt | caggtgaatt | 900 |
| aatagggaag | gagttaggag | aagtgcctat | aaatgaaaaa | aaggctgact | tgctcgatac | 960 |
| tataaattca | tgcatcagga | taggcaagga | gtggcaagga | atttactatg | ccaaaaagaa | 1020 |
| aaacggagat | aatatacaac | aaaatgtgaa | gataatacct | gtcattggac | agggaggaaa | 1080 |
| aattagacac | tatgtgtcca | ttatcagagt | gtgcaatggc | aacaataagg | ctgagaaaat | 1140 |
| atccgaatgt | gttcagtctg | acactcatac | agataatcag | acaggcaaac | ataaagacag | 1200 |
| gagaaaaggc | tcactagacg | tcaaagctgt | tgcctcccgt | gcaactgaag | tttccagcca | 1260 |
| gagacgacac | tcttccatgg | cccggataca | ttccatgaca | attgaggcgc | ccatcaccaa | 1320 |
| ggtaatcaat | attatcaatg | ctgcccagga | aagtagtccc | atgcctgtga | cagaagccct | 1380 |
| agaccgtgtg | ctggaaattc | taagaaccac | tgagttatat | tcaccacagt | ttggtgctaa | 1440 |
| agatgatgat | ccccatgcca | atgaccttgt | tggggcttta | atgtctgatg | gtttgcgaag | 1500 |
| actatcaggg | aatgaatatg | ttctttcaac | aaaaaaacact | caaatggttt | caagcaatat | 1560 |
| aatcactccc | atctcccttg | atgatgtccc | accacggata | gctcgggcca | tggaaaatga | 1620 |
| ggaatactgg | gactttgata | ttttttgaact | ggaggctgcc | acccacaata | ggccctttgat | 1680 |

```
                                    -continued ttatcttggt ctcaaaatgt ttgctcgctt tggaatctgt gaattcttac actgctccga   1740
gtcaacgcta agatcatggt tacaaattat cgaagccaat tatcattcct ccaatcccta   1800
ccacaattct acacattctg ctgatgtgct tcatgccact gcctattttc tctccaagga   1860
gaggataaag gaaactttag atccaattga tgaggtcgct gcactcatcg cagccaccat   1920
tcatgatgtg gatcaccctg ggagaaccaa ctccttcctg tgtaatgctg gaagtgagct   1980
ggccattttg tacaatgaca ctgctgtgct ggagagccac catgcggcct tggccttcca   2040
gctgaccact ggagatgata aatgcaatat atttaaaaac atggagagga atgattatcg   2100
gacactgcgc caggggatta tcgacatggt cttagccaca gaaatgacaa agcactttga   2160
gcatgtcaac aaatttgtca acagcatcaa caaacccttg gcaacactag aagaaaatgg   2220
ggaaactgat aaaaaccagg aagtgataaa cactatgctt aggactccag agaaccggac   2280
cctaatcaaa cgaatgctga ttaaatgtgc tgatgtgtcc aatccctgcc gaccccctgca  2340 gtactgcatc gagtgggctg cacgcatttc ggaagaatat ttttctcaga ctgatgaaga   2400
gaagcagcag ggcttacctg tggtgatgcc agtgtttgac agaaatacct gcagcatccc   2460
caaatcccaa atctctttca ttgattactt catcacagac atgtttgatg cttgggatgc   2520 cttgtagac ctgcctgatt taatgcagca tcttgacaac aactttaaat actggaaagg    2580
actggacgaa atgaagctgc ggaacctccg accacctcct gaatagtggg agacaccacc   2640
cagagccctg aagctttgtt ccttcggtca tttggaattc ctgagggcag ccagagctcc   2700
ttggtccttt cagtactagg cagaacagcc cccgatctgc atagcctgtg aaagcccacg   2760
gggacatcag taaccttctg cagccaccat ccaatgccat tactgtcaag tgagacttgg   2820
ccactgtagc ctgggcctgc tgcaggagct cttcagaaag gcacatgagg accacggttt   2880
gcctcagttt ctggtaaaac acaaggtctg gagtgcccct gcaaagggta ttgatggact   2940
tcctgccagt gacagagcat gtctattgca acaattctc tcagttacgt tcagcactta    3000
agaacggcta atggcaatag gatctttagc aactttttca catcatagaa ggtgcaatcg   3060
ctcacttggg aacactactg agagtgactt ctcttttaaa attgagtagc agatgaaaaa   3120
ttaaaatttg aacttgatta ttaatatcaa ttaaaatgtt ttatttattt tattaaaagc   3180
tcaatatttt ctatgaattc aaaaatactt cagagccaaa gccaacttca ataccgtga    3240 ccaaatttac atgattcata ttcattatgc attacttggt atacagactt attttcataa   3300
tgcaaattaa taaatgaca cttttactgc actatagaaa tattcatgta tgttaaactt    3360
ttctgattga ggctaactgg aaaaagctgg ggtcgtattc taagtgctaa agaaggctgc   3420
ttctactgta tagaacccag ggctctgaaa cagctctagc cgcctaatgc acttcacagg   3480
taactcccca aggtaaaact agactctctt gttggttcgc aaagaaaagt taggacttaa   3540
cacttttttc taaaatttta taattcaatt tccaaaagtc tactctattt tatactgttt    3600
ctacaaaata ttccttataa aaacaaagaa caaaaattga atatttaatg aattgacatt   3660
ttataaccaa cctgttttta tctacggtgg gaatctttga tgccagaaat ttataaagag   3720
gttctgtatc ttcacacctt gaataagcat aataccataa aaaatgacac ttgacatgtc   3780
aatgtatttg tcatttcatt ttaaactcgt atttgtggtt ttttttcccag ataaaaatga   3840 aattaaacca tttcttttta agaaaaaaaa aaaaaaaaa                          3880

<210> SEQ ID NO 51
<211> LENGTH: 829
<212> TYPE: PRT
<213> ORGANISM: Homo sapiens
```

<400> SEQUENCE: 51

```
Met Gly Cys Ala Pro Ser Ile His Ile Ser Glu Arg Leu Val Ala Glu
1               5                   10                  15

Asp Ala Pro Ser Pro Ala Ala Pro Pro Leu Ser Ser Gly Gly Pro Arg
            20                  25                  30

Leu Pro Gln Gly Gln Lys Thr Ala Ala Leu Pro Arg Thr Arg Gly Ala
        35                  40                  45

Gly Leu Leu Glu Ser Glu Val Arg Asp Gly Ser Gly Lys Lys Val Ala
    50                  55                  60

Val Ala Asp Val Gln Phe Gly Pro Met Arg Phe His Gln Asp Gln Leu
65                  70                  75                  80

Gln Val Leu Leu Val Phe Thr Lys Glu Asp Asn Gln Cys Asn Gly Phe
                85                  90                  95

Cys Arg Ala Cys Glu Lys Ala Gly Phe Lys Cys Thr Val Thr Lys Glu
            100                 105                 110

Ala Gln Ala Val Leu Ala Cys Phe Leu Asp Lys His His Asp Ile Ile
        115                 120                 125

Ile Ile Asp His Arg Asn Pro Arg Gln Leu Asp Ala Glu Ala Leu Cys
    130                 135                 140

Arg Ser Ile Arg Ser Ser Lys Leu Ser Glu Asn Thr Val Ile Val Gly
145                 150                 155                 160

Val Val Arg Arg Val Asp Arg Glu Glu Leu Ser Val Met Pro Phe Ile
                165                 170                 175

Ser Ala Gly Phe Thr Arg Arg Tyr Val Glu Asn Pro Asn Ile Met Ala
            180                 185                 190

Cys Tyr Asn Glu Leu Leu Gln Leu Glu Phe Gly Glu Val Arg Ser Gln
        195                 200                 205

Leu Lys Leu Arg Ala Cys Asn Ser Val Phe Thr Ala Leu Glu Asn Ser
    210                 215                 220

Glu Asp Ala Ile Glu Ile Thr Ser Glu Asp Arg Phe Ile Gln Tyr Ala
225                 230                 235                 240

Asn Pro Ala Phe Glu Thr Thr Met Gly Tyr Gln Ser Gly Glu Leu Ile
                245                 250                 255

Gly Lys Glu Leu Gly Glu Val Pro Ile Asn Glu Lys Lys Ala Asp Leu
            260                 265                 270

Leu Asp Thr Ile Asn Ser Cys Ile Arg Ile Gly Lys Glu Trp Gln Gly
        275                 280                 285

Ile Tyr Tyr Ala Lys Lys Asn Gly Asp Asn Ile Gln Gln Asn Val
    290                 295                 300

Lys Ile Ile Pro Val Ile Gly Gln Gly Gly Lys Ile Arg His Tyr Val
305                 310                 315                 320

Ser Ile Ile Arg Val Cys Asn Gly Asn Asn Lys Ala Glu Lys Ile Ser
                325                 330                 335

Glu Cys Val Gln Ser Asp Thr His Thr Asp Asn Gln Thr Gly Lys His
            340                 345                 350

Lys Asp Arg Arg Lys Gly Ser Leu Asp Val Lys Ala Val Ala Ser Arg
        355                 360                 365

Ala Thr Glu Val Ser Ser Gln Arg Arg His Ser Ser Met Ala Arg Ile
    370                 375                 380

His Ser Met Thr Ile Glu Ala Pro Ile Thr Lys Val Ile Asn Ile Ile
385                 390                 395                 400

Asn Ala Ala Gln Glu Ser Ser Pro Met Pro Val Thr Glu Ala Leu Asp
```

```
                    405                 410                 415
Arg Val Leu Glu Ile Leu Arg Thr Thr Glu Leu Tyr Ser Pro Gln Phe
                420                 425                 430
Gly Ala Lys Asp Asp Pro His Ala Asn Asp Leu Val Gly Gly Leu
            435                 440                 445
Met Ser Asp Gly Leu Arg Arg Leu Ser Gly Asn Glu Tyr Val Leu Ser
450                 455                 460
Thr Lys Asn Thr Gln Met Val Ser Ser Asn Ile Ile Thr Pro Ile Ser
465                 470                 475                 480
Leu Asp Asp Val Pro Pro Arg Ile Ala Arg Ala Met Glu Asn Glu Glu
                485                 490                 495
Tyr Trp Asp Phe Asp Ile Phe Glu Leu Glu Ala Ala Thr His Asn Arg
            500                 505                 510
Pro Leu Ile Tyr Leu Gly Leu Lys Met Phe Ala Arg Phe Gly Ile Cys
            515                 520                 525
Glu Phe Leu His Cys Ser Glu Ser Thr Leu Arg Ser Trp Leu Gln Ile
            530                 535                 540
Ile Glu Ala Asn Tyr His Ser Ser Asn Pro Tyr His Asn Ser Thr His
545                 550                 555                 560
Ser Ala Asp Val Leu His Ala Thr Ala Tyr Phe Leu Ser Lys Glu Arg
                565                 570                 575
Ile Lys Glu Thr Leu Asp Pro Ile Asp Glu Val Ala Ala Leu Ile Ala
            580                 585                 590
Ala Thr Ile His Asp Val Asp His Pro Gly Arg Thr Asn Ser Phe Leu
            595                 600                 605
Cys Asn Ala Gly Ser Glu Leu Ala Ile Leu Tyr Asn Asp Thr Ala Val
            610                 615                 620
Leu Glu Ser His His Ala Ala Leu Ala Phe Gln Leu Thr Thr Gly Asp
625                 630                 635                 640
Asp Lys Cys Asn Ile Phe Lys Asn Met Glu Arg Asn Asp Tyr Arg Thr
                645                 650                 655
Leu Arg Gln Gly Ile Ile Asp Met Val Leu Ala Thr Glu Met Thr Lys
            660                 665                 670
His Phe Glu His Val Asn Lys Phe Val Asn Ser Ile Asn Lys Pro Leu
            675                 680                 685
Ala Thr Leu Glu Glu Asn Gly Glu Thr Asp Lys Asn Gln Glu Val Ile
            690                 695                 700
Asn Thr Met Leu Arg Thr Pro Glu Asn Arg Thr Leu Ile Lys Arg Met
705                 710                 715                 720
Leu Ile Lys Cys Ala Asp Val Ser Asn Pro Cys Arg Pro Leu Gln Tyr
                725                 730                 735
Cys Ile Glu Trp Ala Ala Arg Ile Ser Glu Glu Tyr Phe Ser Gln Thr
            740                 745                 750
Asp Glu Glu Lys Gln Gln Gly Leu Pro Val Val Met Pro Val Phe Asp
            755                 760                 765
Arg Asn Thr Cys Ser Ile Pro Lys Ser Gln Ile Ser Phe Ile Asp Tyr
            770                 775                 780
Phe Ile Thr Asp Met Phe Asp Ala Trp Asp Ala Phe Val Asp Leu Pro
785                 790                 795                 800
Asp Leu Met Gln His Leu Asp Asn Asn Phe Lys Tyr Trp Lys Gly Leu
                805                 810                 815
Asp Glu Met Lys Leu Arg Asn Leu Arg Pro Pro Glu
            820                 825
```

<210> SEQ ID NO 52
<211> LENGTH: 2990
<212> TYPE: DNA
<213> ORGANISM: Homo sapiens

<400> SEQUENCE: 52

| | | | | | |
|---|---|---|---|---|---|
| atggaagtgt | gttaccagct | gccggtactg | cccctggaca | ggccggtccc | ccagcacgtc | 60 |
| ctcagccgcc | gaggagccat | cagcttcagc | tccagctccg | ctctcttcgg | ctgccccaat | 120 |
| ccccggcagc | tctctcagag | gcgtggagct | atttcctatg | acagttctga | tcagactgca | 180 |
| ttatacattc | gtatgctagg | agatgtacgt | gtaaggagcc | gagcaggatt | tgaatcagaa | 240 |
| agaagaggtt | ctcacccata | tattgatttt | cgtattttcc | actctcaatc | tgaaattgaa | 300 |
| gtgtctgtct | ctgcaaggaa | tatcagaagg | ctactaagtt | tccagcgata | tcttagatct | 360 |
| tcacgctttt | ttcgtggtac | tgcggtttca | aattccctaa | acattttaga | tgatgattat | 420 |
| aatggacaag | ccaagtgtat | gctggaaaaa | gttggaaatt | ggaattttga | tatctttcta | 480 |
| tttgatagac | taacaaatgg | aaatagtcta | gtaagcttaa | cctttcattt | atttagtctt | 540 |
| catggattaa | ttgagtactt | ccatttagat | atgatgaaac | ttcgtagatt | tttagttatg | 600 |
| attcaagaag | attaccacag | tcaaaatcct | taccataacg | cagtccacgc | tgcggatgtt | 660 |
| actcaggcca | tgcactgtta | cttaaaggaa | cctaagcttg | ccaattctgt | aactccttgg | 720 |
| gatatcttgc | tgagcttaat | tgcagctgcc | actcatgatc | tggatcatcc | aggtgttaat | 780 |
| caacctttcc | ttattaaaac | taaccattac | ttggcaactt | tatacaagaa | tacctcagta | 840 |
| ctggaaaatc | accactggag | atctgcagtg | ggcttattga | gagaatcagg | cttattctca | 900 |
| catctgccat | tagaaagcag | gcaacaaatg | gagacacaga | taggtgctct | gatactagcc | 960 |
| acagacatca | gtcgccagaa | tgagtatctg | tctttgttta | ggtcccattt | ggatagaggt | 1020 |
| gatttatgcc | tagaagacac | cagacacaga | catttggttt | tacagatggc | tttgaaatgt | 1080 |
| gctgatattt | gtaacccatg | tcggacgtgg | gaattaagca | agcagtggag | tgaaaaagta | 1140 |
| acggaggaat | tcttccatca | aggagatata | gaaaaaaaat | atcatttggg | tgtgagtcca | 1200 |
| ctttgcgatc | gtcacactga | atctattgcc | aacatccaga | ttggtaacta | tacatattta | 1260 |
| gatatagctg | gttagaaaaa | tgccactgtt | tttatcaaga | agggaaatat | atttgaaata | 1320 |
| taaaatatta | aaattatgct | catttctatt | tttaaaaata | atttaagaaa | ttttacccTT | 1380 |
| gttttcccTT | gttatggctc | ttctaattct | catttaattt | taggatgtaa | aaagtatatt | 1440 |
| tttgcagaac | aggcagcagc | aataacttgt | ttctgttctt | atgtaaataa | gaatccatta | 1500 |
| ttcgctcatg | tggaagcttc | ttttgcatca | tttgggactg | ccatttaaaa | aaggataggt | 1560 |
| aaacaaagaa | atgacaaaaa | taaatataat | aaaatataaaa | tggataggtg | gtgacccact | 1620 |
| gagcctgatc | ataatacgaa | gaccagcttc | tgccactgcc | tttccagact | cttaccactg | 1680 |
| cctgttgatt | aaatctaact | cttcaacatc | ctagacaggc | ccttataatc | ttgcttcaaa | 1740 |
| tgctgtgcag | ccatcttgcc | tcaacttccc | tctcatttgc | ctacagcatc | tcgggacgct | 1800 |
| tctgtgtttc | ccagtatac | gctgttcttt | cgctctttgt | gcttcgccag | tgctttccat | 1860 |
| gtgcctcgta | gagttatttt | tcttgaagag | gcagctcaaa | tgtcaccttc | tccagaagct | 1920 |
| gctctccact | tgctttaggc | agagtcagtc | acttttcttc | tagattccaa | agtgcctgat | 1980 |
| ccacttggtt | gtggattcct | ggagcctagc | accacaccag | aagcacgagg | ccctggagaa | 2040 |
| ctgtgtgttg | agtgaactaa | taactgtatt | atagaaagca | taatgaaaat | gtcctgtgac | 2100 |

-continued

```
tgaagtatgt gtagcttgtt gcaggagtca caggaaagtt gactaggatt gagtgtgttg    2160
ggctttgggt ataaggagg gggattctac gggggcagta gctcaacaag gaatagaggg    2220
aggagtgtaa ttttggtagc tggtgttgaa tagggccttt gagaatcaga ctgaacacag    2280
tgaaatatgt gcccaaagtt cagaaagatg aagtttccag aaactaagaa ggtagcacaa    2340
tatgtggcat catactcaga aaggaagacc atgccatggg gccagaaatt cagaaacgta    2400
attcttacat tgtgattgca atggatactc atgaaagaaa gtgggtagtg gccgatttgc    2460
cttcagagtg acaggtagag aagggaagag cgtgtagaac tgtggccata ctttaggagt    2520
gtgagggatg ctgaatctcc cagagagctc acactggcca ggaatgctga gagtagcaga    2580 tgctttctt ttgggaggat agtaaaacaa tttagaacca gatatgcttt gtcttgattc    2640
tcaagtagaa taatcttcaa atgcaaaaga atacattaga aatggacaaa agtggccagg    2700
agcggtagct catacttgta acccagcact ttgggaagcc gaggcgggct gatcgcttga    2760
ggtcaggagt tcgagaccag cctggccaaa atagtgaaac tcacgtttct actaaaaata    2820
caaaaattag ctgggtgtga tggccacttg ggaggctgag ataggagaat cgcttgaacc    2880
tgggaggcag aggttgcagt gagccaatat cgtgccactg cattccagcc tgggtgacag    2940
aatgaaactc catcactcca tctcaaaaaa aaaaaaaaaa aaaaaaaaa               2990
```

<210> SEQ ID NO 53
<211> LENGTH: 424
<212> TYPE: PRT
<213> ORGANISM: Homo sapiens

<400> SEQUENCE: 53

```
Met Glu Val Cys Tyr Gln Leu Pro Val Leu Pro Leu Asp Arg Pro Val
1               5                   10                  15

Pro Gln His Val Leu Ser Arg Arg Gly Ala Ile Ser Phe Ser Ser Ser
            20                  25                  30

Ser Ala Leu Phe Gly Cys Pro Asn Pro Arg Gln Leu Ser Gln Arg Arg
        35                  40                  45

Gly Ala Ile Ser Tyr Asp Ser Ser Asp Gln Thr Ala Leu Tyr Ile Arg
    50                  55                  60

Met Leu Gly Asp Val Arg Val Arg Ser Arg Ala Gly Phe Glu Ser Glu
65                  70                  75                  80

Arg Arg Gly Ser His Pro Tyr Ile Asp Phe Arg Ile Phe His Ser Gln
                85                  90                  95

Ser Glu Ile Glu Val Ser Val Ser Ala Arg Asn Ile Arg Arg Leu Leu
            100                 105                 110

Ser Phe Gln Arg Tyr Leu Arg Ser Ser Arg Phe Phe Arg Gly Thr Ala
        115                 120                 125

Val Ser Asn Ser Leu Asn Ile Leu Asp Asp Tyr Asn Gly Gln Ala
    130                 135                 140

Lys Cys Met Leu Glu Lys Val Gly Asn Trp Asn Phe Asp Ile Phe Leu
145                 150                 155                 160

Phe Asp Arg Leu Thr Asn Gly Asn Ser Leu Val Ser Leu Thr Phe His
                165                 170                 175

Leu Phe Ser Leu His Gly Leu Ile Glu Tyr Phe His Leu Asp Met Met
            180                 185                 190

Lys Leu Arg Arg Phe Leu Val Met Ile Gln Glu Asp Tyr His Ser Gln
        195                 200                 205

Asn Pro Tyr His Asn Ala Val His Ala Ala Asp Val Thr Gln Ala Met
    210                 215                 220
```

```
His Cys Tyr Leu Lys Glu Pro Lys Leu Ala Asn Ser Val Thr Pro Trp
225                 230                 235                 240

Asp Ile Leu Leu Ser Leu Ile Ala Ala Ala Thr His Asp Leu Asp His
                245                 250                 255

Pro Gly Val Asn Gln Pro Phe Leu Ile Lys Thr Asn His Tyr Leu Ala
            260                 265                 270

Thr Leu Tyr Lys Asn Thr Ser Val Leu Glu Asn His His Trp Arg Ser
        275                 280                 285

Ala Val Gly Leu Leu Arg Glu Ser Gly Leu Phe Ser His Leu Pro Leu
290                 295                 300

Glu Ser Arg Gln Gln Met Glu Thr Gln Ile Gly Ala Leu Ile Leu Ala
305                 310                 315                 320

Thr Asp Ile Ser Arg Gln Asn Glu Tyr Leu Ser Leu Phe Arg Ser His
                325                 330                 335

Leu Asp Arg Gly Asp Leu Cys Leu Glu Asp Thr Arg His Arg His Leu
            340                 345                 350

Val Leu Gln Met Ala Leu Lys Cys Ala Asp Ile Cys Asn Pro Cys Arg
        355                 360                 365

Thr Trp Glu Leu Ser Lys Gln Trp Ser Glu Lys Val Thr Glu Glu Phe
370                 375                 380

Phe His Gln Gly Asp Ile Glu Lys Lys Tyr His Leu Gly Val Ser Pro
385                 390                 395                 400

Leu Cys Asp Arg His Thr Glu Ser Ile Ala Asn Ile Gln Ile Gly Asn
                405                 410                 415

Tyr Thr Tyr Leu Asp Ile Ala Gly
            420

<210> SEQ ID NO 54
<211> LENGTH: 97
<212> TYPE: PRT
<213> ORGANISM: Mus musculus

<400> SEQUENCE: 54

Ala Glu Ile Cys Ser Val Phe Leu Leu Asp Gln Asn Glu Leu Val Ala
1               5                   10                  15

Lys Val Phe Asp Gly Val Val Asp Asp Glu Ser Tyr Glu Ile Arg
            20                  25                  30

Ile Pro Ala Asp Gln Gly Ile Ala Gly His Val Ala Thr Thr Gly Gln
        35                  40                  45

Ile Leu Asn Ile Pro Asp Ala Tyr Ala His Pro Leu Phe Tyr Arg Gly
    50                  55                  60

Val Asp Asp Ser Thr Gly Phe Arg Thr Arg Asn Ile Leu Cys Phe Pro
65                  70                  75                  80

Ile Lys Asn Glu Asn Gln Glu Val Ile Gly Val Ala Glu Leu Val Asn
                85                  90                  95

Lys

<210> SEQ ID NO 55
<211> LENGTH: 97
<212> TYPE: PRT
<213> ORGANISM: Homo sapiens

<400> SEQUENCE: 55

Ala Glu Ile Cys Ser Val Phe Leu Leu Asp Gln Asn Glu Leu Val Ala
1               5                   10                  15
```

```
Lys Val Phe Asp Gly Val Val Asp Glu Ser Tyr Glu Ile Arg
            20                  25                  30

Ile Pro Ala Asp Gln Gly Ile Ala Gly His Val Ala Thr Gly Gln
            35                  40                  45

Ile Leu Asn Ile Pro Asp Ala Tyr Ala His Pro Leu Phe Tyr Arg Gly
 50                  55                  60

Val Asp Ser Thr Gly Phe Arg Thr Arg Asn Ile Leu Cys Phe Pro
 65                  70                  75                  80

Ile Lys Asn Glu Asn Gln Glu Val Ile Gly Val Ala Glu Leu Val Asn
                 85                  90                  95

Lys

<210> SEQ ID NO 56
<211> LENGTH: 89
<212> TYPE: PRT
<213> ORGANISM: Trypanosoma brucei

<400> SEQUENCE: 56

Ser Ala Arg Cys Ser Leu Phe Leu Val Arg Gly Asp Val Leu Glu Ala
 1               5                  10                  15

His Phe Glu Asp Gly Asn Val Val Thr Ile Pro Arg Gly Ala Gly Ile
                 20                  25                  30

Ala Gly Tyr Val Ala Gln Thr Gly Glu Thr Val Asn Ile Val Asp Ala
            35                  40                  45

Tyr Ala Asp Asp Arg Phe Asn Arg Glu Val Asp Lys Ala Thr Gly Tyr
 50                  55                  60

Arg Thr Lys Thr Ile Leu Cys Met Pro Val Met Tyr Glu Gly Thr Ile
 65                  70                  75                  80

Val Ala Val Ala Gln Leu Ile Asn Lys
                 85

<210> SEQ ID NO 57
<211> LENGTH: 106
<212> TYPE: PRT
<213> ORGANISM: Homo sapiens

<400> SEQUENCE: 57

Ala Asp Arg Tyr Ser Leu Phe Leu Val Cys Glu Asp Ser Ser Asn Asp
 1               5                  10                  15

Lys Phe Leu Ile Ser Arg Leu Phe Asp Val Ala Glu Gly Ser Thr Leu
                 20                  25                  30

Glu Glu Val Ser Asn Asn Cys Ile Arg Leu Glu Trp Asn Lys Gly Ile
            35                  40                  45

Val Gly His Val Ala Ala Leu Gly Glu Pro Leu Asn Ile Lys Asp Ala
 50                  55                  60

Tyr Glu Asp Pro Arg Phe Asn Ala Glu Val Asp Gln Ile Thr Gly Tyr
 65                  70                  75                  80

Lys Thr Gln Ser Ile Leu Cys Met Pro Ile Lys Asn His Arg Glu Glu
                 85                  90                  95

Val Val Gly Val Ala Gln Ala Ile Asn Lys
                100                 105

<210> SEQ ID NO 58
<211> LENGTH: 104
<212> TYPE: PRT
<213> ORGANISM: Homo sapiens

<400> SEQUENCE: 58
```

```
Ala Asp Arg Cys Ala Leu Phe Gln Val Asp His Lys Asn Lys Glu Leu
1               5                   10                  15

Tyr Ser Asp Leu Phe Asp Ile Gly Glu Glu Lys Glu Gly Lys Pro Val
            20                  25                  30

Phe Lys Lys Thr Lys Glu Ile Arg Phe Ser Ile Glu Lys Gly Ile Ala
                35                  40                  45

Gly Gln Val Ala Arg Thr Gly Glu Val Leu Asn Ile Pro Asp Ala Tyr
50                  55                  60

Ala Asp Pro Arg Phe Asn Arg Glu Val Asp Leu Tyr Thr Gly Tyr Thr
65                  70                  75                  80

Thr Arg Asn Ile Leu Cys Met Pro Ile Val Ser Arg Gly Ser Val Ile
                85                  90                  95

Gly Val Val Gln Met Val Asn Lys
            100

<210> SEQ ID NO 59
<211> LENGTH: 94
<212> TYPE: PRT
<213> ORGANISM: Trypanosoma brucei

<400> SEQUENCE: 59

Ala Asp Arg Ser Thr Leu Phe Leu Val Asp Lys Glu Arg Asn Glu Leu
1               5                   10                  15

Cys Ser Arg Met Ala Asp Ser Val Ala Gly Lys Glu Ile Arg Phe Pro
            20                  25                  30

Cys Gly Gln Gly Ile Ala Gly Thr Val Ala Ala Ser Gly Val Gly Glu
                35                  40                  45

Asn Ile Gln Asp Ala Tyr Gln Asp Pro Arg Phe Asn Arg Glu Val Asp
50                  55                  60

Lys Gln Leu Gly Tyr Arg Thr Gln Thr Ile Leu Cys Glu Pro Ile Ile
65                  70                  75                  80

Leu Asn Gly Glu Ile Leu Ala Val Val Gln Leu Val Asn Lys
                85                  90

<210> SEQ ID NO 60
<211> LENGTH: 69
<212> TYPE: PRT
<213> ORGANISM: Trypanosoma brucei

<400> SEQUENCE: 60

Ala Asp Tyr Cys Tyr Cys Phe Phe Cys Leu Leu Asn Asp Val Pro Tyr
1               5                   10                  15

Ser Ile Cys Cys Tyr Leu Ala Phe Ala Arg Gly Leu Gln Asp Asp Pro
            20                  25                  30

Arg Phe Asn Arg Glu Val Asp Lys Gln Leu Gly Tyr Arg Thr Gln Ala
                35                  40                  45

Ile Leu Cys Glu Pro Ile Ile Leu Asn Gly Glu Ile Leu Ala Val Val
    50                  55                  60

Gln Leu Val Asn Lys
65

<210> SEQ ID NO 61
<211> LENGTH: 110
<212> TYPE: PRT
<213> ORGANISM: Homo sapiens

<400> SEQUENCE: 61
```

-continued

```
Val Gln Lys Cys Thr Ile Phe Ile Val Asp Glu Asp Cys Ser Asp Ser
1               5               10              15
Phe Ser Ser Val Phe His Met Glu Cys Glu Glu Leu Glu Lys Ser Ser
                20              25              30
Asp Thr Leu Thr Arg Glu His Asp Ala Asn Lys Ile Asn Tyr Met Tyr
            35              40              45
Ala Gln Tyr Val Lys Asn Thr Met Glu Pro Leu Asn Ile Pro Asp Val
        50              55              60
Ser Lys Asp Lys Arg Phe Pro Trp Thr Thr Glu Asn Thr Gly Asn Val
65              70              75              80
Asn Gln Gln Cys Ile Arg Ser Leu Leu Cys Thr Pro Ile Lys Asn Gly
                85              90              95
Lys Lys Asn Lys Val Ile Gly Val Cys Gln Leu Val Asn Lys
                100             105             110
```

PDES AND USES THEREOF

This application is based on provisional applications, U.S. Ser. No. 60/232,445, filed Sep. 12, 2000, and 60/240,500, filed Oct. 12, 2000, the contents of which are hereby incorporated by reference, in their entirety, into this application.

This work was supported by a Research Grant from the National Institute of Health DK21723 and GMO7750.

Throughout this application various publications are referenced. The disclosures of these publications in their entireties are hereby incorporated by reference into this application in order to more fully describe the state of the art to which this invention pertains.

FIELD OF THE INVENTION

This invention relates to novel amino acid and nucleic acid sequences of novel cyclic nucleotide phosphodiesterases (PDEs) that are involved in T cell activation or from *Trypanosome brucei*. The invention further relates to the use of these sequences in the diagnosis and treatment of immune disorders. The invention also relates to development of specific inhibitors as target of T-cell mediated or modulated diseases, and/or antiprotozoal agents.

BACKGROUND OF THE INVENTION

The second messengers cAMP and cGMP play important roles in mediating the biological effects of a wide variety of first messengers such as transducing a variety of extracellular signals, including hormones, light, and neurotransmitters. The intracellular levels of cAMP and cGMP are controlled by their rates of synthesis by cyclases and their rate of degradation by phosphodiestrases (PDEs).

Multiple families of PDEs have been identified (Beavo, J. A. (1995) *Physiol. Rev.* 75, 725–748; Soderling, S. H., Bayuga, S. J., Beavo, J. A. (1998) *J. Biol. Chem.* 273, 15553–15558; Fisher, D. A., Smith, J. F., Pillar, J. S., St. Denis, S. H., Cheng, J. B. (1998) *J. Biol. Chem.* 273, 15559–15564). Most of these families contain distinct genes, many of which are expressed in different tissues as alternative splice variants. Each PDE family has multiple isozymes and multiple splice variants displaying characteristic kinetic and regulatory properties, sequence homologies, and inhibitor profiles. Several lines of evidence have established an important role for PDEs in a wide variety of physiological processes. Genetic studies have indicated that different PDEs regulate such processes as learning and memory (Kauvar, L. M. (1982) *J. Neurosci.* 2, 1347–1358), development (Shaulsky, G., Escalante, R., Loomis, W. F. (1996) *Proc. Natl. Acad. Sci. USA* 93, 15260–15265), and visual signal transduction (McLaughlin, M. E., Sandberg, M. A., Berson, E. L., Dryja, T. P. (1993) *Nat. Genet.* 4, 130–134). Molecular and pharmacological studies have suggested that PDEs regulate such disparate functions as platelet aggregation (Dickinson, N. T., Jang, E. K., Hasalam, R. J. (1997) *Biochem. J.* 323, 371–377), aldosterone production, (MacFarland, R. T., Zelus, B. D., Beavo, J. A. (1991) *J. Biol. Chem,* 266, 136–142), insulin secretion (Zhao, A. Z., Zhao, H., Teague, J., Fujimoto, W., Beavo, J. A. (1997) *Proc. Natl. Acad Sci. USA* 942, 3223–3228), and olfactory signal transduction (Yan, C., Zhao, A. Z., Bentley, J. K., Loughney, K., Ferguson, K., Beavo, J. A. (1995) *Proc. Natl. Acad. Sci. USA* 92, 9677–9681).

PDEs are typically composed of a catalytic domain (approximately 270 amino acids), an N-terminal regulatory domain responsible for binding cofactors, and, in some cases, a C-terminal domain of unknown function. A conserved motif, HDXXIHXGXXN (SEQ ID NO.: 47), has been found in the catalytic domain of all PDEs. PDE families display roughly 35% amino acid homology within their catalytic domain. Isozymes within the same family typically display 75–95% homology in this region. Within a family, there is often greater than 60% homology outside the catalytic domain, whereas across different PDE families, there is little or no sequence similarity.

A variety of diseases have been suggested to result from decreased levels of cyclic nucleotides based on increased PDE activity. For example, altered PDE3 has been associated with cardiac disease (Smith, C. J., Huang, R., Sun, D., Ricketts, S., Hoegler, C., Ding, J. Z., Moggio, R. A., Hintze, T. H. (1997) *Circulation* 96, 3116–23). A form of diabetes insipidus in the mouse has been associated with increased PDE4 activity (Dousa, T. P. (1999) *Kidney Int.* 55, 29–62). Furthermore, defects in PDE6 have also been associated with retinal disease, such as retinal degeneration in mouse (Tsung, S. H., Gouras, P., Yamashita, C. K., Kjeldbye, H., Fisher, J., Farber, D. B., Goff, S. P. (1996) *Science* 272, 1026–9), autosomal recessive retinitis in humans (Baiget, M., Calaf, M., Valverde, D., del Rio, E., Reig, C., Carballo, M., Calvo, M. T., Gonzales-Duarte, R. (1998) *Med. Clin.* 111, 420–422), and rod/cone dysplasia in some dogs (Dekomien, G., Epplen, J. T. (2000) *Anim. Genet.* 31, 135–139).

PDEs have also been reported to effect cellular proliferation of a number of cell types and have been implicated in various types of cancer (Lerner, A., Kim, D. H., Lee, R. (2000) *Leuk. Lymphoma* 37, 39–51; Kim, D. H., Learner, A. (1998) *Blood* 92, 2484–94). Several of the PDEs, specifically, PDEs 3, 4 (Ekholm, D., Hemmer, B., Gao, G., Vergelli, M., Martin, R., and Manganiello, V. (1997) *Journal Of Immunology* 159, 1520–1529; Erdogan, S. and Houslay, M. D. (1997) *Biochemical Journal* 321,) and 7 (Giembycz, M. A., Corrigan, C. J., Seybold, J., Newton, R., and Barnes, P. J. (1996) *Br J Pharmacol* 118, 1945–58) have been reported to be expressed in human T cells. It is known that activation of CD4$^+$ T cells requires stimulation of the CD3 receptor as well as costimulation of another receptor. Costimulation of the CD28 receptor leads to full activation of CD4$^+$ T cells (Shahinian, A., Pfeffer, K., Lee, K. P., Kundig, T. M., Kishihara, K., Wakeham, A., Kawai, K., Ohashi, P. S., Thompson, C. B., and Mak, T. W. (1993) *Science* 261, 609–612).

It has been shown that PDE7A is upregulated in CD4$^+$ T cells after CD3 and CD28 stimulation and that inhibition of PDE7A upregulation with an antisense oligo leads to inhibition of proliferation (Li, L., Yee, C., and Beavo, J. A. (1999) *Science* 283, 848–851). PDEs 3, 4 (Ekholm, D., Hemmer, B., Gao, G., Vergelli, M., Martin, R., and Manganiello, V. (1997) *Journal Of Immunology* 159, 1520–1529; Erdogan, S. and Houslay, M. D. (1997) *Biochemical Journal* 321) and 7 (Giembycz, M. A., Corrigan, C. J., Seybold, J., Newton, R., and Barnes, P. J. (1996) *Br J Pharmacol* 118, 1945–58) have been reported to be expressed in human T cells.

Furthermore, PDE4 inhibitors have been found to be potent inhibitors of T cell proliferation (Manning, C. D., Burman, M., Christensen, S. B., Cieslinski, L. B., Essayan, D. M., Grous, M., Torphy, T. J., and Barnette, M. S. (1999): *British Journal Of Pharmacology.* December 128, 1393–1398).

Additional forms of PDEs have been described in yeast (*Saccharomyces cerevisiae*) (Nikawa J. et al., Mol Cell Biol 1987; 7: 3629–36), the slime mold *Dictyostelium discoi-*

*deum* (Lacombe M. L. et al, J Biol Chem 1986; 261: 16811–7, *Vibrio fisheri* (Dunlap P. V. et al., J Bacteriol 1993; 175: 4615–24) and *Candida albicans* (Hoyer L. L. et al, Microbiology 1994; 140: 1533–42), that exhibit very little amino acid sequence identity with the previously described enzymes. These enzymes are currently designated as Class II PDEs, and likely have a different evolutionary origin, since, in contrast to all other eukaryotic PDEs, they have catalytic domains unlike those in mammalian Class I enzymes (Nikawa J. et al., Mol Cell Biol 1987; 7: 3629–36).

There is limited information about PDEs in trypanosomatids, a eukaryotic microorganism which causes the fatal human sleeping sickness (Vickerman, K. (1985) *Br. Med*-1. 41,105–114), as well as Nagana, a devastating disease of domestic animals in large parts of sub-Saharan Africa. Chemotherapy of human trypanosomiasis is in a dismal state (Seebeck, T. et al., (1999) Nova Act. *Leopold*. 78. 227–241). The cyclic nucleotide-specific PDEs may constitute a class of new drug targets.

cAMP signaling in trypanosomes is still largely unexplored (Naula, C. and Seebeck, T. (2000) *Parasitol.Today* 16, 35–38; Pays, .E. et al., (1997) In: *Trypanosomiasis and Leishmaniasis* (Hide, G., Mottra, W. C., Coombs, G. H., and Holmes, P. H. eds.), 199–225). cAMP is involved in the regulation of differentiation of bloodstream form trypanosomes from the proliferative "long slender" forms to the insect-preadapted, non-proliferative "short stumpy" forms (Vassella, E. et al., (1997) *J. Cell Sci.* 110, 2661–2671). Several gene families for adenylyl cyclases have been identified in *T. brucei* (Naula, C., and Seebeck,T. (2000) *Parasitol.Today* 16, 35–38; Alexandre, S. et al., (1996) *Mol Biochein. Parasitol.* 77, 173–182; Alexandre, S. et al., (1990) *Mol. Biochem. Parasitol.* 43, 279–288). Even less is known about the trypanosomal phosphodiesterases. An early study demonstrated PDE activity in cell lysates of the bloodstream form *T. brucei* (Walter, R. D., and Opperdoes, F. R. (1982) *Mol Biochem. Parasitol.* 6, 287–295), and experiments with PDE inhibitors suggested that interference with PDE activity might affect cell differentiation (Vassella, E. et al., (1997) *J. Cell Sci.* 110, 2661–2671; Reed, S. L. et al., (1985) *Infect. Immunol.* 49, 844–847).

SUMMARY OF THE INVENTION

The invention provides novel, isolated PDE proteins and nucleic acid molecules thereof, and methods for their uses. The nucleic acid molecules of the invention also include peptide nucleic acids (PNA), and antisense molecules that react with the nucleic acid molecules of the invention.

In one embodiment, the invention provides a full-length, novel T cell associated PDE, designated PDE8A, including the protein and polypeptide molecules, nucleic acid molecules and fragments thereof. The invention also provides another novel T cell associated PDE, designated PDE7A3, including the protein and polypeptide molecules, nucleic acid molecules and fragments thereof. Also included are novel PDEs from *Trypanosome brucei*, designated TbPDE2A, TbPDE2B, TbPDE2C, and TbPDE2E, including, the protein and polypeptide molecules, nucleic acid molecules and fragments thereof.

The present invention also encompasses various nucleotide sequences that represent different forms of the novel PDEs genes and transcripts, such as different allelic forms, polymorphic forms, alternative precursor transcripts, mature transcripts, and differentially spliced transcripts. Additionally, recombinant nucleic acid molecules that are codon usage variants of the novel PDEs sequences are provided.

The present invention includes the polynucleotides encoding novel PDEs in recombinant expression vectors and host-vector systems that include the expression vectors. One embodiment provides various host cells transformed with recombinant vectors that include the novel PDE sequences of the invention.

The present invention also provides recombinant nucleic acid molecules encoding fusion protein sequences. For example, the novel PDE portion of the fusion protein may be joined to a non-PDE protein sequence such as glutathione S-transferase (GST), or an immunoglobulin (Ig) domain.

The present invention further provides recombinant nucleic acid molecules encoding wild type or mutant sequences of novel PDE proteins, or fragments thereof having PDE biological activity.

The present invention provides methods for using isolated and substantially purified novel PDE nucleotide sequences as nucleic acid probes and primers, for using novel PDE polypeptides as antigens for the production of anti-novel PDE antibodies, and for using novel PDE polypeptides for obtaining and detecting novel PDE ligands. The novel PDE probes and primers, and the anti-novel PDE antibodies are useful in diagnostic assays and kits for the detection of naturally occurring novel PDE nucleotide sequences and novel PDE protein sequences present in biological samples.

The invention also relates to antisense molecules capable of reacting with the novel PDE nucleotide sequences of the invention, thereby disrupting expression of genomic novel PDE sequences. The invention also relates to agonists, antibodies, antagonists or inhibitors of the activity of the novel PDE proteins. These compositions are useful for the detection, prevention and/or treatment of conditions associated with the presence or the deficiency of the novel PDE proteins.

BRIEF DESCRIPTION OF THE FIGURES

FIG. 1A shows the complete nucleotide sequence (SEQ ID NO.: 1) and the protein sequence (SEQ ID NO.: 2) of PDE8A, including the N-terminal sequence.

FIG. 1B shows the N-terminal alignment of human (SEQ ID NO.: 3) and mouse PDE8A (SEQ ID NO.: 4) sequences.

FIG. 5A shows the PDE activity profile of a monoQ HPLC profile of hut78 cells using 1 μM of cAMP as a substrate, as described in Example 6, infra.

FIG. 5B shows the PDE activity profile using 0.01 μM cAMP as substrate (●) in the presence of 10 μM rolipram (▲) or 100 μM IBMX (□), as described in Example 6, infra.

FIG. 5C shows that the total PDE activity profile (measured at 0.01 μM cAMP). the PDE activity overlayed with the band intensities of PDE7A or PDE8A from the blots shown in the inset below, and is therefore contributed by both PDE7 and PDE8. PDE8A was blotted with two antibodies, P4G7 and PIL9, as described in Example 6, infra.

FIG. 6A shows that immunoprecipitated PDE8A activity from hut78 cells is inhibited by 100 μM IBMX, as described in Example 7, infra.

FIG. 6B shows that PDE8A activity in CD4+ T cells increases after stimulation with CD3 and CD28 antibodies, as described in Example 7, infra.

FIG. 7A shows that PDE activity of human PDE8A expressed in sf9 cells increases after digestion with trypsin for 2 min (■) or 10 min (▲), as described in Example 8, infra. The inset shows the increase in PDE activity of trypsin digested sf9 expressed human PDE8A by Western blot analysis using PDE8A specific monoclonal (P4G7) or polyclonal (PIL13) antibodies.

FIG. 7B shows that PDE activity of trypsin digested sf9-expressed PDE8A is sensitive to IBMX inhibition, as described in Example 8, infra.

FIG. 8A shows nucleotide sequence of a new splice variant, PDE7A3 (SEQ ID NO.: 5).

FIG. 8B shows amino acid sequence of PDE7A3 ((SEQ ID NO.: 6).

FIG. 9A shows alignment of PDE7A1 (SEQ ID NO.: 7) and PDE7A3 (SEQ ID NO. 8) C-termini, the numbering refers to PDE7A1 sequence.

FIG. 9B shows comparison of the splice variants of PDE7A.

FIG. 9C shows Northern blot analysis of PDE7A3.

FIG. 10A shows upregulation of PDEs 7A1, 7A3 and 8A in CD3+ T cells. The upper panel shows a time course of induction of PDE7A1, 7A3, 8A or G3PDH control; the middle panel shows the quantification of intensities of the bands shown in the upper panel, the lower panel shows RT-PCR of a time course using serially diluted cDNA (The numbers shown above the lanes indicate hours after stimulation).

FIG. 10B shows comparison of methods of preparation of CD4+ T cells. Cells were prepared using a) the CD4+ T cells isolation kit in combination with CD69 kit; b) a mixture of monoclonal antibodies (CD8, CD16, CD20, CD25, HLADr) and goat anti-mouse magnetic beads. cDNA was isolated at 1 hour or 16 hour after stimulation and PCR was performed for PDE7A1, PDE7A3, PDE8A, nad G3PDH.

FIG. 10C shows upregulation of PDE8A in in CD4+ T cells. Left panel shows PCR for PDE8A from cells harvested at 1 and 16 hour after stimulation using either CD3, CD28 or a combination of the monoclonal antibodies; right panel shows Western blot of cells harvested 16 hours after stimulation using PDE8A polyclonal antibody (PIL9).

FIG. 11 shows upregulation of PDE7A and PDE8A by Western blot analysis. A biotinylated monoclonal antibody (P5H7) and a strepavidin horseradish peroxidase conjugate were used for PDE7A blot; a monoclonal antibody (P4G7) and a goat-anti-mouse IgM-horseradish peroxidase conjugate was used for PDE5A blot; a polyclonal antibody (6976) to a C-terminal peptide of PDE7A3 and a goat-anti-rabbit IgG horseradish peroxidase conjugate were used for the PDE7A3 blots; a monoclonal antibody (P5H7) for PDE7A and a goat anti-mouse-kappa-horseradish peroxidase conjugate were used for the PDE7A blot which shows both PDE7A1 (upper band) and PDE7A3 (lower band).

FIG. 16 shows the complete gene (SEQ ID NO.: 9) and amino acid (SEQ ID NO.: 10) sequence of TbPDE2B. Boxed amino acid regions indicate domains identified by sequence similarity to known domains in other proteins. The asterisk indicates the stop codon. Underlined YHN and $HDX_2HX_4N$ motifs indicate PDE catalytic domain, as described in Example 11, infra.

FIG. 17 shows multiple sequence alignment of the TbPDE2B GAF domains (GAF A and GAF B) to the homologous regions of several other representative PDEs. The part of the total GAF domain defined by Hidden Markov Modeling search of the Simple Modular Architecture Research Tool (SMART) database is shown. These include the regions of sequence having highest similarity between enzymes. Alignments were initially done using Clustal W and refined based on visual alignment of the signature motif. Several additional gaps have been added to accommodate apparent additional peptide loops in some of the sequences. The columns marked with*indicate residues which bind cGM7P in the crystal structure of MMPDE2A. MMPDE2A-B (*Mus musculus* PDE2A) (SEQ ID NO.: 54), HSPDE2A-B (*Homo sapiens* PDE2A) (SEQ ID NO.: 55), TBPDE2B-A (*Trypanosoma brucei* PDE2B) (SEQ ID NO.: 56), TBPDE2B-B (*Trypanosoma brucei* PDE2B) (SEQ ID NO.: 59), TBPDE2A (*Trypanosoma brucei* PDE2A) (SEQ ID NO.: 60), HSPDE5A-A (*Homo sapiens* PDE5A, AF043731) (SEQ ID NO.: 57), HSPDE5A-B (*Homo sapiens* PDE5A) (SEQ ID NO.: 61), HSPDE10A (*Homo sapiens* PDE10A) (SEQ ID NO.: 58).

FIG. 19 shows *Saccharomyces cerevisiae* rescue of phenotype, as described in Example 11, infra. The *S. cerevisiae* heat shock sensitivity of cells lacking endogenous PDEs is rescued by a plasmid expressing TbPDE2B. JBS75 (PDE1 PDE2 containing p424), JBS67.2 (pde1 pde2 containing TbPDE2B on p424), and JBS67.1 (pde1 pde2 containing p424) were grown 2d at 30° C. on selective plates, replica plated to fresh selective plates and held at 55° C. or 30° C. for 1 hour before growing 2d at 30° C.

FIG. 21A shows the nucleotide sequence (SEQ ID NO.: 11) of TbPDE2A.

FIG. 21B shows the predicted amino acid sequence (SEQ ID NO.: 12) of TbPDE2A. Grey box: GAF domain. Filled squares denote amino acids predicted to be involved in cGMP binding. Open box: catalytic domain. Filled circles denote amino acids of the catalytic domain which are conserved in at least 12 out of 14 class I PDEs (TbPDE2A, mammalian PDE 1 (Acc Nr. U40372), PDE2 (U21 101), PDE3(M9]667), PDE4 (S75213), PDE5 (NM-00 1083), PDE6 (NM-000283), PDE7 (U6817 1), PDE8 (AF068247), PDE9 (AF031 147), PDEI 0 (A]7–127479), *Drosophila* dunce (PI22252), *S, cerevisiae* PDE2 (M14563) and *Dictyostelium* regA (U60170). Bold underlined amino acids (H269-Y281) represent the phosphodiesterase signature motif.

FIG. 22A shows the nucleotide sequence (SEQ ID NO.: 13) of TbPDE2C.

FIG. 22B shows the predicted amino acid sequence (SEQ ID NO.: 14) of TbPDE2C.

FIG. 23A shows the nucleotide sequence (SEQ ID NO.: 15) of TbPDE2E.

FIG. 23B shows the predicted amino acid sequence (SEQ ID NO.: 16) of TbPDE2E.

FIG. 30 shows a comparison of enzymatic parameters of recombinant TbPDE2A and TbPDE2C, as described in Example 13, infra.

FIG. 33 shows the nucleotide sequence (SEQ ID NO.: 48) and the amino acid sequence (SEQ ID NO.: 49) of a PDE8A variant.

FIG. 34 shows the nucleotide sequence (SEQ ID NO.: 50) and the amino acid sequence (SEQ ID NO.: 51) of another PDE8A variant.

FIG. 35 shows the nucleotide sequence (SEQ ID NO.: 52) and the amino acid sequence (SEQ ID NO.: 53) of a PDE7A3 variant.

DETAILED DESCRIPTION OF THE INVENTION

Definitions

Figure 2:
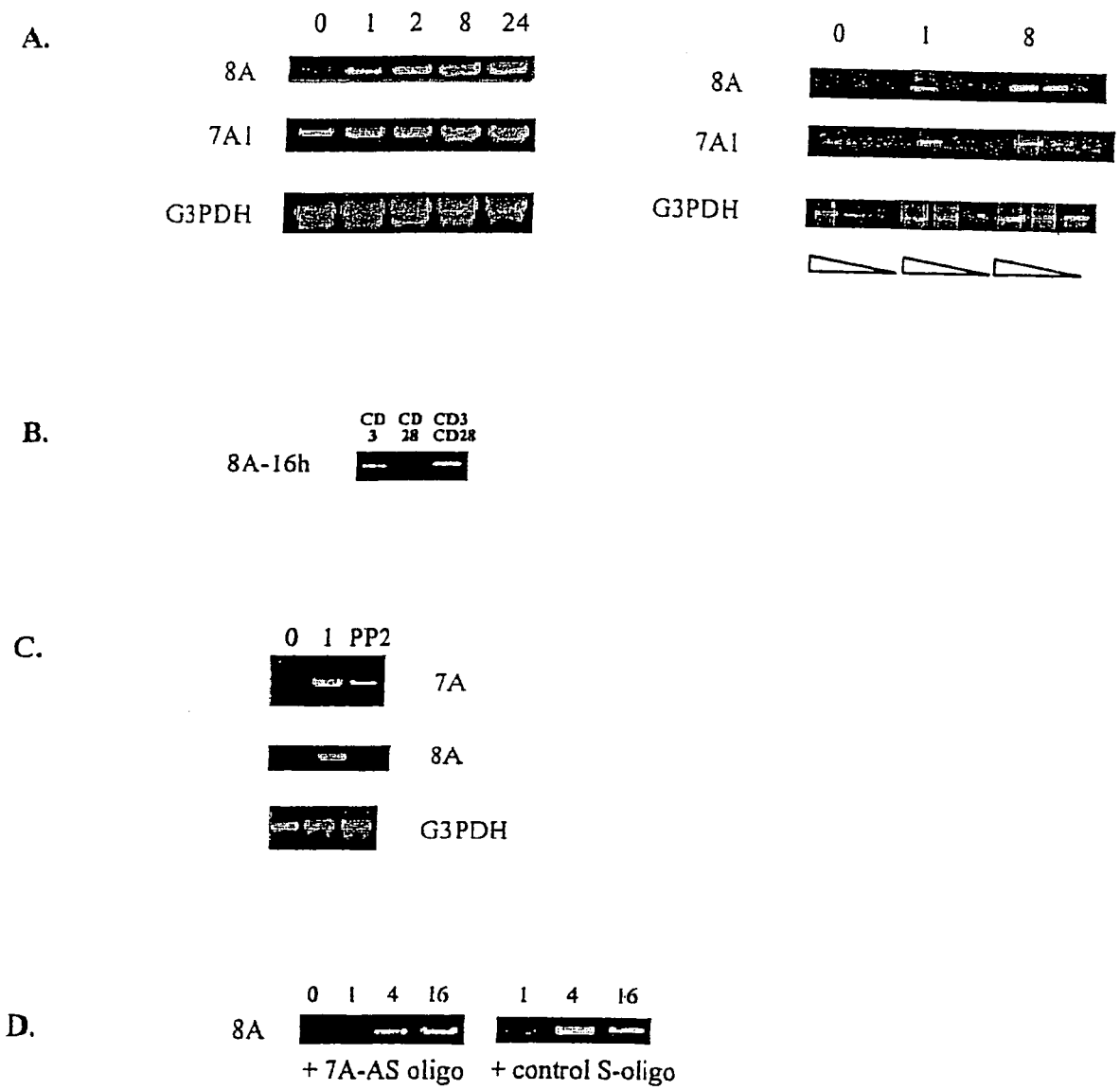
FIG. 2A shows the time course of induction of PDE7A and PDE8A as described in Example 3. The left panel is the time course of induction of PDE7A and PDE8A compared to a G3PDH control. The right panel shows RT-PCR of a time course using serially diluted cDNA.
FIG. 2B shows RT-PCR performed for PDE8A on 16 hour stimulated cells as described in example 3. The cells were stimulated with antibodies to either CD3, CD28, or a combination of the antibodies.
FIG. 2C shows the effect of an inhibitor of lck kinase (PP2) on upregulation of PDE7A and 8A, as described in Example 3, infra.
FIG. 2D shows the effects of a PDE7A-antisense S-oligo or a control S-oligo on PDE8A expression in CD4+ T cells at various times after CD3 and CD28 stimulation, as described in Example 3, infra.

As used in this application, the following words or phrases have the meanings specified.

As used herein, the term "novel PDEs" means any of PDE8A, PDE7A3, TbPDE2A, TbPDE2B, TbPDE2C or TbPDE2E.

As used herein, the term "PDE8", refers to the family of amino acid sequences of substantially purified PDE8 obtained from any species, particularly mammalian, including bovine, ovine, porcine, murine, equine, and preferably human, from any source whether natural, synthetic, semi-synthetic, or recombinant. Examples are shown in FIGS. 1a, 33, and 34. PDE8 encompasses variants or mutants (involving changes such as amino acid substitutions, insertions, deletions, conservative amino acid changes, polymorphic changes, allelic changes, alternative splicing, frame shift changes, or truncations) of the sequence of FIGS. 1a, 33, and 34.

Figure 35:
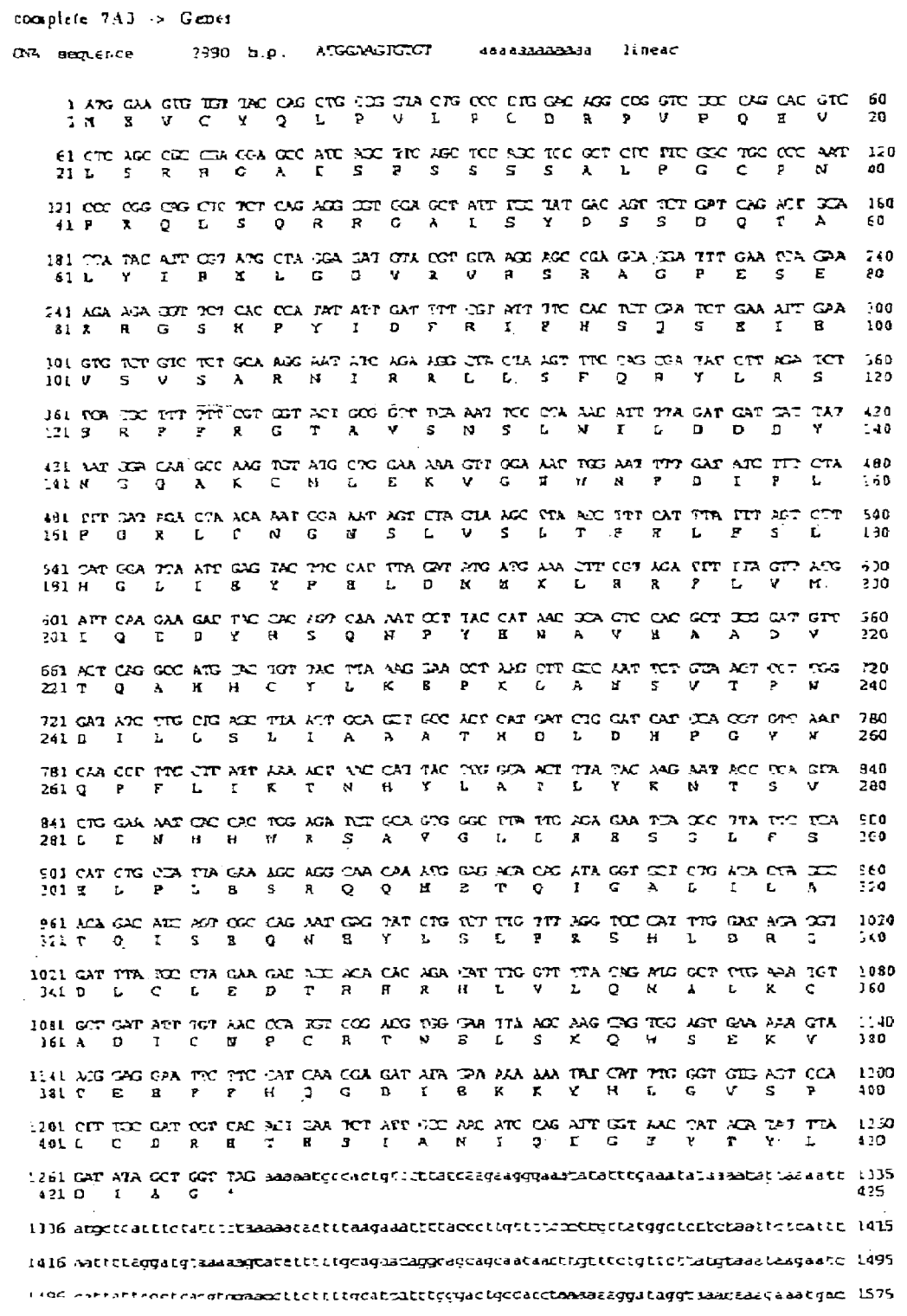
Figure 35:
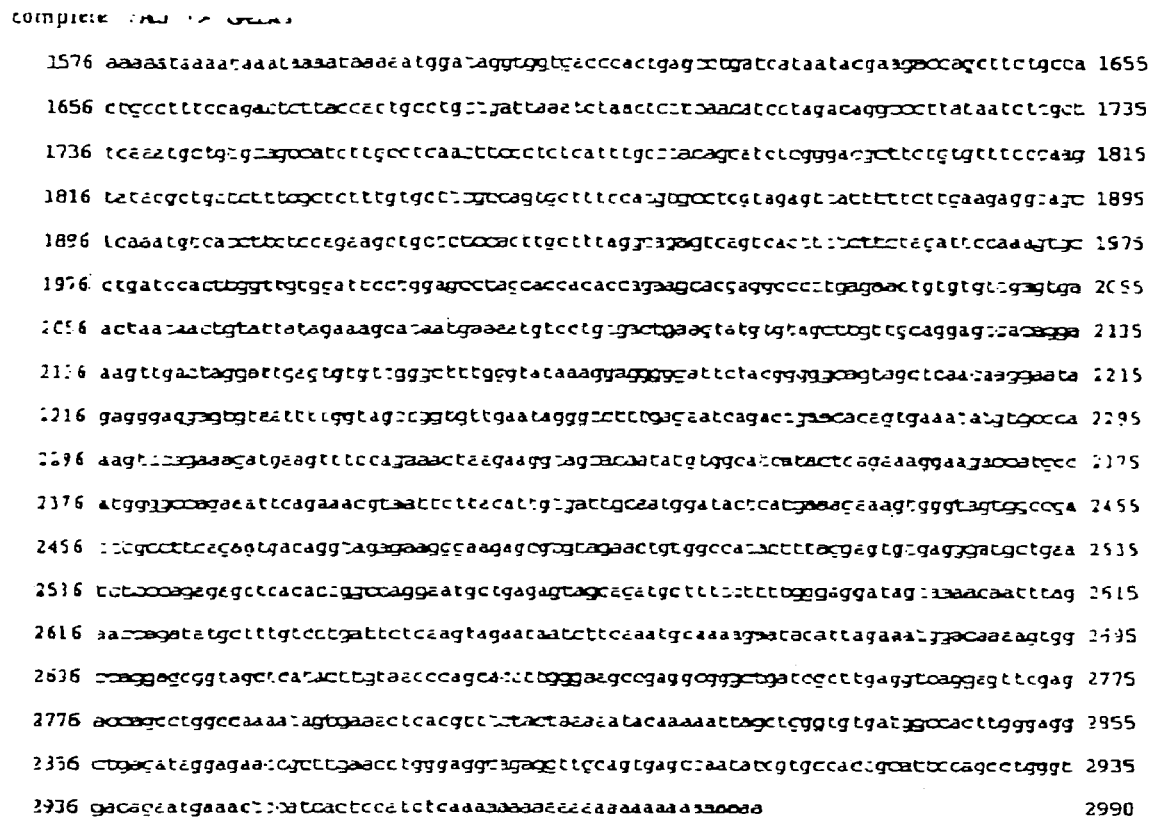

As used herein, the term "PDE7A3", refers to an alternatively spliced form of PDE7A. Substantially purified PDE7A3 can be obtained from any species, particularly mammalian, including bovine, ovine, porcine, murine, equine, and preferably human. PDE7A3 can be from any source whether natural, synthetic, semi-synthetic, or recombinant. Examples are shown in FIGS. 8b and 35. PDE7A3 encompasses variants or mutants (involving changes such as amino acid substitutions, insertions, deletions, conservative amino acid changes, polymorphic changes, allelic changes, alternative splicing, frame shift changes, or truncations) of FIGS. 8b and 35.

As used herein, the term "TbPDE2", refers to a family of amino acids sequences of substantially purified PDE2 from a protozoan species, e.g., *T. brucei*. The TbPDE2 can be natural, synthetic, semi-synthetic, or recombinant. Examples of TbPDE2 include but are not limited to TbPDE2A (FIG. 21B), TbPDE2B (FIG. 16), TbPDE2C (FIG. 22b) and TbPDE2E (FIG. 23B). TbPDE2 encompasses variants or mutants (involving changes such as amino acid substitutions, insertions, deletions, conservative amino acid changes, polymorphic changes, allelic changes, alternative splicing, frame shift changes, or truncations) of any of FIGS. 21B, 16, 22b, or 23B.

The terms "isolated" or "purified" as used herein mean a specific nucleic acid or polypeptide, or a fragment thereof, in which contaminants (i.e. substances that differ from the specific nucleic acid or polypeptide molecule) have been separated or substantially separated from the specific nucleic acid or polypeptide.

As used herein, a first nucleotide or amino acid sequence is said to have sequence "identity" to a second reference nucleotide or amino acid sequence, respectively, when a comparison of the first and the second sequences are exactly alike.

As used herein, a first nucleotide or amino acid sequence is said to be "similar" to a second reference sequence when both the first and second sequences are nearly identical, but have a low level of sequence differences. For example, two sequences are considered to be similar to each other when the percentage of nucleotides or amino acids that differ between the two sequences is between about 60% to 99.99%.

The term "fragment" of a PDE8-, PDE7A3-, or TbPDE2A/2B/2C/2E-encoding nucleic acid molecule refers to a portion of a nucleotide sequence which encodes a polypeptide having the biological activity of a PDE8, PDE7A3 or TbPDE2A/2B/2C/2E protein, e.g., the ability to hydrolyze cAMP (as determined by methods known in the art (Schilling, A. L. et al., (1994) *Anal. Biochem.* 216: 154–158).

The term "fragment" of a PDE8, PDE7A3, or TbPDE2A/2B/2C/2E polypeptide molecule refers to a portion of a polypeptide having the biological activity of a PDE8, PDE7A3 or TbPDE2A/2B/2C/2E polypeptide, e.g., ability to hydrolyze cAMP (as determined by methods known in the art (Schilling, A. L. et al., (1994) *Anal. Biochem.* 216: 154–158).

As used herein, the term "amino acid sequence", refers to amino acids encoding an oligopeptide, peptide, polypeptide, or protein sequence, and fragments thereof, and includes naturally occurring or synthetic molecules.

As used herein, "amplification," refers to the production of additional copies of a nucleic acid sequence and is generally carried out using polymerase chain reaction (PCR) technologies well known in the art (Dieffenbach, C. W. and G. S. Dveksler (1995) PCR Primer, a Laboratory Manual, Cold Spring Harbor Press, Plainview, N.Y.).

As used herein, the term "antagonist," or "inhibitor," refers to a molecule which, when bound to a novel PDE (such as PDE8, PDE7A3, or TbPDE2A/2B/2C/2E), decreases the amount (expression) or the duration of the effect of the biological or immunological activity of the novel PDE. Antagonists may include proteins, nucleic acids, carbohydrates, antibodies or any other molecules which decrease the amount (expression) or effect of novel PDEs present in the sample. The preferred antagonist will selectively inhibit the biological activity of a novel PDE, not affecting any other cellular proteins.

As used herein, an agent is said to agonize or enhance novel PDE (e.g., PDE8, PDE7A3 or TbPDE2A/2B/2C/2E) activity when the agent increases the biological activity of a novel PDE protein of the invention. The preferred agonist will selectively enhance the biological activity of novel PDEs.

As used herein, the term "antibody," refers to intact molecules as well as fragments thereof, such as Fab, F(ab')$_2$ and Fv fragments, which are capable of binding an epitopic determinant on an antigen (e.g., an epitopic determinant(s) on a novel PDE). The antibody can be "polyclonal," "monoclonal," "humanized," or human.

The term "humanized antibody," as used herein, refers to antibody molecules in which amino acids have been replaced in the non-antigen binding regions in order to more closely resemble a human antibody, while still retaining the original binding ability.

As used herein, the term "antigenic determinant," refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

As used herein, the term "biologically active", refers to a protein having structural, regulatory, or biochemical functions of a naturally occurring molecule. Likewise, "immunologically active" refers to the capability of the natural, recombinant, or synthetic novel PDEs of the invention (e.g., PDE8A, PDE7A3 or TbPDE2A/2B/2C/2E), or any oligopeptide thereof, to induce a specific immune response in appropriate animals or cells and to bind with specific antibodies.

As used herein, the term "nucleic acid sequence," refers to an oligonucleotide, nucleotide, or polynucleotide, and fragments thereof, and to DNA or RNA of genomic or synthetic origin which may be single- or double-stranded, and represents the sense or antisense strand.

The term "complementary" as used herein refers to nucleic acid molecules having purine and pyrimidine nucleotides which have the capacity to associate through hydrogen bonding to form double stranded nucleic acid molecules. The following base pairs are related by complementarity: guanine and cytosine; adenine and thymine; and adenine and uracil. Complementary applies to all base pairs comprising two single-stranded nucleic acid molecules, or to all base pairs comprising a single-stranded nucleic acid molecule folded upon itself. Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands.

As used herein, the term "hybridization," refers to any process by which a strand of nucleic acid binds with a complementary strand through base pairing.

As used herein, the term "stringent conditions," refers to conditions which permit hybridization between polynucleotide sequences and the claimed polynucleotide sequences. Suitably stringent conditions can be defined by, for example, the concentrations of salt and/or formamide in the prehybridization and hybridization solutions, or by the hybridization temperature, and are well known in the art. In particular, stringency can be increased by reducing the concentration of salt, increasing the concentration of formamide, or raising the hybridization temperature.

As used herein, the term "antisense," refers to any composition containing nucleotide sequences which are complementary to a specific DNA or RNA sequence. The term "antisense strand" is used in reference to a nucleic acid strand that is complementary to the "sense" strand. Antisense molecules include nucleic acids and may be produced by any method including synthesis or transcription. Once introduced into a cell, the complementary nucleotides combine with natural sequences produced by the cell to form duplexes and block either transcription or translation of the sequences.

As used herein, the term "modulates," refers to a change in the activity of novel PDEs (e.g., PDE8, PDE7A3 or TbPDE2A/2B/2C/2E). For example, modulation may cause an increase or a decrease in protein amount or activity, binding characteristics, or any other biological, functional or immunological properties of novel PDEs of the invention.

As used herein, the term "biological sample," is used in its broadest sense. A biological sample is suspected of containing nucleic acid encoding novel PDEs (e.g., PDE8A, PDE7A3 or TbPDE2,A/2B/2C/2E), or fragments thereof, or a novel PDE (e.g., PDE8, PDE7A3 or TbPDE2A/2B/2C/2E) protein itself or fragments thereof. The suitable biological sample can be from an animal or a human. The sample can be a cell sample or a tissue sample, including samples from spleen, lymph node, thymus, bone marrow, liver, heart, testis, brain, placenta, lung, skeletal muscle, kidney and pancreas. The sample can be a biological fluid, including, urine, blood sera, blood plasma, phlegm, or lavage fluid. Alternatively, the sample can be a swab from the nose, ear or throat.

As used herein, the term "PAS/PAC domain," refers to a region in the N-terminal domain of PDEs that has homology to the PAS/PAC domain found in many signal transduction proteins. The function of this domain is unknown, but it may be involved in protein/protein binding or binding to a small molecule.

As used herein, the term "GAF domain," refers to a highly conserved domain that binds small molecular weight ligands. The GAF domain of some PDEs is known to bind cGMP.

The terms "specific binding," as used herein, refers to that interaction between a protein or peptide and an agonist, an antibody, or an antagonist. The interaction is dependent upon the presence of a particular structure (i.e., the antigenic determinant or epitope) of the protein recognized by the binding molecule.

The term "T cell activation," as used herein refers to a process by which T cells change from a resting state to one where they are proliferating and producing interleukins. In vivo, T cell activation occurs when an antigen-presenting cell (APC) binds to the T cell via the T cell receptor/CD3 complex and another costimulatory molecule, such as CD28. In vitro, T cell induction can be induced by binding anti-mouse antibodies beads to a plate. When antibodies to murine anti-CD3 and anti-CD28 antibodies are added to the plate, they bind to the anti-mouse antibodies by their Fc regions. This leaves the Fab region free to bind CD3 and CD28 receptors on T cells. When T cells are added to the plate, they bind to the antibodies attached to the bottom of the plate and become activated, resulting in T cell proliferation and production of interleukins. The plate with attached antibodies approximates an APC which has receptors that bind to CD3 and CD28.

The term "upregulation," refers to the fact that in resting T cells, there is no detectable PDE8A or PDE7A3 protein or mRNA present. After induction of T cells with CD3 and CD28 antibodies, a time dependent increase in PDE8A or PDE7A3 mRNA and protein is seen, which reaches a maximum level at about 8 hours after stimulation.

Molecules of the Invention

In its various aspects, as described in detail below, the present invention provides proteins, peptides, antibodies, nucleic acid molecules, recombinant DNA molecules, transformed host cells, methods for making the compositions of the invention, screening and diagnostic assays, therapeutic methods, transgenic animals, immunological and nucleic acid-based pharmaceutical or therapeutic assays, and compositions, all involving a novel PDEs or nucleic acids encoding them.

For the sake of convenience, the nucleotide sequences of novel PDEs (e.g., PDE8A, PDE7A3, TbPDE2A, TbPDE2B, TbPDE2C, and TbPDE2E) will be collectively referred to as "novel PDE nucleotides". Additionally, the proteins encoded by the novel PDE nucleotide sequences will be collectively referred to as "novel PDE proteins" and will include any or all of PDE8A, PDE7A3, and TbPDE2A/2B/2C/2E.

Nucleic Acid Molecules of this Invention

The present invention discloses the discovery of nucleic acid molecules herein termed as "novel PDEs " or "novel PDE nucleotide" sequences, that encode novel PDE proteins and polypeptides. In one embodiment, the invention provides polynucleotide sequences (e.g., FIGS. 1a, 33 and 34) encoding PDE8A proteins. For example, the nucleic acid of PDE8 encodes the amino acid sequence beginning with methionine at amino acid position 1 and ending with glutamic acid at amino acid position 829 of any of FIGS. 1a, 33, or A specific embodiment of the nucleic acids of PDE8 is shown at FIG. 1a beginning at adenine at position 137 and ending with adenine at 2623.

In another embodiment, the invention provides polynucleotide sequence encoding a splice variant of PDE7, designated herein as PDE7A3 (FIG. 8A). For example, the nucleic acid of PDE7A3 encodes the amino acid sequence beginning with methionine at amino acid position 1 and ending with glycine at amino acid position 424 of any of FIGS. 8b or 35. A specific embodiment of the nucleic acids of PDE7A3 is shown at FIG. 8b beginning at adenine at position 1 and ending with thymine at 12.

Figure 16:
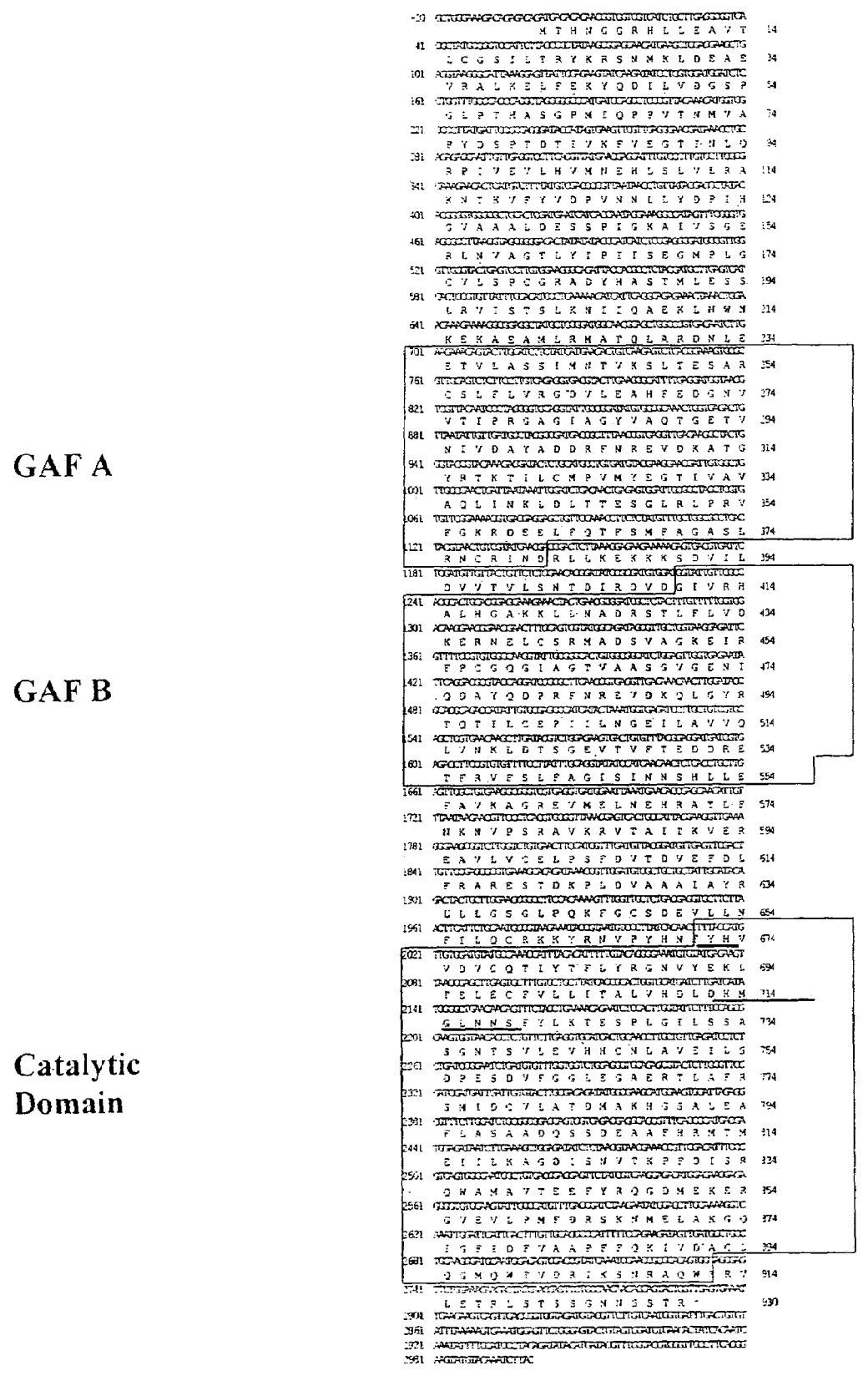

In another embodiment, the invention provides novel PDEs from T. brucei, designated herein as TbPDE2A, TbPDE2B, TbPDE2C, and TbPDE2E (TbPDE2A/2B/2C/2E). For example, the nucleic acid of TbPDE2A encodes the amino acid sequence set forth in FIG. 21b beginning with methionine at amino acid position 1 and ending with serine at amino acid position 485; the nucleic acid of TbPDE2B encodes the amino acid sequence set forth in FIG. 16 beginning with methionine at amino acid position 1 and ending with arginine at amino acid position 930; the nucleic acid of TbPDE2C encodes the amino acid sequence set forth in FIG. 22B beginning with methionine at amino acid position 1 and ending with arginine at amino acid position 930; the nucleic acid of TbPDE2E encodes the amino acid sequence set forth in FIG. 23B beginning with methionine at amino acid position 1 and ending with arginine at amino acid position 367. A specific embodiment of the nucleic acids of TbPDE2A is shown in FIG. 21a beginning at adenine at position 1 and ending with thymine at 1455. A specific embodiment of the nucleic acids of TbPDE2B is shown at FIG. 16 beginning at adenine at position 1 and ending with thymine at 2790. A specific embodiment of the nucleic acids of TbPDE2C is shown at FIG. 22a beginning at adenine at position 1 and ending with thymine at 2790. A specific embodiment of the nucleic acids of TbPDE2E is shown in FIG. 23a beginning at adenine at position 1 and ending with thymine at 1101.

The present invention further provides novel purified and isolated polynucleotides (DNA sequences and fragments thereof, preferably in isolated form, including DNA, RNA transcripts, both sense and complementary antisense strands, encoding novel PDE protein molecules (e.g., PDE8A, PDE7A3, and TbPDE2A/2B/2C/2E), DNA/RNA hybrids, and related molecules. Particularly preferred nucleic acid molecules will have nucleotide sequence substantially identical to or complementary to novel PDE nucleotide sequences herein disclosed. Specifically contemplated are genomic, cDNA, ribozymes, and antisense molecules, as well as nucleic acids based on alternative backbone or including alternative bases, whether derived from natural sources or wholly or partially synthesized. "Wholly" synthesized DNA means that the DNA is produced entirely by chemical means, and "partially" synthesized means that only portions of the resulting DNA were produced by chemical synthesis. Antisense molecules can be RNAs or other molecules, including peptide nucleic acids (PNAs) or non-nucleic acid molecules such as phosphorothioate derivatives that specifically bind DNA or RNA in a base-pair dependent manner. A skilled artisan can readily obtain these classes of nucleic acid molecules using the herein described sequences.

The nucleic acid molecules of the present invention comprise nucleic acid sequences corresponding to differentially spliced transcripts of novel PDEs. In general, a differentially-spliced transcript is a mature RNA transcript that is generated in a cell by the following steps: (1) the cell transcribes precursor RNA transcripts from an intron-containing gene, where the precursor RNA transcripts include all the intron sequences; (2) the cell splices out different introns from different precursor transcripts, resulting in a heterogeneous population of mature RNA transcripts each having different introns; (3) the cell translates some or all of the differentially-spliced transcripts to generate a heterogeneous population of proteins which are encoded by the same intron-containing gene sequence. Thus, a cell may produce a heterogeneous population of novel PDE RNA transcripts that are related to each other as a result of differential splicing of a common precursor transcript. Furthermore, the novel PDE proteins that are translated from the differentially spliced transcripts may have different biological activities.

The present invention further provides nucleotide sequences that selectively hybridize to novel PDE nucleotide sequences (shown in FIGS. 1, 8A, 16, 21A, 22A, and 23A) under high stringency hybridization conditions. Typically, hybridization under standard high stringency conditions will occur between two complementary nucleic acid molecules that differ in sequence complementarity by about 70% to about 100%. It is readily apparent to one skilled in the art that the high stringency hybridization between nucleic acid molecules depends upon, for example, the degree of identity, the stringency of hybridization, and the length of hybridizing strands. The methods and formulas for conducting high stringency hybridizations are well known in the art, and can be found in, for example, Sambrook, et al., *Molecular Cloning* (1989).

In general, stringent hybridization conditions are those that: (1) employ low ionic strength and high temperature for washing, for example, 0.015M NaCl/0.0015M sodium citrate/0.1% SDS at 50° C.; or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

Another example of stringent conditions is the use of 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 mg/ml), 0.1% SDS, and 10% dextran sulfate at 42° C., with washes at 42° C. in 0.2×SSC and 0.1% SDS. A skilled artisan can readily determine and vary the stringency conditions appropriately to obtain a clear and detectable hybridization signal.

The present invention contemplates alternative allelic forms of novel PDE nucleotide sequences that are isolated from different subjects of the same species. Typically, isolated allelic forms of naturally-occurring gene sequences include wild-type and mutant alleles. A wild-type novel PDE gene sequence will encode a novel PDE protein having normal PDE biological activity, such as, for example, a phosphodiesterase function or an immune function. A mutant of novel PDE gene sequence may encode a PDE protein having an activity not found normally in novel PDE proteins, such as, for example, not functioning as a phosphodiesterase. Alternatively, a mutant of a novel PDE gene sequence may encode a PDE protein having normal activity. Accordingly, the present invention provides wild-type and mutant allelic forms of novel PDE sequences.

The present invention further contemplates polymorphic forms of novel PDE nucleotide sequences. Typically, isolated polymorphic forms of naturally-occurring gene sequences are isolated from different subjects of the same species. The polymorphic forms include sequences having one or more nucleotide substitutions that may or may not result in changes in the amino acid codon sequence. These substitutions may result in a wild-type novel PDE gene that encodes a protein having the biological activity of wild-type novel PDE proteins, or encodes a mutant polymorphic form of the novel PDE protein having a different or null activity.

The present invention provides isolated codon-usage variants that differ from the disclosed novel PDE nucleotide sequences, yet do not alter the predicted novel PDE polypeptide sequence or biological activity. The codon-usage variants may be generated by recombinant DNA technology. Codons may be selected to optimize the level of production of the novel PDE transcript or novel PDE polypeptide in a particular prokaryotic or eukaryotic expression host, in accordance with the frequency of codon utilized by the host cell. Alternative reasons for altering the nucleotide sequence encoding a novel PDE polypeptide include the production of RNA transcripts having more desirable properties, such as an extended half-life or increased stability.

| Amino Acid | Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The present invention provides nucleic acid molecules that encode novel PDE proteins. In particular, the RNA molecules of the invention may be isolated full-length or partial mRNA molecules or RNA oligomers that encode the novel PDE proteins.

The nucleic acid molecules of the invention also include derivative nucleic acid molecules which differ from DNA or RNA molecules, and anti-sense molecules. Derivative molecules include peptide nucleic acids (PNAs), and non-nucleic acid molecules including phosphorothioate, phosphotriester, phosphoramidate, and methylphosphonate molecules, that bind to single-stranded DNA or RNA in a base pair-dependent manner (Zamecnik, P. C., et al., (1978) *Proc. Natl. Acad. Sci.* 75:280284; Goodchild, P. C., et al., (1986) *Proc. Natl. Acad. Sci.* 83:4143–4146). Peptide nucleic acid molecules comprise a nucleic acid oligomer to which an amino acid residue, such as lysine, and an amino group have been added. These small molecules, also designated anti-gene agents, stop transcript elongation by binding to their complementary (template) strand of nucleic acid (Nielsen, P. E., et al., (1993) *Anticancer Drug Des* 8:53–63). Reviews of methods for synthesis of DNA, RNA, and their analogues can be found in: *Oligonucleotides and Analogues*, eds. F. Eckstein, (1991) IRL Press, New York; *Oligonucleotide Synthesis*, ed. M. J. Gait, 1984, IRL Press, Oxford, England. Additionally, methods for antisense RNA technology are described in U.S. Pat. Nos. 5,194,428 and 5,110,802. A skilled artisan can readily obtain these classes of nucleic acid molecules using the herein described PDE8 polynucleotide sequences, see for example *Innovative and Perspectives in Solid Phase Synthesis* (1992) Egholm, et al. pp 325–328 or U.S. Pat. No. 5,539,082.

Embodiments of the novel PDE nucleic acid molecules of the invention include DNA and RNA primers, which allow the specific amplification of novel PDE sequences, or of any specific parts thereof, and probes that selectively or specifically hybridize to novel PDE sequences or to any part thereof. The nucleic acid probes can be labeled with a detectable marker. Examples of a detectable marker include, but are not limited to, a radioisotope, a fluorescent compound, a bioluminescent compound, a chemiluminescent compound, a metal chelator or an enzyme. Technologies for generating labeled DNA and RNA probes are well known, see, for example, Sambrook et al., in *Molecular Cloning* (1989).

Recombinant Nucleic Acid Molecules Encoding Novel PDEs

Also provided in this invention are recombinant nucleic acid molecules, such as recombinant DNA molecules (rDNAs) that contain nucleotide sequences encoding a novel PDE polypeptide (e.g., PDE8A, PDE6A3, TbPDE2A/2B/2C/2E) of the invention, or fragments thereof. As used herein, a rDNA molecule is a DNA molecule that has been subjected to molecular manipulation in vitro. Methods for generating rDNA molecules are well known in the art, for example, see Sambrook et al., *Molecular Cloning* (1989), supra. In the preferred rDNA molecules of the present invention, the sequences that encode a novel PDE protein or fragments thereof, are operably linked to one or more expression control sequences and/or vector sequences.

Vectors Comprising Novel PDEs

The nucleic acid molecules of this invention may be recombinant molecules, each comprising the sequence, or portion thereof, of novel PDE nucleotide sequence linked to a non-PDE sequence. For example, the novel PDE sequence may be linked operatively to a vector to generate a recombinant molecule.

The term vector includes, but is not limited to, plasmids, cosmids, and phagemids. A preferred vector for expression will be an autonomously replicating vector comprising a replicon that directs the replication of the rDNA within the appropriate host cell. Alternatively, the preferred vector directs integration of the recombinant vector into a host cell. Various viral vectors may also be used, such as for example, a number of well-known retroviral, adenoviral, and adeno-associated viral (AAV) vectors (Berkner 1988, *Biotechniques* 6:616–629).

The preferred vectors permit expression of novel PDEs transcript or polypeptide sequences in prokaryotic or eukaryotic host cells. The preferred vectors include expression vectors, comprising an expression control element, such as a promoter sequence, which enables transcription of the inserted sequences and can be used for regulating the expression (e.g., transcription and/or translation) of an operably linked sequence in an appropriate host cell such as *Escherichia coli*. Expression control elements are known in the art and include, but are not limited to, inducible promoters, constitutive promoters, secretion signals, enhancers, transcription terminators, and other transcriptional regulatory elements. Other expression control elements that are involved in translation are known in the art, and include the Shine-Dalgarno sequence, and initiation and termination codons.

Specific initiation signals may also be required for efficient translation of novel PDEs sequences. These signals include the ATG-initiation codon and adjacent sequences. In cases where the novel PDEs initiation codon and upstream sequences are inserted into the appropriate expression vector, no additional translation control signals may be needed. However, in cases where only the coding sequence, or a portion thereof, is inserted, exogenous transcriptional control signals including the ATG-initiation codon must be provided. Furthermore, the initiation codon must be in correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf, D., et al, 1994 *Results Probl. Cell. Differ.* 20:125–62; Bittner, et al., 1987 *Methods in Enzymol.* 153: 516–544).

The preferred vectors for expression of the novel PDE nucleotide sequences in eukaryotic host cells include expression control elements, such as the baculovirus polyhedrin promoter for expression in insect cells. Other expression control elements include promoters or enhancers derived from the genomes of plant cells (e. g., heat shock, RUBISCO, storage protein genes), viral promoters or leader sequences or from plant viruses, and promoters or enhancers from the mammalian genes or from mammalian viruses.

The preferred vector includes at least one selectable marker gene that encodes a gene product that confers drug resistance such as resistance to ampicillin or tetracyline. The vector also comprises multiple endonuclease restriction sites that enable convenient insertion of exogenous DNA sequences. Methods for generating a recombinant expression vector encoding the novel PDE proteins of the invention are well known in the art, and are described in Maniatis, T., et al., (1989 *Molecular Cloning, A Laboratory Manual*, Cold Spring Harbor Laboratory, Cold Spring Harbor, N.Y.) and Ausubel et al. (1989 *Current Protocols in Molecular Biology*, John Wiley & Sons, New York N.Y.).

The preferred vectors for generating novel PDE transcripts and/or the encoded novel PDEs polypeptides are expression vectors which are compatible with prokaryotic host cells. Prokaryotic cell expression vectors are well known in the art and are available from several commercial sources. For example, pET vectors (e.g., pET-21, Novagen Corp.), pQE vectors (Qiagen, Chatsworth, Calif.), BLUESCRIPT phagemid (Stratagene, LaJolla, Calif.), pSPORT (Gibco BRL), or ptrp-lac hybrids may be used to express novel PDEs polypeptides in bacterial host cells.

Alternatively, the preferred expression vectors for generating novel PDE transcripts and/or the encoded PDE polypeptides are expression vectors which are compatible with eukaryotic host cells. The most preferred vectors are those compatible with vertebrate cells. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC, #31255), and similar eukaryotic expression vectors.

Host-Vector Systems Comprising Novel PDEs

The invention further provides a host-vector system comprising a vector, plasmid, phagemid, or cosmid comprising a novel PDE nucleotide sequence, or a fragment thereof, introduced into a suitable host cell. A variety of expression vector/host systems may be utilized to carry and express novel PDE sequences. The host-vector system can be used to express (e.g., produce) the novel PDE polypeptides encoded by novel PDE nucleotide sequences. The host cell can be either prokaryotic or eukaryotic. Examples of suitable prokaryotic host cells include bacteria strains from genera such as *Escherichia, Bacillus, Pseudomonas, Streptococcus,* and *Streptomyces*. Examples of suitable eukaryotic host cells include yeast cells, plant cells, or animal cells such as mammalian cells and insect cells. A preferred embodiment provides a host-vector system comprising the pcDNA3 vector (Invitrogen, Carlsbad, Calif.) in COS7 mammalian cells, pGEX vector (Promega, Madison, Wis.) in bacterial cells, or pFastBac HT baculovirus vector (Gibco/BRL) in Sf9 insect cells (ATCC, Manassas, Va.).

Introduction of the recombinant DNA molecules of the present invention into an appropriate host cell is accomplished by well-known methods that depend on the type of vector used and host system employed. For example, prokaryotic host cells are introduced (e.g., transformed) with nucleic acid molecules by electroporation or salt treatment methods, see for example, Cohen et al., (1972) *Proc Natl Acad Sci USA* 69:2110; Maniatis, T., et al., (1989) *Molecular Cloning, A Laboratory Manual,* Cold Spring Harbor Laboratory, Cold Spring Harbor, N.Y. Vertebrate cells are transformed with vectors containing recombinant DNAs by various methods, including electroporation, cationic lipid or salt treatment (Graham et al., (1973) *Virol* 52:456; Wigler et al., (1979) *Proc Natl Acad Sci USA* 76:1373–76).

Successfully transformed cells, i.e., cells that contain a rDNA molecule of the present invention, can be identified by techniques well known in the art. For example, cells resulting from the introduction of recombinant DNA of the present invention are selected and cloned to produce single colonies. Cells from those colonies are harvested, lysed and their DNA content examined for the presence of the rDNA using a method such as that described by Southern, *J Mol Biol* (1975) 98:503, or Berent et al., *Biotech* (1985) 3:208, or the proteins produced from the cell are assayed via a biochemical assay or immunological method.

In bacterial systems, a number of expression vectors may be selected depending upon the use intended for the novel PDE proteins. For example, when large quantities of novel PDE proteins are needed for the induction of antibodies, vectors that direct high level expression of fusion proteins that are soluble and readily purified may be desirable. Such vectors include, but are not limited to, the multifunctional *E. coli* cloning and expression vectors such as BLUESCRIPT (Stratagene, San Diego, Calif.), in which the novel PDE nucleotide sequence may be ligated into the vector in-frame with sequences for the amino-terminal Met and the subsequent 7 residues of β-galactosidase so that a hybrid protein is produced; pIN vectors (Van Heeke & Schuster (1989) *J Biol Chem* 264:5503–5509); and the like. The pGEX vectors (Promega, Madison, Wis.) may also be used to express novel PDE proteins as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned protein of interest can be released from the GST moiety at will.

In yeast, *Saccharomyces cerevisiae,* a number of vectors containing constitutive or inducible promoters such as beta-factor, alcohol oxidase and PGH may be used. For reviews, see Ausubel et al (supra) and Grant et al (1987) *Methods in Enzymology* 153:516–544.

In cases where plant expression vectors are used, the expression of a sequence encoding a novel PDE protein is driven by any of a number of promoters. For example, viral promoters such as the 35S and 19S promoters of CaMV (Brisson, et al., (1984) *Nature* 310:511–514) may be used alone or in combination with the omega leader sequence from TMV (Takamatsu, et al., (1987) *EMBO J* 6:307–311). Alternatively, plant promoters such as the small subunit of RUBISCO (Coruzzi et al (1984) *EMBO J* 3:1671–1680; Broglie et al (1984) *Science* 224:838–843); or heat shock promoters (Winter J and Sinibaldi R M (1991) *Results Probl Cell Differ* 17:85–105) are used. These constructs can be introduced into plant cells by direct DNA transformation or pathogen-mediated transfection. For reviews of such techniques, see Hobbs, S. in: *McGraw Yearbook of Science and Technology* (1992) McGraw Hill New York N.Y., pp 191–196; or Weissbach and Weissbach (1988) in: *Methods for Plant Molecular Biology,* Academic Press, New York N.Y., pp 421–463.

An alternative expression system that can be used to express a novel PDE proteins is an insect system. In one such system, *Autographa californica* nuclear polyhedrosis virus (AcNPV) is used as a vector to express foreign genes in *Spodoptera frugiperda* cells or in *Trichoplusia larvae* (Smith et al (1983) *J Virol* 46:584; Engelhard E. K., et al, 1994 *Proc Nat Acad Sci* 91:3224–7). The sequence encoding a novel PDE protein is cloned into a nonessential region of the virus, such as the polyhedrin gene, and placed under control of the polyhedrin promoter. Successful insertion of a novel PDE nucleotide sequence will render the polyhedrin gene inactive and produce recombinant virus lacking coat protein. The recombinant viruses are then used to infect *S. frugiperda* cells or *Trichoplusia larvae* in which a novel PDE protein is expressed.

In mammalian host cells, a number of viral-based expression systems are utilized. In cases where an adenovirus is used as an expression vector, a novel PDE nucleotide sequence is ligated into an adenovirus transcription/translation vector consisting of the late promoter and tripartite leader sequence. Insertion in a nonessential E1 or E3 region of the viral genome results in a viable virus (Logan and Shenk 1984 *Proc Natl Acad Sci* 81:3655–59) capable of expressing a novel PDE protein in infected host cells. In addition, transcription enhancers, such as the rous sarcoma virus (RSV) enhancer, are used to increase expression in mammalian host cells.

A host cell strain may also be chosen for its ability to modulate the expression of the inserted novel PDE nucleotide sequences or to process the expressed novel PDE protein in the desired fashion. Such modifications of the novel PDE protein include, but are not limited to, acetylation, carboxylation, glycosylation, phosphorylation, lipidation and acylation. Post-translational processing which cleaves a precursor form of the protein (e.g., a prepro protein) may also be important for correct insertion, folding and/or function. Different host cells such as CHO, HeLa, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines that stably express novel PDE proteins are transformed using expression vectors that contain viral origins of replication or endogenous expression elements and a selectable marker gene. Following the introduction of the vector, cells are grown in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate for the cell type used.

Any number of selection systems may be used to recover transformed cell lines. These include, but are not limited to, the herpes simplex virus thymidine kinase (Wigler, M., et al., 1977 *Cell* 11:223–32) and adenine phosphoribosyltransferase (Lowy, I. et al., 1980 *Cell* 22:817–23) genes which can be employed in tk-minus or aprt-minus cells, respectively. Also, antimetabolite, antibiotic or herbicide resistance can be used as the basis for selection; for example, dhfr which confers resistance to methotrexate (Wigler, M., et al., 1980 *Proc Natl Acad Sci* 77:3567–70); npt, which confers resistance to the aminoglycosides neomycin and G-418 (Colbere-Garapin, F., et al., 1981 *J. Mol. Biol.* 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan 1988 *Proc. Natl. Acad. Sci.* 85:8047–51). Recently, the use of visible markers has gained popularity with such markers as anthocyanins, β-glucuronidase and its substrate, GUS, and luciferase and its substrate, luciferin, being widely used not only to identify transformants, but also to quantify the amount of transient or stable protein expression attributable to a specific vector system (Rhodes, C. A., et al., 1995 *Methods Mol. Biol.* 55:121–131).

Proteins and Polypeptides of the Invention

The invention also provides novel PDE proteins and polypeptides. Particular embodiments of the novel PDE proteins of the invention includes mammalian PDE8A and PDE7A3, and TbPDE2A/2B/2C/2E from *T. brucei*. Certain novel PDE protein molecules of the invention (e.g., PDE8A and PDE7A3) can be expressed on activated human CD4⁺ T cell line, and become upregulated in CD4⁺ T cells after stimulation with CD3 and CD28 receptors, and are involved in T cell activation, as certain T cell functions such as T cell proliferation and IL2 production can be inhibited by PDE8A- or PDE7A3-antisense molecules.

Novel PDEs of this invention may be embodied in many forms, preferably in isolated form or in purified form. Novel PDE proteins may also be generated by synthetic, semi-synthetic, or recombinant methods.

A skilled artisan can readily employ standard isolation and purification methods to obtain isolated novel PDE proteins (Marchak, D. R., et al., 1996 in: *Strategies for Protein Purification and Characterization,* Cold Spring Harbor Press, Plainview, N.Y.). The nature and degree of isolation and purification will depend on the intended use. For example., purified novel PDE protein molecules will be substantially free of other proteins or molecules that impair the binding of novel PDE proteins to antibodies or other ligands. Embodiments of the novel PDE proteins include purified novel PDE protein or fragments thereof, having the biological activity of a novel PDE protein. In one form, such purified PDE proteins, or fragments thereof, retain the ability to bind antibody or other ligand.

Various forms of a particular novel PDE protein of the invention may be produced as a result of processes such as post-translational modification, alternative splicing. For example, various forms of isolated novel PDE proteins may include: precursor forms, mature forms, and different mature forms of a novel PDE protein that result from post-translational events, such as, glycosylation, phosphorylation, and intramolecular cleavage.

The present invention provides isolated and purified proteins, polypeptides, and fragments thereof, having an amino acid sequence identical to the predicted sequence of the novel PDE sequences disclosed herein. Accordingly, the amino acid sequences may be identical to a particular novel PDE sequence, as described in FIGS. 1, 8B, 16, 21B, 22B, and 23B).

The present invention also includes proteins having sequence variations from the predicted novel PDE protein sequences disclosed herein. For example, the proteins having the variant sequences include allelic variants, mutant variants, conservative substitution variants, and novel PDE proteins isolated from other organisms. The amino acid sequences may be similar to the disclosed sequences.

The present invention encompasses mutant alleles of novel PDEs that encode mutant forms of novel PDE proteins having one or more amino acid substitutions, insertions, deletions, truncations, or frame shifts. Such mutant forms of proteins typically may not exhibit the same biological activity as wild-type proteins.

Another variant of novel PDE proteins may have amino acid sequences that differ by one or more amino acid substitutions. The variant may have conservative amino acid changes, where a substituted amino acid has similar structural or chemical properties, such as replacement of leucine with isoleucine. Alternatively, a variant may have nonconservative amino acid changes, such as replacement of a glycine with a tryptophan. Similar minor variations may also include amino acid deletions or insertions, or both. Guidance in determining which and how many amino acid residues may be substituted, inserted or deleted may be found using computer programs well known in the art, for example, DNASTAR software.

Conservative amino acid substitutions can frequently be made in a protein without altering either the conformation or the biological activity of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchanged, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant.

The invention also provides peptides comprising biologically and/or immunologically active fragments of novel PDEs. For example, the proteins and peptides of the invention can elicit antibodies that specifically bind an epitope associated with a novel PDE protein of the invention. Accordingly, the novel PDE protein, or any oligopeptide thereof, is capable of inducing a specific immune response in appropriate animals or cells, and/or binding with ligands such as specific antibodies.

The novel PDE-encoding nucleic acid molecules described herein enable the isolation of novel PDE homologues, alternatively sliced isoforms, allelic variants, and mutant forms of the protein as well as their coding and gene sequences.

For example, a portion of the novel PDE-encoding sequence herein described can be synthesized and used as a probe to retrieve DNA encoding a member of the novel PDE family of proteins from organisms other than human, allelic variants of the novel PDE protein herein described, and genomic sequence containing the novel PDE gene. Oligomers containing e.g., about 18–20 nucleotides (encoding about a 6–7 amino acid stretch), can be prepared and used to screen-genomic DNA or cDNA libraries to obtain hybridization under stringent conditions or conditions of sufficient stringency to eliminate an undue level of false positives. In a particular embodiment, cDNA encoding a novel PDE can be used to isolate a full length cDNA encoding a novel PDE homologue.

In addition, the amino acid sequence of the human novel PDE protein may be used to generate antibody probes to screen expression libraries prepared from cells. Typically, polyclonal antiserum from mammals such as rabbits immunized with the purified protein (as described below) or monoclonal antibodies can be used to probe an expression library, prepared from a target organism, to obtain the appropriate coding sequence for a novel PDE homologue. The cloned cDNA sequence can be expressed as a fusion protein, expressed directly using its own control sequences, or expressed by constructing an expression cassette using control sequences appropriate to the particular host used for expression of the enzyme.

Non-human homologues of a novel PDE, naturally occurring allelic variants of a novel PDE and genomic novel PDE sequences may share a high degree of homology to the novel PDE sequences herein described. In general, such nucleic acid molecules will hybridize to the novel PDE sequence under stringent conditions. Such sequences will typically contain at least 70% homology, preferably at least 80%, most preferably at least 90% homology to the a novel PDE sequence. Stringent conditions are those, e.g., that (I)

employ low ionic strength and high temperature for washing, for example, 0.015M NaCl/0.0015M sodium titrate/ 0.1% SDS at 50 EC., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42 EC.

Methods for Generating Novel PDE Proteins

The novel PDE proteins of the invention may be generated by chemical synthesis or by recombinant methods. Recombinant methods are preferred if a high yield is desired. Recombinant methods involve expressing the cloned gene in a suitable host cell. For example, a host cell is introduced with an expression vector having a novel PDE nucleotide sequence, and then the host cell is cultured under conditions that permit production of the novel PDE protein encoded by the sequence.

For example, in general terms, the production of recombinant novel PDE proteins will involve using a host/vector system employing the following steps: A nucleic acid molecule is obtained that encodes a novel PDE protein or a fragment thereof, such as any one of the polynucleotides disclosed in FIGS. 1, 8A, 16, 21A, 22A, or 23A). The novel PDE-encoding nucleic acid molecule is then preferably inserted into an expression vector in operable linkage with suitable expression control sequences (described below), to generate an expression vector containing the novel PDE-encoding sequence. The expression vector is introduced into a suitable host, by standard transformation methods, and the resulting transformed host is cultured under conditions that allow the production and retrieval of the novel PDE protein of the invention. For example, if expression of a novel PDE gene is under the control of an inducible promoter, then suitable growth conditions include the appropriate inducer. The novel PDE protein, so produced, is isolated from the growth medium or directly from the cells; recovery and purification of the protein may not be necessary in some instances where some impurities may be tolerated. A skilled artisan can readily adapt an appropriate host/expression system known in the art (Cohen, et al., supra; Maniatis et al., supra) for use with a novel PDE-encoding sequences to produce a novel PDE protein of the invention.

The novel PDE proteins of the invention, and fragments thereof, can be generated by chemical synthesis methods. The principles of solid phase chemical synthesis of polypeptides are well known in the art and may be found in general texts relating to this area (Dugas, H. and Penney, C. 1981 *Bioorganic Chemistry*, pp 54–92, Springer-Verlag, New York). PDE8 polypeptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl protected amino acids, and other reagents are commercially available from many chemical supply houses.

The present invention provides derivative protein molecules, such as chemically modified novel PDE proteins. Illustrative of such modifications is replacement of hydrogen by an alkyl, acyl, or amino group. The novel PDE protein derivatives retain the biological activities of naturally occurring novel PDEs.

Antibodies Reactive Against Novel PDE Proteins and Polypeptides

The invention further provides antibodies, such as polyclonal, monoclonal, chimeric, fragments, and human plus humanized antibodies, that bind to novel PDE proteins or fragments thereof. The most preferred antibodies will selectively bind to a novel PDE protein and will not bind (or will bind weakly) to a non-PDE protein. These antibodies can be from any source, e.g., rabbit, sheep, rat, dog, cat, pig, horse, mouse and human.

As will be understood by those skilled in the art, the regions or epitopes of a novel PDE protein to which an antibody is directed may vary with the intended application. For example, antibodies intended for use in an immunoassay for the detection of membrane-bound novel PDE on viable cells should be directed to an accessible epitope such as the extracellular domain of a novel PDE protein. Anti-novel PDE mAbs can be used to stain the cell surface of novel PDE—positive cells. The extracellular domain of novel PDE proteins represent potential markers for screening, diagnosis, prognosis, and follow-up assays and imaging methods to detect novel PDE proteins. In addition, novel PDE proteins may be excellent targets for therapeutic methods such as targeted antibody therapy, immunotherapy, and gene therapy to treat conditions associated with the presence or absence of a novel PDE protein of the invention. Additionally, some of the antibodies of the invention may be internalizing antibodies, which internalize (e.g., enter) into the cell upon or after binding. Internalizing antibodies are useful for inhibiting cell growth and/or inducing cell death and for detecting or targeting novel PDEs within damaged or dying cells.

The invention includes a monoclonal antibody, the antigen-binding region of which competitively inhibits the immunospecific binding of any of the monoclonal antibodies of the invention to its target antigen. In one embodiment, this invention discloses a murine monoclonal antibody to PDE8A that was produced using a thioredoxin fusion protein of the PAS domain of PDE8A. Further, the invention provides recombinant proteins comprising the antigen-binding region of any the monoclonal antibodies of the invention.

The invention also encompasses antibody fragments that specifically recognize a novel PDE protein or a fragment thereof. As used herein, an antibody fragment is defined as at least a portion of the variable region of the immunoglobulin molecule that binds to its target, i.e., the antigen-binding region. Some of the constant region of the immunoglobulin may be included. Fragments of the monoclonal antibodies or the polyclonal antisera include Fab, F(ab')$_2$, Fv fragments, single-chain antibodies, and fusion proteins which include the immunologically significant portion (i.e., a portion that recognizes and binds a novel PDE).

The chimeric antibodies of the invention are immunoglobulin molecules that comprise at least two antibody portions from different species, for example a human and non-human portion. Chimeric antibodies are useful, as they are less likely to be antigenic to a human subject than antibodies with non-human constant regions and variable regions. The antigen combining region (variable region) of a chimeric antibody can be derived from a non-human source (e.g. murine) and the constant region of the chimeric antibody, which confers biological effector function to the immunoglobulin, can be derived from a human source (Morrison et al., 1985 *Proc. Natl. Acad. Sci. U.S.A.* 81:6851; Takeda et al., 1985 *Nature* 314:452: Cabilly et al., U.S. Pat. No. 4,816,567; Boss et al., U.S. Pat. No. 4,816.397). The chimeric antibody may have the antigen binding specificity of the non-human antibody molecule and the effector function conferred by the human antibody molecule.

The invention also provides chimeric proteins having different effector functions (Neuberger et al., 1984 *Nature*

312:604), immunoglobulin constant regions from another species and constant regions of another immunoglobulin chain (Sharon et al., 1984 *Nature* 309:364); Tan et al., 1985 *J. Immunol.* 135:3565–3567). Additional procedures for modifying antibody molecules and for producing chimeric antibody molecules using homologous recombination to target gene modification have been described (Fell et al., 1989 *Proc. Natl. Acad. Sci. USA* 86:8507–8511).

Humanized antibodies directed against novel PDE proteins are also useful. As used herein, a humanized novel PDE antibody is an immunoglobulin molecule which is capable of binding to a novel PDE protein. A humanized novel PDE antibody includes variable regions having substantially the amino acid sequence of a human immunoglobulin and the hyper-variable region having substantially the amino acid sequence of non-human immunoglobulin. Humanized antibodies can be made according to several methods known in the art (Teng et al., 1983 *Proc. Natl. Acad. Sci. U.S.A.* 80:7308–7312; Kozbor et al., 1983 *Immunology Today* 4:7279; Olsson et al., 1982 *Meth. Enzymol.* 92:3–16).

Novel antibodies of human origin can be also made to the antigen having the appropriate biological functions. For example, human monoclonal antibodies may be made by using the antigen, e.g. a novel PDE protein or peptide thereof, to sensitize human lymphocytes to the antigen in vitro followed by EBV-transformation or hybridization of the antigen-sensitized lymphocytes with mouse or human lymphocytes, as described by Borrebaeck et al. (*Proc. Nat'l. Acad. Sci. USA* 85:3995–99 (1988)).

Various methods for the preparation of antibodies are well known in the art. For example, antibodies may be prepared by immunizing a suitable mammalian host with an immunogen such as an isolated novel PDE protein, peptide, fragment, or an immunoconjugated form of a novel PDE8 protein (Harlow 1989, in: *Antibodies*, Cold Spring Harbor Press, N.Y.). In addition, fusion proteins of novel PDEs may also be used as immunogens, such as a novel PDE fused to -GST-, -human Ig, or His-tagged fusion proteins. Cells expressing or over-expressing novel PDE proteins may also be used for immunizations. Similarly, any cell engineered to express novel PDE proteins may be used. This strategy may result in the production of monoclonal antibodies with enhanced capacities for recognizing endogenous novel PDE proteins (Harlow and Lane, 1988, in: *Antibodies:* A Laboratory Manual. Cold Spring Harbor Press).

The amino acid sequence of novel PDE proteins, and fragments thereof, may be used to select specific regions of the novel PDE proteins for generating antibodies. For example, hydrophobicity and hydrophilicity analyses of a novel PDE amino acid sequence may be used to identify hydrophilic regions in the novel PDE protein structure. Regions of the novel PDE protein that show immunogenic structure, as well as other regions and domains, can readily be identified using various other methods known in the art such as Chou-Fasman, Garnier-Robson, Kyte-Doolittle, Eisenberg, Karplus-Schultz or Jameson-Wolf analysis (Rost, B., and Sander, C. 1994 *Protein* 19:55–72). Fragments including these regions are particularly suited in generating anti-PDE8 antibodies.

Methods for preparing a protein for use as an immunogen and for preparing immunogenic conjugates of a protein with a carrier such as BSA, KLH, or other carrier proteins are well known in the art. Techniques for conjugating or joining therapeutic agents to antibodies are well known (Amon et al., "Monoclonal Antibodies For Immunotargeting Of Drugs In Cancer Therapy", in: *Monoclonal Antibodies And Cancer Therapy*, Reisfeld et al., (eds.), pp. 243–56 (Alan R. Liss, Inc. 1985); Hellstrom et al., "Antibodies For Drug Delivery", in: *Controlled Drug Delivery* (2nd Ed.), Robinson et al. (eds.), pp. 623–53 (Marcel Dekker, Inc. 1987); Thorpe, "Antibody Carriers Of Cytotoxic Agents In Cancer Therapy: A Review", in: *Monoclonal Antibodies '84: Biological And Clinical Applications*, Pinchera et al. (eds.), pp. 475–506 (1985); and Thorpe et al., "The Preparation And Cytotoxic Properties Of Antibody-Toxin Conjugates", *Immunol. Rev.*, 62:119–58 (1982); Sodee et al., 1997, *Clin. Nuc. Med.* 21: 759–766). In some circumstances, direct conjugation using, for example, carbodiimide reagents may be used; in other instances linking reagents such as those supplied by Pierce Chemical Co., Rockford, Ill., may be effective.

Administration of a novel PDE immunogen is conducted generally by injection over a suitable time period and with use of a suitable adjuvant, as is generally understood in the art. During the immunization schedule; titers of antibodies can be taken to determine adequacy of antibody formation.

While the polyclonal antisera produced in this way may be satisfactory for some applications, for pharmaceutical compositions, monoclonal antibody preparations are preferred. Immortalized cell lines which secrete a desired monoclonal antibody may be prepared using the standard method of Kohler and Milstein (*Nature* 256: 495–497) or modifications which effect immortalization of lymphocytes or spleen cells, as is generally known. The immortalized cell lines secreting the desired antibodies are screened by immunoassay in which the antigen is a novel PDE protein or a fragment thereof. When the appropriate immortalized cell culture secreting the desired antibody is identified, the cells can be cultured either in vitro or by production in ascites fluid. The desired monoclonal antibodies are then recovered from the culture supernatant or from the ascites supernatant.

The antibodies or fragments may also be produced by recombinant means. The antibody regions that bind specifically to the desired regions of a novel PDE protein can also be produced in the context of chimeric or CDR grafted antibodies of multiple species origin.

The antibodies of the invention bind specifically to polypeptides having novel PDE sequences. In one embodiment, the novel PDE antibodies specifically bind to the PAS domain of a novel PDE protein. In another embodiment, the antibodies of the invention specifically bind to the C-terminal domain of a novel PDE protein. In other embodiments, the antibodies of this invention bind to other domains of a novel PDE protein or precursor, for example the antibodies bind to the N-terminal domain of a novel PDE protein.

Uses of the Molecules of the Invention

The nucleic acid molecules encoding novel PDE proteins of the invention are useful for a variety of purposes, including their use in diagnosis and/or prognostic methods. The nucleic acid molecules and proteins of the invention may be used to test the presence and/or amount of novel PDE nucleotide sequences and novel PDE protein in a suitable biological sample. The suitable biological sample can be from an animal or a human. The sample can be a cell sample or a tissue sample, including samples from spleen, lymph node, thymus, bone marrow, liver, heart, brain, placenta, lung, skeletal muscle, kidney and pancreas. The sample can be a biological fluid, including, urine, blood sera, blood plasma, phlegm, or lavage fluid. Alternatively, the sample can be a swab from the nose, ear or throat.

Additionally, the novel PDE protein molecules or fragments thereof are able to elicit the generation of antibodies, which can serve as molecules for use in various therapeutic modalities. A novel PDE protein may also be used to identify and isolate agents that bind to the novel protein (e.g., PDE ligands) and modulate the biological activity of a novel PDE protein.

Uses of Nucleic Acid Molecules Encoding Novel PDEs

The nucleic acid molecules of this invention can be used in various hybridization methods to identify and/or isolate nucleotide sequences related to the novel PDE nucleotide sequence, such as different polymorphic forms, alternatively spliced variants, genomic sequences. Sequences related to a novel PDE nucleotide sequence are useful for developing additional ligands and antibodies. The hybridization methods are used to identify/isolate DNA and RNA sequences that are identical or similar to the novel PDE nucleotide sequences, such as novel PDE homologues, alternatively spliced isoforms, allelic variants, and mutant forms of the novel PDE8 proteins as well as their coding and gene sequences.

Full-length or fragments of the nucleotide sequences that encode the novel PDE proteins, described herein, can be used as a nucleic acid probes to retrieve nucleic acid molecules having sequences related to novel PDE.

In one embodiment, a novel PDE nucleic acid probe is used to screen genomic libraries, such as libraries constructed in lambda phage or BACs (bacterial artificial chromosomes) or YACs (yeast artificial chromosomes), to isolate a genomic clone of a novel PDE gene. The novel PDE nucleotide sequences from genomic libraries are useful for isolating upstream or downstream non-coding sequences, such as promoter, enhancer, and transcription termination sequences. The upstream sequences from a novel PDE gene may be joined to non-PDE sequences in order to construct a recombinant DNA molecule that expresses the non-PDE sequence upon introduction into an appropriate host cell. In another embodiment, a novel PDE probe is used to screen cDNA libraries to isolate cDNA clones expressed in certain tissues or cell types. The novel PDE nucleotide sequences from cDNA libraries are useful for isolating sequences from various cell types, tissue types, or from various mammalian subjects.

Additionally, pairs of oligonucleotide primers can be prepared for use in a polymerase chain reaction (PCR) to selectively amplify or clone nucleic acid molecules encoding novel PDE proteins, or fragments thereof. PCR methods (U.S. Pat. No. 4,965,188) that include numerous cycles of denature/anneal/polymerize steps are well known in the art and can readily be adapted for use in isolating other PDE-encoding nucleic acid molecules.

In addition, the nucleic acid molecules of the invention may also be employed in diagnostic embodiments, using novel PDE nucleic acid probes to determine the presence and/or the amount of novel PDE sequences present in a biological sample.

One embodiment encompasses determining the amount of novel PDE nucleotide sequences present within the suitable biological sample such as in specific cell types, tissues, body fluids, using a novel PDE probe in a hybridization procedure. Alternatively, polynucleotides of this invention may also be used for developing diagnostic methods to detect genetic defects, where a genetic alteration in novel PDE8 sequence may be indicative of a disease.

Another embodiment encompasses quantifying the amount of novel PDE nucleic acid molecules in the biological sample from a test subject, using a novel PDE probe in a hybridization procedure. The amount of novel PDE nucleic acid molecules in the test sample can be compared with the amount of novel PDE nucleic acid molecules in a reference sample from a normal subject. The presence of a measurably different amount of novel PDE nucleic acid molecules between the test and reference samples may correlate with the presence or with the severity of a disease associated with abnormal levels (high or low) of novel PDE nucleic acid molecules as compared to normal levels of the protein.

In another embodiment, monitoring the amount of novel PDE RNA transcripts over time is effected by quantitatively determining the amount of novel PDE RNA transcripts in test samples taken at different points in time. A difference in the amounts of novel PDE RNA transcripts in the various samples being indicative of the course of the disease associated with expression of a novel PDE transcript.

As a further embodiment, diseases or disorders associated with novel PDE transcripts or proteins are detected by an increase or deficiency in novel PDE gene copy number. Methods for detecting gene copy number include chromosome mapping by Fluorescence In Situ Hybridization (FISH analysis) (Rowley et al., (1990) *Proc Natl Acad Sci USA* 87: 9358–9362, H. Shizuya, *Proc Natl Acad Sci USA*, 89:8794). Methods for determining an increase in novel PDE gene copy number are important because the increase may correlate with an increase in the severity of the disease associated with novel PDE protein and poor patient outcome.

To conduct such diagnostic methods, a suitable biological sample from a test subject is contacted with a labelled novel PDE probe, under conditions effective to allow hybridization between the sample nucleic acid molecules and the probe. In a similar manner, a biological sample from a normal subject is contacted with a novel PDE probe and hybridized under similar conditions. The presence of the nucleic acid molecules hybridized to the probe is detected. The relative and/or quantified amount of the hybridized molecules may be compared between the test and reference samples. The novel PDE probes are preferably labeled with any of the known detectable labels, including radioactive, enzymatic, fluorescent, or chemiluminescent labels.

Many suitable variations of hybridization technology are available for use in the detection of nucleic acids having novel PDE sequences. These include, for example, Southern and Northern procedures. Other hybridization techniques and systems are known that can be used in connection with the detection aspects of the invention, including diagnostic assays such as those described in Falkow et al., U.S. Pat. No. 4,358,535. Another hybridization procedure includes in situ hybridization, where the target nucleic acids are located within one or more cells and are contacted with the novel PDE probes. As is well known in the art, the cells are prepared for hybridization by fixation, e.g. chemical fixation, and placed in conditions that permit hybridization of the novel PDE probe with nucleic acids located within the fixed cell.

The nucleic acid molecules of this invention further provide antisense molecules that recognize and hybridize to a novel PDE nucleic acid. Antisense polynucleotides are particularly useful in regulating the expression of a novel PDE protein in those cells expressing a novel PDE mRNA. An antisense molecule corresponding to the N-terminal sequence of the gene is particularly desirable for this approach. This invention provides these full length and fragment antisense polynucleotides.

The polynucleotides of this invention also provide reagents for gene replacement therapy to augment immune functions by enhancing the expression of the novel PDEs in immunocompromised individuals.

The polynucleotide of this invention further provide reagents to develop animal models using "knock-out" strategies through homologous recombination. Methods for generating knock-out animals that fail to express a functional protein molecule are well known in the art (Capechi, *Science* (1989) 244:1288–1292), and will be especially useful for studying in vivo functions of PDE8.

Uses of Novel PDE Protein Molecules

This present invention provides evidence that certain novel PDEs (e.g., PDE8 and PDE7A3) are present in an activated human $CD4^+$ T cell line, and becomes upregulated in $CD4^+$ T cells after stimulation with the CD3 and CD28 receptors. The upregulation of PDE8A and PDE7A3 reaches its maximum level at a much later time point, 8–16 hours after stimulation. The invention further shows that RNA, protein, and activity levels of PDE8A and PDE7A3 all increase at a later time point. A possible advantage of this later upregulation of PDE8A and PDE7A3 may be exploited to design specific inhibitors that will be able to slow down T cell proliferation but not knock it down completely.

The invention further indicates that PDE8A may have different conformations with different states of activation. For example, in $CD4^+$ T cells and hut78 T cell line PDE8A activity is inhibited by IBMX, although recombinant PDE8A is resistant to IBMX inhibition. The invention further shows that the recombinant PDE8A can be activated by limited trypsin digestion and the digested PDE8A is more susceptible to IBMX inhibition than the undigested PDE8A suggesting that PDE8A in T cells may be modified in some way, for instance by phosphorylation, binding of a ligand, or by association with other proteins.

This invention postulates an important role for PDE8A and PDE7A3 in T-cell functions and offers strategies for the development of inhibitors and modulators of PDE8A which may facilitate diagnosis, prevention, and treatment of a number of T-cell mediated disorders.

The novel PDEs (e.g., PDE8A and PDE7A3) proteins are attractive targets for drug development. Drugs directed against these PDEs will likely inhibit an immune system disease such as graft versus host disease (GVHD); psoriasis; immune disorders associated with graft transplantation rejection; T cell lymphoma; T cell acute lymphoblastic leukemia; testicular angiocentric T cell lymphoma; benign lymphocytic angitis; and autoimmune diseases such as lupus erythrmatosis, Hishimoto's thyroiditis, primary myxedema, Grave's disease, pernicious anemia, autoimmune atropic gastritis, Addison's disease, insulin dependent diabetes mellitus, good pasture syndrome, myasthenia gravis, pemphigus, Crohn's disease, sympathetic opthalmia, autoimmune uvetitis, multiple sclerosis, autoimmune hemolytic anemia, idiopathic thrombocytopenia, primary biliary cirrhosis, chronic action hepatitis, ulceratis colitis, Sjogren's syndrome, arthritis (including rheumatoid arthritis, juvenile rheumatoid arthritis, osteoarthritis, psoriatic arthritis), polymositis, scleroderma, or mixed connective tissue disease.

Further, the invention provides cAMP-specific PDEs from *T. brucei*, including isolated PDE proteins TbPDE2A/B/C/E. The invention also provides inhibitors studies demonstrating that these proteins are resistant to most inhibitors tested, including broad-spectrum inhibitors. It is known that cAMP plays a key role in cell growth and differentiation in this parasite and PDEs are responsible for the hydrolysis of this important messenger. Therefore, these parasite PDEs including TbPDE2A/2B/2C/2E, are attractive targets for drug screening assays and to accomplish selective dug design.

The novel PDE (e.g., PDE8A, PDE7A3, and TbPDE2A/2B/2C/2E) proteins and fragments of the invention can be used to elicit the generation of antibodies that specifically bind an epitope associated with a novel PDE protein, as described herein (Kohler and Milstein, supra). The novel PDE antibodies include fragments, such Fv, Fab', and $F(ab')_2$. The antibodies which are immunoreactive with selected domains or regions of a novel PDE protein are particularly useful.

In one embodiment, the novel PDE antibodies are used to screen expression libraries in order to obtain proteins related to novel PDE proteins (e.g., homologues).

In another embodiment, novel PDE antibodies are used to enrich or purify novel PDE proteins from a sample having a heterologous population of proteins. The enrichment and purifying methods include conventional techniques, such as immuno-affinity methods. In general, the immuno-affinity methods include the following steps: preparing an affinity matrix by linking a solid support matrix with a novel PDE antibody, wherein the linked affinity matrix specifically binds with a novel PDE protein; contacting the linked affinity matrix with the sample under conditions that permit the novel PDE protein in the sample to bind to the linked affinity matrix; removing the non-PDE proteins that did not bind to the linked affinity matrix, thereby enriching or purifying for the novel PDE proteins. A further step may include eluting the novel PDE proteins from the affinity matrix. The general steps and conditions for affinity enrichment for a desired protein or protein complex can be found in *Antibodies: A Laboratory Manual* (Harlow, E. and Lane, D., 1988 CSHL, Cold Spring, N.Y.).

The novel PDE antibodies are also used to detect, sort, or isolate cells expressing a novel PDE protein. The novel PDE-positive cells are detected within various biological samples. The presence of novel PDE proteins on cells (alone or in combination with other cell surface markers) may be used to distinguish and isolate cells (e.g., sorting) expressing novel PDE from other cells, using antibody-based cell sorting or affinity purification techniques. The novel PDE antibodies may be used to generate large quantities of relatively pure novel PDE-positive cells from individual subjects or patients, which can be grown in tissue culture. In this way, for example, an individual subject's cells may be expanded from a limited biopsy sample and then tested for the presence of diagnostic and prognostic novel PDE genes, proteins, chromosomal aberrations, gene expression profiles, or other relevant genotypic and phenotypic characteristics, without the potentially confounding variable of contaminating cells. Similarly, patient-specific vaccines and cellular immunotherapeutics may be created from such cell preparations. The methods for detecting, sorting, and isolating novel PDE-positive cells use various imaging methodologies, such as fluorescence or immunoscintigraphy with Induim-111 (or other isotope).

There are multiple diagnostic uses of the antibodies of the invention. For example, CD33 is upregulated in myelodysplastic syndromes (Elghetamy, 1998 supra) and is used as a diagnostic marker for leukemia. The invention provides methods for diagnosing in a subject, e.g., an animal or human subject, a disease associated with the presence or deficiency of the novel PDE protein(s). In one embodiment, the method comprises quantitatively determining the amount of a novel PDE protein in the sample (e.g., cell or biological fluid sample) using any one or combination of the antibodies of the invention. Then the amount so determined can be compared with the amount in a sample from a normal subject. The presence of a measurably different amount in the sample (i.e., the amount of novel PDE proteins in the test sample exceeds or is reduced from the amount of novel PDE proteins in a normal sample) indicates the presence of the disease.

The anti-PDE antibodies of the invention may be particularly useful in diagnostic imaging methodologies, where the antibodies have a detectable label. The invention provides various immunological assays useful for the detection of novel PDE proteins in a suitable biological sample. Suitable detectable markers include, but are not limited to, a radioisotope, a fluorescent compound, a bioluminescent compound, chemiluminescent compound, a chromophore, a metal chelator, biotin, or an enzyme. Such assays generally comprise one or more labeled novel PDE antibodies that recognize and bind a novel PDE protein, and include various immunological assay formats well known in the art, including but not limited to various types of precipitation, agglutination, complement fixation, radioimmunoassays (RIA), enzyme-linked immunosorbent assays (ELISA), enzyme-linked immunofluorescent assays (ELIFA) (H. Liu et al. 1998 *Cancer Research* 58: 4055–4060), immunohistochemical analyses and the like.

In addition, immunological imaging methods that detect cells expressing novel PDEs are also provided by the invention, including but not limited to radioscintigraphic imaging methods using labeled novel PDE antibodies. Such assays may be clinically useful in the detection and monitoring the number and/or location of cells expressing novel PDE proteins in the test and reference samples.

Additionally, the invention provides methods for monitoring the course of disease or disorders associated with novel PDEs in a test subject by measuring the amount of a novel PDE protein in a sample from the test subject at various points in time. This is done for purposes of determining a change in the amount of novel PDE in the sample over time. Monitoring the course of disease or disorders over time may optimize the timing, dosage, and type of treatment. In one embodiment, the method comprises quantitatively determining in a first sample from the subject the presence of a novel PDE protein and comparing the amount so determined with the amount present in a second sample from the same subject taken at a different point in time, a difference in the amounts determined being indicative of the course of the disease.

One embodiment of the invention is a method for diagnosing an immune system disease in a candidate subject. This method comprises: obtaining a biological sample from an candidate subject having an immune system disease (e.g., test sample) and from normal subjects (e.g., reference samples); contacting the test and reference sample(s) with an anti-PDE antibody that specifically forms a complex with a novel PDE protein; detecting the complex so formed in the test and reference samples; comparing the amount of complex formed in the test and reference samples, where a measurable difference in the amount of the complex formed in the test and reference samples is indicative of an immune system disease. Elevated levels of novel PDE in the bloodstream or lavage fluid may be a way of detecting immune system disease. This detection can be done by ELISA or similar methods using labeled antibodies that react with novel PDE proteins.

The novel PDE antibodies may also be used therapeutically to modulate (e.g., inhibit or activate) the biological activity of novel PDE proteins, or to target therapeutic agents, such as anti-inflammatory and anti-protozoal drugs to cells expressing novel PDE proteins. For example, cells expressing novel PDEs can be targeted, using antibodies that bind with cells expressing novel PDE proteins. The binding of the novel PDE antibody with the cells decreases the biological activity of novel PDE proteins, thereby inhibiting the growth of the novel PDE-expressing cells and decreasing the disease associated with abnormal cellular expression of novel PDE proteins.

Screening for Novel PDE Ligands

Another aspect of the invention relates to screening methods for identifying agents of interest and/or cellular constituents that bind to novel PDE proteins (e.g., ligands) and/or modulate the biological activity of novel PDE proteins.

Because certain novel PDEs (e.g., PDE8A and PDE7A3) are expressed in activated T cells, these proteins may be involved in immune cell functions. Thus, agents that bind with and modulate the biological activity of these novel PDE proteins may be effective in modulating novel PDE functions and therefore, may facilitate diagnosis, prevention, and treatment of a number of T cell mediated disorders.

Further, certain novel PDE (TbPDE2A/2B/2C/2E) proteins are phosphodiesterases from *T. brucei* that work as key components in the regulation of intracellular levels of cAMP by catalyzing its hydrolysis, and together with the adenylyl cyclases ultimately control the biological responses mediated by this messenger molecule. Regulation of intracellular levels of cAMP is crucial in the processes of cell transformation and proliferation The intracellular levels of cAMP are significantly different depending on the life cycle and cell stage of the protozoal parasite, *Trypanosome*. For example, *T. brucei*, differentiates from long slender bloodstream forms into short stumpy forms that are infectious to the insect (Reed S. L. et al., Infec Immun 1985; 49: 844–7). TbPDEs including TbPDE2A/2B/2C/2E are attractive targets for screening for agents that bind with and modulate the biological activity of TbPDE2A/2B/2C/2E proteins may be effective in modulating TbPDE2A/2B/2C/2E functions and therefore, may facilitate development of novel and effective anti-protozoal agents for the treatment of parasitic diseases.

Typically, the goal of such screening methods is to identify an agent(s) that binds to the target novel PDEs (e.g., PDE8A, PDE7A and TbPDE2A/2B/2C/2E) and causes a change in the biological activity of the target polypeptide, such as activation or inhibition of the target polypeptide, thereby decreasing diseases associated with abnormal cellular expression of novel PDE proteins. The agents of interest are identified from a population of candidate agents.

In one embodiment, a screening assay comprises the following: contacting a labeled novel PDE protein with a test agent or cellular extract, under conditions that allow association (e.g., binding) of the novel PDEs protein with the test agent or component of the cellular extract; and determining if a complex comprising the agent or component associated with the novel PDE protein is formed. The screening methods are suitable for use in high throughput screening methods.

The binding of an agent with a novel PDE protein can be assayed using a shift in the molecular weight or a change in biological activity of the unbound PDE protein, or the expression of a reporter gene in a two-hybrid system (Fields, S. and Song, O., 1989, *Nature* 340:245–246). The method used to identify whether an agent/cellular component binds to a novel PDE protein will be based primarily on the nature of the novel PDE protein used. For example, a gel retardation assay can be used to determine whether an agent binds to a novel PDE, or a fragment thereof. Alternatively, immunodetection and biochip (e.g., U.S. Pat. No. 4,777,019) technologies can be adopted for use with the novel PDE protein. An alternative method for identifying agents that bind with a novel PDE protein employs TLC overlay assays using glycolipid extracts from immune-type cells (K. M. Abdullah, et al., 1992 *Infect. Immunol.* 60:56–62). A skilled artisan can readily employ numerous art-known techniques for determining whether a particular agent binds to a novel PDE protein of the invention.

Alternatively or consecutively, the biological activity of a novel PDE protein, as part of the complex, can be analyzed as a means for identifying agonists and antagonists of PDE activity. For example, a method used to isolate cellular components that bind CD22 (D. Sgroi, et al., 1993 *J. Biol. Chem.* 268:7011–7018; L. D. Powell, et al., 1993 *J. Biol. Chem.* 268:7019–7027) can be adapted to isolate cell-surface glycoproteins that bind to novel PDE proteins by contacting cell extracts with an affinity column having immobilized anti-novel PDE antibodies.

Another embodiment of the assays includes screening agents and cellular constituents that bind to novel PDE proteins using a yeast two-hybrid system (Fields, S. and Song, O., supra) or using a binding-capture assay (Harlow, supra). Generally, the yeast two-hybrid system is performed in a yeast host cell carrying a reporter gene, and is based on the modular nature of the GAL transcription factor which has a DNA binding domain and a transcriptional activation domain. The two-hybrid system relies on the physical interaction between a recombinant protein that comprises the DNA binding domain and another recombinant protein that comprises the transcriptional activation domain to reconstitute the transcriptional activity of the modular transcription factor, thereby causing expression of the reporter gene. Either of the recombinant proteins used in the two-hybrid system can be constructed to include the novel PDE-encoding sequence to screen for binding partners of novel PDEs. The yeast two-hybrid system can be used to screen cDNA expression libraries (G. J. Hannon, et al. 1993 *Genes and Dev.* 7: 2378–2391), and random aptmer libraries (J. P. Manfredi, et al. 1996 *Molec. And Cell. Biol.* 16: 4700–4709) or semi-random (M. Yang, et al. 1995 *Nucleic Acids Res.* 23: 1152–1156) aptmer libraries for novel PDE ligands. In one embodiment, using yeast two hybrid screening assay, this invention discloses three classes of cellular proteins that are involved in protein/protein interaction with PDE8A (Example 9).

Novel PDE proteins which are used in the screening assays described herein include, but are not limited to, an isolated novel PDE protein, a fragment of a novel PDE protein, a cell that has been altered to express a novel PDE protein, or a fraction of a cell that has been altered to express a novel PDE protein.

The candidate agents to be tested for binding with novel PDE proteins and/or modulating the activity of novel PDE proteins can be, as examples, peptides, small molecules, and vitamin derivatives, as well as carbohydrates. A skilled artisan can readily recognize that there is no limit as to the structural nature of the agents tested for binding to novel PDE proteins. One class of agents is peptide agents whose amino acid sequences are chosen based on the amino acid sequence of the novel PDE protein. Small peptide agents can serve as competitive inhibitors of novel PDE protein.

Candidate agents that are tested for binding with novel PDE proteins and/or modulating the activity of novel PDE proteins can be randomly selected or rationally selected. As used herein, an agent is said to be randomly selected when the agent is chosen randomly without considering the specific sequences of the novel PDE protein. Examples of randomly selected agents are members of a chemical library, a peptide combinatorial library, a growth broth of an organism, or plant extract.

As used herein, an agent is said to be rationally selected when the agent is chosen on a nonrandom basis that is based on the sequence of the target site and/or its conformation in connection with the agent's action. Agents can be rationally selected by utilizing the peptide sequences that make up the novel PDE protein. For example, a rationally selected peptide agent can be a peptide whose amino acid sequence is identical to a selected fragment of a novel PDE protein.

The cellular extracts to be tested for binding with novel PDE proteins and/or modulating the activity of novel PDE proteins can be, as examples, aqueous extracts of cells or tissues, organic extracts of cells or tissues or partially purified cellular fractions. A skilled artisan can readily recognize that there is no limit as to the source of the cellular extracts used in the screening methods of the present invention.

Uses of Novel PDE Proteins and Antibodies in Immunotherapy

The invention provides various immunotherapeutics methods for treating novel PDE-associated disorders, including antibody therapy, in vivo vaccines, and ex vivo immunotherapy approaches. In one approach, the invention provides novel PDE antibodies which may be used systematically to treat novel PDE-associated disorders.

Treatment will generally involve the repeated administration of the antibody preparation via an acceptable route of administration such as intravenous injection (IV), at an effective dose. Dosages will depend upon various factors generally appreciated by those of skill in the art, including without limitation the type of disorder and the severity, grade, or stage of the disorder, the binding affinity and half life of the mAb or mAbs used, the degree of novel PDE protein expression in the subject, the extent of circulating PDE protein, the desired steady-state antibody concentration level, frequency of treatment, and the influence of chemotherapeutic or immune regulating agents used in combination with the treatment method of the invention. Typical daily doses may range from about 0.1 ug/kg to 100 mg/kg Doses in the range of 1–500 mg mAb per week may be effective and well tolerated, although even higher weekly doses may be appropriate and/or well tolerated. The principal determining factor in defining the appropriate dose is the amount of a particular antibody necessary to be therapeutically effective in a particular context. Repeated administrations may be required. Initial loading doses may be higher. The initial loading dose may be administered as an infusion. Periodic maintenance doses may be administered similarly, provided the initial dose is well tolerated.

For example, novel PDE antibodies or fragments thereof may be conjugated to a second molecule, such as a therapeutic agent (e.g., a cytotoxic agent) resulting in an immunoconjugate. The immunoconjugate can be used for targeting the second molecule to a novel PDE positive cell, thereby inhibiting the growth of the novel PDE positive cell (Vitetta, E. S. et al., 1993 "Immunotoxin Therapy" pp. 2624–2636, in: *Cancer: Principles and Practice of Oncology*, 4th ed., ed.: DeVita, Jr., V. T. et al., J.B. Lippincott Co., Philadelphia).

For example, the therapeutic agents include, but are not limited to, anti-tumor drugs, cytotoxins, radioactive agents, cytokines, and a second antibody or an enzyme. Examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, *Pseudomonas* exotoxin (PE) A, PE40, abrin, and glucocorticoid and other chemotherapeutic agents, as well as radioisotopes. Further, the invention provides an embodiment wherein the antibody of the invention is linked to an enzyme that converts a prodrug into a cytotoxic drug. Alternatively, the antibody is linked to enzymes, lymphokines, or oncostatin.

Use of immunologically reactive fragments, such as the Fab, Fab', or F(ab')$_2$ fragments is often preferable, especially in a therapeutic context, as these fragments are generally less immunogenic than the whole immunoglobulin. The invention also provides pharmaceutical compositions having the monoclonal antibodies or anti-idiotypic monoclonal antibodies of the invention, in a pharmaceutically acceptable carrier.

The invention further provides vaccines formulated to contain novel PDE protein or fragment thereof. The use of a protein antigen in a vaccine for generating humoral and cell-mediated immunity is well known in the art and can be readily practiced for employing a novel PDE protein or fragments thereof, or a novel PDE-encoding nucleic acid molecule and recombinant vectors capable of expressing and appropriately presenting the novel PDE immunogen.

Dosages of novel PDE proteins will depend upon various factors generally appreciated by those of skill in the art, including without limitation the type of disorder and the severity, grade, or stage of the disorder, the binding affinity and half life of the protein used, the desired steady-state protein concentration level, frequency of treatment, and the influence of chemotherapeutic and/or immune regulating agents used in combination with the treatment method of the invention. Typical daily doses may range from about 0.1 ug/kg to 100 mg/kg. Doses in the range of 1–500 mg mAb per week may be effective and well tolerated, although even higher weekly doses may be appropriate and/or well tolerated. The principal determining factor in defining the appropriate dose is the amount of a particular protein necessary to be therapeutically effective in a particular context. Repeated administrations may be required.

For example, viral gene delivery systems may be used to deliver a novel PDE-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a novel PDE protein or fragment thereof introduced into the patient (e.g., intramuscularly) to induce an appropriate immune response. In one embodiment, the full-length human novel PDE cDNA may be employed. In another embodiment, novel PDE nucleic acid molecules encoding specific cytotoxic T lymphocyte (CTL) epitopes may be employed. CTL epitopes can be determined using specific algorithms (e.g., Epimer, Brown University) to identify peptides within a novel PDE protein which are capable of optimally binding to specified HLA alleles.

Various ex vivo strategies may also be employed. One approach involves the use of dendritic cells to present novel PDE antigen to a patient's immune system. Dendritic cells express MHC class I and II, B7 costimulator, and IL-12, and are thus highly specialized antigen-presenting cells. Dendritic cells can be used to present novel PDE peptides to T cells in the context of MHC class I and II molecules. In one embodiment, autologous dendritic cells are pulsed with PDE8 peptides capable of binding to MHC molecules. In another embodiment, dendritic cells are pulsed with the complete novel PDE protein. Yet another embodiment involves engineering the overexpression of a novel PDE gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182).

Anti-idiotypic anti-PDE antibodies can also be used in anti-cancer therapy as a vaccine for inducing an immune response to cells expressing a novel PDE protein. Specifically, the generation of anti-idiotypic antibodies is well known in the art and can readily be adapted to generate anti-idiotypic anti-PDE antibodies that mimic an epitope on a novel PDE protein (see, for example, Wagner et al., 1997, Hybridoma 16: 33–40; Foon et al., 1995, J Clin Invest 96: 334–342; Herlyn et al., 1996, Cancer Immunol Immunother 43: 65–76). Such an anti-idiotypic antibody can be used in anti-idiotypic therapy.

Genetic immunization methods may be employed to generate prophylactic or therapeutic humoral and cellular immune responses directed against a novel PDE. Using the novel PDE-encoding DNA molecules described herein, constructs comprising DNA encoding a novel PDE protein/imunogen and appropriate regulatory sequences may be injected directly into muscle or skin of an individual, such that the cells of the muscle or skin take-up the construct and express the encoded novel PDE. The novel PDE8 protein/immunogen may be expressed as a cell surface protein or be secreted. Expression of a novel PDE protein/immunogen results in the generation of prophylactic or therapeutic humoral and cellular immunity. Various prophylactic and therapeutic genetic immunization techniques known in the art may be used (for review, see information and references published at internet address www.genweb.com).

The invention further provides methods for inhibiting cellular activity (e.g., cell proliferation, activation, or propagation) of a cell expressing a novel PDE protein on its cell surface. This method comprises reacting the immunoconjugates of the invention (e.g., a heterogenous or homogenous mixture) with the cell so that the novel PDE or antigens on the cell surface forms a complex with the immunoconjugates. The greater the number of novel PDE antigens on the cell surface, the greater the number of novel PDE-antibody complexes. The greater the number of novel PDE-antibody complexes, the greater the cellular activity that is inhibited. A subject with a neoplastic or preneoplastic condition can be treated in accordance with this method when the inhibition of cellular activity results in cell death.

A heterogenous mixture includes novel PDE antibodies that recognize different or the same epitope, each antibody being conjugated to the same or different therapeutic agent. A homogenous mixture includes antibodies that recognize the same epitope, each antibody being conjugated to the same therapeutic agent.

The invention further provides methods for inhibiting the biological activity of novel PDEs by blocking novel PDEs from binding its respective ligand. The methods comprises contacting an amount of novel PDE with an antibody or immunoconjugate of the invention under conditions that permit a novel PDE-immunoconjugate or novel PDE-antibody complex thereby blocking the novel PDE from binding its ligand and inhibiting the activity of novel PDE.

Novel PDE Promoters and Other Expression Regulatory Elements

The invention further provides the expression control sequences found 5' of the of the novel PDE genes in a form that can be used in generating expression vectors and transgenic animals. Specifically, the novel PDE expression control elements, such as the PDE8 or TbPDE2A/2B/2C/2E promoter that can readily be identified as being 5' from the ATG start codon in the PDE8 or TbPDE2A/2B/2C/2E gene, can be used to direct the expression of an operably linked protein encoding DNA sequence. A skilled artisan can readily use the novel PDE gene promoter and other regulatory elements in expression vectors using methods known in the art.

Generation of Transgenic Animals

Another aspect of the invention provides transgenic non-human mammals comprising novel PDE nucleic acids. For example, in one application, novel PDE-deficient non-human animals can be generated using standard knock-out procedures to inactivate a novel PDE homologue or, if such animals are non-viable, inducible novel PDE homologue antisense molecules can be used to regulate novel PDE homologue activity/expression. Alternatively, an animal can be altered so as to contain a novel PDE-encoding nucleic acid molecule or an antisense-novel PDE expression unit that directs the expression of novel PDE protein or the antisense molecule in a tissue specific fashion. In such uses, a non-human mammal, for example a mouse or a rat, is generated in which the expression of the novel PDE homologue gene is altered by inactivation or activation and/or replaced by a novel PDE gene. This can be accomplished using a variety of art-known procedures such as targeted recombination. Once generated, the novel PDE homologue deficient animal, the animal that expresses novel PDE (human or homologue) in a tissue specific manner, or an animal that expresses an antisense molecule can be used to (1) identify biological and pathological processes mediated by the novel PDE protein, (2) identify proteins and other genes that interact with the novel PDE proteins, (3) identify agents that can be exogenously supplied to overcome a novel PDE protein deficiency and (4) serve as an appropriate screen for identifying mutations within the novel PDE genes that increase or decrease activity.

For example, it is possible to generate transgenic mice expressing the human minigene encoding PDE8A or PDE7A, or TbPDE2A/2B/2C/2E in a tissue specific-fashion and test the effect of over-expression of the protein in tissues and cells that normally do not contain the these novel PDE proteins. This strategy has been successfully used for other genes, namely bcl-2 (Veis et al. Cell 1993 75:229). Such an approach can readily be applied to a novel PDE protein/gene and can be used to address the issue of a potential beneficial or detrimental effect of the novel PDE proteins in a specific tissue.

COMPOSITIONS

The invention provides a pharmaceutical composition comprising a novel PDE nucleic acid molecule of the invention or an expression vector encoding a novel PDE protein or encoding a fragment thereof and, optionally, a suitable carrier. The invention additionally provides a pharmaceutical composition comprising an antibody or fragment thereof which recognizes and binds a novel PDE protein. In one embodiment, the antibody or fragment thereof is conjugated or linked to a therapeutic drug or a cytotoxic agent.

Suitable carriers for pharmaceutical compositions include any material which when combined with the nucleic acid or other molecule of the invention retains the molecule's activity and is non-reactive with the subject's immune systems. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods. Such compositions may also be formulated within various lipid compositions, such as, for example, liposomes as well as in various polymeric compositions, such as polymer microspheres.

The invention also provides a diagnostic composition comprising a novel PDE nucleic acid molecule, a probe that specifically hybridizes to a nucleic acid molecule of the invention or to any part thereof, or a novel PDE antibody or fragment thereof. The nucleic acid molecule, the probe or the antibody or fragment thereof can be labeled with a detectable marker. Examples of a detectable marker include, but are not limited to, a radioisotope, a fluorescent compound, a bioluminescent compound, a chemiluminescent compound, a metal chelator or an enzyme. Further, the invention provides a diagnostic composition comprising a novel PDE-specific primer pair capable of amplifying novel PDE-encoding sequences using polymerase chain reaction methodologies, such as RT-PCR.

EXAMPLES

The following examples are presented to illustrate the present invention and to assist one of ordinary skill in making and using the same. The methodology and results may vary depending on the intended goal of treatment and the procedures employed. The examples are not intended in any way to otherwise limit the scope of the invention.

Example 1

The following example provides the method used for PDE8A sequence determination.

The complete N-terminus of PDE8A was obtained as follows. The truncated human PDE8A was previously published (Leu$_{117}$-end) (Fisher, D. A., Smith, J. F., Pillar, J. S., StDenis, S. H., and Cheng, J. B. (1998) *Biochem. Biophys. Res. Commun.* 246, 570–577). Using primers synthesized to the known sequence, the sequence of PDE8A was extended to Gly$_{58}$ using 5'RACE (Clontech, Palo Alto, Calif.) of a preparation of mRNA from stimulated CD4$^+$ T cells. 3' RACE confirmed the previously published human PDE8A 3' sequence. BLAST (Basic Local Alignment Search Tool) (Altschul, S. F., Gish, W. et al. (1990) *J. Mol. Biol.* 215, 403–10) was used to search the human EST database using the published human PDE8A sequence as query. An EST clone (AI474074) was purchased from Genome Systems (St. Louis, Mo.) and sequenced. Sequencing was performed using an ABI Prism Model 377 sequencer and BigDye terminator cycle sequencing kit (Perkin-Elmer, Foster City, Calif.). Sequencing reactions were purified using centri-sep columns (Princeton separations, Adelphia, N.J.). Sequences were assembled using the program terminus which overlapped with both the published sequence and the RACE determined sequence (FIG. 1A). This sequence is very similar to the N-terminus of the published mouse PDE8A sequence (Soderling, S. H., Bayuga, S. J., and Beavo, J. A. (1998) *Proc. Natl. Acad. Sci. USA* 95, 8991–8996), although there is a small area of difference indicating the possibility of more splice variants (FIG. 1B). The 5' end was further confirmed by immunoblotting of CD4$^+$ T cells with a peptide antibody (PIL9) corresponding to the first 15 residues of mouse PDE8A. The PAS/PAC motif of PDE8 was identified by Hidden Markov Modeling search (Schuler, G. D., Altschul, S. F., Lipman, D. J. (1991) *Proteins* 9:180–190) of the Simple Modular Architecture Research Tool (SMART) database (Ponting, C. P., Schultz, S. F. et al. (1999) *Nucleic Acids Res.* 27, 229–32). Homology of PDE8 N-terminus to other PAS/PAC containing proteins was detected by Position-Specific Iterated BLAST (PSI-BLAST) searches of the nonredundant GenBank database and by use of the Multiple Alignment Construction and Analysis Worldbench (MACAW (Schuler, G. D., Altschul, S. F., Lipman, D. J. (1991) *Proteins* 9:180–190). The nucleotide sequence of PDE8A shown in FIG. 1A encodes for a protein of 829 amino acids. This sequence is highly homologous to the mouse PDE8A sequence (Soderling, S. et al. (1998) *J Biol Chem* 273, 15553–15558.). However, there is a stretch of about 50 residues where the sequence diverges from the mouse PDE8A sequence (FIG. 1B). This may be a species difference, or may indicate the presence of splice variants. Two additional variants of PDE8A were also obtained. The nucleotide and amino acid sequences of these PDE8A variants are shown in FIGS. 33 and 34. The presence of the predicted N-terminal sequence in CD4+ T cells and a human T cell line, Hut78, was further confirmed by Western blot analusis with antibody PIL9 which is specific for the mouse PDE8A (see below).

Example 2

The following Example describes the method for the detecting the presence of PDE8A in human CD4$^+$ T cells.

Peripheral blood mononuclear cells were isolated from one human buffy coat (50 mL) by centrifugation through a layer of Ficoll-Paque Plus (2000 rpm, 30 min). Cells from the interface were removed and further purified by negative selection. CD4$^+$ T cells were usually isolated using a mixture of monoclonal antibodies (CD8, CD16, CD20, CD25 and HLADr) and goat anti-mouse IgG conjugated to magnetic beads according to the manufacturers protocol (Dynal, Lake Success, N.Y.). In some cases the CD4$^+$ T cell isolation kit was used in combination with the CD69 microbead kit (to remove activated cells). The labeled cells were removed by passage through a CS column (Miltenyi Biotec, Auburn, Calif.) placed in a magnetic field. The CD4$^+$ T cells passing through the column (at least 98% pure as determined by FACS analysis) were resuspended in RPMI/10% FBS/pen/strep/glutamine medium. The cells were stimulated as follows. Plates (Corning, Acton, Mass.) were precoated with goat anti-mouse IgG (10 µg/mL) for 2 hours at 37° C. and then washed with PBS. Cells were added to the plate together with CD3 (0.01 µg/mL) and CD28 (0.1 ug/mL) monoclonal antibodies and were harvested at various time points. The presence of PDE8A protein and RNA in activated CD4$^+$ T cells was detected by Western blotting and RT-PCR (see example 3). The present invention has shown for the first time that PDE8A is present in a pure preparation of activated human CD4$^+$ T cells and more importantly that it is not present at detectable levels in the non activated cells. This in turn supports the idea that induction of this PDE is important to the activation and function of T cells.

Example 3

The following example provides the method of detection of PDE8A and PDE7A1 by Reverse Transcription-PCR analysis.

RNA was isolated from the cytoplasm of CD4$^+$ cells using the Qiagen RNeasy kit (Qiagen, Valencia, Calif.) and cDNA was synthesized using the Promega reverse transcription system. PCR was performed using 1 µL of undiluted or serially diluted cDNA and gene specific primers for 35 cycles (94° C., 1 min., 55° C., 1 min., 72° C., 2 min.). The primers used had the following sequences:

```
7A1p1:
GATATTTGTAACCCATGTCGGACG        (SEQ ID NO.: 17)
and

7A1p2:
GAAAGCTTGGCGGTACTCTACGAT        (SEQ ID NO.: 18)

7A3p1:
ACGCAGGAATTCTTCCATCAAGGAGAT     (SEQ ID NO.: 19)
and

7A3p2:
AGCTTCCACATGAGCGAATAATGGATT     (SEQ ID NO.: 20)

8Ap1:
GTAATGCCTTTCAATTCTGCTGGATTTACA  (SEQ ID NO.: 21)
and

8Ap2:
ACGAGTGTCAGACTGAA-CACATTCGGATAT (SEQ ID NO.: 22)
```

It was previously shown that PDE7A is essential for T cell activation and becomes upregulated during T cell activation (Li, L., Yee, C., and Beavo, J. A. (1999) *Science* 283, 848–851). There is; however, a small amount of basal PDE7A. This amount varies depending on the donor as well as the method of preparation of CD4$^+$ cells. The method of preparation using the monoclonal antibodies and anti-mouse magnetic beads is preferred since the CD4$^+$ T cell isolation kit leads to activation of T cells as measured by the presence of PDE7A. PDE7A becomes upregulated early with a distinct difference in levels shown as early as 1 hour after stimulation. The PDE8A becomes upregulated later reaching a maximum between 8 and 16 hours. The time course shown in FIG. 2A is very likely quantitative as the right panel with dilutions of cDNA demonstrates that the signal is linear under the conditions used in this method. Similar to PDE7A (Li, L., Yee, C., and Beavo, J. A. (1999) *Science* 283, 848–851), both CD3 and CD28 are required for PDE8A upregulation (FIG. 2B). The effect of inhibitors on upregulation of PDE8A is shown in FIGS. 2C and 2D. PP2 is an inhibitor of lck kinase (Hanke, J. H., Gardner, J. P., Dow, R. L., Changelian, P. S., Brissette, W. H., Weringer, E. J., Pollok, B. A., and Connelly, P. A. (1996) *J. Biol. Chem.* 271, 695–701). Lck kinase activation and subsequent tyrosine phosphorylation is an important first step in T cell activation (Veillette, A., Bookman, M. A., Horak, E. M., Samelson, L. E., and Bolen, J. B. (1989) *Nature* 338, 257–259). FIG. 2C shows that PP2 leads to reduction of PDE7A upregulation 1 hour after stimulation. The PDE8A activity is also greatly reduced. Li et al. (Li, L., Yee, C., and Beavo, J. A. (1999) *Science* 283, 848–851) have shown that a PDE7A antisense S-oligo has a large effect on proliferation of T cells and also reduces PDE7A RNA levels to some extent. FIG. 2D shows that the PDE7A antisense oligo also has an effect on PDE8A upregulation by delaying the time course of upregulation.

The data from these inhibitor studies suggests that upregulation of PDE8A is dependent upon earlier upregulation of PDE7A. The data further suggests that inhibiting the upregulation of PDE7A, which occurs at an early time point, also has an effect on inhibiting the upregulation of PDE8A.

Example 4

The following example provides the method for the characterization of PDE8A, PDE7A1 and PDE7A3 by Western blot analysis.

CD4+ T cells were stimulated and isolated at various time points. Cells ($5 \times 10^6$) were harvested by centrifugation and resuspended in 20 µL 20 mM Tris pH7.5. The cells were sonicated, SDS sample buffer was added and the samples were boiled. The samples were run on SDS-gels (8% acrylamide) and blotted onto PVDF membrane. Membranes were blocked with blocking buffer (10 mM Tris pH7.5, 100 mM NaCl, 0.2% Tween 20, 3% non-fat milk). PDE7A and PDE8A monoclonal or polyclonal primary antibodies, and anti-mouse IgM or anti-rabbit IgG HRP conjugated secondary antibodies, were each incubated with the blot for 1 hour. The blot was developed using SuperSignal Chemiluminescent substrate (Pierce, Rockford, Ill.) and exposure to X-ray film.

Figure 3:
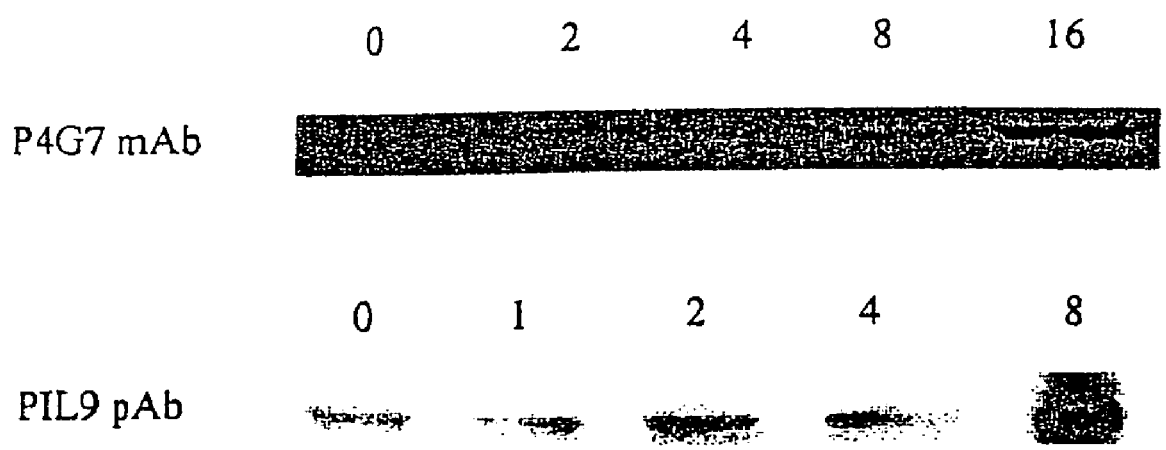
FIG. 3 is a Western blot analysis showing upregulation of PDE8A protein at various times after T cell stimulation, as described in Example 4, infra. Two PDE8A antibodies were used: a monoclonal antibody to a PAS domain fusion (P4G7) and a polyclonal antibody to a N-terminal peptide (PIL9).

Western blot analysis (FIGS. 3 and 11) was performed using a time course of CD4+ T cell activation. PDE7A (P5H7) and PDE8A (P4G7A) monoclonal antibodies were obtained from hybridoma cell lines developed by injecting mice with a GST fusion protein of the C-terminal 100 residues of PDE7A or a thioredoxin fusion of a PAS domain of PDE8A respectively. In addition, a peptide antibody specific for the N-terminus of mouse PDE8A (PIL9: MGCAPSIHTSENRTF (SEQ ID NO.: 23) or the C-terminus of human PDE8A (PIL13: KGLDEMKLRNLRPPPE (SEQ ID NO.: 24) was used. The PDE7A3 peptide polclonal antibody is specific for C-terminus (6976: QIGNYTYL-DIAG (SEQ ID NO.: 25). The N-terminus contains a FLAG tag and has the following sequence: MDYKDDDDKG-SYNM<u>EWQGI</u> (SEQ ID NO.: 26). The underlined sequence is the start of the PDE8A1 which is residue E285 using the numbering shown in FIG. 1A. For PDE7A blots, a biotinylated monoclonal antibody for PDE7A (P5H7) and a strepavidin horseradish peroxidase conjugate were used.

As shown in FIG. 6, both of the PDE8A antibodies (P4G7 and PIL13) recognize a band of the same size which migrates at approximately 100 kDa, similar to the predicted molecular weight of 93,235 Da for PDE8A.

The PDE7A1 band migrates at 55 kDa (FIG. 11). One of the problems encountered when detecting upregulation of PDE7A1 in CD4+ T cells by Western blot is due to the fact that cells are stimulated with antibodies to CD3 and CD28 which remain in cell extract and are detected by secondary antibody in Western blots. The heavy chain of these antibodies migrates at about 55 kDa which is the same size as PDE7A1. Therefore, the PDE7A1 Western blot analysis was performed with biotin-conjugated monoclonal antibody and strepavidin-horseradish peroxidase.

A Western blot using the monoclonal antibody P4H7 and a goat anti-mouse-kappa-horseradish peroxidase conjugate shoes both PDE7A1 (upper band, FIG. 11, bottom panel) and PDE7A3 (lower band, FIG. 11, bottom panel). Further, a polyclonal antibody to the C-terminal peptide of PDE7A3 (6976) and a goat-anti-rabbit IgG horseradishperoxidase conjugate were used for the PDE7A3 blot, and a single band for PDE7A3 was detected (FIG. 11, third panel).

The Western blot data (FIGS. 3 and 11) further confirms that in CD4+ T cells, the protein levels of PDEs 8A, and 7A are also upregulated after CD3 and CD28 stimulation.

Example 5

This example shows that PDE8A is involved in T cell proliferation and the T cell proliferative activity is reduced if PDE8A can be inhibited by antisense molecules.

A 96 well plate was precoated with goat anti-mouse IgG (10 µg/mL in PBS). CD4+ cells were seeded at 100000 cells/well in 200 µL medium and stimulated with 0.2 ng/mL CD3 and 0.2 µg/mL anti CD28 antibodies. The cells were incubated for 2–3 days at 37° C. at which point 1 µCi $^3$H-thymidine/well was added. The cells were grown an additional 16 hours and then harvested with a PHD cell harvester. Ultima Gold scintillation fluid (Packard) was added to the filter paper disks and 3H-thymidine incorporation into cells was measured by scintillation counting. In some cases antisense oligos were added at the time of stimulation and their effect on T cell proliferation was examined.

Figure 4:
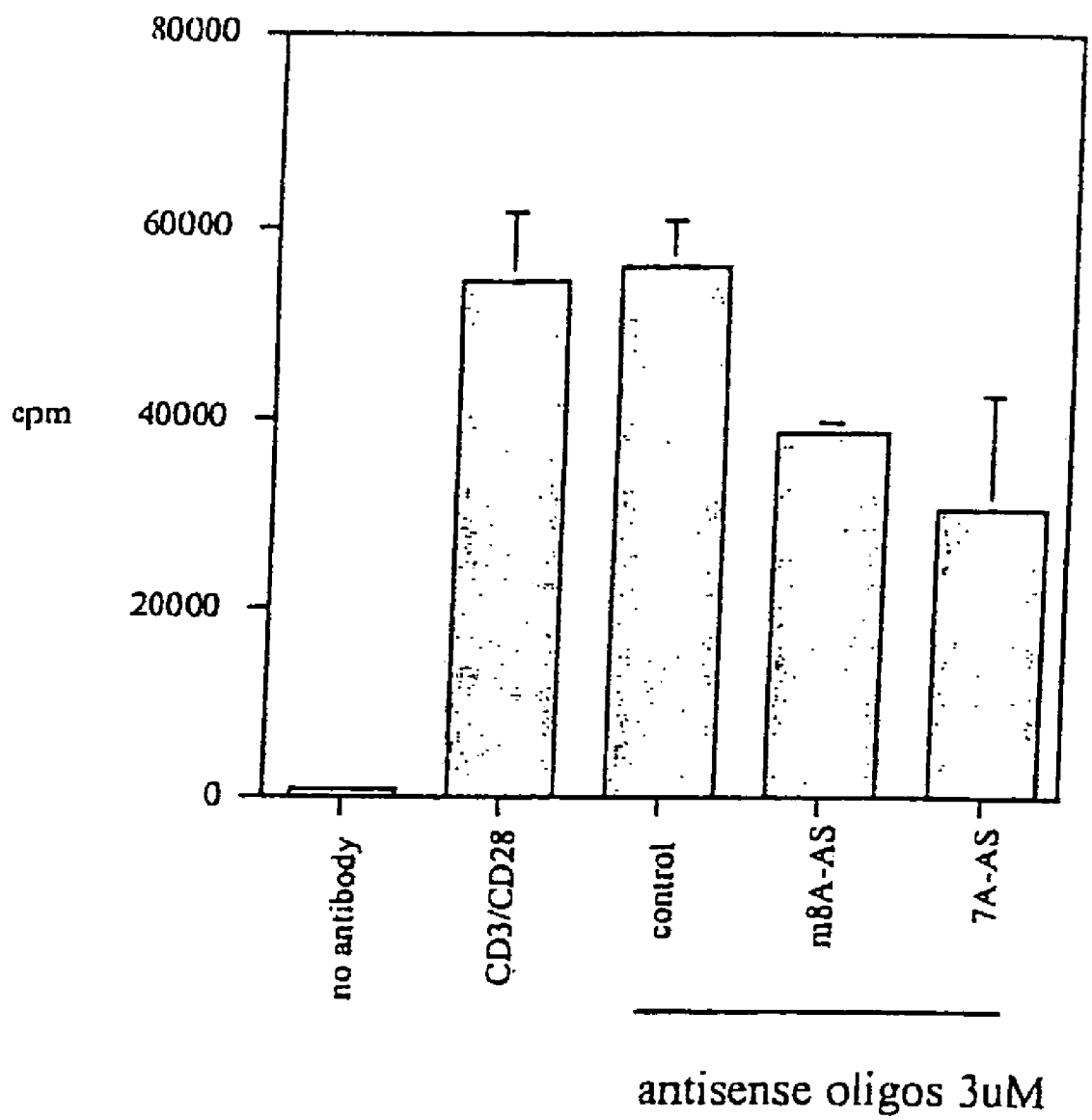
FIG. 4 shows inhibition of proliferation of CD4+ T cells by a PDE8A antisense oligonucleotide, as described in Example 5, infra.

The PDE7A and PDE8A both inhibited T cell proliferation (FIG. 4). Under the conditions used, the 7A-AS sequence (PDE7A specific antisense) inhibited T cell proliferation about 50% while the PDE8A antisense sequence inhibited T cell proliferation about 30%. It has been previously shown that antisense inhibitors of PDE7A can almost completely inhibit T cell proliferation. The paper of Li et al. (Li, L., Yee, C., and Beavo, J. A. (1999) *Science* 283, 848–51) showed about 90% inhibition of proliferation of CD4+ T cells. Data shown here suggests that a PDE8A inhibitor may have less of an effect on T cell proliferation since the upregulation of PDE8A is at a later time point and there are other pathways involved in proliferation. A possible advantage of PDE8A inhibitor over a PDE7A inhibitor may be that it would be able to slow down T cell proliferation but not knock it out completely. This could have substantial therapeutic advantage, as it may be less likely to compromise the immune system.

Example 6

The following example describes that the PDE8A activity that is expressed on a human CD4+ T cell line hut78 is distinct from that of recombinantly expressed PDE8A in terms of sensitivity to inhibitors.

Since pure CD4+ T cells can only be obtained in limited quantities, a human CD4+ T cell line, hut78, (ATCC, Manassas, Va.), was used to study the activity of PDE8A. Hut78 cells ($2 \times 10^8$) were resuspended in 20 mM Tris pH 7.5 buffer containing protease inhibitors (Boehringer Mannheim, Indianapolis, Ind.) and sonicated. The supernatant was removed after centrifugation at 15000×g for 10 minutes and applied to a Mono Q column attached to a Rainin Dynamax HPLC system (Ameryville, Calif.). A NaCl gradient (0–0.8M) was passed through the column and 250 uL fractions were collected. The fractions were assayed for activity using either 1 µM or 0.01 µM cAMP as substrate and the indicated concentration of inhibitor (FIG. 5). Western blot analysis was also performed (10 µL/well) using PDE7A or 8A antibodies.

As shown in FIG. 5A, there are two main peaks of PDE activity as measured with 1 µM cAMP as substrate. It has been previously shown that two peaks contain PDEs 7 and 4 respectively (Bloom, T. J. and Beavo, J. A. (1996) *Proc. Natl. Acad. Sci. USA* 93, 14188–14192; Ichimura, M. and Kase, H. (1993) *Bioch. Bioph. Res. Comm.* 193, 985–990). When the fractions were assayed with 0.01 µM cAMP, only one peak was seen (FIG. 5B). At this low concentration, there is negligible contribution to activity by PDE4 and only low Km PDEs are detected. This peak was resistant to rolipram but sensitive to IBMX. Western blot analysis across the peak showed that it was actually made up of PDE8A in the front part of the peak and PDE7A in the back part of the peak. (FIG. 5C). Two or three of the fractions contained only PDE8A and the activity of those fractions that contained only PDE8A was also inhibited by IBMX. This was not predicted to be the case as the recombinant expressed PDE8A has been shown to be resistant to IBMX (Fisher, D. A., Smith, J. F., Pillar, J. S., StDenis, S. H., and Cheng, J. B. (1998) Biochem. Biophys. Res. Commun. 246, 570–577).

These results suggest that the PDE8A as it is expressed in the activated T cells may be in a form which is sensitive to IBMX, different from the recombinant form of PDE8A. To address this question, PDE8A from hut78 cells was immunoprecipitated and the immunoprecipitated activity was assayed with 0.01 µM cAMP in the presence of different concentration of IBMX (See example 7). This result strongly implies that the activated recombinant PDE8A or that isolated from cells expressing the activated forms but not normally expressed recombinant PDE8A is the most appropriate target for drug screening.

Example 7

The following example describes immunoprecipitation of PDE8A and shows that the biochemical activity of PDE8A localizes with the immunoprecipitated protein.

From the experiments discussed in Example 6, it seemed likely that PDE8A as it is expressed in the activated human T cell line may be in a form that is sensitive to IBMX, a different form from the recombinant form. In an attempt to verify this result, immunoprecipitation of PDE8A was performed.

Hut78 or CD4+ cells were harvested at various points after stimulation with CD3 and CD28 antibodies. Cells were resuspended in IP buffer (20 mM Tris pH7.5, 100 mM NaCl, 1 mM benzamidine, 1 µg/mL leupeptin, 1 µg/mL pepstatin, 50 mM NaF, 2 mM EDTA) and sonicated. The cells were centrifuged at 15000×g for 10 minutes. The supernatant was precleared for 2 hours with 0.5 µg mouse IgG and 10 µL protein-G agarose (Santa Cruz Biotechnology, Santa Cruz, Calif.). PDE8A monoclonal antibody was preloaded onto 10 µL protein G-agarose and added to the precleared supernatant. The immunoprecipitations were agitated overnight at 4° C. and the beads washed three times with IP buffer containing 1M NaCl followed by one wash with IP buffer. The beads were assayed for activity with 0.01 µM cAMP in the presence or absence of IBMX.

The results shown in FIGS. 6A and 6B demonstrate that PDE8A activity from hut78 CD4+ T cells is IBMX sensitive and increases after stimulation. Hut78 cells were immunoprecipitated with a PDE8A monoclonal antibody, and the precipitated activity was assayed in the presence or absence of IBMX (FIG. 6A). The $IC_{50}$ value was determined to be 13 µM (FIG. 6A). FIG. 6B shows that immunoprecipitated activity of PDE8A from CD4+ T cells increases after activation. This increase in activity could be inhibited by IBMX.

Example 8

The following example shows that trypsin digestion of recombinant PDE8A results in increased sensitivity to IBMX.

To determine mechanism by which PDE8A might show an increased sensitivity to inhibitors, limited trypsin digestion of sf9 expressed PDE8A was performed. Briefly, human PDE8A was expressed in Sf9 cells (ATCC, Manassas, Va.). This PDE8A was already N-terminally truncated at position 285. The supernatant ($10^6$ cells/digestion) was isolated and digested with the indicated amounts of trypsin at the indicated times at 30° C. The digestion was stopped with a 100-fold excess of soybean trypsin inhibitor. The activity was assayed with 1 µM cAMP. In some cases IBMX was added. The digested PDE8A was analyzed by Western blot analysis using a peptide antibody specific to the C-terminus (PIL13) or the P4G7 monoclonal antibody.

Figure 13:
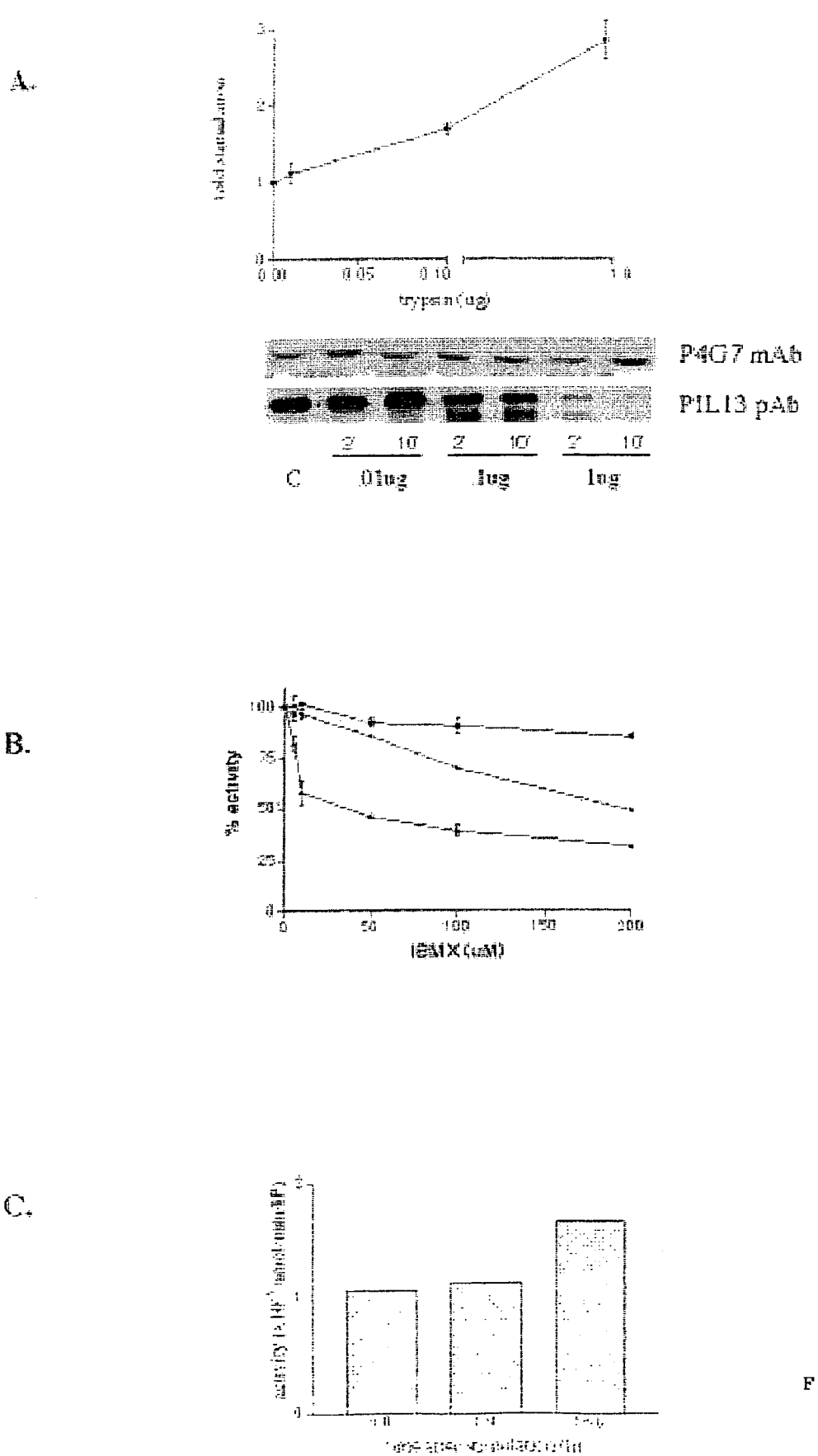
FIG. 13A shows that PDE activity of human PDE8A expressed in sf9 cells increases after digestion with trypsin for 2 min (■), as described in Example 8, infra. The inset the graph shows Western blot analysis of the 2 min or 10 min digested samples performed with the monoclonal PDE8A antibody (P4G7) or the polyclonal antibody specific For the C-terminal peptide (PIL13).
FIG. 13B shows that PDE8A activity of trypsin digested sf9-expressed PDE8A is sensitive to IBMX inhibition. IBMX inhibition of undigested PDE8A/sf9 extract (■), the two minute trypsin digested extract (♦) and PDE8A immunoprecipitated from Hut78 cells (▲). The cell extracts were immunoprecipitated with PDE8A monoclonal antibody ($3 \times 10^7$ cells/IP) and assayed with 0.01 μM cAMP, as described in Example 8, infra.
FIG. 13C shows the activity of immunoprecipitated PDE8A from CD4+ T cells with 0.01 μM cAMP.

The results of this experiment shown in FIGS. 6, 7 and 13, show that the PDE activity (Vmax) can be increased up to 3 fold after trypsin digestion. The inset below the graph shows Western blotting of samples using either a C-terminal antibody (PIL13) or the PAS domain antibody (P4G7), which recognizes the N-terminus of this construct. The PIL13 blot shows that the N-terminus becomes digested with 0.1 µg trypsin and the epitope is cleaved from the C-terminus with 1 µg trypsin. It is possible that PDE8A has a C-terminal inhibitory domain and activity increases after this is cleaved. FIG. 7B shows that the digested PDE8A had a differing sensitivity to IBMX. At 1 µM IBMX, the activity of undigested PDE8A was unchanged while trypsin digested PDE8A retained only 40% of its activity. While the undigested PDE8A was resistant to IBMX inhibition, the trypsin digested PDE8A was inhibited by IBMX with an IC50 of approximately 200 µM (FIG. 13B). The Km of trypsin digested PDE8A was increased about four fold from 0.07 µM to 0.29 µM. In order to evaluate IBMX sensitivity of PDE8A in T cells, immunoprecipitation of PDE8A from Hut78 cell line, was performed. As shown in FIG. 13B, PDE8A was inhibited by IBMX with an IC50 of 39 µM. The Km of immunoprecipitated PDE8A was 0.18 µM. FIGS. 6B and 13C show that immunoprecipitated activity of PDE8A from CD4+ T cells increases after activation.

From the experiments discussed in Examples 6, 7 and 8, it appears that PDE8A activity in CD4+ T cells is distinct from that of the recombinant PDE8A protein in its susceptibility to inhibitors. This invention further shows that even the recombinant PDE8A when treated with trypsin demonstrates an increased sensitivity to IBMX. Therefore, it is possible that PDE8A in T cells may be modified in some way, for instance by phosphorylation or binding of a ligand to its PAS domain. It may also be a part of a complex with other proteins. These modifications may decrease the affinity for cAMP and thereby may make it more susceptible to IBMX inhibition. This raises an interesting possibility that inhibitors which were previously not considered to be useful for PDE8A may actually be effective in vivo. A somewhat similar observation has been seen previously for PDE4A which had a 17 fold lower IC50 for rolipram when complexed with a Lyn-SH3 domain (McPhee, I., Yarwood, S. J., Scotland, G., Huston, E., Beard, M. B., Ross, A. H., Houslay, E. S., and Houslay, M. D. (1999) *J. Biol. Chem.* 274, 11796–11810) and PDE4D which has an 8 fold lower IC50 for tolipram when activated by PKA phosphorylation at Serine 54.

Example 9

The following Example describes a new PDE7A splice variant, PDE7A3 and demonstrates that PDE7A3 is upregulated in CD4+ T cells at alater time point than PDE7A1.

The PDE7A3 sequence was obtained by performing RACE of a preparation of mRNA from 16 hour stimulated CD4+ T cells. 3' and 5' RACE were performed using the SMART RACE cDNA amplification kit (Clontech) and a pair of nested gene specific primers. RACE PCR products were cloned into a pCRII-TOPO vector (Invitrogen) and sequenced as discussed in Example 1. The new sequence information was obtained with 3' RACE which demonstrated that PDE7A3 is a C-terminal splice variant. Additionally, PDE7A1 N-terminal sequence was obtained using 5' RACE and confirmed that this belonged to the PDE7A3 C-terminus by RT-PCR which amplified the whole PDE7A3 sequence. The nucleotide and amino acid sequence of PDE7A3 are shown in FIGS. 8A and 8B respectively. In addition, another variant of PDE7A3 was obtained and had the nucleotide and amino acid sequences as shown in FIG. 35.

A new 3' splice variant of PDE7A was isolated in CD4+ T cells by 3'RACE using known 7A1 sequence (Bloom, T. J. & Beavo, J. A. (1996) *Proc Natl Acad Sci USA* 93, 14188–14192). The new variant is designated PDE7A3. The nucleotide sequence of PDE7A3 shown in FIG. 8A encodes a protein of amino acids. The predicted amino acid sequence pf PDE7A3 is shown in FIG. 8B. The FIG. 9A shows a C-terminal alignment between PDE7A1 and PDE7A3. The sequence of PDE7A3 diverges at position G415 (PDE7A1 numbering) leading to a truncation immediately after the catalytic domain. We have determined that PDE7A3 has the same N-terminus as PDE7A1 by amplifying the entire sequence by RT-PCR. FIG. 9B shows the relationship of PDE7A3 to the other PDE7A splice variants. FIG. 9C is a Northern blot using a 7A3 probe. This probe is able to react with all splice variants of PDE7A because of the small amount of sequence difference between them. These results are similar to the results of Li et. al. (*Pathobiology* (1995) 63, 175–87) who used a PDE7A1 probe. PDE7A1 mRNA is the most abundant PDE7A variant in the tissues tested and has a transcript size of 4.2 kb. PDE7A2 is highly expressed in skeletal muscle and heart with a transcript size of 3.8 kb. The PDE7A3 transcript is smaller at about 3.0 kb and is expressed in heart and skeletal muscle. Faint bands are also seen in spleen, thymus, testis and peripheral blood leukocytes. Further, PDE7A3 is present in testis, skeletal muscle, CD4+ T cells, CD8+ T cells, B cells and the cell lines, Hut78 and Jurkat, as confirmed by sequencing RT-PCR products. The fact that only a faint band is seen in the peripheral blood leukocyte fraction on the Northern blot is probably due to the fact that PDE7A3 is upregulated at a late time point after cell stimulation.

PDE7A3 RNA (FIG. 10) and protein (FIG. 11) are both upregulated in CD4+ T cells after stimulation. The band reacting with the PDE7A3 specific polyclonal antibody (FIG. 11) becomes upregulated at a late time point and migrates at approximately 50 kDa. This is close to the predicted molecular weight of 48.8 kDa. Western blot analysis was also performed with the PDE7A monoclonal antibody followed by an anti-kappa light chain secondary antibody. The bands were very faint due to the lower level of amplification of the antibody signal, but the 7A blot (lower panel of FIG. 11) showed that two bands were upregulated. The top band migrates at the position of PDE7A1, 55 kDa, while the bottom band migrates at the position of PDE7A3, 50 kDa.

Figure 12:
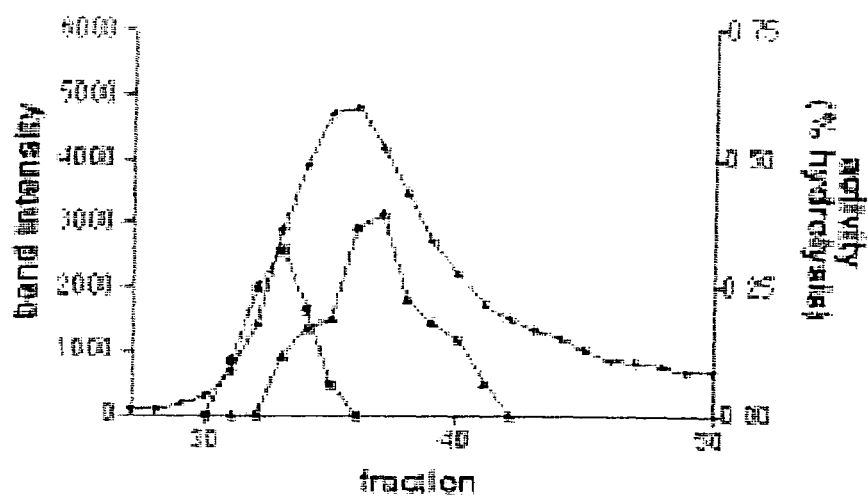
FIG. 12 shows PDE activity profile of a monoQ HPLC profile of hut78 cells using cAMP as a substrate, as described in Example 6, infra. A) PDE activity of profile of Hut cells using 1 μM cAMP as a substrate; B) PDE activity profile using 0.01 μM cAMP as substrate (●) in the presence of 10 μM rolipram (▲) or 100 μM IBMX (□); C) the PDE activity profile (0.01 μM cAMP) overlayed with the band intensities (in arbitrary units) of PDE7A (▲) or PDE8A (■) from the blots shown in the inset below, PDE7A1 was detected with P5H7 monoclonal antibody and PDE8 was detected with PIL9 polyclonal antibody, PDE7A3 was detected with both the P5H7 monoclonal antibody and the 6976 polyclonal antibody and eluted in a region with low activity.

PDE7A3 eluted in a part of the monoQ HPLC profile that had very low activity (FIG. 12C). A band at about 50 kDa was detected with both the PDE7A monoclonal antibody and with the 7A3 peptide antibody. Further, PEDE7A3 expressed in sf9 cells has very low level of activity compared to PDE7A1.

The gene for human PDE7A is found on chromosome 8 and the PDE7A3 C-terminus and 3' untranslated regions mapped to sequence AC055822.

Example 10

The following example describes the yeast two hybrid screening assay for detecting PDE8A protein/protein interaction in vivo.

The yeast two hybrid screening assay (S. Fields and O. K. Song, Nature 340:245–246, (1989), a genetic assay for the detection of protein/protein interactions in vivo, was used to detect and identify molecules involved in protein/protein interaction with PDE8A.

This assay is based on the observation that transcriptional activators contain two distinct domains, a DNA binding domain, which binds DNA promoter elements and an activator domain that recruits the transcriptional machinary necessary to stimulate transcription. Each domain may be seperated and fused with heterologous proteins. If the heterologous proteins interact with each other, then this interaction will bring together the DNA binding domain and activation domain such that transcription is initiated. By assaying for the transcription for two reporter genes in yeast (LacZ which imparts a blue color to positive yeast in the presence of X-gal, and His3, which allows positive yeast to grow on plates lacking histidine) libraries of proteins fused to the activation domain can be screened with a bait protein fused to the DNA binding protein. Library clones containing interacting proteins are identified from yeast that are positive for both selectable markers.

As the PAS/PAC domain has been described as a protein/protein interaction domain (N. Gekakis, L. Saez Science 270(5237): 811–5 (1995)), the N-terminus of murine PDE8, containing the PAS/PAC domain was subcloned into the LexA DNA binding domain vector pBTM115 (referred to as PDE8/LexA). The yeast strain L40 was co-transformed with PDE8/LexA and a cDNA library from testis (Clontech, Palo Alto, Calif.) using the lithium acetate method according to the instructions of the manufacturer (Clontech, Palo Alto, Calif.). Yeast were selected for growth in the absence of histidine and assayed for the LacZ activation by filter lifts using "Z-buffer" according to the Clontech yeast two-hybrid assay protocol. From the initial screen, 414 positive yeast colonies were picked. These clones were then put through a high stringency screen by streaking each colony onto plates lacking histidine and containing the competitive HIS3 inhibitor 3-AT. At this concentration of 3-AT only strongly interacting proteins retain the ability to grow in the absence of histidine. This high stringency screen identified 78 "high affinity" interacting proteins. These 78 clones were sequenced and found to contain several PDE8 interacting proteins, two of which were represented multiple times by independent cDNA clones.

Figure 14:
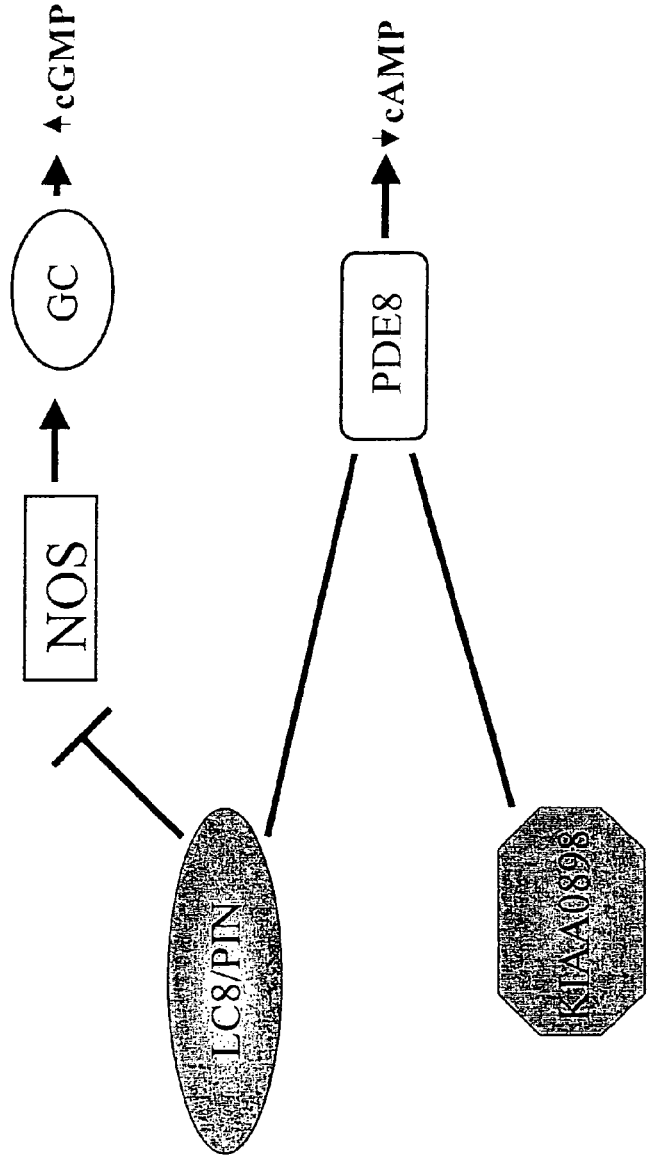
FIG. 14 shows the three classes of PDE8 interacting proteins that were identified using the Yeast Two Hybrid Screening Assay, as described in Example 10, infra.

As shown in Table 1, a total of 45 cDNA clones identified in the PDE8 two-hybrid screen were identified as the LC8 or PIN protein. LC8/PIN (dynein 8 kDa light chain) is a component of the dynein motor complex which is activated by PKA (R. I. Stephens, G. Prior, J Cell Sci 103, (1992)) and also binds stoichiometrically to and inhibits the function of nitric oxide synthase (S. E. Benashski, et al., J Biol Chem 272, (1997), P. Crepieux, et al., *Mol Cell Biol* 17, (1997)) (FIG. 14). Thus LC8/PIN may function to localize and or modulate the function of PDE8.

A second abundant cDNA type (identified in 8 cDNA clones) corresponds to a novel protein identified as a partial cDNA in Genbank as "KIAA0898" (Table 1). KIAA0898 is a multidomain protein, containing a RING domain, a B-box domain, and a merpin/TRAF homology domain (MATH domain). RING and B-box domains often occur together, are thought to serve protein/protein interactions and the cordinated binding of zinc, and may be involved in regulating protein degradation via the ubiquitination pathway (K L. Borden, *Biochem Cell Biol* 1998;76(2–3):351–8; P. S. Freemont, Curr Biol 2000 Jan. 27;10(2):R84–7) (FIG. 8). The MATH domain has an unknown function, however it is conserved between the metalloprotease Merpin and the Tumor Necrosis Factor Receptor Associated Factor (TRAF) (A. G. Uren, D. L. Vaux, *Trends Biochem Sci* 1996 July;21 (7):244–5) suggesting it may play a role in regulating cell survival or death.

TABLE 1

Yeast Two Hybrid Screen

| Protein Family | # of clones |
| --- | --- |
| LC8/PIN | 30 |
| LC8/PIN (Novel) | 15 |
| KIAA0898 | 8 |

Example 11

The following Example describes the cloning, sequence, expression and characterization of a cAMP specific PDE (TbPDE2B) from *Trypanosoma brucei*.

Materials and Methods

Database Searching. The amino acid sequences of mammalian PDEs (PDEs1 to 10) were used as queries to search the EST database. The program used was the Basic Local Alignment Search Tool (BLAST) (Altschul S. F. et al., *J. Mol. Biol.* 1990; 215: 403–10.), accessed from the database search and analysis "Search Launcher". Smith R. F. et al., Genome Res. 1996; 6: 454–62).

Other Databases or Programs The GAF and catalytic domain boundaries were identified both by Hidden Markov Modeling searches of the Simple Modular Architecture Research Tool (SMART) database, and PFAM: Multiple alignments and profile HMMs of protein domains Release 5.1 (Washington University, St. Louis). Alignment of GAF domains were constructed by using CLUSTAL W 1.8 and refined by visual alignment of known signature sequences. Pairwise sequence alignments were made using the SIM-Local Similarity Program accessed from the BCM search launcher. For $K_m$ calculations enzyme activity data were analyzed with the GraphPad PRISM program (GraphPad Software, San Diego, Calif.) using the one site nonlinear regression fit.

Primers. Primers were designed using the program AMPLIFY[21] and were purchased from Operon Technologies (Alameda, Calif.). Their sequences and designations are as follows:

| | | |
| --- | --- | --- |
| AA06.1s (GGAGCTGTTCCAAACCTTCTCTATGTTTG), | (SEQ ID NO.: 27) |
| AA06.2s (CTGGCGCCTCACTACGTAACTGTCGTATC), | (SEQ ID NO.: 28) |
| AA06.1as (GTTGTTTGTCAACTCACGGTTGAAGCG), | (SEQ ID NO.: 29) |
| AA06.2As (CCTGGTACGCGTCCTGAATATTCTCACC), | (SEQ ID NO.: 30) |
| W8.1s (GAAGTTAAGAAGCACCGTAATGTCCC), | (SEQ ID NO.: 31) |
| W8.1as (GATTCCGGATCAGAGAGGATCTCAAC), | (SEQ ID NO.: 32) |
| W8.2as (GCAAGGTTGCAGTGATGCACCTCAAG), | (SEQ ID NO.: 33) |
| AA.c5 (GTAAGATTTGTACATACTTCCGTGAAGGC), | (SEQ ID NO.: 34) |
| GAF.1s (GCTGGGAAAGACAGAGACAGATGACAC), | (SEQ ID NO.: 35) |
| AP1 (GTAATACGACTCACTATAGGGC), | (SEQ ID NO.: 36) |
| AP2 (ACTATAGGGCACGCGTGGT). | (SEQ ID NO.: 37) |

DNA Sequencing and Sequence Assembly. All PCR products were subcloned into the PCRII-TOPO vector (Invitrogen). Plasmid DNA was prepared by using the SNAP kit (Invitrogen). Sequencing was done by using Applied Biosystems ABI PRISM dye terminator cycle-sequencing kit (Perkin-Elmer), and sequencing reactions were purified by using Centri-sep columns (Princeton Separations, Adelphia, N.J.). Sequences were assembled by using the program SEQUENCHER 3.0 (Gene Codes, Ann Harbor, Mich.).

Sequence Amplification. Advantage Genomic Polymerase PCR mix was purchased from Clontech. Reactions were set up as follows: 0.2 μg of *Trypanosoma brucei* DK-4 Istar 1.1 genomic DNA, 0.2 μM W8.1s primer, 0.2 μM AA06.1as primer, 2.5 μl of 10× reaction buffer (supplied with Advantage polymerase), 0.2 mM dNTP, 0.5 μl Advantage genomic polymerase mix, in a final volume of 25 μl, with the following cycling protocol on a GeneMate Genius PCR machine (ISC BioExpress, Kaysville, Utah): 94° C. for 30 sec, 5 cycles of 94° C. for 5 sec, 72° C. for 3 min; 5 cycles of 94° C. for 5 sec, 70° C. for 3 min; 30 cycles of 94° C., for 5 sec, 68° C. for 3 min. To obtain the missing 5' and 3' ends of the open reading frame the Universal Genome Walker Kit (Clontech) was used to produce five Genome Walker genomic "libraries" with the set of restriction enzymes: Dra I, EcoR V, Pvu II, Sca I and Stu I. Each batch of digested genomic DNA was ligated separately to the Genome Walker Adaptor according to the user manual. PCR reactions were set up as follows: 1 μl of each DNA library, 0.2 μM W8.1as or AA06.1s primer, 0.2 μM AP1 primer, 5 μl of 10× Tth PCR reaction buffer (supplied with Advantage Tth polymerase), 0.2 mM dNTP, 1 μl Advantage Tth polymerase mix (50×), in a final volume of 50 μl, with the following cycling protocol: 94° C. for 1 min, 7 cycles of 94° C. for 25 sec, 72° C. for 3 min; 32 cycles of 94° C. for 25 sec, 67° C. for 3 min; 1 cycle of 67° C. for 7 min. A second PCR amplification was carried out using the first PCR products diluted 50 times as template, and the primers W8.2as or AA06.2s and the AP2 primer with the same cycling protocol.

Generation of the complete open reading frame To obtain the ORF sequence of the *T. brucei* PDE, the same protocol was used as for the sequence amplification described above but with the primer AAc5 and GAF Is. This reaction was repeated three times and each PCR product subcloned and sequenced separately to avoid PCR artifacts.

Expression of *T. brucei* PDE. The ORF sequence for *T. brucei* PDE was subcloned into the pcDNA 3.1-TOPO vector (Invitrogen) according to the manual (Eukaryotic TOPO TA Cloning, version C) and plasmid DNA purified as described above. Human embryonic kidney 293 (HEK 293) cells were transfected with 12 µg of DNA in 60 µl of GenePORTER Transfection Reagent (Gene Therapy Systems, San Diego, Calif.) in 100-mm dishes and kept at 37° C. in 5% $CO_2$ for 24 h. After this period fresh medium was added, and incubated under the same conditions for an additional 24 h. The same amount of pcDNA vector containing the sequence for the Green Fluorescent Protein (GFP) was transfected under identical conditions as a positive control for expression and as a negative control for PDE activity. Two plates were harvested at a time and homogenized with 1 ml of homogenization buffer containing 40 mM Tris-HCl, pH 7.5; 15 mM benzamidine; 15 mM 2-mercaptoethanol; 1 µg/ml pepstatin A; 1 µg/ml leupeptin and 5 mM EDTA. The cell suspension was immediately subjected to sonication (3×5 s) on ice. One volume of glycerol and 1 mg/ml of bovine serum albumin were added immediately to the homogenate. A pool from 10 plates was stored at −70° C. in aliquots and did not lose appreciable activity over 1.5 months.

*Sacchromyces cerevisiae* methods. The yeast strain JBS21.51 (mat a; ade2-1oc; can1-100; his3-11,15; leu2–3, 112; trp1–1; ura3-1; pde1::HIS3; pde2::Kan$^r$) was generated from Cry1 (mat a; ade2-1oc; can1-100; his3-11,15; leu2-3, 112; trp1-1; ura3-1), a generous gift of Trisha Davis (University of Washington, Department of Biochemistry), using standard techniques of PCR-based gene replacement. The plasmid JBS52.19, containing the TbPDE2B entire open reading frame on a BstXI fragment was cloned into the SmaI site of p424 (2 µm origin, GPD promoter, TRP1 selection) (Beavo, J. A. and D. H. Reifsnyder, Trends Pharmacol Sci, 1990. 11(4): p. 150–5). Sequencing of the splice junctions confirmed the plasmid construction. Strains JBS67.1 and JBS75 contain p424 in JBS21.51 or Cry1, respectively. Strain JBS67.2 is JBS21.51 containing JBS52.19. All transformations were carried out with the lithium acetate method of Geitz, et al.(Gietz, R. D., et al., Mol Cell Biochem, 1997. 172 (1–2): 67–79). Strains with TRP1 plasmids were maintained on selective media.

Heat shock was performed by replica plating cells to pre-warmed (55° C.) plates after 2 days of growth at 30° C. Plates were maintained at 55° C. for 10 min to 2 h and allowed to cool to room temperature. After two days at 30° C. plates were scored for growth. Soluble extracts were obtained from yeast according to the method of Atienza and Colicelli (Atienza, J. M. and J. Colicelli, Methods, 1998. 14 (1): 35–42).

Phosphodiesterase assay. PDE activities were assayed at different concentrations of [$^3$H] cAMP or [$^3$H] cGMP according to the method of Hansen and Beavo ((Hansen R. S, Beavo J. A., Proc Natl Acad Sci USA 1982;79: 2788–92). The reactions were performed in a buffer containing 40 mM Mops (pH 7.5), 0.8 mM EGTA, 15 mM Mg acetate, 0.2 mg/ml BSA in a final reaction volume of 250 µl. Concentrations from 0.03–300 µM [$^3$H]cAMP were used to determine the $K_m$ value in HEK293 cell lysates and concentrations from 0.002–10 uM[$^3$H]cAMP were used for $K_m$ determination in yeast cell extracts. Hydrolysis of substrate did not exceed 20% under these conditions and PDE activity was proportional to time and enzyme concentration. For inhibition studies, assays were performed in the presence of rolipram (Biomol, Plymouth Meeting, Pa.), Ro 20–1724 (Hoffman-La Roche, Nutley, N.J.), zaprinast (May & Baker, Dagenham, UK), enoximone (Merrell Dow Research Institute), sildenafil (Pfizer Central Research, Sandwich, UK), cGMP, papaverine, 3-Isobutyl-1-methylxanthine (IBMX), EHNA (erythro-9-[3-(2-hydroxynonyl)]-adenine), pentoxifylline, etazolate or dipyridamole obtained from Sigma (St. Louis, Mo.) using 1 µM [$^3$H]cAMP as substrate.

Results

Figure 15:
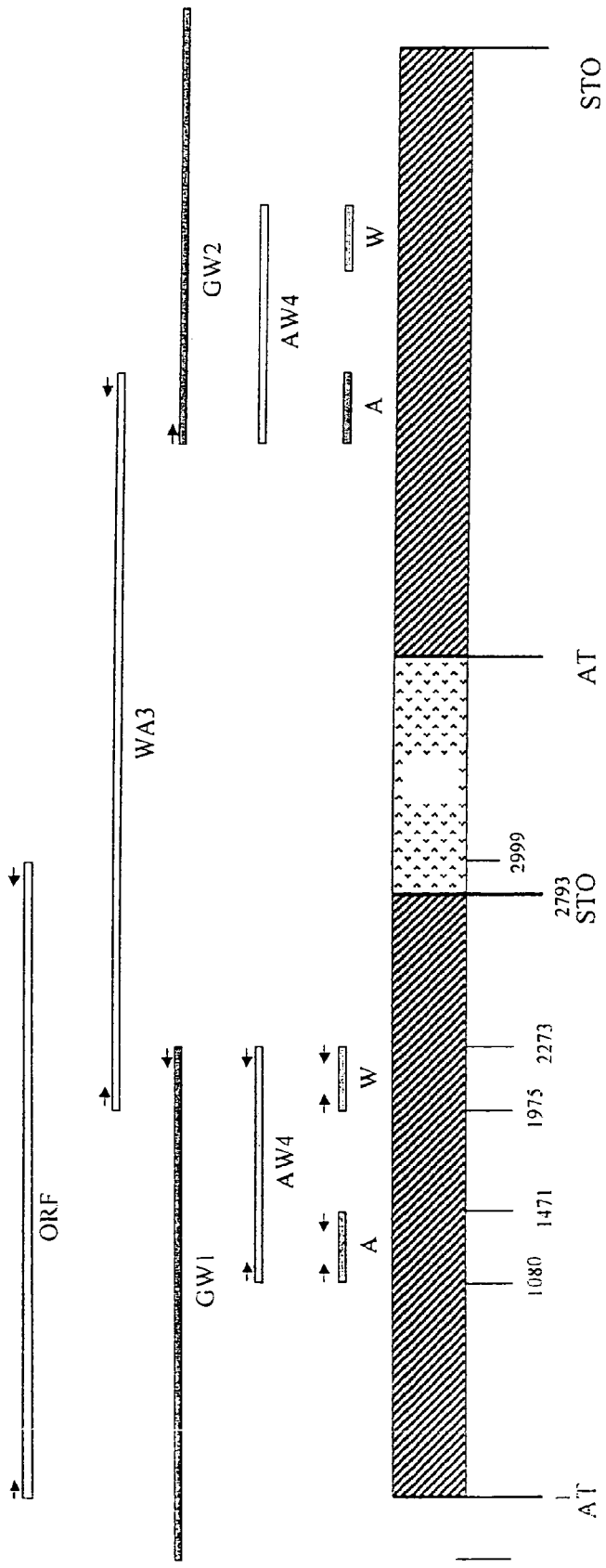
FIG. 15 shows a diagram of overlapping genomic clones for TbPDE2B. The bottom scale is based on the nucleotide sequence of the full-length gene and drawn approximately to scale. The open reading frames are indicated by ATG and STOP marked on the scale. A, EST # AA063739; W, EST # W84103; IR, Intergenomic Region. Arrows indicate the primers used to amplify each clone, as described in Example 11, infra.

Cloning and Sequencing. Searches of the EST databases using sequences from the first 10 previously cloned mammalian PDEs resulted in two probable *Trypanosoma brucei rhodesiense* EST PDE sequences. The first one (clone ID AA063739) corresponded most closely to the non-catalytic domain of PDE10A, PDE2, PDE5 and PDE6. The second (clone ID W84103) was homologous to the catalytic domain of all Class I PDEs, including the conserved YHN PDE catalytic domain motif (Beavo J. A. et al., Trends Pharm Sci 1990; 11: 150–5). Oligonucleotide primers were synthesized based on the sequence of these two EST clones and combined to amplify by PCR the gene sequence yielding a clone 4.7 kb in length (clone WA3). This clone contained the EST sequence W84103 on the 5' end and AA063739 on the 3' end, indicating the possibility of two PDE genes in tandem. To extend the 5' and 3' ends of each gene five "genomic libraries" were prepared using a Gene Walker kit and screened with the adapter primer AP1 together with the W8.1as primer (clone GW1) for the 5' end and the primer AA06.1s (clone GW2) for the 3' end (FIG. 15). The sequence alignment of all these clones yielded a sequence with two identical ORFs in tandem separated by a pyrimidine rich intergenomic region of 1390 base pairs (FIG. 15).

To confirm the result of primers AA06.Is and W8.Ias were used for a new PCR reaction that yielded a single band of 1.2 kb (clone AW4). This product contained the sequence of the clones AA063739 and W84103 as flanking regions and a sequence of 500 base pairs in the middle corresponding to the 5' and 3' ends of the gene missing in the first amplification (FIG. 15).

Figure 17:
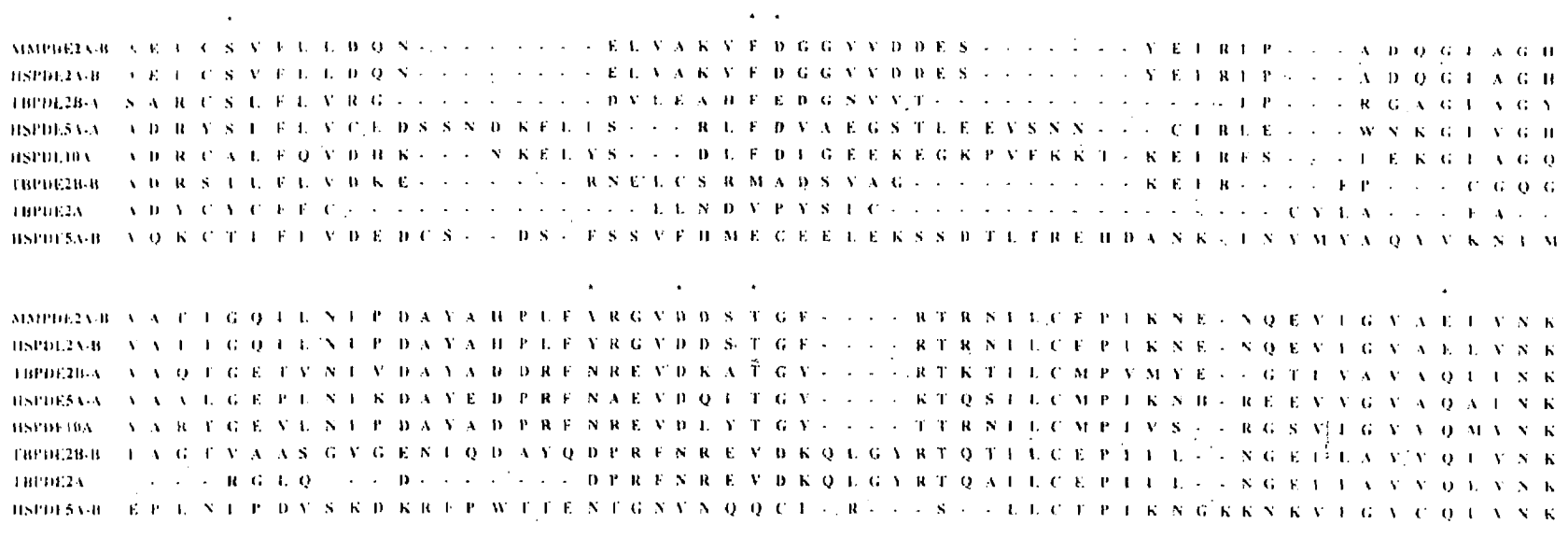

The complete gene (2793 base pairs) was amplified as described in Materials and Methods, and the ORF sequence predicts a 930 amino-acid protein with a molecular mass of 103,253 Da (FIG. 16). A consensus PDE catalytic domain is located between amino acids 668 and 908. The homology of this domain to other PDE catalytic domains suggests that TbPDE2B is a novel member of the recently described TbPDE2 family of class I PDEs (FIG. 17) (Soderling, S. H. and J. A. Beavo, Curr Opin Cell Biol, 2000. 12(2): 174–9; Zoraghi, R., et al., J Biol Chem, 2001. 276(15): p. 11559–66). Two conserved GAF (for cGMP binding and stimulated PDEs, *Anabaena* adenylyl cyclases and *Escherichia coli* Fh1A) domains in tandem are also predicted between amino acids 234–379 and 407–552 similar to those found in PDE2, PDE5, PDE6, PDE10 and PDE11 (FIGS. 16 and 17).

Expression and characterization of recombinant *T. brucei* PDE activity. To confirm that the isolated gene encodes an active PDE, a plasmid containing the complete ORF was expressed in HEK 293 cells. The cAMP hydrolyzing activity at 1 µM substrate concentration of the transfected cells, harvested at 48 h after transfection, showed on average a 10 fold increase (depending on the batch) above cells transfected with the same plasmid containing GFP coding sequence or non-transfected cells. However, no increase in cGMP hydrolysis was observed (data not shown), indicating that this sequence encodes for a cAMP specific PDE. A more detailed kinetic characterization of the enzyme showed a $K_m$ of 2.4 µM (±0.6), as the average of three separate experiments. The catalysis of cAMP was not stimulated or inhibited by cGMP, at concentrations up to 200 µM.

Inhibitor specificity of recombinant *T. brucei* PDE activity. The inhibitory profile of the enzyme (Table 2) shows an extremely low sensitivity to the non-specific PDE inhibitors papaverine, pentoxifylline and IBMX. No inhibition was observed in presence of specific inhibitors of the mammalian cAMP specific PDE (PDE4) rolipram and RO 20–1724 for the recombinant enzyme; however the endogenous PDE activity from the HEK 293 cells was completely abolished with the lowest concentration of these compounds used in the assay (10 µM). No $IC_{50}$ could be obtained even at very high concentrations for specific inhibitors of the PDE 2, 3, 5 and 6 families (EHNA, enoximone, zaprinast and sildenafil). Only dipyridamole at a concentration of 27 µM was able to inhibit 50% of the total activity in the assay and this value is from 6–71 times higher than those obtained for PDE5, PDE6, PDE8 and PDE 10 at similar substrate concentrations. Etazolate had a weak inhibitory effect with an $IC_{50}$ of 127 µM.

Complementation of *Sacchromyces cerevisiae* PDE deficiency. To test whether this PDE retains activity in vivo, TbPDE2B was expressed in a PDE-deficient yeast strain (JBS21.51, FIG. 18) and rescues this strain from heat shock sensitivity. Yeast cells lacking endogenous PDEs are sensitive to heat shock; they cannot survive incubation at 55° C. (Pillai, R., et al., Proc Natl Acad Sci USA, 1993. 90(24): p. 11970–4). Several Class I PDEs have been shown to complement this defect to varying degrees (Zoraghi, R., et al., J Biol Chem, 2001. 276(15): p. 11559–66; Michaeli, T., et al., J Biol Chem, 1993. 268(17): p. 12925–32). TbPDE2B expressing yeast are tolerant of a strong (60 min at 55° C.) heat shock, suggesting that the enzyme is highly active in yeast.

Discussion

Figure 18:
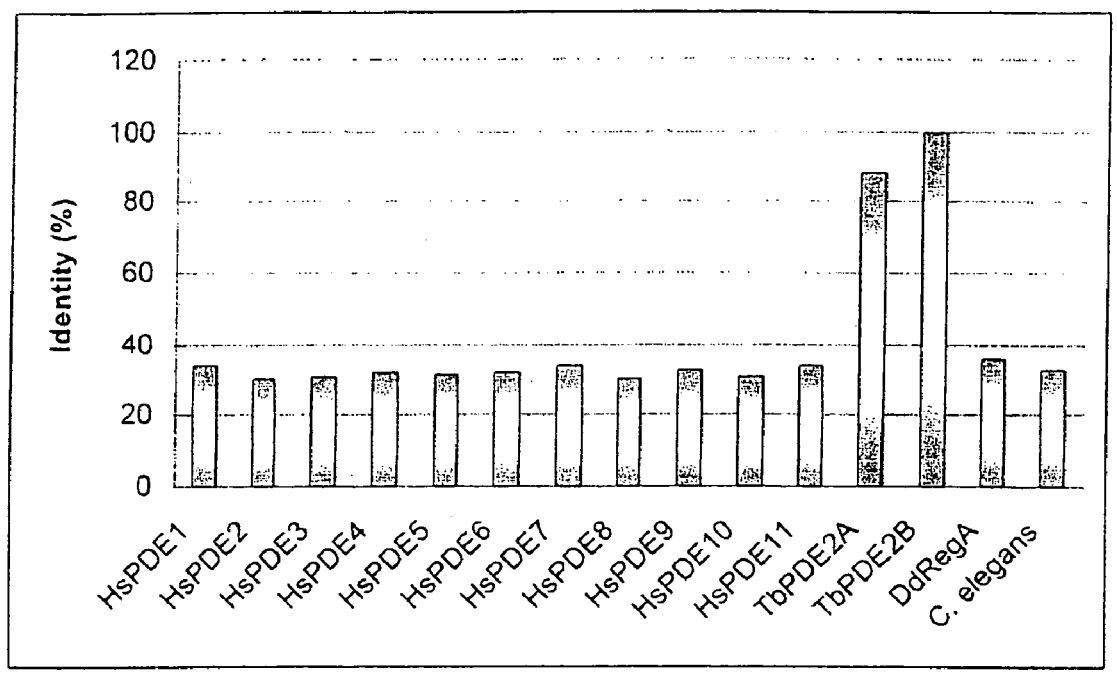
FIG. 18 shows a graphical representation of pairwise alignments of TbPDE2B catalytic domain with the catalytic domains of one member of each of the known human Class I PDEs as well as Class I PDEs from *Dictyostelium, C. elegans* and *T. brucei* PDE2A. Catalytic domains were defined by the PFAM motifs program. The catalytic domain for the "A" gene of each of the 11 human PDEs was compared to the catalytic domain of TbPDE2B.

Through an initial bioinformatic approach, a *T. brucei* gene encoding a cyclic AMP specific phosphodiesterase, was isolated. Sequence comparisons indicate that the *T. brucei* PDE2B is highly homologous to TbPDE2A and similar to other eukaryotic Class I PDEs but has no extended homology to Class II PDEs. This conclusion is based on the 30–35% sequence identity of a deduced catalytic domain of 241 amino acids with those of the 11 mammalian PDEs (Nikawa, J., et al., *Mol Cell Biol*, 1987. 7(10): p. 3629–36), the *Dyctiostelim discoideum*, RegA (Gietz, R. D., et al., *Mol Cell Biochem*, 1997. 172(1–2): p. 67–79), and a probable PDE from *Caenorhabditis elegans* (GeneBank accession # Q22000). This is essentially the same as the homology shown among families of mammalian Class I PDEs. A graphical representation of the amino acid identity scores for TbPDE2B with the human, *C. elegans* and *Dictyostelium* PDEs is shown in FIG. 18. TbPDE2B contains the conserved PDE catalytic domain initiating YHN motif, as well as the putative metal binding motif $HDX_2HX_4N$ (Dousa, T. P., Kidney Int, 1999. 55(1): p. 29–62) between amino acids 709–718 (FIG. 16). Since this gene product rescues a *S. cerevisiae* PDE deficiency, measurably catalyzes the hydrolysis of cAMP, is homologous to known PDEs and contains these PDE motifs, it is apparent that this gene encodes an active PDE.

TbPDE2B and TbPDE2A appear to be recently diverged genes. The GAF and catalytic domains of the two genes match with >89% identity at the amino acid and DNA levels. but the genes are organized differently. TbPDE2A is a single gene flanked by two unrelated genes while TbPDE2B is arranged as two consecutive identical open reading frames (Zoraghi, R., et al., J Biol Chem, 2001. 276(15): p. 11559–66). TbPDE2B also encodes a second GAF domain, one which is more likely to bind cGMP (see below). It is plausible that TbPDE2A is a recent duplication of TbPDE2B, and that TbPDE2B duplicated even more recently to form a head-to-tail concatemer.

TbPDE2B contains two GAF domains at the N terminus of the protein. These sequences are similar to those found in the GAF domains of mammalian PDE2, PDE5, PDE6, PDE10 and PDE11 (Soderling, S. H. and J. A. Beavo, Curr Opin Cell Biol, 2000. 12(2): p. 174–9). These motifs were first identified as cGMP binding domains in the PDE2s and the photoreceptor PDE6s, but the subsequent identification of a similar motif in *Anabaena* adenylate cyclases and *Escherichia coli* Fh1A, organisms which do not make cGMP, required a more general name for these motifs (Reviewed in Aravind, L. and C. P. Ponting, Trends Biochem Sci, 1997. 22(12): p. 458–9). Homologous domains are also present in a number of other signaling molecules that include transcription regulators and sensory histidine kinases in bacteria, ethylene-responsive factors and phytochromes in plants, and nitrogen fixation proteins in *Azotobacter* (Schultz, J., et al., Proc Natl Acad Sci USA, 1998. 95(11): p. 5857–64). Because of the probable different ligand specificities of this domain in the many different enzymes containing GAF domains, there is no consensus function for these domains. However, in most of the other PDEs cGMP binding to the GAF domains acts as a means for regulation of the enzyme. For example the phosphorylation state of PDE5 (Thomas, M. K. et al., J Biol Chem, 1990. 265(25): p. 14971–8; Wyatt, T. A., et al., Am J Physiol, 1998. 274(2 Pt 2): p. H448–55.) and the interaction between small molecules such as formic acid as in the case of *E. coli* Fh1A transcription factor (Aravind, L. and C. P. Ponting, *The GAF domain: an evolutionary link between diverse phototransducing proteins.* Trends Biochem Sci, 1997. 22(12): p. 458–9).

The entire catalytic domain of TbPDE2A and TbPDE2B are very highly conserved, consistent with the similar $K_m$ found for the two isozymes (2.4±0.6 and 2.3±0.6, respectively) and the fact that each is specific for cAMP hydrolysis. Additionally, both isozymes are relatively insensitive to mammalian PDE inhibitors (selective or non-selective), a finding in keeping with the other described PDEs from the *Trypanosomatidae* family.

Non-selective PDE inhibitors slightly affected PDE activities present in *T. cruzi*[16], *T. gambiense* (Walter, R. D., Hoppe Seylers Z Physiol Chem, 1974. 355(11): p. 1443–50), *Leishmania donovani* (Walter, R. D., et al., Tropenmed Parasitol, 1978. 29(4): p. 439–42), *L. mexicana* (Rascon, A., et al., Mol Biochem Parasitol, 2000. 106(2): p. 283–92) and TbPDE2A (Zoraghi, R., et al., J Biol Chem, 2001. 276(15): p. 11559–66). An extremely low inhibition by the selective PDE inhibitors for PDE3 (enoximone), PDE4 (rolipram, Ro 20–1724) and PDE5 has been also shown for *L. mexicana* PDEs (Rascon, A., et al., Mol Biochem Parasitol, 2000. 106(2): p. 283–92) and TbPDE2A (Zoraghi, R., et al., J Biol Chem, 2001. 276(15): p.

11559–66). The sequence differences between the catalytic domains of the two members of the TbPDE2 family, clustered between the amino acids 787–819 for TbPDE2B (347–392 for TbPDE2A), likely account for the differences in sensitivity observed for TbPDE2B the towards sildenafil, dipyridamole, zaprinast, etazolate and IBMX (Table 2). It is striking that there is a >10-fold difference in sensitivity to Sildenafil, given the high homology between these isozymes. The significant differences between sensitivities of trypanosomatid PDEs and their mammalian counterparts is makes these enzymes potentially good targets for development of selective drugs.

TABLE 2

Effect of different compounds on *T. brucei* PDEs

| Inhibitor | PDE Selectivity (IC$_{50}$) | [a]TbPDE2A IC$_{50}$ (μM) | [b]TbPDE2B IC$_{50}$ (μM) (n = 3) |
|---|---|---|---|
| IBMX | Non-selective (2–50 μM) | 545 | >1000 |
| Papaverine | Non-selective (5–25 μM) | ND | 304 ± 19 |
| Pentoxifylline | Non-selective (45–150 μM) | ND | >800 |
| Rolipram | PDE 4 (2 μM) | >100 | >300 |
| Ro 20-1724 | PDE 4 (2 μM) | ND | >300 |
| Etazolate | PDE 4 (1.2 μM) | 30.3 | 127 ± 4 |
| Enoximone | PDE 3 (1 μM) | ND | >100 |
| [c]cGMP | PDE 3 | >100 | >200 |
| Zaprinast | PDE 5 (0.76 μM) PDE 6 (0.15 μM) | 42.5 | >50 |
| Sildenafil | PDE 5 (0.0039 μM) | 9.4 | >100 |
| EHNA | PDE 2 (1 μM) | ND | >180 |
| Dipyridamole | PDE 5 (0.9 μM) PDE 6 (0.38 μM) PDE 8 (4.5 μM) PDE 10 (1.1 μM) | 5.9 | 27 ± 3 |

ND: not determined,
[a]from reference (Altschul, S. F., et al., J Mol Biol, 1990. 215 (3): p. 403–10.) [19],
[b]Substrate concentration 1 μM [$^3$H]-cAMP,
[c]No inhibition or activation was observed.

The high IC$_{50}$ obtained with the PDE4 selective inhibitor etazolate (127 μM) for the TbPDE2B reported here, does not support the idea of this enzyme being the target of the effects described for this compound in the induction of in vitro transformation of slender to stumpy forms of *T. brucei* since it occurs at concentrations of 1–2 μM etazolate (Vassella, E., et al., J Cell Sci, 1997. 110(Pt 21): p. 2661–71). Therefore, the observed effect of etazolate in the differentiation process of these parasites could be through the inhibition of another PDE or perhaps through actions on some other target. For example in mammals, etazolate is also an adenosine receptor antagonist and can interact with GABA channels (Williams, M. and M. F. Jarvis, Pharmacol Biochem Behav, 1988. 29(2): p. 433–41).

There are at least two copies of the gene coding for this cAMP specific PDE in *T. brucei*. These genes are tandemly repeated in the genomic DNA, and not a single copy as the TbPDE2A that is part of a small gene family (Zoraghi, R., et al., J Biol Chem, 2001. 276(15): p. 11559–66). The presence of more than one copy of a gene at a single locus is common for genes that encode enzymes essential for normal metabolism in *Trypanosomatids*. For example, phosphoglucose isomerase, aldolase and glycosomal glyceraldehyde phosphate dehydrogenases are all multiple copy genes in *T. brucei* ( ) [39]. The fact that there are also multiple copies of this PDE gene may suggest that it is not a functionally redundant enzyme and has important functions to the life of the trypanosomatid.

Example 12

This Example describes the identification, cloning, and characterization of a cAMP specific PDE (TbPDE2A) from *T. brucei*.

Materials and Methods

Cell culture. *Trypanosoma brucei* strain 427 (derived form MiTat 15a) was grown as procyclic form at 27° C. in SDM medium (Brun, R., and Schonenberger, M. (1979) Acta Tropica 36, 289–292). Monomorphic bloodstream forms of strain 221 (MiTat 1.2) were cultivated as described by Hesse et al. (Hesse, F. et al., (1995) Mol. *Biochem. Parositol.* 70, 157–166). The yeast strain PP5 (MATa leu2-3 leu2-112 ura3-52 his3-532 his4 cam pde1::URA3 pde2:: HIS3: (Pillai, R. et al., (1993) *Proc Natl Acad Sci. U.S.A.* 90,11970–11974). was a gift of John Colicelli, UCLA. Yeast transformation was done as described (Atienza, J. M. et al., (1998) *Melhods* 14, 35–42). Transformants were selected on liquid minimal medium containing 0.67% yeast nitrogen base without amino acids (DIFCO) and 2% glucose, supplemented with an amino acid mixture lacking leucine (SC-leu). Heat shock experiments were performed by replica-plating patches onto YPD plates prewarmed to 55° C., and the heat shock was continued for 15 min. After cooling the plates to room temperature, they were incubated for 2–3 days at 30° C.

Construction of TbPDE2A constructs Full length TbPDE2A: The 3'-end of the open reading frame of TbPDE2A was amplified from the cDNA plasmid pT'2928 using the forward primer pde2tyfor (5'-ATGACAATG-GATGGATGTGCTTAT-3') (SEQ ID NO.: 38) and the reverse primer pde2tyrev (5'-CTTCTCGAGGGATC-CCTATCCATGGGCAGACGAAGCCCCTGTACTC-3') (SEQ ID NO.: 39), containing XhoI, BamHI and NcoI sites (underlined) and a stop codon (bold italics). The resulting PCR fragment (366 bp) was cloned into pGEM-T-Easy (Promega) and verified by sequencing. The fragment was then excised by digestion with EcoRV and XhoI and was inserted into pT2928 digested with the same enzymes. This step removed the 3'-UTR and introduced an NcoI site immediately, before the stop codon and resulted in plasmid pTPDE23U.

The 5'-end of the open reading frame was amplified from a fragment of genomic DNA, using the forward primer pde2gtf2 (5'-GA<u>GAATTC</u>AAAC<u>ATG</u>TATG TGCAC-GACGTACGCATGTTC-3') (SEQ ID NO.: 40), containing an EcoRI site (underlined) followed by a Kozak sequence and the start codon (bold underlined), and the reverse primer pde2gr (5'-TTCAACCCCATATGATCAAGATCATG-CACCAG-3') (SEQ ID NO.: 41). The PCR product (804 bp) was cloned into pGEM-T-Easy, verified by sequencing and then excised by digestion with EcoRI and NdeI and cloned into pTPDE23U cut with the same enzymes. This step generated a full-length copy of TbPDE2A (pTPDE2A) containing an NcoI site immediately bet-ore the stop codon.

For generating an N-terminally truncated form of TbPDE2A without the noncatalytic cGMP-binding domain (starting at M124 of the full sequence), the corresponding region was amplified from genomic DNA using the forward primer pde2gfl (5'-GA<u>GAATTC</u>AAAC <u>ATG</u>GAAGTTAACGAACACCGAGCAACATTG-3') (SEQ ID NO.: 42), containing an EcoRI site (underlined) followed by a Kozak sequence and the codon for M124 (bold underlined), and the reverse primer pde2gr (see above). The PCR product (475 bp) was cloned and sequenced as indicated above, Finally it was excised by digestion with EcoRI and NdeI and inserted into the corresponding sites of pTPDE23U, to generate pTPDE2AT.

For inserting a hemagglutinin tag (amino acid sequence: YPYDVPDYAGIPM (SEQ ID NO.: 43) at the C-teminus of both constructs, two complementary oligonucleotides, Htfor (5-CATGGTTACCCATACGATGTCCCAGATTACGCCG GTATTCCAATGTAGG-3') (SEQ ID NO.: 44); open NcoI site underlined, stop signal bold underlined) and Htrev (5'-GATCCCTACATTGGAATACCGGCGTAATCTGGGACA TCGTATGGGTAAC-3') (SEQ ID NO.: 45); open BamHI site underlined) were annealed and then inserted into pTPDE2A and pTPDE2AT digested with NcoI and BamHI. The resulting tagged constructs (pTPDE2Ahm and pTPDE2AThm) were finally verified by sequencing. Similar constructs were also made which contain the TY-1 tag (Bastin, P. et al., (1996) Mol. Biochem. Parasitol. 77, 235–239) instead of the hemagglutinin tag at their C-termini.

For expression in S. cerevisiae, the tagged genes were introduced into the yeast expression vector p4215cyc 1 containing an attenuated CYC 1 promoter (Mumberg, D. et al., (1995) Gene 156, 119–122), and into pLT1 which allows high-level expression from a strong TEF2 promoter. PLT1 was derived from p425CYC1 by replacing its expression cassette with the TEF2 promoter, including the original TEF2 Kozak sequence. The initiation codon is followed by two restriction sites which allow cloning of the gene to be expressed. The resulting sequence of the expression site is as follows: TEF2 promoter: -412 through -7, followed by 5'-CTAAACATGAGTCGACCTCGAGT-3' (SEQ ID NO.: 46) (Kozak sequence bold, start-codon bold underlined, SalI site underlined, XhoI site italics). Protein expression and stability of the enzyme under assay conditions were monitored by immunoblotting, using a monoclonal antibody against the hemagglutinin tag (Roche Molecular Biochemicals).

Yeast cell lysis. Yeast cells grown to mid- to end-log phase in SC-leu medium were collected, resuspended quickly in an original volume of prewarmed YPD medium and incubated for an additional 3 h at 30° C. in order to maximize protein expression. Cells were then harvested, washed once in water and once in HBB buffer (Hank's balanced salt solution, containing 50 mM HEPES, pH 7.5). The washed cell pellet was suspended in an equal volume of HBB containing a protease inhibitor cocktail (Complete™, Roche Molecular Biochemicals). Cells were lysed by grinding with glass beads (425 µm; Sigma) using a FastPrep FP 120 (3×45 s at setting 4). The cell lysate was clarified by centrifugation for 15 min at 15,000×g. To the resulting supernatant, glycerol was added to a final concentration of 25% v/v and it was stored at −70° C. Under these conditions, TbPDE2A activity is stable for at least several months.

Phosphodiesterase Assay. PDE assays were done according to Schilling et al. (Schilling, R. J. et al., (1994) Anal. Biochem. 216, 154–158). The reaction contained 50 mM HEPES, pH 7.5, 0.5 mM EDTA, 10 mM $MgCl_2$ and $^3$H-cAMP or $^3$H-cGMP (50,000 dpm per reaction; 5 µM) in a total volume of 100 µl. Incubation was at 30° C. for 20 min. Reactions were stopped by the addition of 50 µl 21.5 mM $ZnCl_2$, followed by 50 µl 17.5 µM $Ba(OH)_2$ and incubated on ice for 30 min. The precipitates were filtered through GF-C glass fiber fitters and filters were washed 3 times with ice-cold 1 mM NaOH/100 mM NaCl and were then dried and counted in liquid scintillation fluid (4 g/l omnifluor in toluene). All assays were carried out in triplicates and with three independent enzyme preparations. Controls for the efficiency of precipitation of cAMP and of AMP were always included. When assaying yeast cell extracts, control lysates from the PDE deletion strains transfected with empty vector was used as a background control. Inhibitor studies were done at a cAMP concentration of 1 µM, i.e. close to the Km of TbPDE2A, so that the IC50 values should approximate the Ki. Inhibitors were dissolved in DMSO or ethanol, and the final concentration of the solvent never exceeded 1% in the assays reaction. Incubation times and enzyme concentrations were always adjusted so that less than 30% of the input substrate was hydrolyzed (2–5 µg total protein/100 µl assay). IC50 values were calculated by curve fitting on a four parameter dose-response model with variable slope, using the Prism software package of Graph Pad Inc., San Diego, Calif.

Cytotoxicity Determination. Cytotoxicity of PDE inhibitors was determined for bloodstream forms in culture by determining acid phosphatase activity as described (Bodley, A. L. et al., (1995) J. Infect. Dis. 172, 1157–1159). Exponentially growing monomorphic bloodstream forms MiTat 1.2 were transferred into colorless medium (Sbicego, S. et al., (1999) Mol. Biochem. Parasitol. 104, 311–32) (cell density $3 \times 10^5$ cells/ml culture) and were seeded into microtiter wells (199 µl per well) containing 1 µl of inhibitor or solvent control. Plates were incubated for both 20 and 40 h at 37° in a humidified incubator with a 5% $CO_2$ atmosphere. At the end of the growth period, cells were lysed by the addition of 20 µl of lysis/substrate buffer (20 mg/ml p-nitrophenyl-phosphate in 1 M Na-acetate, pH 5.5, 1% Triton X-100), and the incubation was continued for another 4 h at 37° C. Production of p-nitrophenol was determined at 405 nm on a microtiter plate reader. In order to control for intrinsic absorbance by the inhibitors, control series containing inhibitor dilutions but no cells were run for every experiment, and the resulting absorbance values were subtracted as background from the experimental readings. All assays were run in triplicates.

Results

Figure 20A:
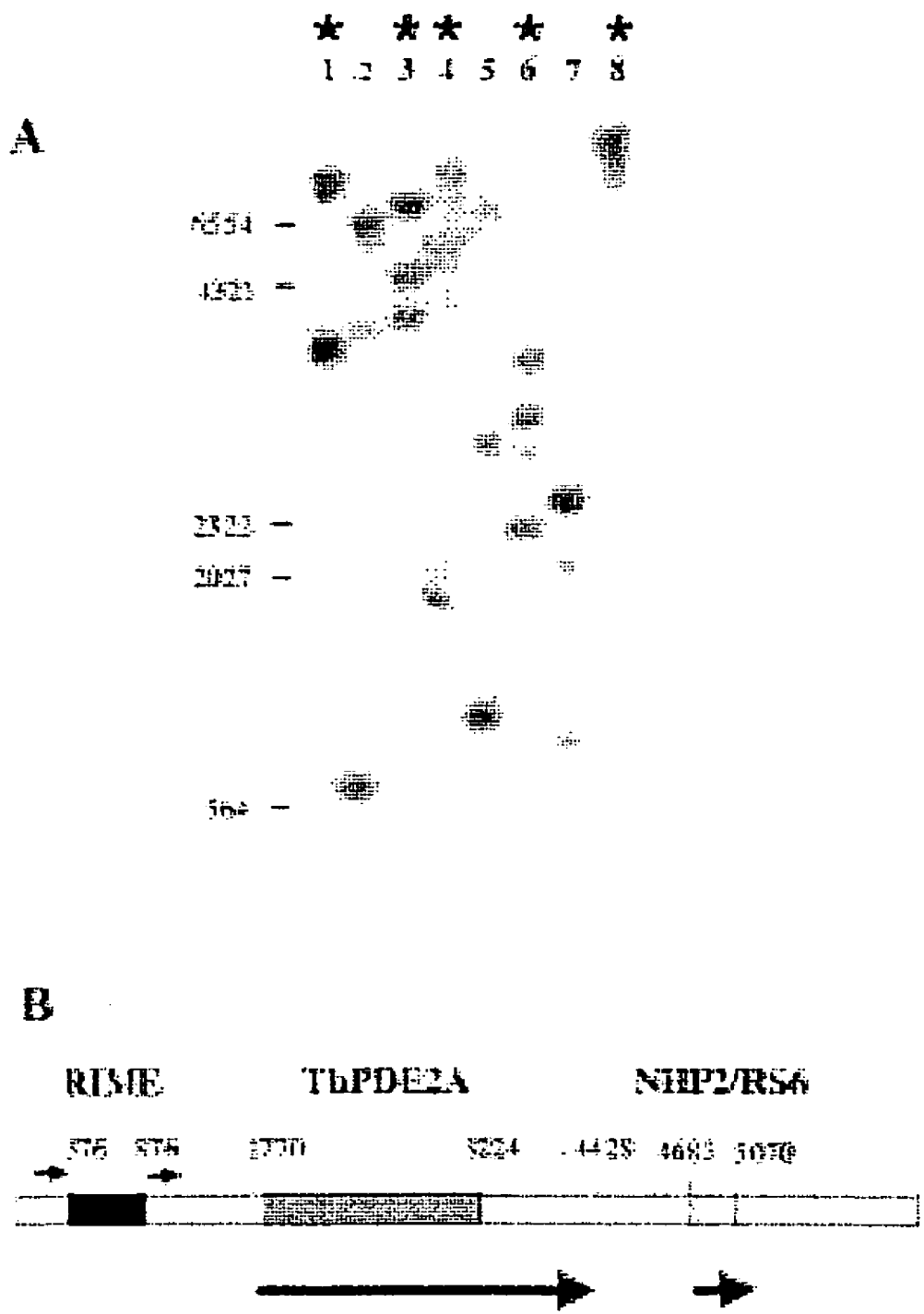
FIG. 20 shows the genomic organization of the TbPDE2 gene. Panel A: Restriction digests of -genomic DNA hybridized with the cDNA insert of pT2928, representing catalytic domain and 3' UTR of TbPDE2A. Restriction enzymes used: lane 1: BamHI; 2: BclI; 3: HindIII; 4: EcoRI, 5: EcoRV; 6: PstI; 7: SalI; 8: XhoI. The enzymes designated by asterisks (BamHI, HindIII, EcoRI, PstI, and XhoI) do not cut within the fragment used for hybridization. Panel B: Organization of the 6317 bp genomic EcoRI fragment which contains the TbPDE2A locus. n376–876: RIME element. Arrows above: 12 bp direct repeats. n1770–3224: open reading frame of TbPDE2A. n4428: polyA addition site of TbPDE2A mRNA. n4693–5070: open reading frame of an NHP2/RS6 homologue. Arrows underneath indicate the direction of transcription.
FIG. 20B shows the structure of the TbPDE2 family members.
Figure 20B:
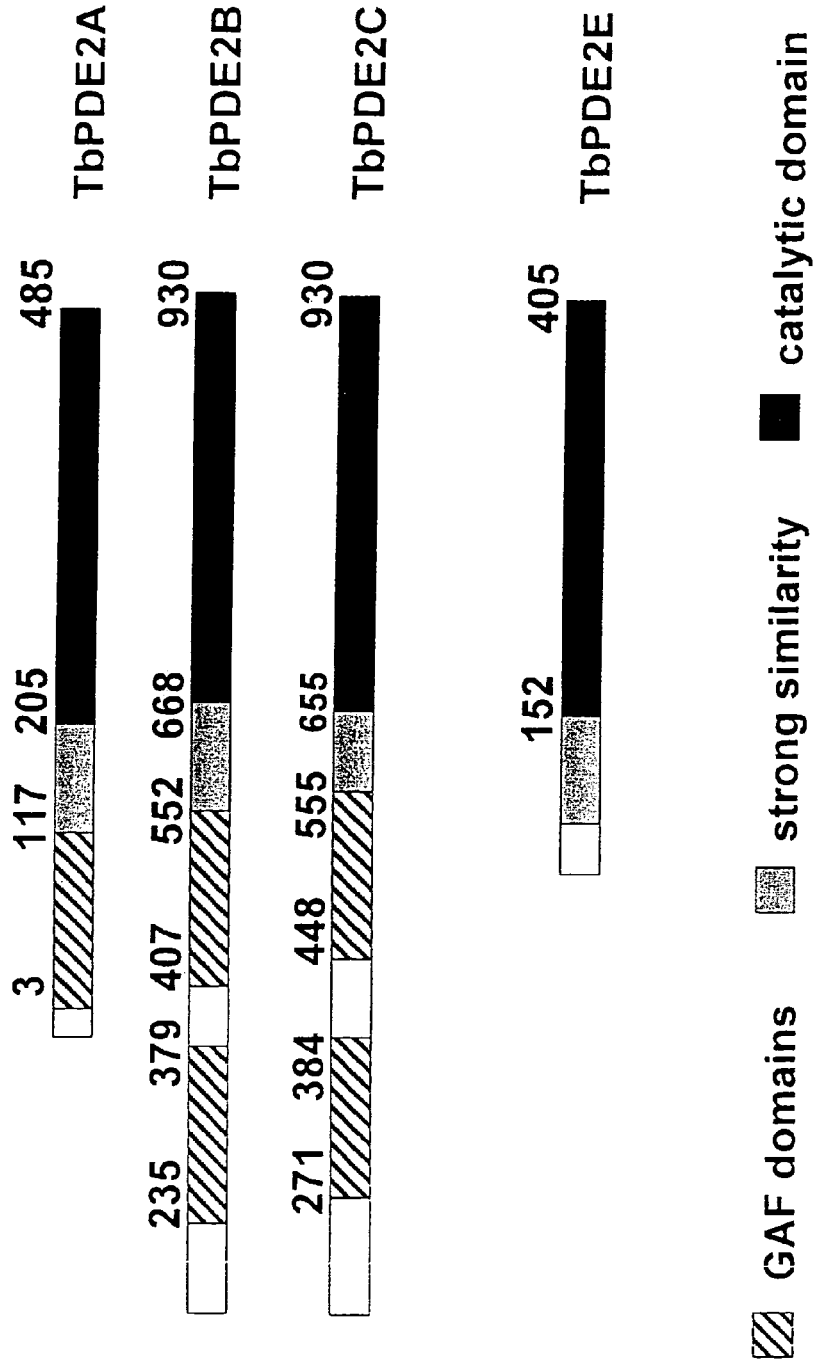

The TbPDE2A Locus. Upon searching the T. brucei EST database for potential phosphodiesterase genes, an EST clone (pT2928) was identified. The corresponding plasmid was sequenced. The cDNA fragment contained the 3'-part of a cDNA which unambiguously represented a phosphodiesterase gene, termed TbPDE2A according to the recently proposed rules for the nomenclature of trypanosomatid genes (Clayton C. et al., (1998) Mol. Biochem Parasitol. 97, 221–224). Southern blot analysis of genomic DNA demonstrated that TbPDE2A is not a single gene, but a member of small gene family (FIGS. 20A and B). This was further confirmed by screening a cDNA library, which resulted in the identification of several cDNA clones which represent different PDE2 family members. The cDNA fragment from pT2928 was then used to screen a genomic library of T. brucei. and the TbPDE2A locus was recovered on a 6 Kb genomic EcoRI DNA fragment. The fragment was sequenced, as were several cDNA clones for TbPD2A. The nucleotide sequence of TbPDE2A cDNA is shown in FIG. 21A. The organization of the ThPDE2A locus (FIG. 20B) demonstrates that it contains three different, closely spaced genes. The first one is a RIME element (nucleotides 376–876), a member of a family of abundant, highly transcribed, repetitive transposable elements (Murphy, N. B. et al., (1987) J. Mol. Biol. 195, 855–871). Within this element, nucleotides 868–632 on the reverse strand represent the open reading frame coding for a RIME-associated protein. The RIME element is flanked by two 12 bp direct repeats (n 364–375 and 877–888). The open reading frame for TbPDE2A extends from nucleotides 1770–3225 (FIG. 21A) and codes for a protein of 485 amino acids. The predicted start methionine was functional, and the predicted open reading frame coded for an active protein when expressed in *S. cerevisiae* (see below). The coding region is followed by a long 3'-untranslated region of 1196 nucleotides, and the polyA-addition site is represented by nucleotide 4420. Downstream of the TbPDE2A gene, a gene for a member of the NHP2/RS6 family of nuclear proteins (Henras, A. et al., (1998) *EMBO J.* 17, 7078–7090) is coded for by nucleotides 4635–5062. The presence of unrelated genes upstream and downstream of TbPDE2A demonstrated that the members of this PDE family are not closely linked.

Expression of TbPDE2A was analyzed both by Northern blot hybridization and by RT-PCR. Both approaches demonstrated that TbPDE2A is expressed both in the bloodstream and the procyclic (insect stage) form of the trypanosome life cycle.

The screening the cDNA library resulted in the identification of several cDNA clones which represent different PDE2 family members, including ThPDE2C and TbPDE2E. The nucleotide and amino acid sequences of TbPDE2C are shown in FIGS. 22A and 22B respectively. The nucleotide and amino acid sequences of TbPDE2E are shown in FIGS. 23A and 23B respectively.

Predicted amino acid sequence of TbPDE2A. The open reading frame of TbPDE2A predicts a protein of 485 amino acids, with a calculated molecular mass of 55,348 (FIG. 21B). The N-terminus of TbPDE2A contains a single GAF domain (V3-V117; (Aravind, L. and Ponting, C. P. (1997) *Trends Biochem. Sci.* 22, 458–459) which may function in cGMP binding. The presence of a single GAF domain in TbPDE2A is reminiscent of the human PDE11A which also has a single GAF domain, while all other mammalian PDEs with such domains (PDEs 2, 5, 6 and 10) contain two of them in a closely spaced arrangement. The overall sequence identity between the single GAF domain of TbPDE2A and either of the corresponding domains of mammalian PDEs 2, 5, 6, 10 and 11 varies between 30 and 50%, with several residues (L59, C60 P62, N77, K78, F88, and D91) strongly or absolutely conserved. For mammalian PDE5A, where cGMP-binding by the GAF domain was experimentally demonstrated, the interaction with cGMP was predicted to occur via N77, K78 and D91, all of which are strongly conserved (Turko J. V. et al., (1996) *J. Biol. Chem.* 271, 22240–22244).

The catalytic domain of TbPDE2A is located between F205 and F438, as predicted by analogy with other PDEs. All class I PDEs known to date contain a conserved region of approximately 250 amino acids which represent the catalytic domain (Charbonneau, H. et al., (1986) *Proc Natl Acad Sci. U.S.A.* 83, 9308–9312). Several residues within this domain are absolutely or chemically conserved between PDE families, and across species from yeast to humans. The predicted catalytic domain contains the signature sequence for cyclic nucleotide-specific phosphodiesterases (H269-Y281) (Beavo, J. A. et al., (1990) *Trends Pharinacol. Sci.* 11, 150–155). Two putative $Zn^{2+}$-binding motifs are represented by H229, H233 and E252, and H269, D-270, H-273 and E302, respectively (Francis, S. H. et al., (1994) *J. Biol. Chem.* 269, 22477–22480). The putative nucleotide-binding site is formed by amino acids K389-F438 (McAllister-Lucas, L. M. et al (1995) *J. Biol. Chem.* 270, 30671–30679). The neighboring histidine residues (H304 and H305), which are located outside this conserved nucleotide-binding region, may correspond to the vicinal histidine residues shown to be involved in cAMP binding in the human PDE4A (Jacobitz, S. et al., (1997) *Mol Pharmacol.* 51, 999–1006). Many amino acid residues of the catalytic domain are highly conserved between TbPDE2A and representatives of the 11 mammalian PDE families (H229 (identical between TbPDE2A and 10 out of the 11 mammalian PDE families), N230 (10/11), H269 (11/11), D270 (11/11), D272 (10/11), H273, (11/11), G275 (11/11), N278 (10/11), E302 (11/11), H304 (11/11), H305 (11/11), A342 (11/11), T343 (11/11), D344 (11/11), D383 (11/11), E404 (11/11), F405 (9/11), Q408 (10/11), G409 (9/11), D410 (11/11), D424 (9/11), Q435 (11/11) and F438 (10/11)). Interestingly, the linker region between the cGMP-binding domain and the catalytic domain contains a phosphorylation site for cAMP/cGMP kinases (K144–T147). The functional significance of this regulatory site remains to be established.

Figure 24:
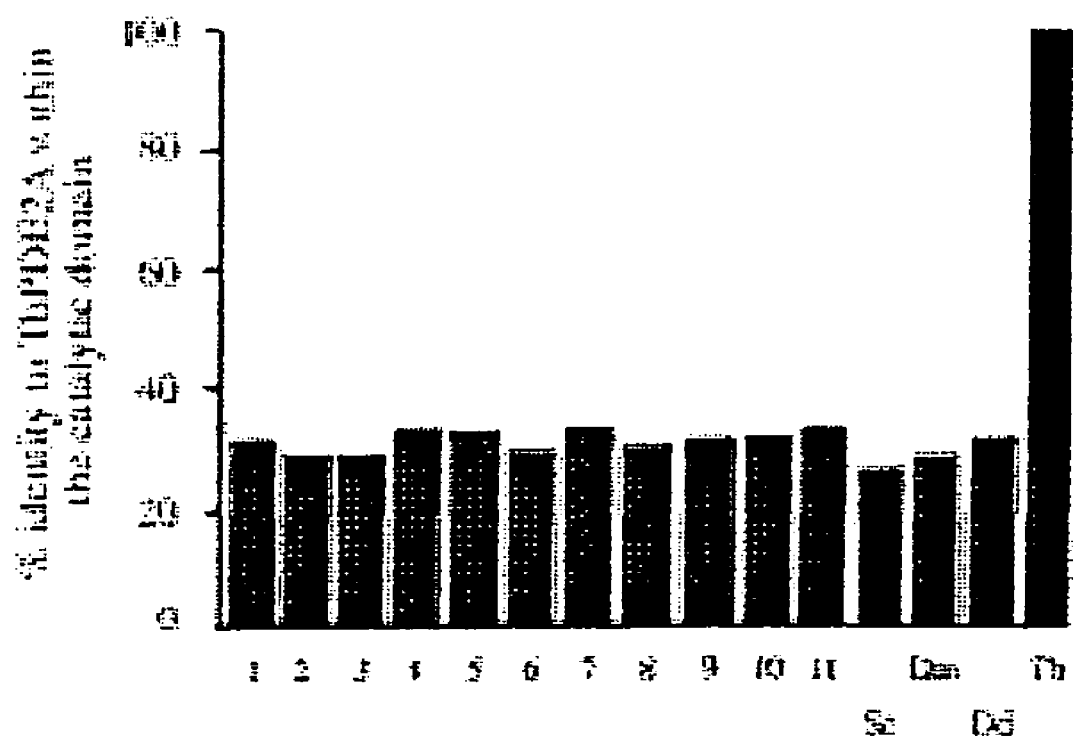
FIG. 24 shows comparison of catalytic domains. Graphic representation of the extent of sequence identity between the catalytic domains of TbPDE2A (Tb) and the 11 mammalian PDEs (1-11), *Saccharomyces cerevisiae* PDE2 (Sc), *Drosophila rnelanogaster* dunce (Dm), and *Dictyostelium* regA (Dd).

The overall sequence conservation between catalytic domains of phosphodiesterases which belong to the same family is >50%, while between families, the extent of identity is less than 40% (Soderling, S. H. et al., (1998) *J. Biol. Chem.* 273,15553–15558). In FIG. 24, the conservation of the catalytic domain of TbPDE2A is compared to representatives of the 11 currently known mammalian PDE families. TbPDE2A exhibits no sequence identity of more than 40% with any of them, nor with class I PDEs from lower organisms, such as PDE2 from *S. cerevisiae,* dunce from *Drosophila* or the regA of Dietyostelium.

Figure 25:
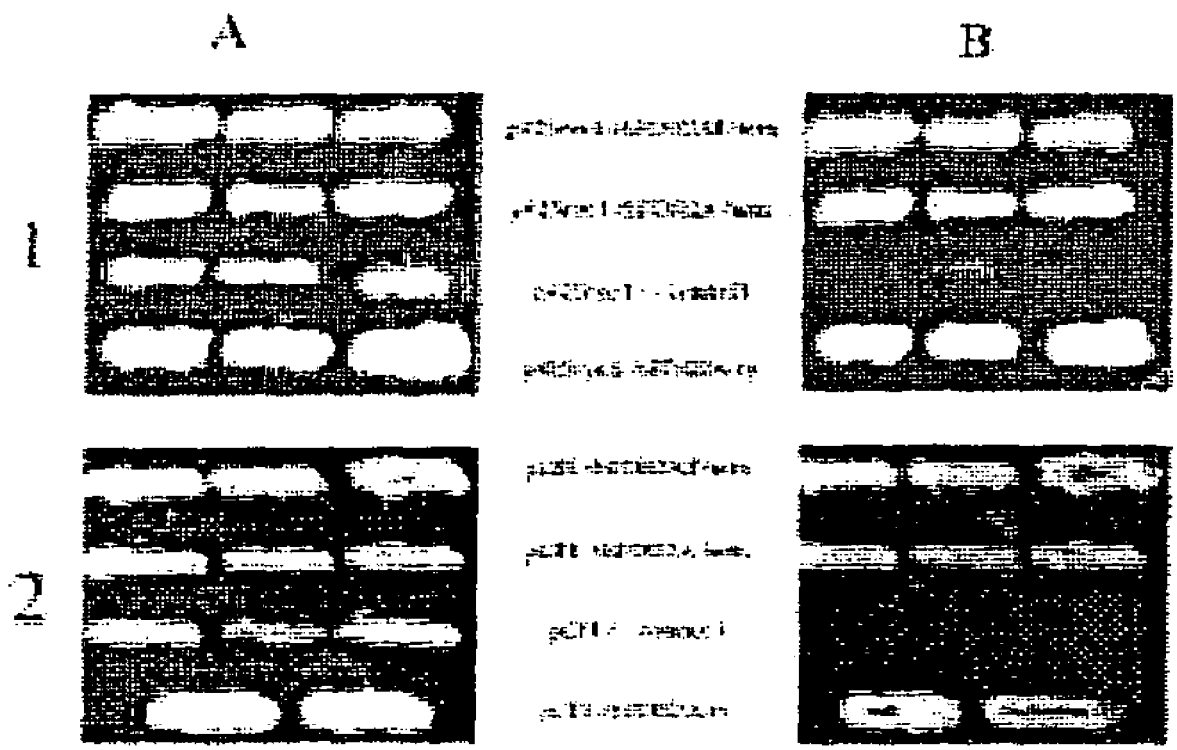
FIG. 25 shows heat shock resistance, as described in Example 12, infra. The heat-shock sensitive PDE-deletion strain of *S. cerevisiae,* PP5, was transformed with plasmids containing a weak promotor (attenuated CYC1; series 1) or a strong promotor (TEF2; series 2) and expressing the following constructs: a: N-terminally truncated TbPDE2A containing a C-terminal hemagglutinin tag; b: full-size TbPDE2A, containing a C-terminal hemagglutinin tag; c: empty vector; d: full-size TbPDE2A containing a C-terminal TY-1 tag. A. control plate without heat shock; B: plate with heat shock. Two or three independent clones were tested for each construct.

TbPDE2A complements PDE deficient *S. cerevisiae.* TbPDE2A was expressed, either as the full size enzyme or as the truncated form without the N-terminal cGMP binding domain (aa 124–485), in a *S. cerevisiae* strain from which both endogenous phosphodiesterase genes had been deleted (PP5; (Pillai, R. et al., (1993) *Proc. Natl Acad. Sci. U.S.A.* 90,11970–11974). PP5 is exquisitely heat-shock sensitive due to the absence of phosphodiesterase activity. Transformants were tested for heat shock resistance (FIG. 25). Both, the full size enzyme and the truncated form fully restored heat-shock resistance of the indicator strain, indicating that TbPDE2A is active in *S. cerevisiae,* and that the N-terminal domain is not required for the activity of the catalytic domain. Two promoters of different strengths were used for these expression experiments (an attenuated form of CYC 1 as a weak, and TEF2 as a strong promoter), but essentially identical results were obtained. Thus, minimal amounts of TbPDE2A are apparently sufficient to rescue the heat shock resistance phenotype of the PP5 strain.

Characterization of TbPDE2A activity. For the characterization of TbPDE2A activity, the enzyme was expressed in the PDE-deficient yeast strain PP5, using plasmid pLT1 with the strong TEF2 promoter. TbPDE2A was expressed either as the full-length enzyme, or in its N-terminally truncated form (amino acids 124–485) which lacks the GAF domain. In order to be able to monitor protein expression and stability, both constructs contained a hemagglutinin tag at their C-termini. In vivo activity of all constructs was first assessed by analysis of the heat-shock phenotype conferred to the host strain, and stability under assay conditions was monitored by immunoblotting with an anti-hemagglutinin antibody.

Both constructs exhibited very similar activities with cAMP as the substrate, with a Km in the range of 2 μM and a Vmax of 1 μmol/mg×min (Table 3). These Km values are well within the range of other class I PDEs. With both constructs, cAMP hydrolysis was unaffected by the presence of a 100-fold excess of cGMP in the reaction (data not shown). This observation defines the catalytic activity of TbPDE2A as that of a cAMP specific phosphodiesterase. In addition, it indicates that cGMP either does not bind to the GAF domain, or that such a binding does not directly influence the catalytic activity of the enzyme under the conditions of the assay.

TABLE 3

Comparison of MW and enzyme parameters of full-size (TbPDE2A) and N-terminally truncated (TbPDE2AT) phosphodiesterase

|  | MW | Km (μM) | Vmax (μmol × mg-1min − 1) |
|---|---|---|---|
| TbPDE2A | 55,313 | 228 ± 0.56 | 1.17 ± 0.20 |
| TbPDE2AT | 41,248 | 1.18 ± 0.26 | 0.81 + 0.14 |

Figure 26:
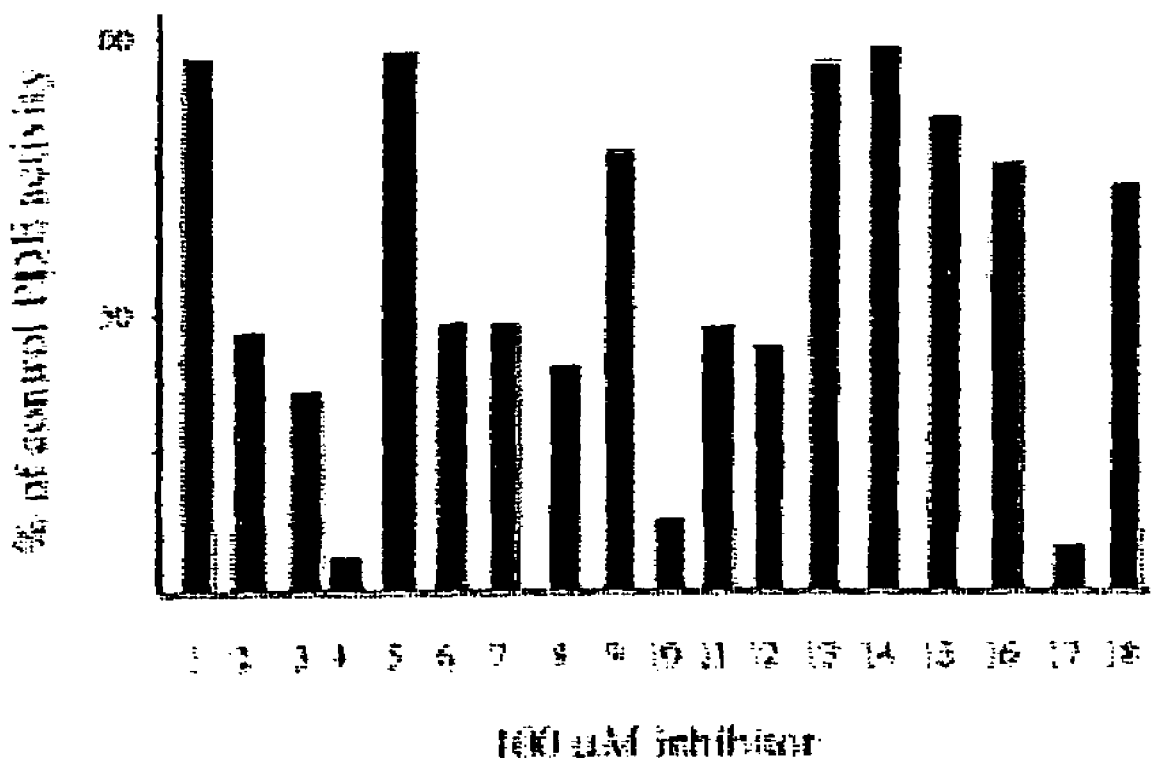
FIG. 26 shows the potency of PDE inhibitors against TbPDE2A. The activity of full-size recombinant TbPDE2A was determined in the presence of 100 μM of inhibitor. 1: no inhibitor (control); 2: etazolate; 3: erythro-9-(2-hydroxy-3-nonyl)adenine (EHNA); 4: trequinsin: 5: rolipram. 6: zardaverine. 7: pentoxifylline-8: 8-methoxy-IBMX. 9: theophylline; 10: ethaverine; 11: milrinone; 12: papaverine; 13: RO 20-1724; 14: IBMX; 15: zaprinast; 16: cilostamide; 17: dipyridamole; 18: vinpocetine.

Inhibitor Profile of ThPDE2A. Inhibitor studies were performed on lysates from PP5 expressing the full-size TbPDE2A. For the initial screening, all inhibitors were used at a concentration of 100 μM, with a substrate concentration of 1 μM cAMP (FIG. 26). Only a few of all inhibitors tested demonstrated a significant effect on enzyme activity, even at the high concentration used for the screen. Most notably, several broad-spectrum PDE inhibitors such as IBMX were ineffective. In this respect, TbPDE2A is similar to the mammalian PDE9 family (Soderling, S. H. et al., (1998). *J. Biol. Chem.* 273, 15553–15558). Rolipram, an effective and specific inhibitor of the mammalian cAMP-specific PDE4 family, showed no appreciable activity against TbPDE2A. Zaprinast, an inhibitor of the mammalian cGMP-binding PDEs 5 and 6, showed only very little effect, as did cilostamide or milrinone (both inhibitors of PDE3) and vinpocetine and 8-methoxymethyl-IBMX (inhibitors of PDE1). Unexpectedly, ethaverine proved to be significantly more effective as an inhibitor of TbPDE2A than its parent compound papaverine. This compound, the ethoxy-derivative of papaverine, was so far only known as a calcium channel blocker (Wang, Y. et al., (1991) *Mol. Pharmacol.* 40, 750–755).

Subsequently, IC50 were determined for several inhibitors, using yeast lysates expressing the full-size construct pTPDE2Ahm (FIG. 26). The concentration of cAMP as substrate was set at 1 μM, i.e. the range of its Km. Several structurally unrelated inhibitors showed similar potency against TbPDE2A, with Kis in the low micromolar range. The potency of these inhibitors toward TbPDE2A is not correlated with their family-specificity for mammalian PDE (Table 4). Trequinsin is an inhibitor of the PDE3 family, dipyridamole inhibits families 5, 6, 9, 10 and 11 (Fawcett, L. et al., (2000) *Proc Natl Acad. Sci.* U.S.A. 97, 3702–3707), and sildenafil is quite specific for family 5. Ethaverine was not known so far as a PDE inhibitor at all.

TABLE 4

Potency against TbPDE2A and mammalian family-specificity of selected PDE inhibitors

| Inhibitor TbPDE'2A | mammalian PDE family inhibited | IC$_{50}$ for (μM) |
|---|---|---|
| Trequinsin | 3 | 5.4 |
| Dipyridamole | 5 and 6 | 5.9 |
| Sildenafil | 5 | 9.4 |
| Ethaverine | — | 14.2 |
| Etazolate | 4 | 30.3 |
| Zaprinast | 5 and 6 | 42.4 |
| IBMX | non-selective | 545 |
| Cilostamide | 3 | >100 |
| Rolipram | 4 | >100 |
| Theophylline | non-selective | >100 |
| Vinpocetine | 1 | >100 |

Figure 27:
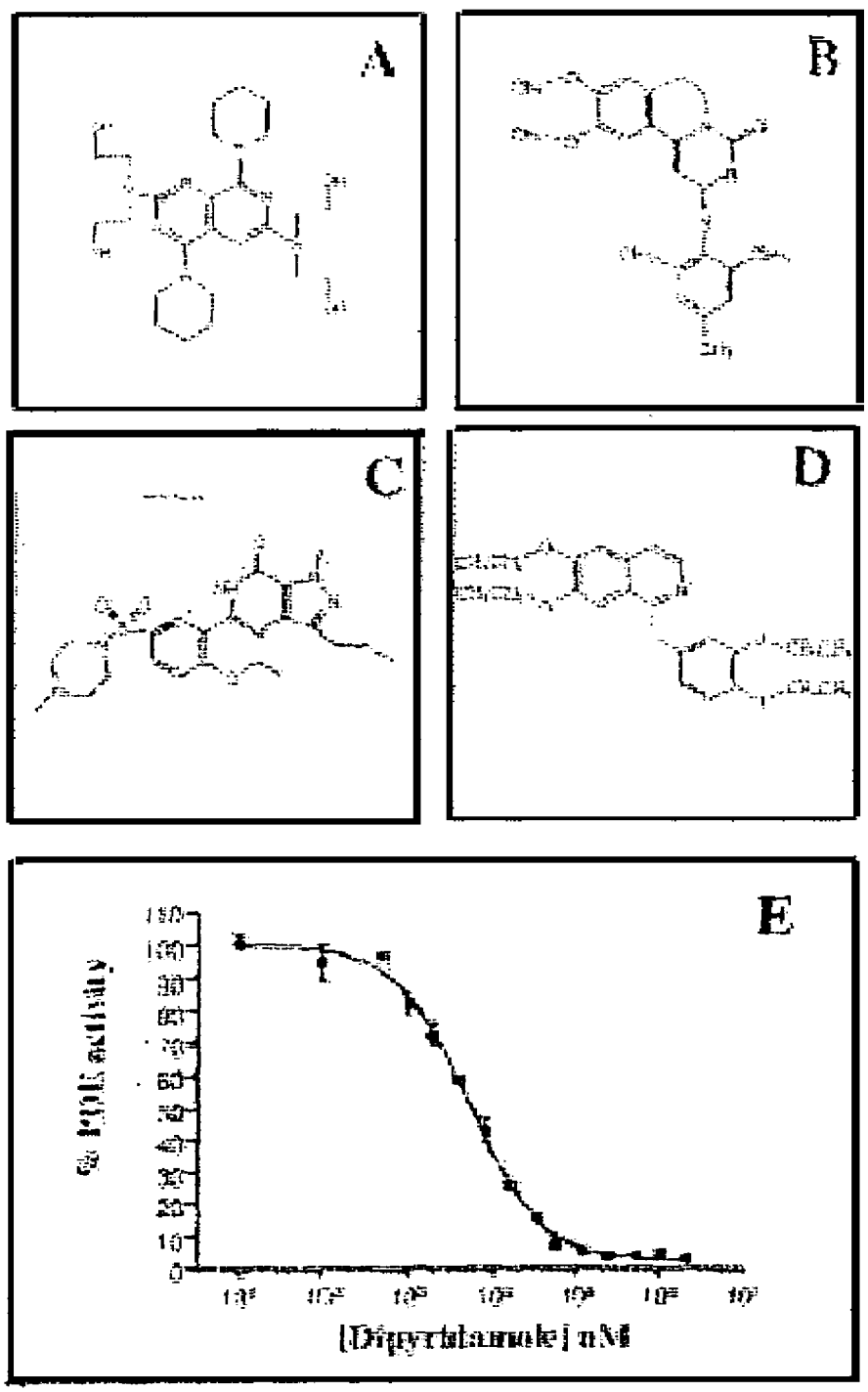
FIG. 27 shows that TbPDE2A is inhibited by inhibitors of different structares and with specificities for different mammalian PDE families, as described in Example 12, infra. Panel A. Dipyridamole; panel B Trequinsin; panel C: Sildenafil; panel D: Ethaverine; panel E: example of a dose response curve (dipyridamote).
Figure 28:
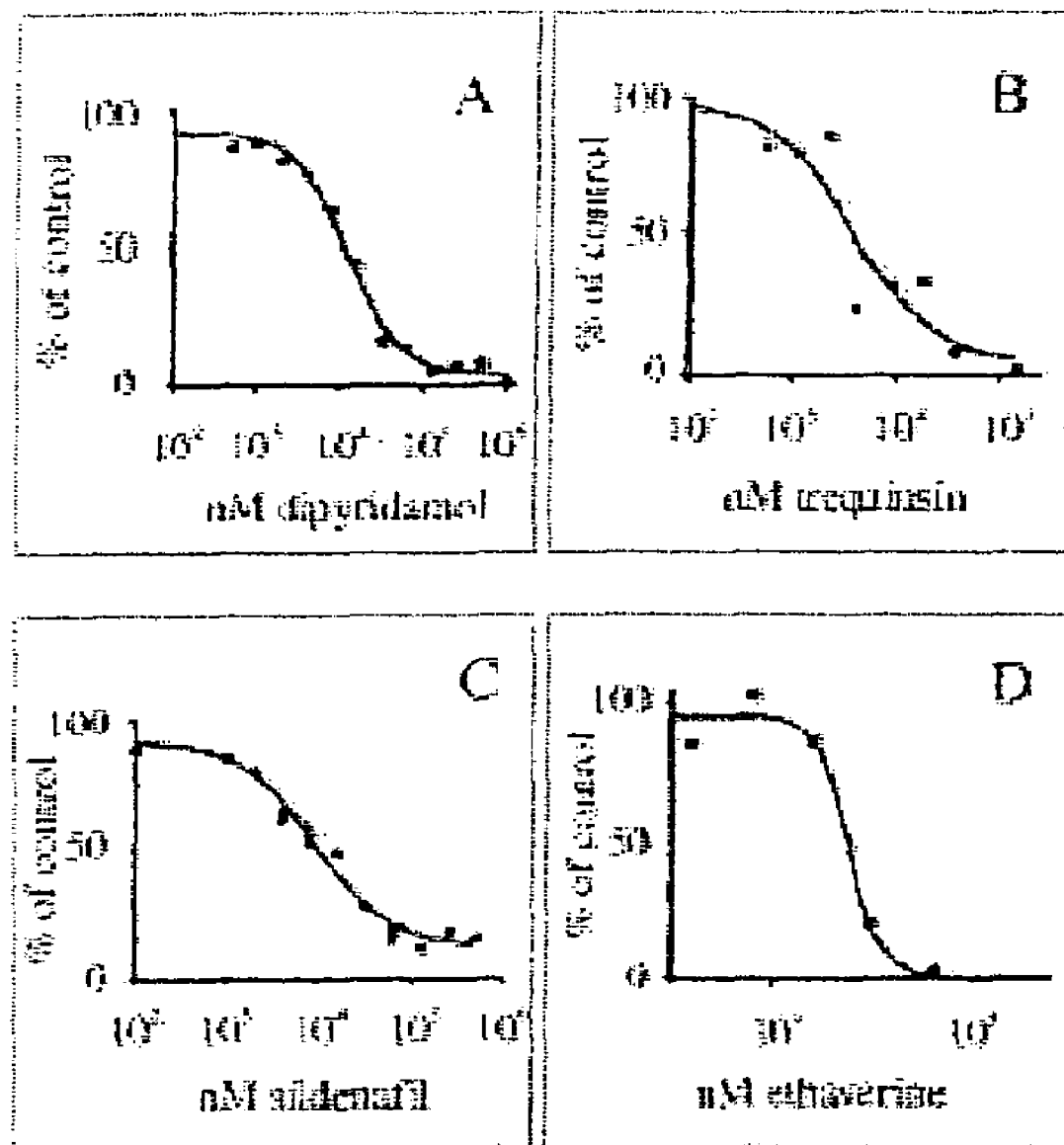
FIG. 28 shows the cytotoxicity of selected PDE inhibitors for bloodstream form trypanosomes, as described in Example 12, infra. Representative examples of IC50 determinations of PDE inhibitors against 427 bloodstream cultures. Cytotoxicity was determined after 40 h of cell growth. A: Dipyridamole; B: Trequisine; C: Sildenafil; D: Ethaverine.

The four compounds were further analyzed for their effects on cell growth in culture (FIGS. 27 and 28). Bloodstream form trypanosomes were grown in microtiter plates for 20 or 40 h in the presence of serial dilutions of the inhibitors (FIG. 28), and cell proliferation was determined by an acid phosphatase-based assay (Bodley, A. L. et al., (1995) *J. Infect. Dis.* 172, 1157–1159). All four compounds inhibited trypanosome growth with IC50, which were about 10-fold higher than those determined with the soluble enzyme. The Hill slopes of the dose-response curves were close to 1 for three of the compounds (dipyridamole: 1.38±021; sildenafil: 1.73±0.69; trequinsin: 1.09±0.63), while it was 5.19±1.52 for ethaverine. This indicates that the observed inhibition of cell proliferation by the first three compounds is indeed due to the inhibitory effect of the compounds on PDE activity, while the inhibition by ethaverine may be due to the combined effects of calcium channel blocking and inhibition of PDE activity. The results obtained with the first three compounds establish that the activity of TbPDE2A, and possibly other members of this family, is essential for trypanosome proliferation in culture, Discussion The invention discloses the identification and characterization of a member of a small family of cAMP-specific phosphodiesterases from the parasitic protozoon *Trypanosoma brucei*. This is the first report of cloning a gene for a phosphodiesterase from a parasitic protozoon. TbPDE2A is coded for by a gene which represents a small family of related but different genes. DNA sequence analysis of the locus revealed the presence of genes unrelated to phosphodiesterases upstream and downstream of the open reading frame for TbPDE2A, demonstrating that the genes of this PDE family are not clustered. The open reading frame predicts a protein consisting of 485 amino acids, with a molecular mass of 55,313. The predicted start codon is functional, as demonstrated by expression of the recombinant protein in *S. cerevisiae,* and no potential extension of the open reading frame upstream of this start codon is predicted from the DNA sequence. The open reading frame codes for a protein with a C-terminal catalytic domain with strong homology to all class I PDEs. The extent of sequence conservation, as well as the inhibitor profile, unambiguously classify TbPDE2A as a new family of the class I PDEs. The N-terminal moiety contains a single, well-conserved GAF domain (Aravind, L. et al., (1997) *Trends Biochem. Sci.* 22, 458–459) which is separated from the downstream catalytic domain by a linker region of about 80 amino acids. The GAF domain is very similar to those of the mammalian PDE families which contain such domains (families 2, 5, 6, 10 and 11). TbPDE2A only contains a single such domain, while the mammalian PDEs 2, 5, 6 and 10 all contain two closely spaced such domains. In this respect, it most closely resembles the mammalian PDE11A (Fawcett, L. et al., (2000) *Proc. Natl Acad. Sci.* U.S.A. 97, 3702–3707). The functional significance of this unusual architecture of TbPDE2A remains to be explored. The fact that GAF domains can potentially bind cGMP may indicate that cGMP signaling is also present in *T. brucei,* lending support to an earlier claim that cGMP signaling might exist in *T. cruzi* (Paveto, C. et al., (1995) *J. Biol. Chem.* 270, 16576–16579). The domain may serve as an integrator for cAMP- and a cGMP-mediated signaling cascades. On the other hand, GAF domains are representatives of a large family of domains which bind assorted small molecules other than cGMP (Aravind L. et al., (1997) *Trends Biochem. Sci.* 22, 458–459). Thus, not every domain predicted from its amino acid sequence to be a cGMP binding domain may actually function by binding cGMP. For instance, several *E. coli* proteins contain predicted cGMP-binding domains, though *E. coli* does not contain a guanylyl cyclase, and cGMP is unlikely to play a role in this organism.

Analysis of recombinant TbPDE2A demonstrated that it is a cAMP-specific phosphodiestrase with a Km for cAMP in the 2 µM range. This Km is typical for many of the class I PDEs. It is also in good agreement with the available estimates of the intracellular concentration of cAMP in *T. brucei* (1–10 µM); (Vassella, E. et al., (1997) *J. Cell Sci.* 110, 2661–2671). Recombinant proteins with or without the GAF domain exhibited similar activities with cAMP as a substrate, and the activity of both constructs was not affected by the presence of excess cGMP. These observations confirm that TbPDE2A is a cAMP-specific phosphodiesterase, and that cGMP either does not bind to the GAF domain, or that such a binding does not directly affect its catalytic activity. Thus, the GAF domain may be involved in the interaction with other components of the cell.

TbPDE2A displays a unique pharmacology which sets it apart from all previously characterized PDE families. IBMX and theophylline, two non-selective inhibitors of most PDEs are not effective on TbPDE2A. Three compounds which were found to inhibit TbPDE'2A at the low micromolar level are specific inhibitors of different mammalian PDE families. Trequinsin (IC50 for TbPDE2A=5.4 µM) is an inhibitor of family 3, dipyridamole (IC50=5.8 µM) is an inhibitor of the mammalian families 5 and 6, as is sildenafil (IC50=9.4 µM). Unexpectedly, ethaverine, a derivative of the non-specific inhibitor papaverine with only marginal activity against TbPDE2A, is rather effective inhibitor of TbPDE2A, with an IC50 of 14 µM. This was unexpected since ethaverine pharmacologically used so far mostly as a calcium channel blocker (Wang, Y. et al., (1991) *Mol. Pharmacol.* 40, 750–755), A similar pattern of inhibition was observed when cytotoxicity was determined with cultured bloodstream forms. Interestingly, the dose-response curve for ethaverine showed a very steep Hill slope (5.19±1.52), indicating that the effect of this compound on cell proliferation might be due to a combined effect of calcium channel blockage and PDE inhibition. In contrast to ethaverine, dipyridamole, a potent inhibitor of adenosine transporters besides its activity as a PDE inhibitor, showed a Hill slope of around 1 (1.37±0.21), with no sign of cooperative inhibition of cell proliferation. This suggests that even in the presence of dipyridamole, sufficient amounts of purines can be taken up by the trypanosomes to allow unconstrained proliferation in culture.

The identification of inhibitors of this enzyme has provided the necessary tools for the experimental dissection of cAMP signaling in trypanosomes. The observations that inhibitors of TbPDE2A prevent cell proliferation in culture demonstrate that TbPDE2A or the TbPDE2 family as a whole, may be essential for cell proliferation. This is also supported by the observation that TbPDE2 mRNA is constitutively expressed. In conjunction, these data indicate that TbPDE2A and its isoenzymes may represent interesting targets for the development of a new generation of trypanocidal drugs, based on phosphodiesterase inhibitors. TbPDE2A and its relatives in *T. brucei* as well as in other protozoa may offer a new class of targets for the development of novel and effective anti-protozoal drugs.

Example 13

This Example provides validation of the novel PDEs of *T. brucei* as a dru target.

Figure 29:
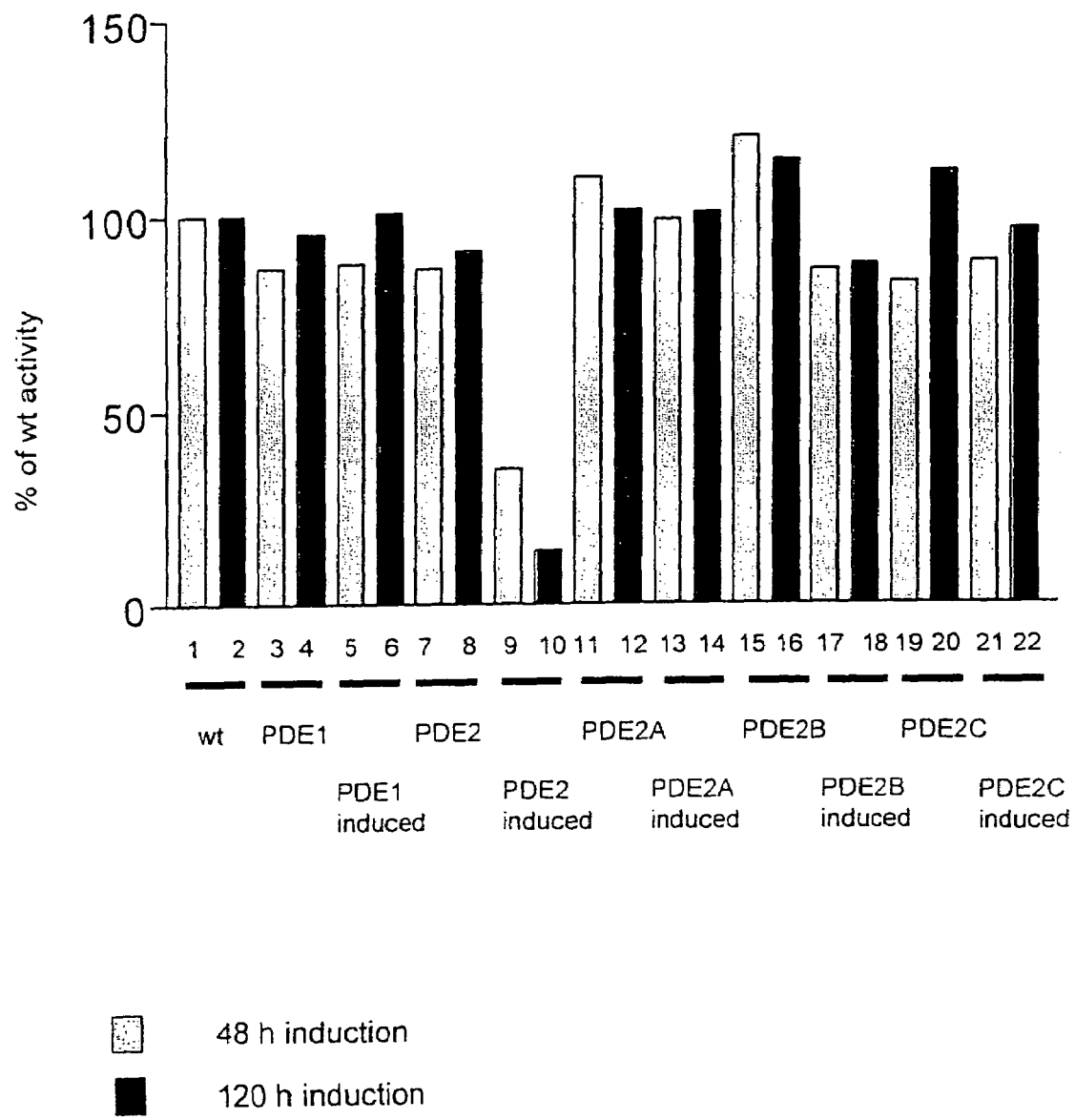
FIG. 29 shows that RNAi inactivation of the TbPDE2 mRNAs reduces the overall PDE activity in whole trypanosome lysates. Trypanosomes transfected with the appropriate RNAi constructs were incubated in the absence (noninduced) or presence (induced) of tetracyclin in the culture medium for 48 and 120 h, respectively. Cell lysates were prepared, and the overall PDE activity was determined. Activities are given as percentage of wild-type cell lysates.

Chemical validation of the TbPDE2 family as a potential drug target. One of the novel PDEs of the invention, TbPDE2A, was expressed as a recombinant protein and was characterized in detail (see above). TbPDE2A is a low $K_m$, cAMP-specific phosphodiesterase, and its activity is neither inhibited nor stimulated by cGMP. We have established that a number of well-known PDE inhibitors inhibit recombinant TbPDE2A with $IC_{50}$ values in the low micromolar range (dipyridamole, ethaverine, trequinsin and sildenafil). We have determined that the application of these inhibitors to trypanosomal cell extracts leads to a marked, if not complete, reduction of total PDE activity (FIG. 29).

We also have expressed a second family member, TbPDE2C, as a recombinant protein in the yeast *S. cerevisiae* and have characterized it was previously done for TbPDE2A. As predicted from the high sequence conservation between the catalytic domains of TbPDE2A and TbPDE2C, the catalytic properties of TbPDE2C and its sensitivity to PDE inhibitors were very similar to those found earlier for TbPDE2A (FIG. 30). cGMP does not affect the activity of TbPDE2C, despite the fact that this enzyme contains two potentially cGMP-binding GAF domains.

We have further demonstrated that application of PDE inhibitors to live trypanosomes leads to an increase in intracellular cAMP, and that they completely inhibit the proliferation of bloodstream form trypanosomes in culture. The $IC_{50}$ values of inhibition of cell proliferation by the PDE inhibitors dipyridamole, ethaverine, trequinsin and sildenalfil were similar to those observed for inhibition of the recombinant enzyme (Zoraghi et al., J. Biol. Chem. 276, 2001, 11559–11566). These data imply that the inhibition of cell proliferation is caused by an inhibition of the TbPDE2 family.

Genetic validation of the TbPDE2 family as a potential drug target. RNA interference (subsequently called RNAi) was used to further establish that the TbPDE2 family is essential for trypanosome proliferation. RNAi constructs were based on the vector pZJM (Wang et al., J. Biol. Chem. 275, 2000, 40174–40179) which allows inducible expression of double-stranded RNA from two opposing T7 RNA polymerase promotors which are under the control of a bacterial tetracyclin repressor. The constructs were targeted either against the divergent N-termini of each TbPDE2 family member (to allow a specific inactivation of individual family members), or against the conserved catalytic domain (allowing the combined inactivation of the entire gene family). The plasmid constructs were introduced into cultured procyclic (insect form) trypanosomes via electroporation, and expression of the double-stranded RNA was induced by addition of tetracyclin to the growth medium in order to to release the tetracyclin repressor.

PCR analysis. PCR analysis of the various transgenic trypanosome strains was performed to determine the efficacy of the various RNAi constructs. The results demonstrated that the mRNAs for TbPDE2A and TbPDE2C were the most abundant. Induction of RNAi lead to the elimination of TbPDE2 mRNAs in all strains.

Figure 31:
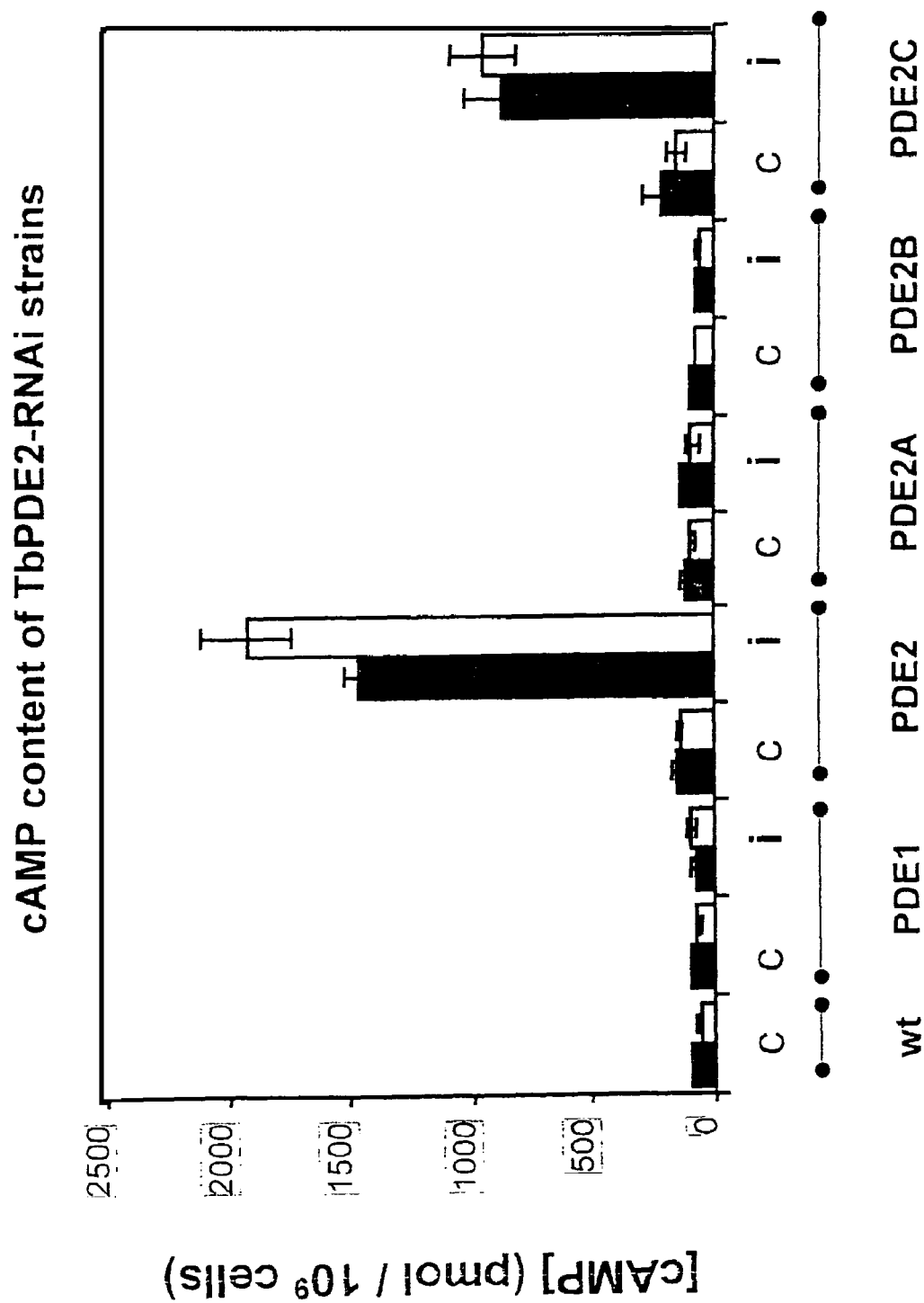
FIG. 31 shows that inactivation of TbPDE2 by RNAi increases intracellular cAMP. Procyclic trypanosomes were transfected with control plasmid (wt), or with RNAi constructs directed against the unrelated TbPDE1 (PDE1), against the entire TbPDE2 family (PDE2), against TbPDE2A (PDE2A), against TbPDE2B (PDE2B9 or against TbPDE2C (PDE2C). Inactivation of the corresponding mRNAs was induced by the addition of tetracyclin to the growth medium for 48 h (solid bars) and 120 h (open bars). respectively. i: induction of double-stranded RNA with tetracyclin; c: uninduced controls FIG. 32 shows the sensitivity of bloodstream trypanosomes to an increase in intracellular cAMP. Trypanosomes were incubated in culture medium containing various concentrations of the membrane-permeable cAMP analog 8-bromo-cAMP. The extent of cell proliferation was determined after 70 h of culture.

Analysis of intracellular cAMP. Determination of intracellular cAMP concentrations demonstrated that inactivation of the TbPDE2 family mRNAs by RNAi leads to an increase in intracellular cAMP. This increase was most pronounced when TbPDE2C was inactivated, which is in good agreement with the relatively high abundance of TbPDE2C mRNA which indicated that this isoenzyme is the predominant form. An even stronger increase of intracellular cAMP was observed when all TbPDE2 family members were simultaneously inactivated using the RNAi construct directed against that conserved catalytic domain (FIG. 31).

Figure 32:
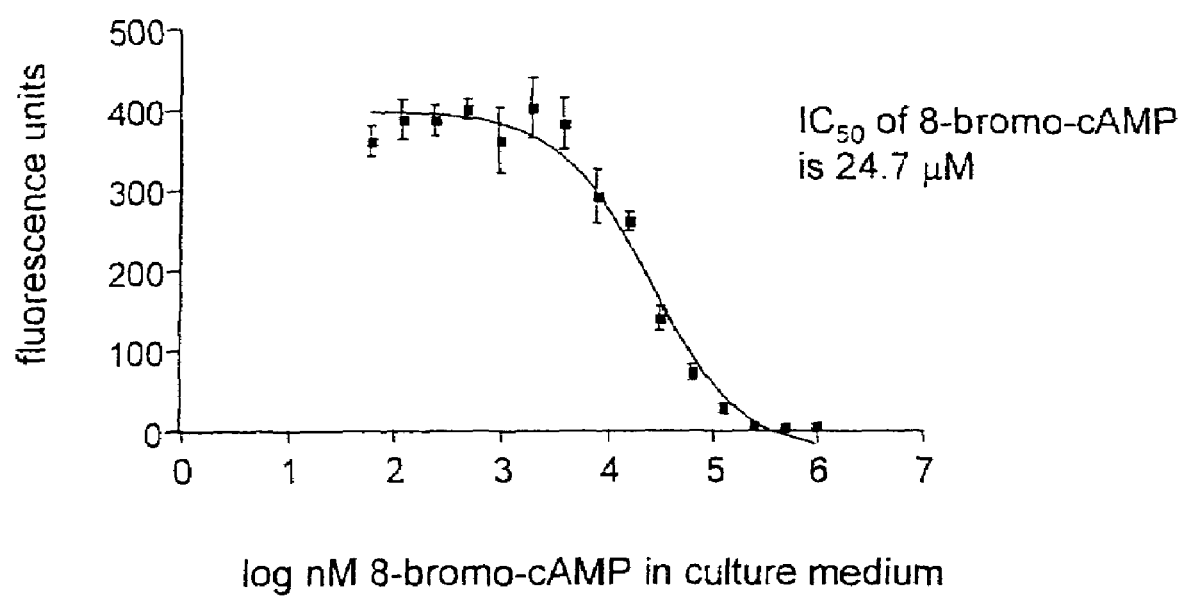

Exquisite sensitivity of bloodstream form trypanosomes against elevated concentrations of cAMP. Following up these findings, we have used membrane-permeable cAMP analogues to demonstrate that bloodstream form trypanosomes are exquisitely sensitive against elevated concentrations of cAMP (FIG. 32). We conclude from these data that an inactivation of the TbPDE2 family either by PDE inhibitors or by genetic means such as RNAi leads to an accumulation of intracellular cAMP which is lethal to the trypanosomes.

This conclusion is further strengthened by our observations from many experiments that knocking out the gene for TbPDE2C is consistently lethal for bloodstream trypanosomes. Independent genetic validation for these observations was obtained by our findings that it is impossible to introduce RNAi constructs directed against the TbPDE2 family into bloodstream form trypanosomes. The (well-established) small amount of leakiness of these constructs is sufficient to reduce the TbPDE2 mRNAs to a level which is lethal for the bloodstream forms. When the same constructs are introduced into the physiologically distinct procyclic forms, a dramatic change in intracellular cAMP concentration (see FIG. 31) is observed, but this does not grossly interfere with the proliferation of procyclic trypanosomes in culture.

Various publications are cited herein that are hereby incorporated by reference in their entirety.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

What is claimed is:

1. An PDE8A protein having the amino acid sequence set forth in SEQ ID NO:2 beginning with methionine at amino acid position 1 and ending with glutamic acid at amino acid position 829.

2. An isolated or purified nucleic acid molecule encoding the protein of claim 1.

3. The nucleic acid molecule of claim 2 having the nucleotide sequence set forth in
   a. SEQ ID NO:1 beginning at adenine at position 137 and ending with adenine at 2623;
   b. FIG. 8a beginning at adenine at position 1 and ending with thymine at 1272;
   c. FIG. 21a beginning at adenine at position 1 and ending with thymine at 1455;
   d. FIG. 16 beginning at adenine at position 1 and ending with thymine at 2790;
   e. FIG. 22a beginning at adenine at position 1 and ending with thymine at 2790; or
   f. FIG. 23a beginning at adenine at position 1 and ending with thymine at 1101.

4. The nucleic acid molecule of claim 3, which is a DNA molecule.

5. The nucleic acid molecule of claim 4, wherein the DNA is a cDNA molecule.

6. An isolated or purified nucleic acid molecule polynucleotide having the sequence of SEQ ID NO:1;
   hybridizes under high stringency conditions to the complement of a polynucleotide encoding the amino acid sequence of SEQ ID NO:3; and
   encodes a protein having phosphodiesterase activity.

7. A vector comprising the nucleic acid molecule of claim 2.

8. A host vector system comprising the vector of claim 7 in a host cell.

9. The host vector system of claim 8, wherein the host cell is a bacterial cell.

10. The host vector system of claim 8, wherein the host cell is a eukaryotic call.

11. A method of producing a PDE protein comprising culturing the host vector system of claim 8 under suitable condition so as to produce the PDE protein in the host and recovering the PDE protein so produced.

12. A method for modulating the expression of a PDE protein, comprising:
   contacting the nucleic acid molecule of claim 6, which nucleic acid encodes PDE8A protein or a variant thereof, with a polynucleotide that hybridizes to the complement of a second nucleic acid encoding the amino acid sequence of SEQ ID NO:3,
   whereby expression of the PDE8A protein is inhibited.

13. The method of claim 12, wherein the contacting occurs in a host cell.

* * * * *